(12) United States Patent
Alam et al.

(10) Patent No.: US 12,258,354 B2
(45) Date of Patent: Mar. 25, 2025

(54) AhR MODULATORS

(71) Applicant: IDEAYA BIOSCIENCES, INC., South San Francisco, CA (US)

(72) Inventors: Muzaffar Alam, South San Francisco, CA (US); Hilary Plake Beck, South San Francisco, CA (US); Michael Patrick Dillon, South San Francisco, CA (US); Marcos Gonzalez-Lopez, South San Francisco, CA (US); James Clifford Sutton, Jr., South San Francisco, CA (US)

(73) Assignee: IDEAYA Biosciences, Inc., South San Francisco, CA (US)

( * ) Notice: Subject to any disclaimer, the term of this patent is extended or adjusted under 35 U.S.C. 154(b) by 0 days.

(21) Appl. No.: 17/853,647

(22) Filed: Jun. 29, 2022

(65) Prior Publication Data

US 2023/0039955 A1    Feb. 9, 2023

Related U.S. Application Data

(62) Division of application No. 17/023,980, filed on Sep. 17, 2020, now Pat. No. 11,407,764, which is a division of application No. 16/268,444, filed on Feb. 5, 2019, now Pat. No. 10,815,250.

(60) Provisional application No. 62/793,260, filed on Jan. 16, 2019, provisional application No. 62/626,739, filed on Feb. 6, 2018.

(51) Int. Cl.
| | |
|---|---|
| *C07D 519/00* | (2006.01) |
| *A61P 35/00* | (2006.01) |
| *C07D 471/04* | (2006.01) |
| *C07D 487/04* | (2006.01) |
| *C07D 491/107* | (2006.01) |
| *C07D 498/04* | (2006.01) |
| *C07D 513/04* | (2006.01) |

(52) U.S. Cl.
CPC ............ *C07D 498/04* (2013.01); *A61P 35/00* (2018.01); *C07D 471/04* (2013.01); *C07D 487/04* (2013.01); *C07D 491/107* (2013.01); *C07D 513/04* (2013.01); *C07D 519/00* (2013.01)

(58) Field of Classification Search
CPC .................................................. C07D 519/00
See application file for complete search history.

(56) References Cited

U.S. PATENT DOCUMENTS

| | | |
|---|---|---|
| 10,815,250 B2 | 10/2020 | Alam et al. |
| 11,407,764 B2 | 8/2022 | Alam et al. |
| 2005/0272728 A1 | 12/2005 | Altenbach et al. |
| 2015/0031672 A1 | 1/2015 | Ren et al. |
| 2021/0002297 A1 | 1/2021 | Alam et al. |
| 2021/0254006 A1 | 8/2021 | Alam et al. |

FOREIGN PATENT DOCUMENTS

| | | |
|---|---|---|
| WO | WO-2000064888 A1 | 11/2000 |
| WO | WO-2003016292 A1 | 2/2003 |
| WO | WO-2006105081 A2 | 10/2006 |
| WO | WO-2007016525 A2 | 2/2007 |
| WO | WO-2008054599 A2 | 5/2008 |
| WO | WO-2009100130 A1 | 8/2009 |
| WO | WO-2009134973 A1 | 11/2009 |
| WO | WO-2009155001 A2 | 12/2009 |
| WO | WO-2010104851 A1 | 9/2010 |
| WO | WO-2010148350 A1 | 12/2010 |
| WO | WO-2012015914 A2 | 2/2012 |
| WO | WO-2012050500 A1 | 4/2012 |
| WO | WO-2012064973 A2 | 5/2012 |
| WO | WO-2012106343 A2 | 8/2012 |
| WO | WO-2013086436 A1 | 6/2013 |
| WO | WO-2005113551 A1 | 10/2015 |
| WO | WO-2015197861 A1 | 12/2015 |

(Continued)

OTHER PUBLICATIONS

CAS, Registry No. 857834-18-5, 1H-Isoindole-1,3(2H)-dione, 2-[4-(2-quinolinyl)phenyl], entered Aug. 1, 2005.
Neunhoeffer et al., Synthese und Fluorescenzverhalten chinolinsubstituierster 1.3.5-Triphenyl-pyrazoline, Chemische Berichte, 1955, v. 88, pp. 1123-1133.
CAS, Registry No. 332403-33-5, 2-(4-(6-(5-carboxy-1,3-dioxoisoindolin-2-yl)-4-phenylquinazolin-2-yl)phenyl)-1,3-dioxoisoindoline-5-carboxylic acid, accessed Jun. 24, 2023.
CAS, Registry No. 332403-34-6, 4-chloro-2-(4-(6-(4-chloro-1,3-dioxoisoindolin-2-yl)-4-phenylquinazolin-2-yl)phenyl)isoindoline-1,3-dione, accessed Jun. 24, 2023.
CAS, Registry No. 332403-37-9, 4-nitro-2-(4-(6-(4-nitro-1,3-dioxoisoindolin-2-yl)-4-phenylquinazolin-2-yl)phenyl)isoindoline-1,3-dione, accessed Jun. 24, 2023.

(Continued)

*Primary Examiner* — Susanna Moore
(74) *Attorney, Agent, or Firm* — Mintz Levin Cohn Ferris Glovsky and Popeo PC

(57) ABSTRACT

Provided herein are compounds, compositions and methods of using the compounds and compositions for the treatment of diseases modulated, as least in part, by AhR. The compounds are represented by formulae:

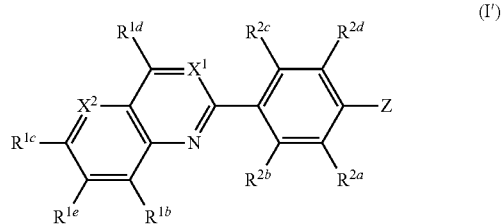

wherein the letters and symbols $X^1$, $X^2$, Z, $R^{1b}$, $R^{1c}$, $R^{1d}$, $R^{1e}$, $R^{2a}$, $R^{2b}$, $R^{2c}$ and $R^{2d}$ have the meanings provided in the specification.

14 Claims, No Drawings

(56) References Cited

FOREIGN PATENT DOCUMENTS

| | | |
|---|---|---|
| WO | WO-2016210292 A1 | 12/2016 |
| WO | WO-2017184547 A1 | 10/2017 |
| WO | WO-2018141855 A1 | 8/2018 |
| WO | WO-2018141857 A1 | 8/2018 |
| WO | WO-2018153893 A1 | 8/2018 |
| WO | WO-2018195397 A2 | 10/2018 |
| WO | WO-2019018562 A1 | 1/2019 |
| WO | WO-2019156987 A1 | 8/2019 |
| WO | WO-2019236766 A1 | 12/2019 |

OTHER PUBLICATIONS

CAS, Registry No. 356079-78-2, 2-(4-(4-phenylquinazolin-2-yl)phenyl)isoindoline-1,3-dione, accessed Jun. 24, 2023.
CAS, Registry No. 499975-52-9, 2-(4-(6-(1,3-dioxoisoindolin-2-yl)-4-phenylquinazolin-2-yl)phenyl)isoindoline-1,3-dione, accessed Jun. 24, 2023.
CAS, Registry No. 512194-33-1, 2-(4-(1,3-dioxo-1,3,3a,4,7,7a-hexahydro-2H-isoindol-2-yl)phenyl)quinoline-4-carboxylic acid, accessed Jun. 24, 2023.
CAS, Registry No. 512194-34-2, 6-chloro-2-(4-(1,3-dioxo-1,3,3a,4,7,7a-hexahydro-2H-isoindol-2-yl)phenyl)quinoline-4-carboxylic acid, accessed Jun. 24, 2023.
CAS, Registry No. 512194-35-3, 2-(4-(1,3-dioxo-1,3,3a,4,7,7a-hexahydro-2H-isoindol-2-yl)phenyl)-8-methylquinoline-4-carboxylic acid, accessed Jun. 24, 2023.
CAS, Registry No. 512194-36-4, 6-bromo-2-(4-(1,3-dioxo-1,3,3a,4,7,7a-hexahydro-2H-isoindol-2-yl)phenyl)-8-ethylquinoline-4-carboxylic acid, accessed Jun. 24, 2023.
CAS, Registry No. 512194-37-5, 6-bromo-2-(4-(1,3-dioxo-1,3,3a,4,7,7a-hexahydro-2H-isoindol-2-yl)phenyl)-8-methylquinoline-4-carboxylic acid, accessed Jun. 24, 2023.
CAS, Registry No. 512194-38-6, 2-(4-(1,3-dioxooctahydro-2H-isoindol-2-yl)phenyl)quinoline-4-carboxylic acid, accessed Jun. 24, 2023.
CAS, Registry No. 512194-39-7, 6-chloro-2-(4-(1,3-dioxooctahydro-2H-isoindol-2-yl)phenyl)quinoline-4-carboxylic acid, accessed Jun. 24, 2023.
CAS, Registry No. 512194-40-0, 6-bromo-2-(4-(1,3-dioxooctahydro-2H-isoindol-2-yl)phenyl)quinoline-4-carboxylic acid, accessed Jun. 24, 2023.
CAS, Registry No. 512194-41-1, 2-(4-(1,3-dioxooctahydro-2H-isoindol-2-yl)phenyl)-8-methylquinoline-4-carboxylic acid, accessed Jun. 24, 2023.
CAS, Registry No. 512194-42-2, 6-bromo-2-(4-(1,3-dioxooctahydro-2H-isoindol-2-yl)phenyl)-8-ethylquinoline-4-carboxylic acid, accessed Jun. 24, 2023.
CAS, Registry No. 512194-43-3, 7-chloro-2-(4-(1,3-dioxooctahydro-2H-isoindol-2-yl)phenyl)-8-methylquinoline-4-carboxylic acid, accessed Jun. 24, 2023.
CAS, Registry No. 512194-44-4, 6-bromo-7-chloro-2-(4-(1,3-dioxooctahydro-2H-isoindol-2-yl)phenyl)-8-methylquinoline-4-carboxylic acid, accessed Jun. 24, 2023.
CAS, Registry No. 512194-45-5, 6-bromo-2-(4-(1,3-dioxooctahydro-2H-isoindol-2-yl)phenyl)-8-methylquinoline-4-carboxylic acid, accessed Jun. 24, 2023.
CAS, Registry No. 512194-46-6, 2-(4-(1,3-dioxoisoindolin-2-yl)phenyl)quinoline-4-carboxylic acid, accessed Jun. 24, 2023.
CAS, Registry No. 512194-47-7, 6-chloro-2-(4-(1,3-dioxoisoindolin-2-yl)phenyl)quinoline-4-carboxylic acid, accessed Jun. 24, 2023.
CAS, Registry No. 512194-48-8, 2-(4-(1,3-dioxoisoindolin-2-yl)phenyl)-6-methylquinoline-4-carboxylic acid, accessed Jun. 24, 2023.
CAS, Registry No. 512194-49-9, 2-(4-(1,3-dioxoisoindolin-2-yl)phenyl)-8-methylquinoline-4-carboxylic acid, accessed Jun. 24, 2023.
CAS, Registry No. 512194-50-2, 6-bromo-2-(4-(1,3-dioxoisoindolin-2-yl)phenyl)-8-ethylquinoline-4-carboxylic acid, accessed Jun. 24, 2023.
CAS, Registry No. 512194-51-3, 7-chloro-2-(4-(1,3-dioxoisoindolin-2-yl)phenyl)-8-methylquinoline-4-carboxylic acid, accessed Jun. 24, 2023.
CAS, Registry No. 512194-52-4, 6-bromo-7-chloro-2-(4-(1,3-dioxoisoindolin-2-yl)phenyl)-8-methylquinoline-4-carboxylic acid, accessed Jun. 24, 20231.
CAS, Registry No. 512194-53-5, 6-bromo-2-(4-(1,3-dioxoisoindolin-2-yl)phenyl)-8-methylquinoline-4-carboxylic acid, accessed Jun. 24, 2023.
CAS, Registry No. 669741-08-6, 8-chloro-2-(4-(1,3-dioxo-1,3,3a,4,7,7a-hexahydro-2H-isoindol-2-yl)phenyl)quinoline-4-carboxylic acid, accessed Jun. 24, 2023.
CAS, Registry No. 669741-57-5, 2-(4-(1,3-dioxooctahydro-2H-isoindol-2-yl)phenyl)-6-methylquinoline-4-carboxylic acid, accessed Jun. 24, 2023.
CAS, Registry No. 669742-09-0, 2-(4-(1,3-dioxo-1,3,3a,4,7,7a-hexahydro-2H-isoindol-2-yl)phenyl)-6-methylquinoline-4-carboxylic acid, accessed Jun. 24, 2023.
CAS, Registry No. 886701-66-2, 6-bromo-7-chloro-2-(4-(1,3-dioxo-1,3,3a,4,7,7a-hexahydro-2H-isoindol-2-yl)phenyl)-8-methylquinoline-4-carboxylic acid, accessed Jun. 24, 2023.
CAS, Registry No. 886729-14-2, 7-chloro-2-(4-(1,3-dioxo-1,3,3a,4,7,7a-hexahydro-2H-isoindol-2-yl)phenyl)-8-methylquinoline-4-carboxylic acid, accessed Jun. 24, 2023.
CAS, Registry No. 895756-49-7, 4-((1,3-dioxo-2-(4-(4-phenylquinazolin-2-yl)phenyl)isoindolin-5-yl)oxy)benzoic acid, accessed Jun. 24, 2023.
CAS, Registry No. 903237-01-4, 8-chloro-2-(4-(1,3-dioxoisoindolin-2-yl)phenyl)quinoline-4-carboxylic acid, accessed Jun. 24, 2023.
CAS, Registry No. 932835-31-9, 6-bromo-2-(4-(1,3-dioxo-1,3,3a,4,7,7a-hexahydro-2H-isoindol-2-yl)phenyl)quinoline-4-carboxylic acid, accessed Jun. 24, 2023.
CAS, Registry No. 932925-77-4, 6-bromo-2-(4-(1,3-dioxoisoindolin-2-yl)phenyl)quinoline-4-carboxylic acid, accessed Jun. 24, 2023.
CAS, Registry No. 1005188-55-5, 6-methyl-2-(4-(5-methyl-1,3-dioxooctahydro-2H-isoindol-2-yl)phenyl)quinoline-4-carboxylic acid, accessed Jun. 24, 2023.
CAS, Registry No. 1022029-19-1, 6-bromo-8-ethyl-2-(4-(5-methyl-1,3-dioxooctahydro-2H-isoindol-2-yl)phenyl)quinoline-4-carboxylic acid, accessed Jun. 24, 2023.
CAS, Registry No. 1022356-23-5, 6-bromo-2-(4-(5-methyl-1,3-dioxooctahydro-2H-isoindol-2-yl)phenyl)quinoline-4-carboxylic acid, accessed Jun. 24, 2023.
CAS, Registry No. 1022403-15-1, 6-bromo-2-(4-(5,6-dibromo-1,3-dioxooctahydro-2H-isoindol-2-yl)phenyl)-8-methylquinoline-4-carboxylic acid, accessed Jun. 24, 2023.
CAS, Registry No. 1022464-24-9, 6-bromo-7-chloro-2-(4-(5,6-dibromo-1,3-dioxooctahydro-2H-isoindol-2-yl)phenyl)-8-methylquinoline-4-carboxylic acid, accessed Jun. 24, 2023.
CAS, Registry No. 1022510-65-1, 2-(4-(5,6-dibromo-1,3-dioxooctahydro-2H-isoindol-2-yl)phenyl)-8-methylquinoline-4-carboxylic acid, accessed Jun. 24, 2023.
CAS, Registry No. 1023476-69-8, 6-bromo-7-chloro-8-methyl-2-(4-(5-methyl-1,3-dioxooctahydro-2H-isoindol-2-yl)phenyl)quinoline-4-carboxylic acid, accessed Jun. 24, 2023.
CAS, Registry No. 1023479-76-6, 8-methyl-2-(4-(5-methyl-1,3-dioxooctahydro-2H-isoindol-2-yl)phenyl)quinoline-4-carboxylic acid, accessed Jun. 24, 2023.
CAS, Registry No. 1023496-95-8, 6-bromo-2-(4-(5,6-dibromo-1,3-dioxooctahydro-2H-isoindol-2-yl)phenyl)quinoline-4-carboxylic acid, accessed Jun. 24, 2023.
CAS, Registry No. 1023510-67-9, 8-chloro-2-(4-(5-methyl-1,3-dioxooctahydro-2H-isoindol-2-yl)phenyl)quinoline-4-carboxylic acid, accessed Jun. 24, 2023.
CAS, Registry No. 1023514-06-8, 6-bromo-7-chloro-8-methyl-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1023515-24-3, 6-bromo-8-methyl-2-(4-(4-methyl-1,3-dioxo-1,3,3a,4,7,7a-hexahydro-2H-isoindol-2-yl)phenyl)quinoline-4-carboxylic acid, accessed Jun. 24, 2023.

(56) References Cited

OTHER PUBLICATIONS

CAS, Registry No. 1023548-81-3, 8-chloro-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1023565-72-1, 6-chloro-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1023810-53-8, 6-bromo-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1023815-77-1, 2-(4-(5,6-dibromo-1,3-dioxooctahydro-2H-isoindol-2-yl)phenyl)quinoline-4-carboxylic acid, accessed Jun. 24, 2023.
CAS, Registry No. 1023816-02-5, 6-bromo-8-ethyl-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1023861-09-7, 7-chloro-8-methyl-2-(4-(5-methyl-1,3-dioxooctahydro-2H-isoindol-2-yl)phenyl)quinoline-4-carboxylic acid, accessed Jun. 24, 2023.
CAS, Registry No. 1024052-36-5, 2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1024083-96-2, 2-(4-(5,6-dibromo-1,3-dioxooctahydro-2H-isoindol-2-yl)phenyl)-6-methylquinoline-4-carboxylic acid, accessed Jun. 24, 2023.
CAS, Registry No. 1024123-04-3, 2-(4-(5-methyl-1,3-dioxooctahydro-2H-isoindol-2-yl)phenyl)quinoline-4-carboxylic acid, accessed Jun. 24, 2023.
CAS, Registry No. 1024233-59-7, 6-chloro-2-(4-(5,6-dibromo-1,3-dioxooctahydro-2H-isoindol-2-yl)phenyl)quinoline-4-carboxylic acid, accessed Jun. 24, 2023.
CAS, Registry No. 1024266-91-8, 6-methyl-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1024310-86-8, 7-chloro-2-(4-(5,6-dibromo-1,3-dioxooctahydro-2H-isoindol-2-yl)phenyl)-8-methylquinoline-4-carboxylic acid, accessed Jun. 24, 2023.
CAS, Registry No. 1024314-04-2, 8-chloro-2-(4-(5,6-dibromo-1,3-dioxooctahydro-2H-isoindol-2-yl)phenyl)quinoline-4-carboxylic acid, accessed Jun. 24, 2023.
CAS, Registry No. 1024324-97-7, 6-bromo-2-(4-(5,6-dibromo-1,3-dioxooctahydro-2H-isoindol-2-yl)phenyl)-8-ethylquinoline-4-carboxylic acid, accessed Jun. 24, 2023.
CAS, Registry No. 1024399-70-9, 7-chloro-8-methyl-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1024511-57-6, 8-methyl-2-(4-(4-methyl-1,3-dioxo-1,3,3a,4,7,7a-hexahydro-2H-isoindol-2-yl)phenyl)quinoline-4-carboxylic acid, accessed Jun. 24, 2023.
CAS, Registry No. 1052645-27-8, 6-chloro-2-(4-(5-methyl-1,3-dioxooctahydro-2H-isoindol-2-yl)phenyl)quinoline-4-carboxylic acid, accessed Jun. 24, 2023.
CAS, Registry No. 1052645-43-8, 6-bromo-8-methyl-2-(4-(5-methyl-1,3-dioxooctahydro-2H-isoindol-2-yl)phenyl)quinoline-4-carboxylic acid, accessed Jun. 24, 2023.
Database Caplus, Chemical Abstracts Service, Columbus, Ohio, US, Jan. 1, 1956, XP002789704, Database accession No. 1956:73937, 5 pages.
International Search Report for PCT/US2019/016705, mailed Jul. 29, 2019, 4 pages.
International Search Report for PCT/US2019/035671, mailed Aug. 27, 2019, 5 pages.
Joseph et al., Abstract 4719: Small-molecule antagonists of the Aryl Hydrocarbon receptor (AhR) promote activation of human PBMCs in vitro and demonstrate significant impact on tumor growth and immune modulation in vivo, Immunology, Apr. 14, 2018, p. 4719, Abstract.
Written Opinion for PCT/US2019/016705, mailed Jul. 29, 2015, 7 pages.
Written Opinion for PCT/US2019/035671, mailed Aug. 27, 2019, 8 pages.

AhR MODULATORS

CROSS-REFERENCES TO RELATED APPLICATIONS

This application is a divisional application of U.S. application Ser. No. 17/023,980, filed Sep. 17, 2020, which is a divisional of U.S. application Ser. No. 16/268,444, filed Feb. 5, 2019, now U.S. Pat. No. 10,815,250, which claims the benefit of priority under 35 U.S.C § 119(e) to U.S. Provisional Application Ser. No. 62/626,739, filed Feb. 6, 2018 and U.S. Provisional Application Ser. No. 62/793,260 filed Jan. 16, 2019, each of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The aryl hydrocarbon receptor (AhR) is a helix-loop-helix ligand-activated transcription factor that mediates biological responses to aromatic hydrocarbons. AhR is localized in the cytoplasm, where upon binding to a hydrocarbon based ligand agonist such as 2,3,7,8-tetrachlorodibenzo-p-dioxin (TCDD), it migrates to the nucleus and forms a heterodimer with aryl hydrocarbon receptor nuclear translocator (ARNT). Formation of the AhR/ARNT complexes subsequently enables binding to and transcription of the xenobiotic response element (XRE) and associated genes. AhR can also activate a non-XRE dependent protein-protein interaction pathway.

Through its XRE-dependent and independent activity, AhR modulates numerous critical innate and adaptive immune responses. Chief among those responses, AhR agonists promote development of IL-17 producing T-helper cells (Th17) and regulatory T-cells (Tregs). AhR activation further induces trans-differentiation of Th17 cells to Tregs and enhances the suppressive activity of Tregs. Studies have also demonstrated that AhR agonism results in suppression of innate inflammatory responses mediated by macrophages (e.g. Reduced LPS-induced IL-1b, IL-6, IL-12 and TNFa expression) and dendritic cells (DCs) (inhibits activation of DCs and promotes expression of IL-10).

To mount an effective anti-tumor immune response, antigen presenting cells (APCs) are required to process, present and consequently activate helper CD4+ T-cells (Th) and cytotoxic CD8+ T-cells (Tc) which act in concert to effectively lyse tumor cells. Tumor cells have developed several mechanisms to evade the immune mediated lysis of Th and Tc. One such mechanism is the release of high concentrations of kynurenine and other potential AhR ligands in the tumor microenvironment (TME). High AhR ligand concentrations activate the AhR in the TME resulting in suppression of APCs, Th and Tc directly, as well as recruitment, generation and activation of Tregs and Th17 which further suppress the activity of Th and Tc. Through this mechanism, tumor cells are capable of evading anti-tumor immune responses. An antagonist of the AhR pathway would therefore block the AhR-dependent immune evasion mechanisms employed by malignant cells and restore effective anti-tumor immunity.

Recent insights into tumor immunobiology has revealed that malignant cells employ a composite of immune-evasion mechanisms. Blocking or enhancing these mechanisms through a combination of therapeutic applications such as immune check point inhibition and vaccines has been demonstrated pre-clinically and clinically to provide an optimal restoration of the anti-tumor immune response. While it is expected that AhR antagonism in monotherapy will restore anti-tumor immunity, a combination of an AhR modulator with a check point inhibitor and/or vaccine is predicted to work in concert with other therapeutics to potentiate the immunotherapeutic response.

Immune mechanisms regulated by AhR have also been associated with autoimmune and inflammatory diseases such as multiple sclerosis and inflammatory bowel diseases. The activation of AhR by agonists could therefore be beneficial for the therapeutic treatment of autoimmune and inflammatory diseases. While agonists of AhR are described in the art, there remains a need for improved compositions and methods for immunological modulation of treating autoimmune and inflammatory diseases via modulation of AhR.

BRIEF SUMMARY OF THE INVENTION

Provided herein are compounds, compositions and methods of using the compounds and compositions for the treatment of diseases modulated, at least in part, by AhR. The compounds are represented by formula (I'):

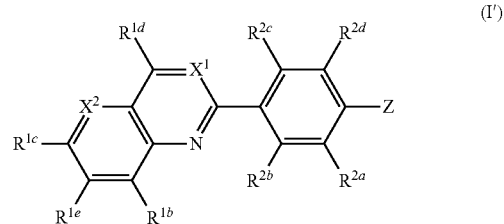

wherein the letters and symbols $X^1$, $X^2$, Z, $R^{1b}$, $R^{1c}$, $R^{1d}$, $R^{1e}$, $R^{2a}$, $R^{2b}$, $R^{2c}$ and $R^{2d}$ have the meanings provided below.

BRIEF DESCRIPTION OF THE DRAWINGS

Not Applicable

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The present invention is drawn to, inter alia, small molecule compounds having AhR modulator activity, as well as compositions thereof, and methods of using the compounds and compositions for the treatment and prevention of the diseases, disorders and conditions described herein.

Definitions

Unless otherwise indicated, the following terms are intended to have the meaning set forth below. Other terms are defined elsewhere throughout the specification.

The term "alkyl", by itself or as part of another substituent, means, unless otherwise stated, a saturated straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "deuteroalkyl", by itself or as part of another substituent, refers to an alkyl group wherein from one to five hydrogen atoms have been replaced by deuterium. An example of a "deuteroalkyl" group is —$CD_3$.

The term "alkylene" refers to a divalent alkyl group as defined herein. Examples of alkylene include methylene, ethylene, and the like.

The term "alkenyl", by itself or as part of another substituent, means, unless otherwise stated, a straight or branched chain hydrocarbon radical containing one or two double bonds and having the number of carbon atoms designated (i.e. $C_{2-6}$ means two to six carbons). Examples of alkenyl groups include ethenyl, n-propenyl, isopropenyl, n-butenyl, and the like.

The term "alkynyl", by itself or as part of another substituent, means, unless otherwise stated, a straight or branched chain hydrocarbon radical containing a triple and having the number of carbon atoms designated (i.e. $C_{2-6}$ means two to six carbons). Examples of alkynyl groups include ethynyl, propynyl, and the like.

The term "cycloalkyl" refers to hydrocarbon rings having the indicated number of ring atoms (e.g., $C_{3-6}$ cycloalkyl) and being fully saturated or having no more than one double bond between ring vertices.

The term "heterocycloalkyl" refers to a ring having the indicated number of vertices ($C_{3-7}$ refers to a 3- to 7-membered ring) and having from one to five heteroatoms selected from N, O, and S, which replace one to five of the carbon vertices, and wherein the nitrogen and sulfur atoms are optionally oxidized, and the nitrogen atom(s) are optionally quaternized. More specifically, the subscript refers to the total number of ring vertices including the carbon and heteroatom ring vertices. The heterocycloalkyl may be a monocyclic, a bicyclic or a polycyclic ring system. Non-limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

As used herein, a wavy line, "⁓", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—$CH_2CH_2$—" is meant to include both —O—$CH_2CH_2$— and —$CH_2CH_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. The terms "deuteroalkoxy is used in its conventional sense, and refer to deuteroalkyl, as defined herein, that is attached to the remainder of the molecule via an oxygen atom.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to a 5- to 10-membered aromatic ring (or fused ring system) that contains from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal). In one embodiment, the patient is human.

The term "spiroheterocycloalkyl" means a saturated bicyclic ring having 6 to 12 ring atoms in which one of the ring atoms is nitrogen and may contain one or two additional heteroatoms selected from N, O, and S(O)$_n$, where n is an integer from 0 to 2, the remaining ring atoms being C and the rings are connected via a single atom is also called the spiroatom, most often a quaternary carbon ("spiro carbon"). Representative examples include, but are not limited to, 2,6-diazaspiro[3.3]heptane, 2,6-diazaspiro[3.4]octane, 2-azaspiro[3.4]octane, 2-azaspiro[3.5]-nonane, 2,7-diazaspiro[4.4]nonane, and the like.

The terms "administration", "administer" and the like, as they apply to, for example, a subject, cell, tissue, organ, or biological fluid, refer to contact of, for example, an AhR modulator, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an AhR modulator or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an AhR modulator or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an AhR modulator (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of AhR, either directly or indirectly. A modulator may act alone, or it may use a cofactor, e.g., a protein, metal ion, or small molecule. Examples of modulators include small molecule compounds and other bioorganic molecules.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

AhR and Modulation Thereof

Identification of AhR Modulators Possessing Desirable Characteristics

The present invention is drawn, in part, to the identification of AhR modulators with at least one property or characteristic that is of therapeutic relevance. Candidate AhR modulators can be identified by using, for example, an art-accepted assay or model, examples of which are will be apparent to the skilled artisan. The assay used to determine the AhR modulatory activity of the compounds described herein is set forth in the Experimental section.

After identification, candidate modulators can be further evaluated by using techniques that provide data regarding characteristics of the modulators (e.g., pharmacokinetic parameters). Comparisons of the candidate modulators to a reference standard (which may be the "best-of-class" of current modulators) are indicative of the potential viability of such candidates.

AhR modulators that can serve as reference or benchmark compounds include CH223191, StemRegenin-1, kynurenine, ITE, GNF351, and CB7993113. Other reference compounds subsequently identified by the skilled artisan can also be used to assess the viability of candidate AhR modulators.

Compounds

Provided herein are compound having the formula (I'):

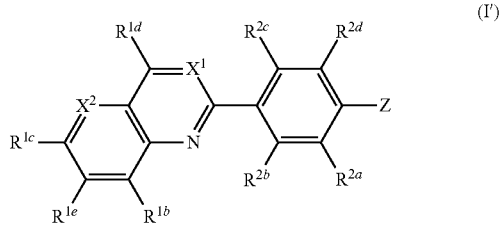

or a pharmaceutically acceptable salt, solvate or hydrate thereof, wherein:

each of ring vertices $X^1$ and $X^2$ is independently selected from the group consisting of $C(R^{1a})$ and N;

Z is selected from the group consisting of:

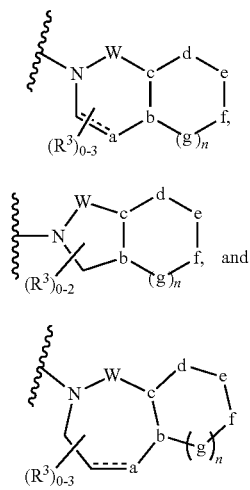

wherein:
the dashed bonds are single or double bonds;
n is 0 or 1;
W is —C(O)— or —SO$_2$—;
each of ring vertices a, b, c, d, e, f, and g are independently selected from the group consisting of O, S, N, C(R$^4$) and N(R$^4$), and the bonds joining the ring vertices are independently single or double bonds;

each $R^{1a}$, $R^{1b}$, $R^{1c}$, $R^{1d}$ and $R^{1e}$ is independently selected from the group consisting of hydrogen, deuterium, halogen, —CN, —NO$_2$, —R$^c$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^a$, and —S(O)$_2$NR$^a$R$^b$; wherein each R$^a$ and R$^b$ is independently selected from hydrogen, C$_{1-8}$ alkyl, C$_{3-6}$ cycloalkyl and C$_{1-8}$ haloalkyl, or when attached to the same nitrogen atom can be combined with the nitrogen atom to form a four-, five- or six-membered ring having from 0 to 2 additional heteroatoms as ring members selected from N, O, S, SO or SO$_2$; each R$^c$ is independently selected from the group consisting of C$_{1-8}$ alkyl, C$_{1-8}$ haloalkyl, C$_{1-8}$ deuteroalkyl, C$_{2-6}$ alkenyl, C$_{2-6}$ alkynyl, and C$_{3-6}$ cycloalkyl, and wherein the aliphatic and cyclic portions of R$^a$, R$^b$ and R$^c$ can be further substituted with from one to three halogen, hydroxy, C$_{1-4}$ alkyl, C$_{1-4}$ alkoxy, amino, C$_{1-4}$ alkylamino, di C$_{1-4}$ alkylamino and carboxylic acid groups;

each $R^{2a}$, $R^{2b}$, $R^{2c}$ and $R^{2d}$ is independently selected from the group consisting of hydrogen, halogen, C$_{1-3}$ alkyl, C$_{1-3}$ deuteroalkyl, C$_{1-3}$ haloalkyl, C$_{1-3}$ alkoxy, C$_{1-3}$ deuteroalkoxy and C$_{1-3}$ haloalkoxy;

$R^3$ is selected from the group consisting of hydrogen, deuterium, C$_{1-3}$ alkyl, C$_{1-3}$ deuteroalkyl, C$_{1-3}$ alkylene-OR$^d$, C$_{1-3}$ alkylene-CO$_2$R$^d$, C$_{1-3}$ alkylene-NR$^d$R$^e$, C$_{1-3}$ alkylene-CONR$^d$R$^e$, C$_{1-3}$ alkylene-OC(O)NR$^d$R$^e$, and C$_{1-3}$ alkylene-NR$^e$C(O)$_2$R$^f$; or two R$^3$ groups are combined to form oxo (=O);

each R$^4$ is independently selected from the group consisting of hydrogen, halogen, —CN, —R$^e$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$R$^e$, —OR$^a$, —S(O)$_2$NR$^d$R$^e$, —X$^a$—CN, —X$^a$—CO$_2$R$^d$, —X$^a$—CONR$^d$R$^e$, —X$^a$—C(O)R$^d$, —X$^a$—OC(O)NR$^d$R$^e$, —X$^a$—NR$^e$C(O)R$^d$, —X$^a$—NR$^e$C(O)$_2$Rt, —X$^a$—NR$^d$C(O)NR$^d$R$^e$, —X$^a$—NR$^d$R$^e$, —X$^a$—OR$^d$, —X$^a$—S(O)$_2$NR$^d$R$^e$, and —X$^a$—OP(O)(OH)$_2$; wherein each X$^a$ is independently C$_{1-6}$alkylene; and each R$^d$ and R$^e$ is independently selected from hydrogen, C$_{1-8}$ alkyl, and C$_{1-8}$ haloalkyl, or when attached to the same nitrogen atom can be combined with the nitrogen atom to form either (i) a four-, five- or six-membered ring having from 0 to 3 additional heteroatoms as ring members selected from N, O, C(O), S, SO or SO$_2$ or (ii) a spiroheterocycloalkyl ring;

each R$^f$ is independently selected from the group consisting of C$_{1-8}$ alkyl, C$_{1-8}$ haloalkyl, C$_{1-8}$ deuteroalkyl, C$_{3-6}$ cycloalkyl, C$_{3-6}$ heterocycloalkyl, phenyl and 5- or 6-membered heteroaryl;

and wherein the aliphatic and cyclic portions of R$^d$, R$^e$ and R$^f$ are can be further substituted with from one to three halogen, hydroxy, benzyloxy, C$_{1-4}$ alkyl, C$_{1-4}$ alkoxy, amino, C$_{1-4}$ alkylamino, di C$_{1-4}$ alkylamino, tetrazolyl, and carboxylic acid groups.

In a first embodiment, the compounds of formula (I'), are wherein Z is selected from the group consisting of:

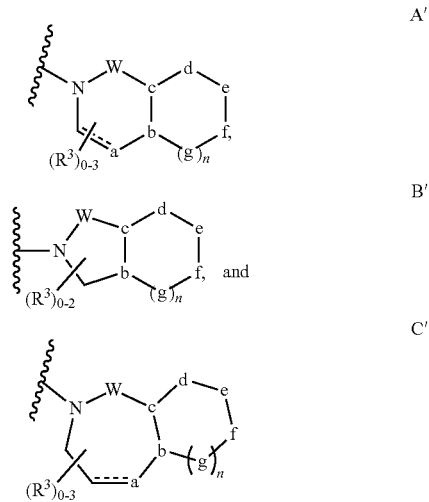

wherein:
the dashed bonds (i.e., ======) are single bonds;
vertex a is selected from the group consisting of O, S, N, CH($R^4$) and N($R^4$) and each of ring vertices b, c, d, e, f, and g are independently selected from the group consisting of O, S, N, C($R^4$) and N($R^4$), and the bonds joining the ring vertices are independently single or double bonds (i.e., b, c, d, e, f, and g form an aromatic ring).

In one group of embodiments, the compounds of formula (I') and compounds of formula (I') in a first embodiment, are wherein Z has subformula A' (formula I'A').

In another group of embodiments, the compounds of formula (I') and compounds of formula (I') in a first embodiment, are wherein Z has subformula B' (formula I'B').

In yet another group of embodiments, the compounds of formula (I') and compounds of formula (I') in a first embodiment, are wherein Z has subformula C' (formula I'C').

In yet another group of embodiments, the compounds of formula (I') and compounds in any one of the embodiments above, are wherein n is 0.

In yet another group of embodiments, the compounds of formula (I') and compounds in any one of the embodiments above, are wherein n is 1.

Within compounds of formula (I'), compounds of formula (I') in a first embodiment, and embodiments referred to above as formula I'A', in selected embodiments, Z is selected from the group consisting of:

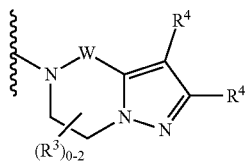
A'1

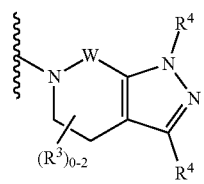
A'2

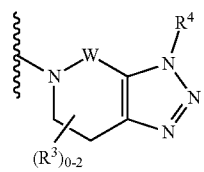
A'3

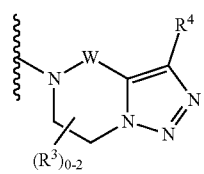
A'4

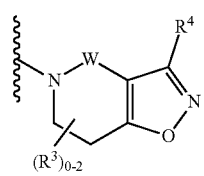
A'5

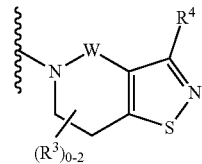
A'6

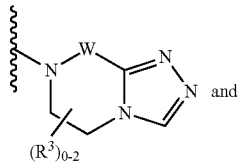
A'7
and

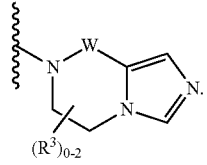
A'8

Within above selected embodiments, in further selected embodiments, Z is A'1. Within above selected embodiments, in another further selected embodiments, Z is A'2. Within above selected embodiments, in yet another further selected embodiments, Z is A'3. Within above selected embodiments, in yet another further selected embodiments, Z is A'4. Within above selected embodiments, in yet another further selected embodiments, Z is A'5. Within above selected embodiments, in yet another further selected embodiments, Z is A'6. Within above selected embodiments, in yet another further selected embodiments, Z is A'7. Within above selected embodiments, in a further selected embodiments, Z is A'8.

Within compounds of formula (I'), compounds of formula (I') in a first embodiment, embodiments referred to herein as formula I'A', and selected and further selected embodiments thereof above, in further selected embodiments, W is —C(O)—.

Within compounds of formula (I'), embodiments referred to herein as formula I'A', compounds of formula (I') in a first embodiment, and selected and further embodiments thereof above, in another further selected embodiments, W is —SO$_2$—.

Within compounds of formula (I'), compounds of formula (I') in a first embodiment, and embodiments referred to above as formula I'B', in selected embodiments, Z is selected from the group consisting of:

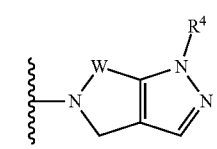
B'1

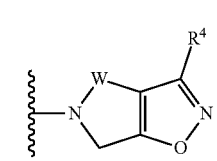
B'2

-continued

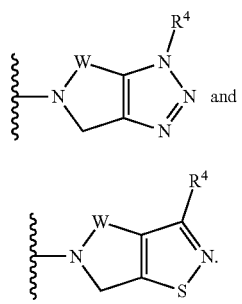
B'3 and

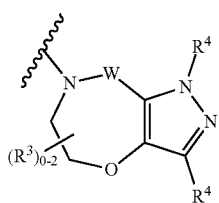
B'4

Within above selected embodiments, in further selected embodiments, Z is B'1. Within above selected embodiments, in another further selected embodiments Z is B'2. Within above selected embodiments, in another further selected embodiments Z is B'3. Within above selected embodiments, in another further selected embodiments Z is B'4.

Within compounds of embodiments referred to herein as formula I'B', and selected and further embodiments thereof above, in further selected embodiments, W is —C(O)—.

Within compounds of embodiments referred to herein as formula I'B' and selected and further embodiments thereof above, in another further selected embodiments, W is —SO$_2$—.

Within compounds of formula (I'), compounds of formula (I') in first embodiment, and embodiments referred to above as formula I'C'; in selected embodiments, Z is selected from the group consisting of:

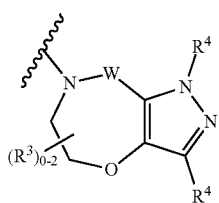
C'1

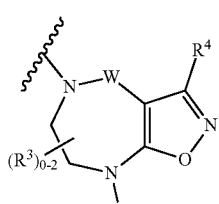
C'2

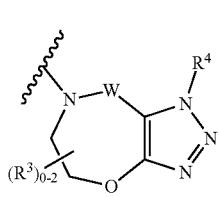
C'3

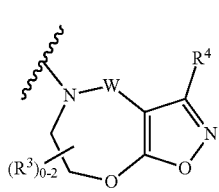
C'4

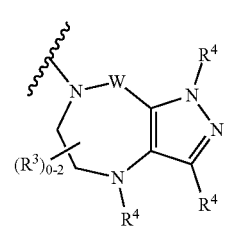
C'5

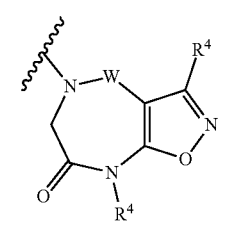
C'6

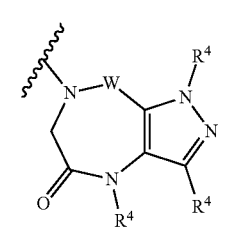
C'7

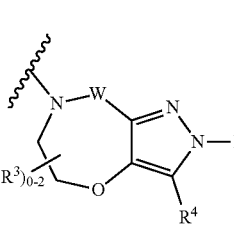
C'8

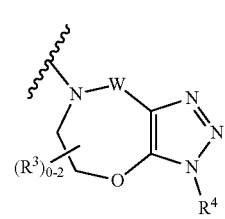
C'9

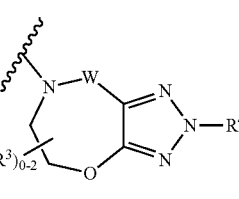
C'10

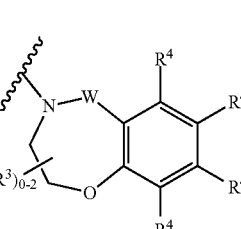
C'11

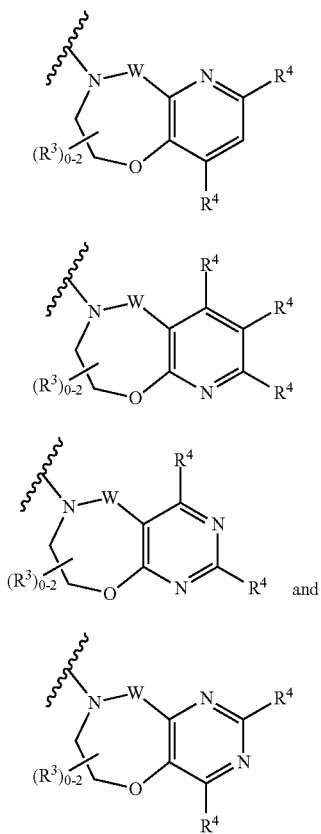

Within above selected embodiments, in further selected embodiments, Z is C'1. Within above selected embodiments, in another further selected embodiments, Z is C'2. Within above selected embodiments, in yet another further selected embodiments, Z is C'3. Within above selected embodiments, in yet another further selected embodiments, Z is C'4. Within above selected embodiments, in yet another further selected embodiments, Z is C'5. Within above selected embodiments, in yet another further selected embodiments, Z is C'6. Within above selected embodiments, in a further selected embodiments, Z is C'7. Within above selected embodiments, in another further selected embodiments, Z is C'8. Within above selected embodiments, in yet another further selected embodiments, Z is C'9. Within above selected embodiments, in yet another further selected embodiments, Z is C'10. Within above selected embodiments, in yet another further selected embodiments, Z is C'11. Within above selected embodiments, in yet another further selected embodiments, Z is C'12. Within above selected embodiments, in a further selected embodiments, Z is C'13. Within above selected embodiments, in a further selected embodiments, Z is C'14. Within above selected embodiments, in a further selected embodiments, Z is C'15.

Within compounds of embodiments referred to herein as formula I'C', and selected and further embodiments thereof above, in further selected embodiments, W is —C(O)—.

Within compounds of embodiments referred to herein as formula I'C' and selected and further embodiments thereof above, in another further selected embodiments, W is —SO$_2$—.

In some selected embodiments, compounds of formula I' and compounds of any one of the embodiments above, are wherein $X^1$ is N.

In some selected embodiments, compounds of formula I' and compounds of any one of the above embodiments, are wherein $X^2$ is N.

In some selected embodiments, compounds of formula I' and compounds of any one of above embodiments, are wherein $X^1$ and $X^2$ are both N.

In some selected embodiments, compounds of formula I' and compounds of any one of above embodiments, are wherein $R^{1b}$ is selected from the group consisting of H, deuterium, halogen, $C_{1-4}$ alkyl, —$OC_{1-4}$ alkyl, $C_{1-4}$ haloalkyl, and —$OC_{1-4}$ haloalkyl. In further selected embodiments, $R^{1b}$ is selected from the group consisting of H, deuterium, and $CH_3$.

In some selected embodiments, compounds of formula I' and compounds of any one of above embodiments, are wherein $R^{1c}$ is selected from the group consisting of H, deuterium, halogen, $C_{1-4}$ alkyl, $C_{1-4}$ haloalkyl and —$OC_{1-4}$ haloalkyl. In further selected embodiments, $R^{1c}$ is selected from the group consisting of H, deuterium, fluoro, $CH_2$, $CF_3$, —$OCF_2$, and —$OCF_3$. In still further selected embodiments, $R^{1c}$ is selected from the group consisting of H, fluoro, deuterium, and $CF_3$. In another still further selected embodiments, $R^{1c}$ is selected from the group consisting of H, fluoro, deuterium, and $CF_3$. In another still further selected embodiments, $R^{1c}$ is selected from the group consisting of fluoro, deuterium, and $CF_3$.

In some selected embodiments, compounds of formula I' and compounds of any one of above embodiments, are wherein $R^{1d}$ and $R^{1e}$ are each independently selected from the group consisting of H, deuterium, halogen, $C_{1-4}$ alkyl, $C_{1-4}$ haloalkyl and $OC_{1-4}$ haloalkyl. In a further selected embodiment, $R^{1d}$ and $R^{1e}$ are hydrogen.

In some selected embodiments, compounds of formula I' and compounds of any one of above embodiments, are wherein $R^{2a}$ is selected from the group consisting of H, deuterium, halogen, $C_{1-4}$ alkyl and $C_{1-4}$ haloalkyl. In further selected embodiments, $R^{2a}$ is selected from the group consisting of H, deuterium, fluoro, methyl, or trifluoromethyl.

In some selected embodiments, compounds of formula I' and compounds of any one of above embodiments, are wherein $R^{2b}$ is selected from the group consisting of H, deuterium, halogen, $C_{1-4}$ alkyl and $C_{1-4}$ haloalkyl. In further selected embodiments, $R^{2b}$ is selected from the group consisting of H, deuterium, fluoro, methyl, or trifluoromethyl.

In some selected embodiments, compounds formula I' and compounds of any one of above embodiments, are wherein $R^{2e}$ is selected from the group consisting of H, deuterium, halogen, $C_{1-4}$ alkyl and $C_{1-4}$ haloalkyl. In further selected embodiments, $R^{2e}$ is selected from the group consisting of H, deuterium, fluoro, methyl, or trifluoromethyl.

In some selected embodiments, compounds of formula I' and compounds of any one of above embodiments, are wherein $R^{2a}$ is selected from the group consisting of H, deuterium, halogen, $C_{1-4}$ alkyl and $C_{1-4}$ haloalkyl. In further selected embodiments, $R^{2a}$ is selected from the group consisting of H, deuterium, fluoro, methyl, or trifluoromethyl.

In some selected embodiments, compounds of formula I' and compounds of any one of above embodiments are wherein each of $R^{2a}$, $R^{2b}$, $R^{2e}$ and $R^{2a}$ are independently selected from the group consisting of H, deuterium, fluoro and $CH_3$ and $R^{1a}$ is hydrogen.

In some selected embodiments, compounds of formula I' and compounds of any one of above embodiments, are wherein each $R^4$ is independently selected from the group consisting of H, halogen, CN, —$R^f$, —$CO_2R^d$, —$CONR^dR^e$, —$C(O)R^d$, —$NR^eC(O)R^d$, —$NR^eC(O)_2R^f$—$NR^dC(O)NR^dR^e$, —$NR^dR^e$, —$OR^d$, —$X^a$—CN, —$X^a$—$CO_2R^d$, —X$^a$—CONR$^d$R$^e$, —X$^a$—C(O)R$^d$, —X$^a$—OC(O)NR$^d$R$^e$, —X$^a$—NR$^e$C(O)R$^d$, —X$^a$—NR$^e$C(O)$_2$R, —X$^a$—NR$^d$C(O)NR$^d$R$^e$, —X$^a$—NR$^d$R$^e$ and —X$^a$—OR$^d$; wherein each X$^a$ is independently C$_{1-4}$alkylene. In further selected embodiments, each R$^4$ is independently selected from the group consisting of hydrogen, halogen, —CN, —R$^f$, —CO$_2$R$^d$, —CONR$^d$R$^e$, —C(O)R$^d$, —NR$^d$R$^e$, —OR$^d$, —X$^a$—CN, —X$^a$—CO$_2$R$^d$, X$^a$—NR$^d$R$^e$, and —X$^a$—OR$^d$ wherein each X$^a$ is independently C$_{1-6}$alkylene. In still further selected embodiments, each R$^4$ is independently H, halogen, or R$^f$. In further selected embodiments, each R$^4$ is independently H, halogen, C$_{1-6}$alkyl, C$_{1-6}$haloalkyl, C$_{1-6}$deuteroalkyl, or C$_{3-6}$cycloalkyl. In another further selected embodiments, each R$^4$ is independently H, fluoro, chloro, bromo, cyano, methyl, ethyl, propyl, hydroxymethyl, 2-hydroxyethyl, 1-hydroxyethyl, 2-hydroxyprop-2-yl, cyanomethyl, methoxycarbonyl, ethoxycarbonyl, carboxy, morpholin-4-yl, 3-oxo-morpholin-4-yl, morpholin-4-ylmethyl, morpholin-4-ylethyl, 2-methylmorpholin-4-ylmethyl, piperidin-1-ylmethyl, piperidin-1-ylethyl, 4-hydroxypiperidin-1-ylethyl, 4,4-difluoropiperidin-1-ylethyl, 4-oxopiperidin-1-ylmethyl, 4-fluoropiperidin-1-ylmethyl, 4-hydroxypiperidin-1-ylmethyl, 1,1-dioxothiomorpholin-1-ylmethyl, 4-methylpiperazin-1-ylmethyl, 4-ethylpiperazin-1-ylmethyl, 4-methylpiperazin-1-ylethyl, 4-ethylpiperazin-1-ylethyl, 3-oxo-4-methylpiperazin-1-ylmethyl, 2-oxa-7-azaspiro[3.5]nonan-7-ylmethyl, 2-oxa-7-azaspiro[3.5]nonan-7-ylethyl, 6-hydroxy-2-azaspiro[3.3]heptan-2-ylmethyl, 6-hydroxy-2-azaspiro[3.3]heptan-2-ylethyl, 2-oxa-6-azaspiro[3.5]nonan-6-ylmethyl, 2-oxa-6-azaspiro[3.5]nonan-6-ylethyl, 2-oxa-6-azaspiro[3.4]octan-6-ylmethyl, 2-oxa-6-azaspiro[3.4]-octan-6-ylethyl, aminocarbonyl, 3-hydroxyprop-2-ylaminocarbonyl, morpholin-4-ylcarbonyl, piperidin-1-ylcarbonyl, 4-methylpiperazin-1-ylcarbonyl, amino, dimethylaminomethyl, diethylaminoethyl, dimethylaminoethyl, diethylaminoethyl, tetrazolylmethyl, tetrazolylethyl, carboxymethyl, carboxyethyl, 3-hydroxyprop-2-ylamino, 2-hydroxyethyloxy, 3-hydroxy-propyloxy, or 2,4-dioxoimidazolidin-5-yl.

In some selected embodiments, compounds of formula I' and compounds of any one of above embodiments, are wherein X$^1$ is N, X$^2$ is CH, R$^{1b}$ is H or CH$_3$, R$^{1c}$ is CF$_3$, R$^{2a}$ is H, F or CH$_3$, R$^{2b}$ and R$^{2d}$ are H, and R$^{2c}$ is H or CH$_3$.

In some selected embodiments, compounds of formula I' compounds of any one of above embodiments, are wherein X$^1$ is N, X$^2$ is N, R$^{1b}$ is H or CH$_3$, R$^{1c}$ is CF$_3$, R$^{2a}$ is H, F or CH$_3$, R$^{2b}$ and R$^{2d}$ are H, and R$^{2c}$ is H or CH$_3$.

In some selected embodiments, compounds of formula I' and compounds of any one of above embodiments, are wherein X$^1$ is CH, X$^2$ is N, R$^{1b}$ is H or CH$_3$, R$^{1c}$ is CF$_3$, R$^{2a}$ is H, F or CH$_3$, R$^{2b}$ and R$^{2d}$ are H, and R$^{2c}$ is H or CH$_3$.

In some selected embodiments, compounds of formula I' and compounds of any one of above embodiments, are wherein X$^1$ is CH, X$^2$ is CH, R$^{1b}$ is H or CH$_3$, R$^{1c}$ is CF$_3$, R$^{2a}$ is H, F or CH$_3$, R$^{2b}$ and R$^{2d}$ are H, and R$^{2c}$ is H or CH$_3$.

In some selected embodiments, compounds of formula I' and compounds of any one of above embodiments, are wherein each R$^3$ is hydrogen or C$_{1-3}$alkyl.

In some selected embodiments, compounds of formula I' and compounds of any one of above embodiments, are wherein two R$^3$ are combined to form oxo.

In some selected embodiments, in the compounds of formula I' and compounds of any one of above embodiments, when two R$^4$ are present, then one of R$^4$ is H, methyl, or ethyl and the other of R$^4$ is H, bromo, cyano, methyl, ethyl hydroxymethyl, 2-hydroxyethyl, 1-hydroxyethyl, 2-hydroxyprop-2-yl, cyanomethyl, methoxycarbonyl, ethoxycarbonyl, carboxy, morpholin-4-yl, 3-oxo-morpholin-4-yl, morpholin-4-ylmethyl, morpholin-4-ylethyl, 2-methylmorpholin-4-ylmethyl, piperidin-1-ylmethyl, piperidin-1-ylethyl, 4-hydroxypiperidin-1-ylethyl, 4,4-difluoropiperidin-1-ylethyl, 4-oxopiperidin-1-ylmethyl, 4-fluoropiperidin-1-ylmethyl, 4-hydroxypiperidin-1-ylmethyl, 1,1-dioxothiomorpholin-1-ylmethyl, 4-methylpiperazin-1-ylmethyl, 4-ethylpiperazin-1-ylmethyl, 4-methylpiperazin-1-ylethyl, 4-ethylpiperazin-1-ylethyl, 3-oxo-4-methylpiperazin-1-ylmethyl, 2-oxa-7-azaspiro[3.5]nonan-7-ylmethyl, 2-oxa-7-azaspiro[3.5]nonan-7-ylethyl, 6-hydroxy-2-azaspiro[3.3]heptan-2-ylmethyl, 6-hydroxy-2-azaspiro[3.3]heptan-2-ylethyl, 2-oxa-6-azaspiro[3.5]nonan-6-ylmethyl, 2-oxa-6-azaspiro[3.5]nonan-6-ylethyl, 2-oxa-6-azaspiro[3.4]octan-6-ylmethyl, 2-oxa-6-azaspiro[3.4]octan-6-ylethyl, aminocarbonyl, 3-hydroxyprop-2-ylaminocarbonyl, morpholin-4-ylcarbonyl, piperidin-1-ylcarbonyl, 4-methylpiperazin-1-ylcarbonyl, amino, dimethylaminomethyl, diethylaminoethyl, dimethylaminoethyl, diethylaminoethyl, tetrazolylmethyl, tetrazolylethyl, carboxymethyl, carboxyethyl, 3-hydroxyprop-2-ylamino, 2-hydroxyethyloxy, 3-hydroxypropyloxy, or 2,4-dioxoimidazolidin-5-yl.

In still other selected embodiments, the compound of formula I' has a structure of formula (II'a), (II'b), (II'c), (II'd), (II'e) or (II'f):

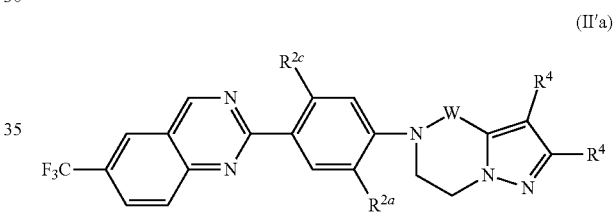

(II'a)

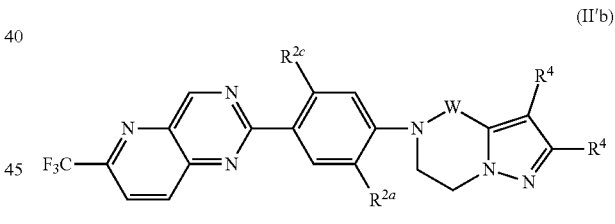

(II'b)

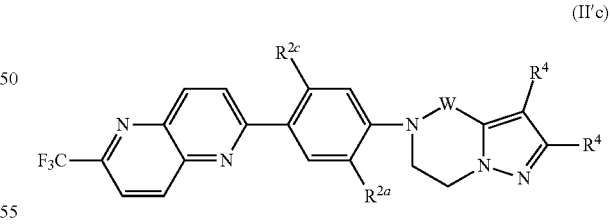

(II'c)

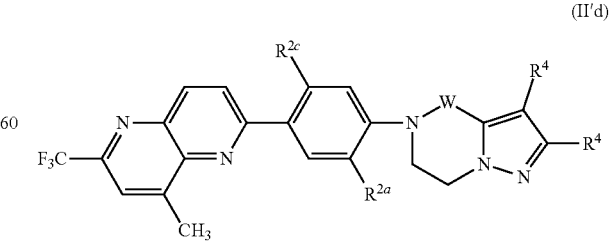

(II'd)

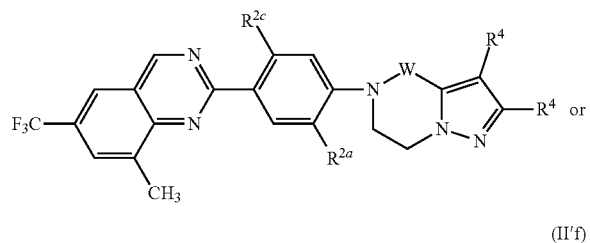
(II'e)

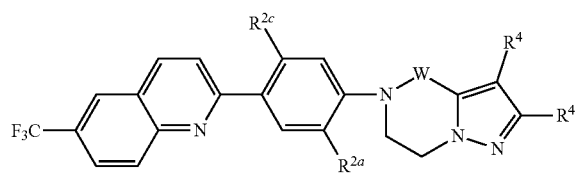
(II'f)

In further selected embodiments, the compound has formula (II'a). In further selected embodiments, the compound has formula (II'b). In further selected embodiments, the compound has formula (II'c). In further selected embodiments, the compound has formula (II'd). In further selected embodiments, the compound has formula (II'e). In further selected embodiments, the compound has formula (II'f).

Within compounds of formulae (II'a) to (II'f), in further selected embodiments, W is C(O).

Within compounds of formulae (II'a) to (II'f), in another further selected embodiments, W is S(O)$_2$.

In yet other selected embodiments, the compound of formula I' has a structure of formula (III'a), (III'b), (III'c), or (III'd):

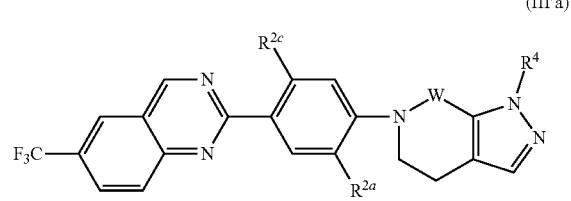
(III'a)

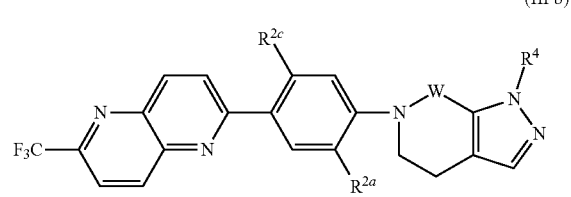
(III'b)

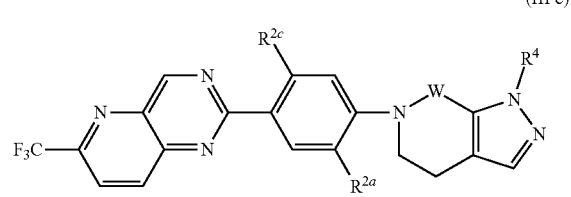
(III'c)

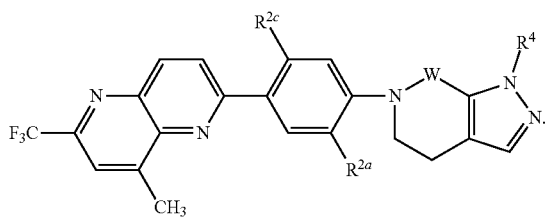
(III'd)

In further selected embodiments, the compound has formula (III'a). In further selected embodiments, the compound has formula (III'b). In further selected embodiments, the compound has formula (III'c). In further selected embodiments, the compound has formula (III'd).

Within compounds of formulae (III'a) to (III'd), in further selected embodiments, W is C(O).

Within compounds of formulae (III'a) to (III'd), in another further selected embodiments, W is S(O)$_2$.

In other selected embodiments, the compound of formula I' has a structure of formula (IV'a), (IV'b), (IV'c) or (IV'd):

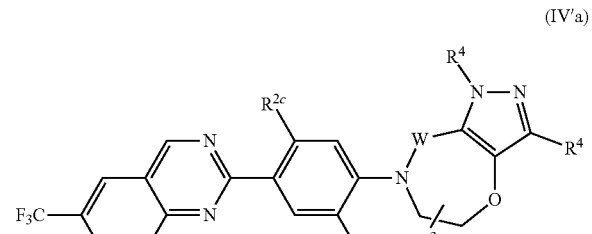
(IV'a)

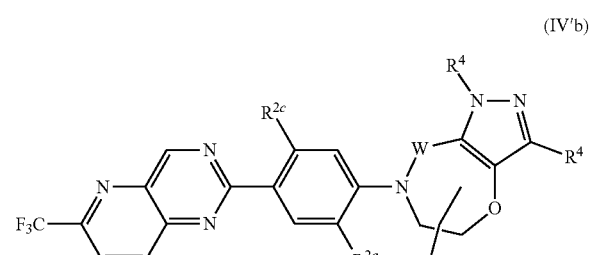
(IV'b)

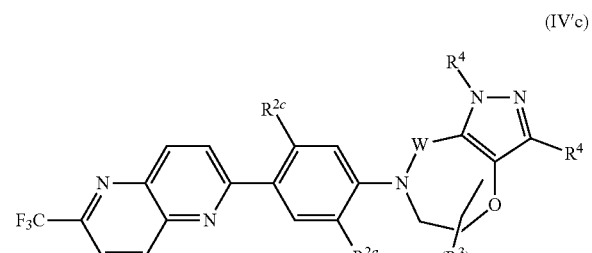
(IV'c)

21
-continued

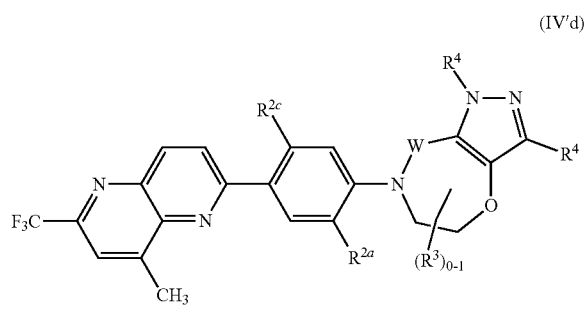
(IV'd)

In further selected embodiments, the compound has formula (IV'a). In further selected embodiments, the compound has formula (IV'b). In further selected embodiments, the compound has formula (IV'c). In further selected embodiments, the compound has formula (IV'd).

Within compounds of formulae (IV'a) to (IV'd), in further selected embodiments, W is C(O).

Within compounds of formulae (IV'a) to (IV'd), in another further selected embodiments, W is $S(O)_2$.

Within compounds of formulae (IV'a) to (IV'd) and in further selected embodiments contained therein, in a still further selected embodiments, $R^3$ is hydrogen or $C_{1-3}$ alkyl, preferably $R^3$ is hydrogen or methyl.

In other selected embodiments, the compound of formula I' has a structure of formula (V'a), (V'b), (V'c) or (V'd):

22
-continued

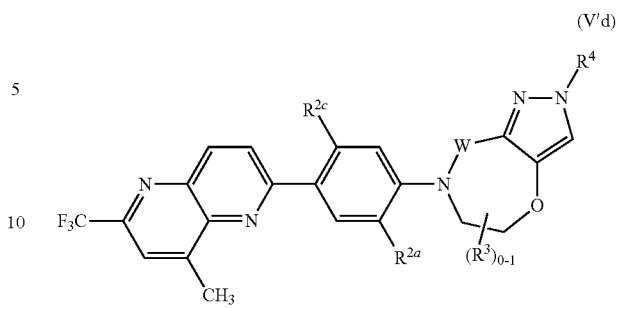
(V'd)

In further selected embodiments, the compound has formula (V'a). In further selected embodiments, the compound has formula (V'b). In further selected embodiments, the compound has formula (V'c). In further selected embodiments, the compound has formula (V'd).

Within compounds of formulae (V'a) to (V'd) and in further selected embodiments thereby, W is C(O).

Within compounds of formulae (V'a) to (V'd) and in another further selected embodiments therein, W is $S(O)_2$.

Within compounds of formulae (V'a) to (V'd) and in further selected embodiments contained therein, in a still further selected embodiments, $R^3$ is hydrogen or $C_{1-3}$ alkyl, preferably $R^3$ is hydrogen or methyl.

In other selected embodiments, compounds are provided having formula (VI'a), (VI'b), (VI'c) or (VI'd):

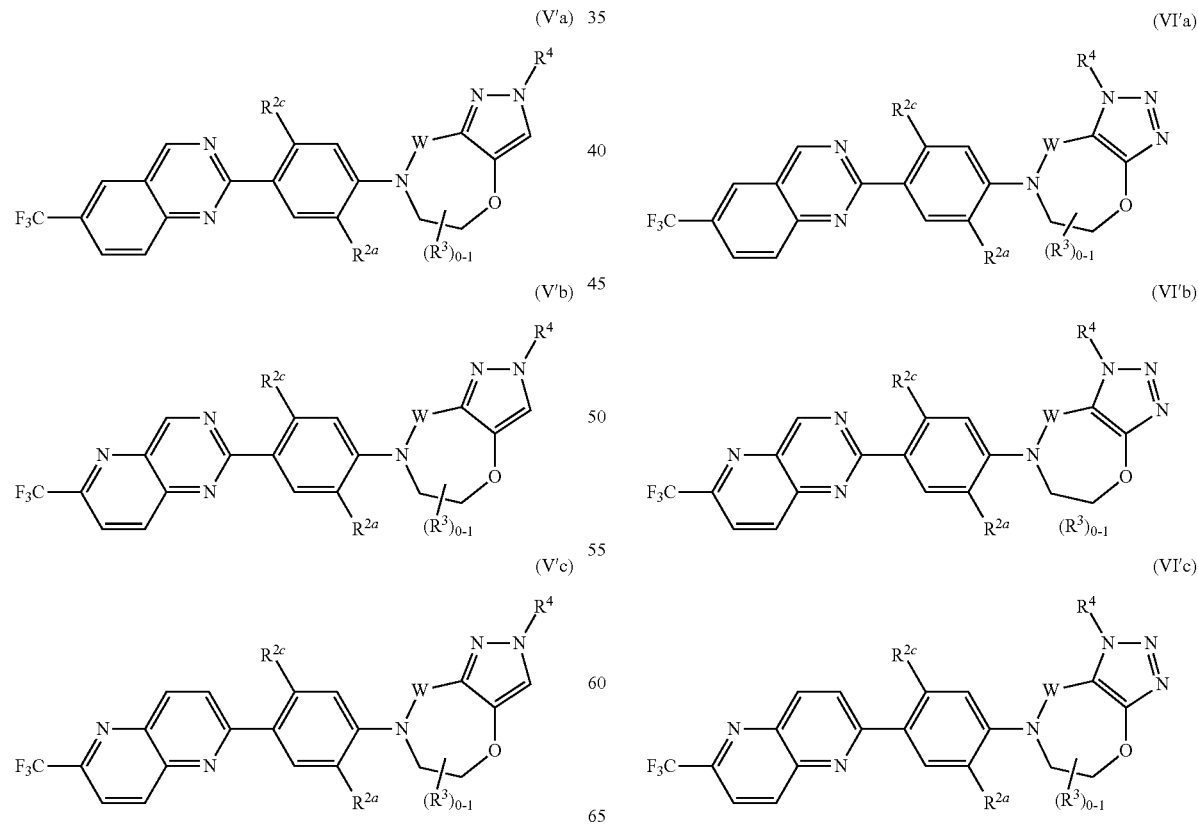

(VI'd)

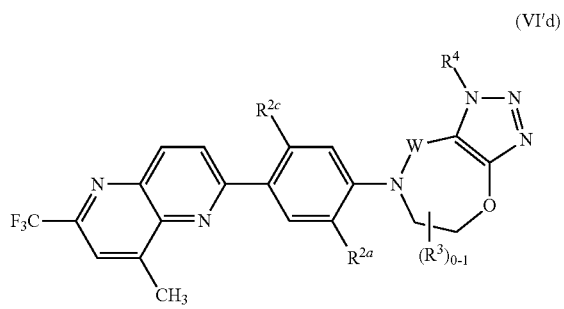

(VII'd)

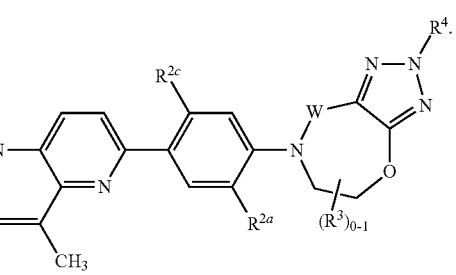

In further selected embodiments, the compound has formula (VI'a). In further selected embodiments, the compound has formula (VI'b). In further selected embodiments, the compound has formula (VI'c). In further selected embodiments, the compound has formula (VI'd).

Within compounds of formulae (VI'a) to (VI'd) and in further selected embodiments therein, W is C(O).

Within compounds of formulae (VI'a) to (VI'd) and in further selected embodiments therein, in another further selected embodiments, W is $S(O)_2$.

Within compounds of formulae (VI'a) to (VI'd) and in further selected embodiments therein, in a still further selected embodiments, $R^3$ is hydrogen or $C_{1-3}$ alkyl, preferably $R^3$ is hydrogen or methyl.

In other selected embodiments, the compound of formula I' has a structure of formula (VII'a), (VII'b), (VII'c) or (VII'd):

In further selected embodiments, the compound has formula (VII'a). In further selected embodiments, the compound has formula (VII'b). In further selected embodiments, the compound has formula (VII'c). In further selected embodiments, the compound has formula (VII'd).

Within compounds of formulae (VII'a) to (VII'd) and further selected embodiments therein, in further selected embodiments W is C(O).

Within compounds of formulae (VII'a) to (VII'd) and further selected embodiments therein, in another further selected embodiments, W is $S(O)_2$.

Within compounds of formulae (VII'a) to (VII'd) and further selected embodiments therein, in a still further selected embodiments, $R^3$ is hydrogen or $C_{1-3}$ alkyl, preferably $R^3$ is hydrogen or methyl.

In other selected embodiments, the compound of formula I' has a structure of formula (VIII'a), (VIII'b), (VIII'c) or (VIII'd):

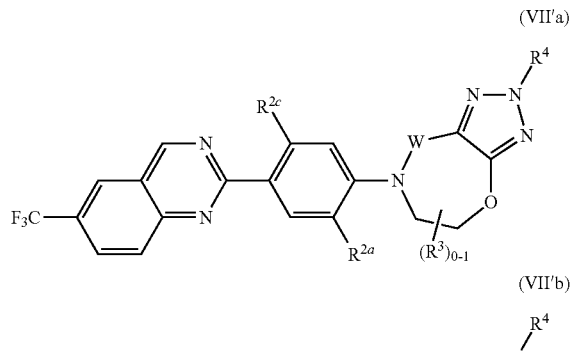

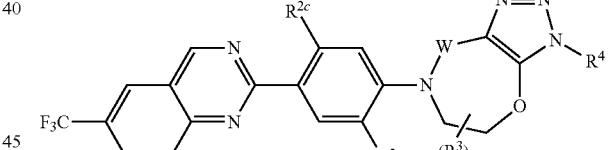

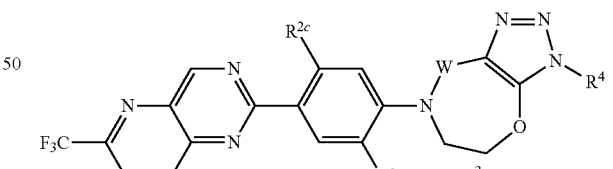

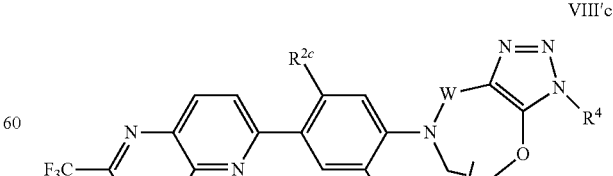

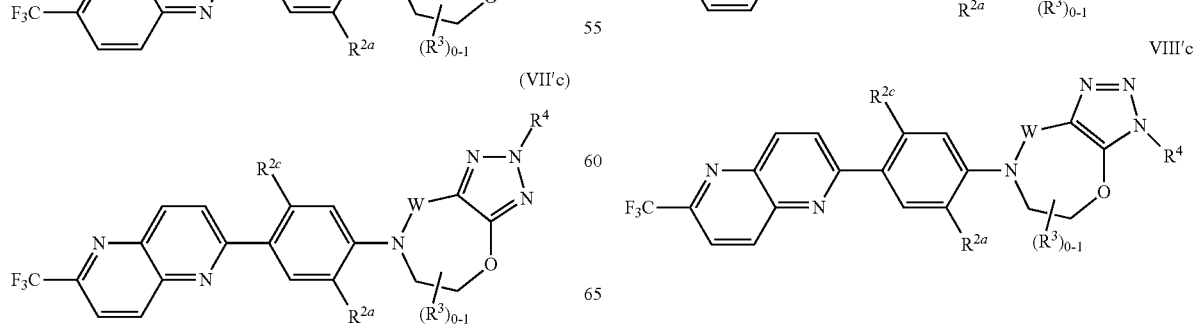

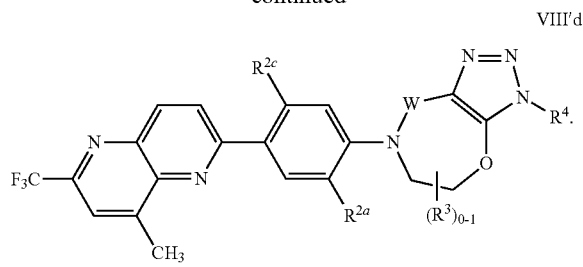

In further selected embodiments, the compound has formula (VIII'a). In further selected embodiments, the compound has formula (VIII'b). In further selected embodiments, the compound has formula V(III'c). In further selected embodiments, the compound has formula (VIII'd).

Within compounds of formulae (VIII'a) to (VIII'd) and in further selected embodiments therein, W is C(O).

Within compounds of formulae (VIII'a) to (VIII'd) and in further selected embodiments therein, W is S(O)$_2$.

Within compounds of formulae (VIII'a) to (VIII'd) and in further selected embodiments therein, in a still further selected embodiments, $R^3$ is hydrogen or $C_{1-3}$ alkyl, preferably $R^3$ is hydrogen or methyl.

Within compounds of formulae (II'a) to (II'e), (III'a) to (III'd), (IV'a) to (IV'd), (V'a) to (V'd), (VI'a) to (VI'd), (VII'a) to (VII'd), and (VIII'a) to (VIII'd) and further embodiments contained therein, in further selected embodiments, each $R^4$ is independently selected from the group consisting of H, halogen, CN, —$R^e$, —$CO_2R^d$, —$CONR^dR^e$, —$C(O)R^d$, —$NR^eC(O)R^d$, —$NR^eC(O)_2R^f$, —$NR^dC(O)NR^dR^e$, —$NR^dR^e$, —$OR^d$, —$X^a$—CN, —$X^a$—$CO_2R^d$, —$X^a$—$CONR^dR^e$, —$X^a$—$C(O)R^d$, —$X^a$—$OC(O)NR^dR^e$, —$X^a$—$NR^eC(O)R^d$, —$X^a$—$NR^eC(O)_2Rt$, —$X^a$—$NR^dC(O)NR^dR^e$, —$X^a$—$NR^dR^e$ and —$X^a$—$OR^d$; wherein each $X^a$ is independently $C_{1-4}$alkylene. In further selected embodiments, each $R^4$ is independently selected from the group consisting of hydrogen, halogen, —CN, —$R^f$, —$CO_2R^d$, —$CONR^dR^e$, —$C(O)R^d$, —$NR^dR^e$, —$OR^d$, —$X^a$—CN, —$X^a$—$CO_2R^d$, $X^a$—$NR^dR^e$, and —$X^a$—$OR^d$ wherein each $X^a$ is independently $C_{1-6}$alkylene. In further selected embodiments, each $R^4$ is independently H, halogen, or $R^f$. In another further selected embodiments, each $R^4$ is independently H, halogen, $C_{1-6}$alkyl, $C_{1-6}$haloalkyl, $C_{1-6}$deuteroalkyl, or $C_{3-6}$cycloalkyl. In still another further selected embodiments, each $R^4$ is independently H, fluoro, chloro, bromo, cyano, methyl, ethyl, propyl, hydroxymethyl, 2-hydroxyethyl, 1-hydroxyethyl, 2-hydroxyprop-2-yl, cyanomethyl, methoxycarbonyl, ethoxycarbonyl, carboxy, morpholin-4-yl, 3-oxo-morpholin-4-yl, morpholin-4-ylmethyl, morpholin-4-ylethyl, 2-methylmorpholin-4-ylmethyl, piperidin-1-ylmethyl, piperidin-1-ylethyl, 4-hydroxypiperidin-1-ylethyl, 4,4-difluoropiperidin-1-ylethyl, 4-oxopiperidin-1-ylmethyl, 4-fluoropiperidin-1-ylmethyl, 4-hydroxypiperidin-1-ylmethyl, 1,1-dioxothiomorpholin-1-ylmethyl, 4-methylpiperazin-1-ylmethyl, 4-ethylpiperazin-1-ylmethyl, 4-methylpiperazin-1-ylethyl, 4-ethylpiperazin-1-ylethyl, 3-oxo-4-methylpiperazin-1-ylmethyl, 2-oxa-7-azaspiro[3.5]nonan-7-ylmethyl, 2-oxa-7-azaspiro[3.5]nonan-7-ylethyl, 6-hydroxy-2-azaspiro[3.3]heptan-2-ylmethyl, 6-hydroxy-2-azaspiro[3.3]heptan-2-ylethyl, 2-oxa-6-azaspiro[3.5]nonan-6-ylmethyl, 2-oxa-6-azaspiro[3.5]nonan-6-ylethyl, 2-oxa-6-azaspiro[3.4]octan-6-ylmethyl, 2-oxa-6-azaspiro[3.4]octan-6-ylethyl, aminocarbonyl, 3-hydroxyprop-2-ylaminocarbonyl, morpholin-4-ylcarbonyl, piperidin-1-ylcarbonyl, 4-methylpiperazin-1-ylcarbonyl, amino, dimethylaminomethyl, diethylaminoethyl, dimethylaminoethyl, diethylaminoethyl, tetrazolylmethyl, tetrazolylethyl, carboxymethyl, carboxyethyl, 3-hydroxyprop-2-ylamino, 2-hydroxyethyloxy, 3-hydroxypropyloxy, or 2,4-dioxoimidazolidin-5-yl.

In still another further selected embodiments, in compounds where two $R^4$ are present, then one of $R^4$ is H, methyl, or ethyl and the other of $R^4$ is H, bromo, cyano, methyl, ethyl hydroxymethyl, 2-hydroxyethyl, 1-hydroxyethyl, 2-hydroxyprop-2-yl, cyanomethyl, methoxycarbonyl, ethoxycarbonyl, carboxy, morpholin-4-yl, 3-oxo-morpholin-4-yl, morpholin-4-ylmethyl, morpholin-4-ylethyl, 2-methylmorpholin-4-ylmethyl, piperidin-1-ylmethyl, piperidin-1-ylethyl, 4-hydroxypiperidin-1-ylethyl, 4,4-difluoropiperidin-1-ylethyl, 4-oxopiperidin-1-ylmethyl, 4-fluoropiperidin-1-ylmethyl, 4-hydroxypiperidin-1-ylmethyl, 1,1-dioxothiomorpholin-1-ylmethyl, 4-methylpiperazin-1-ylmethyl, 4-ethylpiperazin-1-ylmethyl, 4-methylpiperazin-1-ylethyl, 4-ethylpiperazin-1-ylethyl, 3-oxo-4-methylpiperazin-1-ylmethyl, 2-oxa-7-azaspiro[3.5]nonan-7-ylmethyl, 2-oxa-7-azaspiro[3.5]nonan-7-ylethyl, 6-hydroxy-2-azaspiro[3.3]heptan-2-ylmethyl, 6-hydroxy-2-azaspiro[3.3]heptan-2-ylethyl, 2-oxa-6-azaspiro[3.5]nonan-6-ylmethyl, 2-oxa-6-azaspiro[3.5]nonan-6-ylethyl, 2-oxa-6-azaspiro[3.4]octan-6-ylmethyl, 2-oxa-6-azaspiro[3.4]octan-6-ylethyl, aminocarbonyl, 3-hydroxyprop-2-ylaminocarbonyl, morpholin-4-ylcarbonyl, piperidin-1-ylcarbonyl, 4-methylpiperazin-1-ylcarbonyl, amino, dimethylaminomethyl, diethylaminoethyl, dimethylaminoethyl, diethylaminoethyl, tetrazolylmethyl, tetrazolylethyl, carboxymethyl, carboxyethyl, 3-hydroxyprop-2-ylamino, 2-hydroxyethyloxy, 3-hydroxypropyloxy, or 2,4-dioxoimidazolidin-5-yl;

$R^{2a}$ is H, F or $CH_3$; and $R^{2e}$ is H or $CH_3$.

Also, provided herein are compounds having the formula (I):

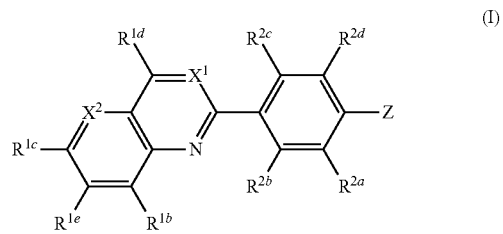

or a pharmaceutically acceptable salt, solvate or hydrate thereof, wherein:

each of ring vertices $X^1$ and $X^2$ is independently selected from the group consisting of $C(R^{1a})$ and N;

Z is selected from the group consisting of:

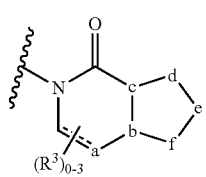

A

-continued

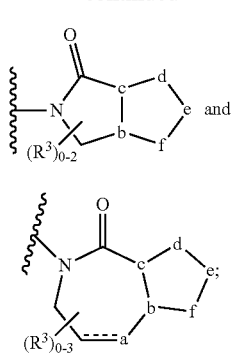

wherein the dashed bonds are single or double bonds, each of ring vertices a, b, c, d, e and f are independently selected from the group consisting of O, S, N, C($R^4$) and N($R^4$), and the bonds joining the ring vertices are independently single or double bonds;

each $R^{1a}$, $R^{1b}$, $R^{1c}$, $R^{1d}$ and $R^{1e}$ is independently selected from the group consisting of hydrogen, deuterium, halogen, —CN, —$NO_2$, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O, S, SO or $SO_2$; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, and $C_{3-6}$ cycloalkyl, and wherein the aliphatic and cyclic portions of $R^a$, $R^b$ and $R^c$ can be further substituted with from one to three halogen, hydroxy, $C_{1-4}$ alkyl, $C_{1-4}$ alkoxy, amino, $C_{1-4}$ alkylamino, di $C_{1-4}$ alkylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$; or two $R^3$ groups are combined to form oxo (=O);

each $R^4$ is independently selected from the group consisting of hydrogen, halogen, —CN, —$R^e$, —$CO_2R^d$, —$CONR^dR^e$, —C(O)$R^d$, —OC(O)$NR^dR^e$, —$NR^eC(O)R^d$, —$NR^eC(O)_2Rt$, —$NR^dC(O)NR^dR^e$, —$NR^dR^e$, —$OR^d$, —$S(O)_2NR^dR^e$, —$X^a$—CN, —$X^a$—$CO_2R^d$, —$X^a$—$CONR^dR^e$, —$X^a$—C(O)$R^d$, —$X^a$—OC(O)$NR^dR^e$, —$X^a$—$NR^eC(O)R^d$, —$X^a$—$NR^eC(O)_2Rt$, —$X^a$—$NR^dC(O)NR^dR^e$, —$X^a$—$NR^dR^e$, —$X^a$—$OR^d$, and —$X^a$—$S(O)_2NR^dR^e$; wherein each $X^a$ is independently $C_{1-6}$ alkylene; and each $R^d$ and $R^e$ is independently selected from hydrogen, $C_{1-8}$ alkyl, and $C_{1-8}$ haloalkyl, or when attached to the same nitrogen atom can be combined with the nitrogen atom to form a four-, five- or six-membered ring having from 0 to 2 additional heteroatoms as ring members selected from N, O, S, SO or $SO_2$;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, $C_{3-6}$ heterocycloalkyl, phenyl and 5- or 6-membered heteroaryl;

and wherein the aliphatic and cyclic portions of $R^d$, $R^e$ and $R^f$ are can be further substituted with from one to three halogen, hydroxy, $C_{1-4}$ alkyl, $C_{1-4}$ alkoxy, amino, $C_{1-4}$ alkylamino, di $C_{1-4}$ alkylamino and carboxylic acid groups.

In one group of embodiments, the compounds of formulae (I), are those wherein Z has subformula A (formula IA).

In another group of embodiments, the compounds of formulae (I), are those wherein Z has subformula B (formula IB).

In yet another group of embodiments, the compounds of formulae (I), are those wherein Z has subformula C (formula IC).

In those embodiments referred to herein as formula IA; in selected embodiments, Z is selected from the group consisting of:

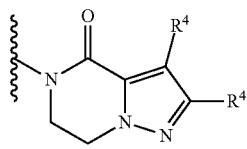

A1

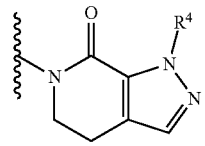

A2

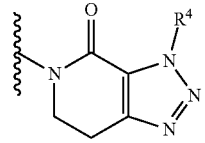

A3

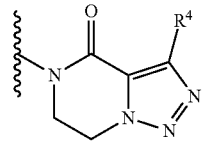

A4

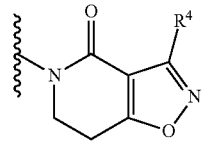

A5

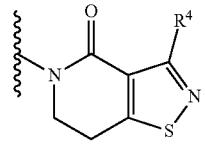

A6

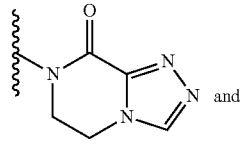

A7 and

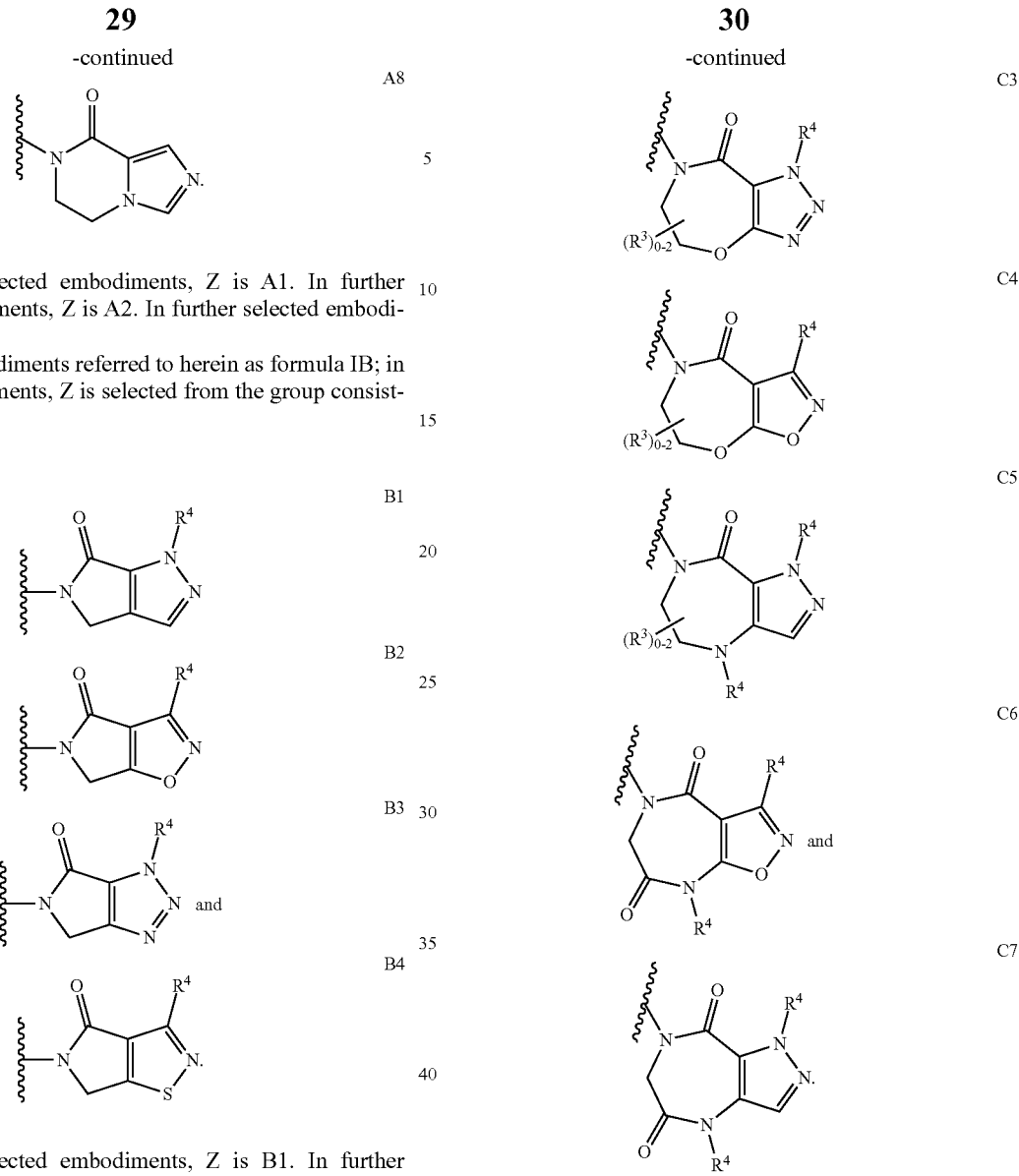

In further selected embodiments, Z is A1. In further selected embodiments, Z is A2. In further selected embodiments, Z is A5.

In those embodiments referred to herein as formula IB; in selected embodiments, Z is selected from the group consisting of:

In further selected embodiments, Z is B1. In further selected embodiments, Z is B2.

In those embodiments referred to herein as formula IC; in selected embodiments, Z is selected from the group consisting of.

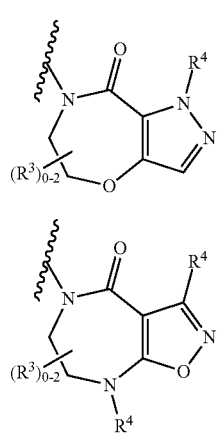

In further selected embodiments, Z is C1. In further selected embodiments, Z is C5.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^1$ is N.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^2$ is N.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^1$ and $X^2$ are both N.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{1b}$ is selected from the group consisting of H, deuterium, $C_{1-4}$ alkyl and $C_{1-4}$ haloalkyl. In further selected embodiments, $R^{1b}$ is selected from the group consisting of H, deuterium and $CH_3$.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{1c}$ is selected from the group consisting of H, deuterium, $C_{1-4}$ alkyl and $C_{1-4}$ haloalkyl. In further selected embodiments, $R^{1c}$ is selected from the group consisting of H, deuterium and $CF_3$.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{1d}$ and $R^{1e}$ are each independently selected from the group consisting of H, deuterium, $C_{1-4}$ alkyl and $C_{1-4}$ haloalkyl.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{2a}$ is selected from the group consisting of H, deuterium, halogen, $C_{1-4}$ alkyl and $C_{1-4}$ haloalkyl.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{2b}$ is selected from the group consisting of H, deuterium, halogen, $C_{1-4}$ alkyl and $C_{1-4}$ haloalkyl.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{2c}$ is selected from the group consisting of H, deuterium, halogen, $C_{1-4}$ alkyl and $C_{1-4}$ haloalkyl.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $R^{2a}$ is selected from the group consisting of H, deuterium, halogen, $C_{1-4}$ alkyl and $C_{1-4}$ haloalkyl.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein each of $R^{2a}$, $R^{2b}$, $R^{2c}$ and $R^{2d}$ are independently selected from the group consisting of H, deuterium, fluoro and $CH_3$.

In some selected embodiments, compounds are provided having formula IC, wherein two $R^3$ are combined to form oxo.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein each $R^4$ is independently selected from the group consisting of H, halogen, —$R^e$, —$CO_2R^d$, —$CONR^dR^e$, —$C(O)R^d$, —$NR^eC(O)R^d$, —$NR^eC(O)_2Rt$, —$NR^dC(O)NR^dR^e$, —$NR^dR^e$, —$OR^d$, —$X^a$—CN, —$X^a$—$CO_2R^d$, —$X^a$—$CONR^dR^e$, —$X^a$—$C(O)R^d$, —$X^a$—$OC(O)NR^dR^e$, —$X^a$—$NR^eC(O)R^d$, —$X^a$—$NR^eC(O)_2Rt$, —$X^a$—$NR^dC(O)NR^dR^e$, —$X^a$—$NR^dR^e$ and —$X^a$—$OR^d$; wherein each $X^a$ is independently $C_{1-4}$alkylene. In further selected embodiments, each $R^4$ is independently H, halogen, or R. In further selected embodiments, each $R^4$ is independently H, halogen, $C_{1-6}$alkyl, $C_{1-6}$haloalkyl, $C_{1-6}$deuteroalkyl, or $C_{3-6}$cycloalkyl.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^1$ is N, $X^2$ is CH, $R^{1b}$ is H or $CH_3$, $R^{1c}$ is $CF_3$, $R^{2a}$ is H, F or $CH_3$, $R^{2b}$ is H, and $R^{2c}$ is H or $CH_3$.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^1$ is N, $X^2$ is N, $R^{1b}$ is H or $CH_3$, $R^{1c}$ is $CF_3$, $R^{2a}$ is H, F or $CH_3$, $R^{2b}$ is H, and $R^{2c}$ is H or $CH_3$.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^1$ is CH, $X^2$ is N, $R^{1b}$ is H or $CH_3$, $R^{1c}$ is $CF_3$, $R^{2a}$ is H, F or $CH_3$, $R^{2b}$ is H, and $R^{2c}$ is H or $CH_3$.

In some selected embodiments, compounds are provided having any one of formula IA, IB, IC, IA1, IA2, IA3, IA4, IA5, IA6, IA7, IA8, IB1, IB2, IB3, IB4, IC1, IC2, IC3, IC4, IC5, IC6, or IC7, wherein $X^1$ is CH, $X^2$ is CH, $R^{1b}$ is H or $CH_3$, $R^{1c}$ is $CF_3$, $R^{2a}$ is H, F or $CH_3$, $R^{2b}$ is H, and $R^{2c}$ is H or $CH_3$.

In still other selected embodiments, formula (IIa), (IIb), (IIc), (IId), (IIe) or (IIf):

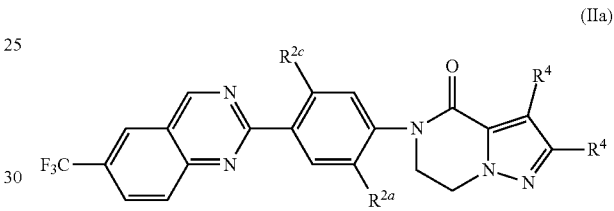

(IIa)

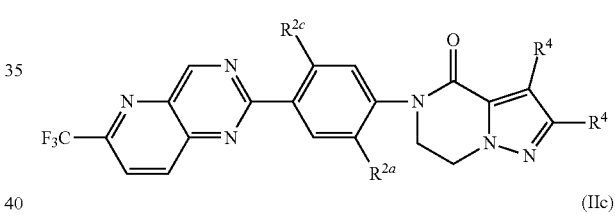

(IIb)

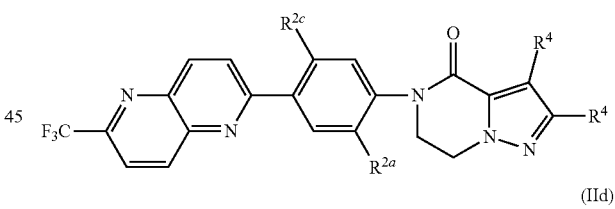

(IIc)

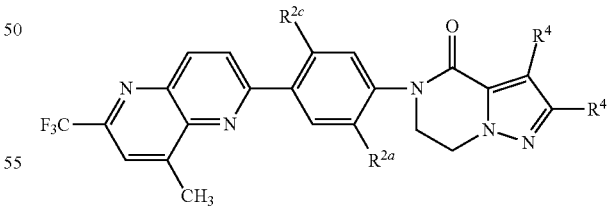

(IId)

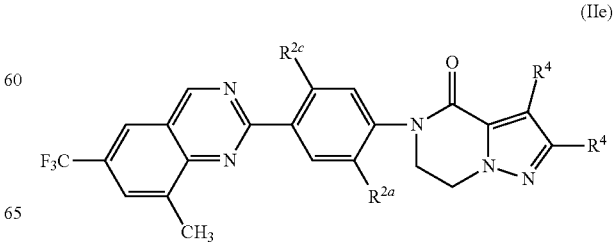

(IIe)

(IIf)
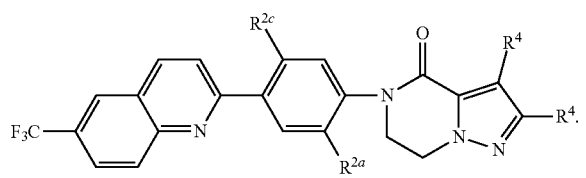

(IVa)
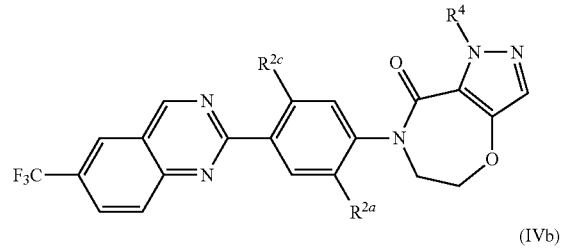

(IVb)
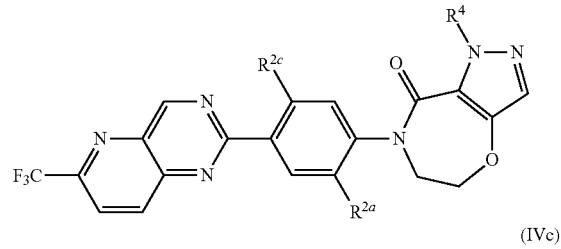

In further selected embodiments, each $R^4$ is independently H, halogen, or R. In further selected embodiments, each $R^4$ is independently H, halogen, $C_{1-6}$alkyl, $C_{1-6}$ haloalkyl, $C_{1-6}$deuteroalkyl, or $C_{3-6}$cycloalkyl.

In yet other selected embodiments, compounds are provided having formula (IIIa), (IIIb), (IIIc) or (IIId):

(IIIa)
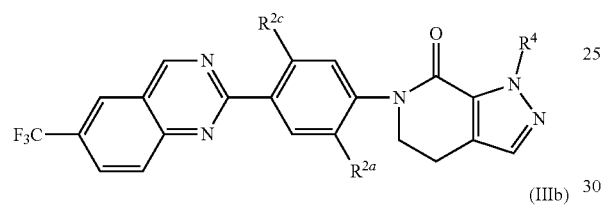

(IVc)
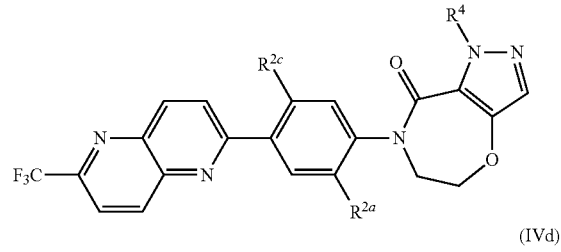

(IIIb)
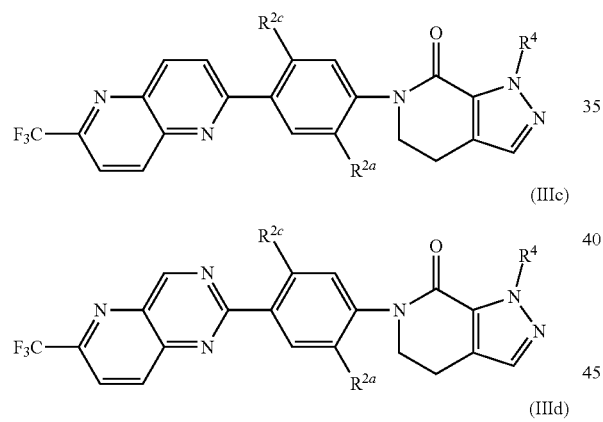

(IVd)
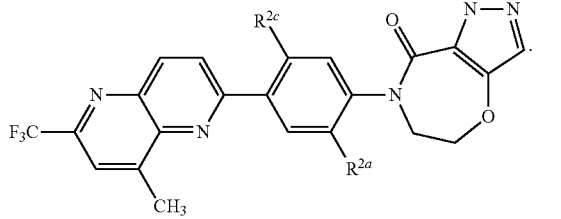

(IIIc)

(IIId)
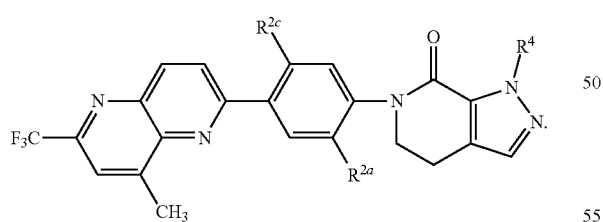

In further selected embodiments, each $R^4$ is independently H, halogen, or $R^f$. In further selected embodiments, each $R^4$ is independently H, halogen, $C_{1-6}$alkyl, $C_{1-6}$ haloalkyl, $C_{1-6}$deuteroalkyl, or $C_{3-6}$cycloalkyl.

In some selected embodiments, provided herein are compounds in Table 1 having +++ or ++++ activity.

In some selected embodiments, the compound has the formula 3-methyl-5-(2-methyl-4-(6-(trifluoromethyl)quinazolin-2-yl)phenyl)-6,7-dihydropyrazolo[1,5-a]pyrazin-4(5H)-one-6,6,7,7-d4

Intermediates:
Also provided herein are intermediates of formula (X):

(X)
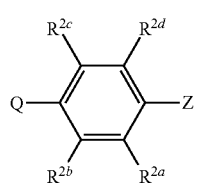

In further selected embodiments, each $R^4$ is independently H, halogen, or $R^f$. In further selected embodiments, each $R^4$ is independently H, halogen, $C_{1-6}$alkyl, $C_{1-6}$ haloalkyl, $C_{1-6}$deuteroalkyl, or $C_{3-6}$cycloalkyl.

In other selected embodiments, compounds are provided having formula (IVa), (IVb), (IVc) or (IVd):

or a pharmaceutically acceptable salt, solvate or hydrate thereof, wherein:

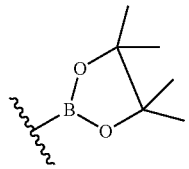 [SMILES: *B1OC(C)(C)C(C)(C)O1]

Q is CHO, halo, —B(OH)$_2$, or; and

Z, R$^{2e}$, R$^{2d}$, R$^{2e}$, R$^{2f}$ are as defined in compounds of Formula (I') and embodiments thereof described above.

In some embodiments, provided herein is an intermediate having the formula

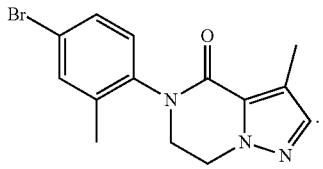

Therapeutic and Prophylactic Uses

The present invention contemplates the use of the AhR modulators described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, an AhR modulator can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. In another particular embodiments, the tumor or cancer is melanoma, lung cancer, pancreatic cancer, glioblastoma, or multiple myeloma. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an AhR modulator and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the AhR modulators described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The AhR modulators provided herein can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The AhR modulators can also be used to stimulate the immune system of patients suffering from iatrogenically-induced immune suppression, including those who have undergone bone marrow transplants, chemotherapy, or radiotherapy.

In particular embodiments of the present disclosure, the AhR modulators are used to increase or enhance an immune response to an antigen by providing adjuvant activity. In a particular embodiment, at least one antigen or vaccine is administered to a subject in combination with at least one AhR modulator as provided herein to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one AhR modulator as provided herein.

Microbial-related Disorders. By inhibiting the immunosuppressive and anti-inflammatory activity of AhR, the present disclosure contemplates the use of the AhR modulators described herein in the treatment and/or prevention of any viral, bacterial, fungal, parasitic or other infective disease, disorder or condition for which treatment with an AhR modulator may be beneficial. Examples of such diseases and disorders include HIV and AIDS, staphylococcal and streptococcal infections (e.g., *Staphylococcus aureus* and *Streptococcus sanguinis*, respectively), leishmania, toxoplasma, trichomonas, giardia, *Candida albicans, Bacillus anthracis,* and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of AhR may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments provided herein also contemplate the administration of the AhR modulators described herein to a subject for the treatment or prevention of any other disorder that may benefit from at least some level of AhR modulation. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the AhR modulators provided herein may be used to inhibit statin-induced adenosine production, or reduce or decrease increases in blood glucose caused by a statin in a subject taking a statin (e.g., lovastatin and pravastatin)

Pharmaceutical Compositions

The AhR modulators provided herein may be in the form of compositions suitable for administration to a subject. In general, such compositions are "pharmaceutical compositions" comprising an AhR modulator(s) and one or more pharmaceutically acceptable or physiologically acceptable diluents, carriers or excipients. In certain embodiments, the AhR modulator is present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., a modulator of AhR function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneooxycetanol), or condensation products of ethylene oxide with partial esters derived from fatty acids and a hexitol (e.g., polyoxy-ethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an AhR modulator as provided herein and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an AhR modulator, including implants (e.g., implantable pumps) and catheter systems, slow injection pumps and devices, all of which are well known to the skilled artisan.

Depot injections, which are generally administered subcutaneously or intramuscularly, may also be utilized to release the AhR modulators disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the AhR modulators in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The AhR modulators contemplated by the present invention may be in the form of any other suitable pharmaceutical composition (e.g., sprays for nasal or inhalation use) currently known or developed in the future.

Routes of Administration

The present invention contemplates the administration of one or more AhR modulators as provided herein, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the AhR modulators disclosed herein over a defined period of time.

Particular embodiments of the present invention contemplate oral administration.

Combination Therapy

The present invention contemplates the use of AhR modulators in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the AhR modulators are administered or applied sequentially, e.g., where one agent is administered prior to one or more other agents. In other embodiments, the AhR modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The AhR modulators of the present invention may be used in combination with at least one other (active) agent in any manner appropriate under the circumstances. In one embodiment, treatment with the at least one active agent and at least one AhR modulator of the present invention is maintained over a period of time. In another embodiment, treatment with the at least one active agent is reduced or discontinued (e.g., when the subject is stable), while treatment with an AhR modulator of the present invention is maintained at a constant dosing regimen. In a further embodiment, treatment with the at least one active agent is reduced or discontinued (e.g., when the subject is stable), while treatment with an AhR modulator of the present invention is reduced (e.g., lower dose, less frequent dosing or shorter treatment regimen). In yet another embodiment, treatment with the at least one active agent is reduced or discontinued (e.g., when the subject is stable), and treatment with the AhR modulator of the present invention is increased (e.g., higher dose, more frequent dosing or longer treatment regimen). In yet another embodiment, treatment with the at least one active agent is maintained and treatment with the AhR modulator of the present invention is reduced or discontinued (e.g., lower dose, less frequent dosing or shorter treatment regimen). In yet another embodiment, treatment with the at least one active agent and treatment with the AhR modulator of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an AhR modulator and at least one additional therapeutic or diagnostic agent.

In certain embodiments, the present invention provides methods for tumor suppression of tumor growth comprising administration of an AhR modulator described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more AhR modulators described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; abraxane; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylomithine (DMFO); retinoic acid; esperamicins; capecitabine; VEGF inhibitors such as bevacizumab; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4 (5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with an AhR modulator include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the modulators of AhR function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints checkpoints include but are not limited to CTLA-4, PD-1/L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present invention contemplates the use of the AhR modulators described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1/PDL1 inhibitors include lambrolizumab, nivolumab, atezolizumab, avelumab, and durvalumab. PD1 inhibitors in development include pidilizumab (Cure Tech), AMP-224 and AMP-514 (GSK), PDR001 (Novartis) and cemiplimab (Regeneron and Sanofi) and anti-PDL1 antibodies in development include BMS-936559 (BMS) and CK-301 (Checkpoint Therapeutics). Nivolumab has shown promise in patients with melanoma, lung and kidney cancer.

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an AhR modulator and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the AhR modulators described herein include various supplements and herbs (e.g., garlic, policosanol, and guggul).

The present invention encompasses pharmaceutically acceptable salts, acids or derivatives of any of the above.

Immune-related Disorders and Disorders Having an Inflammatory Component. The present invention provides methods for treating and/or preventing immune-related diseases, disorders and conditions; and diseases, disorders and conditions having an inflammatory component; with an AhR modulator and at least one additional therapeutic or diagnostic agent.

Examples of therapeutic agents useful in combination therapy are specific to the underlying disease, disorder or condition, and are known to the skilled artisan.

Microbial Diseases. The present invention provides methods for treating and/or preventing viral, bacterial, fungal and parasitic diseases, disorders and conditions, as well as disorders associated therewith, with an AhR modulator and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an AhR modulator include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the AhR modulators described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the AhR modulators described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolones). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the AhR modulators described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolites (e.g., 5-fluorocytosine).

The present invention encompasses pharmaceutically acceptable salts, acids or derivatives of the agents (and members of the classes of agents) set forth above.

Dosing

The AhR modulators provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of an AhR modulator, as provided herein, may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the AhR modulators contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired AhR modulator is contained in a "unit dosage form". The phrase "unit dosage form" refers to physically discrete units, each unit containing a predetermined amount of the AhR modulator, either alone or in combination with one or more additional agents, sufficient to produce the desired effect. It will be appreciated that the parameters of a unit dosage form will depend on the particular agent and the effect to be achieved.

Kits

The present invention also contemplates kits comprising an AhR modulator, and pharmaceutical compositions thereof. The kits are generally in the form of a physical structure housing various components, as described below, and may be utilized, for example, in practicing the methods described above.

A kit can include one or more of the AhR modulators disclosed herein (provided in, e.g., a sterile container), which may be in the form of a pharmaceutical composition suitable for administration to a subject. The AhR modulators can be provided in a form that is ready for use (e.g., a tablet or capsule) or in a form requiring, for example, reconstitution or dilution (e.g., a powder) prior to administration. When the AhR modulators are in a form that needs to be reconstituted or diluted by a user, the kit may also include diluents (e.g., sterile water), buffers, pharmaceutically acceptable excipients, and the like, packaged with or separately from the AhR modulators. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: μg=microgram; μl or μL=microliter; mM=millimolar; μM=micromolar; aa=amino acid(s); Ac$_2$O=acetic anhydride; AcCl=acetylchloride; ACN=acetonitrile; AIBN=2,2'-Azobis(2-methylpropionitrile); BID=twice daily; BINAP=2,2'-bis(diphenylphosphino)-1,1'-binaphthyl; Boc$_2$O or (Boc)$_2$O=di-tert-butyl dicarbonate; bp=base pair(s); BSA=bovine serum albumin; BW=body weight; d=doublet; dd=doublet of doublets; DEAD=diethyl azodicarboxylate; DIBAL=diisobutylaluminium hydride DIEA=N,N-diisopropylethylamine; DIPEA=N,N-diisopropylethylamine; dl or dL=deciliter; DMA=dimethylacetamide; DMAP=dimethylaminopyridine; DME=1,2-dimethoxyethane; DMEM=Dulbecco's Modification of Eagle's Medium; DMF=N,N-dimethylformamide; DMSO=dimethylsulfoxide; dppf=1,1'-Bis(diphenylphosphino)ferrocene; DTT=dithiothreitol; EDTA=ethylenediaminetetraacetic acid; ES=electrospray; EtOAc=ethyl acetate; EtOH=ethanol; g=gram; h or hr=hour(s); HATU=2-(1H-7-azabenzotriazol-1-yl)-1,1,3,3-tetramethyluronium hexafluorophosphate; HEPES=4-(2-hydroxyethyl)-1-piperazineethylanesulfonic acid; HOAc=acetic acid; HPLC=high performance liquid chromatography; HPLC=high pressure liquid chromatography; i.m.=intramuscular(ly); i.p.=intraperitoneal(ly); IHC=immunohistochemistry; IPA=isopropyl alcohol; kb=kilobase(s); kDa=kilodalton; kg=kilogram; 1 or L=liter; LC=liquid chromatography; LCMS=liquid chromatography and mass spectrometry; m/z=mass to charge ratio; M=molar; m=multiplet; MeCN=acetonitrile; MeOH=methanol; MeSO$_2$Cl=methanesulfonylchloride; mg=milligram; min=minute(s); min=minutes; ml or mL=milliliter; mM=millimolar; MS=mass spectrometry; MsCl=methanesulfonylchloride; N=normal; NADPH=nicotinamide adenine dinucleotide phosphate; NBS=N-bromosuccinamide; ng=nanogram; nm=nanometer; nM=nanomolar; NMP=N-methylpyrrolidone; NMR=nuclear magnetic resonance; ns=not statistically significant; nt=nucleotides(s); PBS=phosphate-buffered saline; Pd/C=palladium on carbon; Pd$_2$(dba)$_3$=Tris(debenzylideneactone) dipalladium; Pd(dppf)Cl$_2$=1,1'-bis(diphenylphosphino)ferrocene-palladium(II)dichloride; PE=petroleum ether; QD=daily; QM=monthly; QW=weekly; rac=racemic; Rt=retention time; s=singlet; s or sec=second(s); sat.=saturated; SC or SQ=subcutaneous(ly); t=triplet; TBAB=tetra-n-butylammonium bromide; TEA=triethylamine; TFA=trifluoroacetic acid; THF=tetrahydrofuran; TLC=thin layer chromatography; TMSCl=trimethylsilylchloride; TsOH=p-toluenesulfonic acid; U=unit; wt=wildtype.

Example 1

Synthesis of 1-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

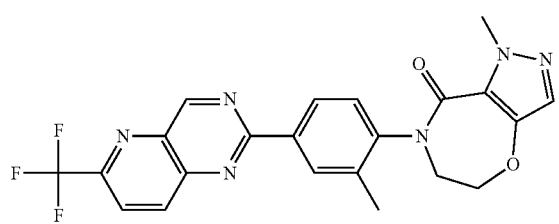 [SMILES: Cc1cc(-c2ncc3nc(C(F)(F)F)ccc3n2)ccc1N1CCOc2cnn(C)c2C1=O]

Step 1: Synthesis of 2-bromo-6-(trifluoromethyl)pyridin-3-amine

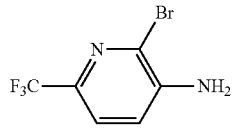

Into a 15-L 3-necked round-bottom flask, was placed 6-(trifluoromethyl)pyridin-3-amine (200 g, 1.23 mol, 1 equiv) and ACN (8 L) NBS (219.6 g, 1.23 mol, 1 equiv) was added in portions. The resulting solution was stirred for 3 h at 0° C. The reaction mixture was then quenched with water and the resulting solution was extracted with ethyl acetate. The organic layer was concentrated and the residue was applied onto a silica gel column and eluted with ethyl acetate/petroleum ether (1/10) to give (146 g, 48.99%) of the title compound as a yellow solid. LC-MS: (ES, m/z): [M+H]+ 241

Step 2: Synthesis of 3-amino-6-(trifluoromethyl)picolinonitrile

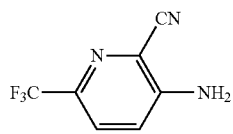 [SMILES: N#Cc1nc(C(F)(F)F)ccc1N]

Into a 3-L 3-necked round-bottom flask under $N_2$ atmosphere, was placed 2-bromo-6-(trifluoromethyl)pyridin-3-amine (146 g, 605.7 mmol, 1 equiv), CuCN (271 g, 3029.5 mmol, 5 equiv), and DMSO (1400 mL). The resulting solution was stirred for 2 h at 120° C. The reaction was then quenched with water and the solids were filtered. The resulting solution was extracted with ethyl acetate and the organic layer concentrated. The residue was applied onto a silica gel column and eluted with ethyl acetate/petroleum ether (1/1) to give 85 mg of the title compound as a yellow solid. LC-MS: (ES, m/z): [M+H]+ 187

Step 3: Synthesis of 6-(trifluoromethyl)pyrido[3,2-d]pyrimidine-2,4(1H,3H)-dione

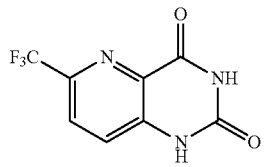 [SMILES: O=c1[nH]c(=O)c2nc(C(F)(F)F)ccc2[nH]1]

Into a 2-L 3-necked round-bottom flask, was placed 3-amino-6-(trifluoromethyl)picolinonitrile (30 g, 160.32 mmol, 1 equiv), DMF (300 mL), and DBU (73.2 g, 480.96 mmol, 3 equiv) under $CO_2$ atmosphere. The resulting solution was stirred for 14 h at 100° C. The reaction mixture was quenched with water. The pH value of the solution was adjusted to 5 with HCl (1 mol/L) and the solids were filtered to give (15 g, 40.54%) of the title compound as a yellow solid. LC-MS: (ES, m/z): [M+H]+ 231.

Step 4: Synthesis of 2,4-dichloro-6-(trifluoromethyl)pyrido[3,2-d]pyrimidine

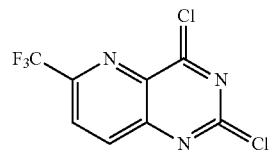

Into a 100 mL 3-necked round-bottom flask, was placed 6-(trifluoromethyl)pyrido[3,2-d]pyrimidine-2,4(1H,3H)-dione (15 g, 64.91 mmol, 1 equiv), $POCl_3$ (75 mL), and $PCl_5$ (67.5 g, 325.05 mmol, 5 equiv). The resulting solution was stirred for 6 at 105° C. The resulting mixture was concentrated under vacuum, quenched with water/ice, and extracted with MTBE. The combined organic layers were concentrated and the residue was applied onto a silica gel column and eluted with ethyl acetate/petroleum ether (1/50) to give (9.5 g, 54.59%) of the title compound as a white solid.

Step 5: Synthesis of 2-chloro-6-(trifluoromethyl)pyrido[3,2-d]pyrimidine

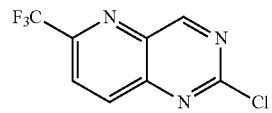 [SMILES: FC(F)(F)c1ccc2nc(Cl)ncc2n1]

Into a 250-mL 3-necked round-bottom flask under $N_2$ atmosphere, was placed 2,4-dichloro-6-(trifluoromethyl)pyrido[3,2-d]pyrimidine (9.5 g, 35.58 mmol, 1 equiv), THF (100 mL), $PPh_3$ (13.93 g, 53.37 mmol, 1.5 equiv), $SnBu_3H$ (10.29 g, 35.48 mmol, 1.1 equiv), and $Pd(PPh_3)_4$ (4.09 g, 3.54 mmol, 0.1 equiv). The resulting solution was stirred for 2 h at 0° C. The resulting mixture was concentrated under vacuum and then applied onto a silica gel column and eluted with ethyl acetate/petroleum ether (1/50) to give (4.5 g, 54.28%) of the title compound as a red solid.

Step 6: Synthesis of 4-(2-(benzyloxy)ethoxy)-1-methyl-1H-pyrazole-5-carboxylic acid

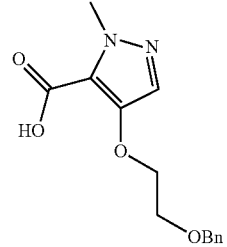 [SMILES: Cn1ncc(OCCOCc2ccccc2)c1C(=O)O]

To a stirred mixture of 4-bromo-1-methyl-1H-pyrazole-5-carboxylic acid (60 g, 292.67 mmol, 1 equiv) in 2-(benzyloxy)ethan-1-ol (300 mL) were added $Cs_2CO_3$ (286.1 g, 878.00 mmol, 3.00 equiv) and $CuCl_2$ (3.9 g, 29.27 mmol, 0.10 equiv). The resulting mixture was stirred for overnight at 130° C. under nitrogen atmosphere. The reaction was quenched with water and extracted with EtOAc. The aqueous phase was acidified to pH 2 with conc. HCl and the resulting mixture was extracted with EtOAc. The combined organic layers were concentrated under reduced pressure. The residue was purified by reverse flash chromatography under the following conditions: column, C18 silica gel; mobile phase, MeCN in water, 0% to 35% gradient in 25 min; detector, UV 254 nm to give (19.2 g, 23.74%) of the title compound as a white solid. LC-MS: (ES, m/z): [M+H]$^+$ 277.

Step 7: Synthesis of 4-(2-(benzyloxy)ethoxy)-1-methyl-1H-pyrazole-5-carbonyl chloride

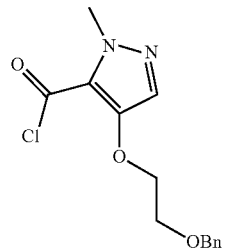 [SMILES: Cn1ncc(OCCOCc2ccccc2)c1C(=O)Cl]

To a stirred solution of 4-(2-(benzyloxy)ethoxy)-1-methyl-1H-pyrazole-5-carboxylic acid (10 g, 36.19 mmol, 1 equiv) and DMF (0.3 g, 3.62 mmol, 0.10 equiv) in DCM (200 mL) was added (COCl)$_2$ (6.9 g, 54.29 mmol, 1.5 equiv) dropwise at 0° C. under nitrogen atmosphere. The resulting mixture was stirred for 3 h at room temperature under nitrogen atmosphere and then concentrated under vacuum to give (11.5 g, crude) of the title compound as a white solid.

Step 8: Synthesis of 4-(2-(benzyloxy)ethoxy)-N-(4-bromo-2-methylphenyl)-1-methyl-1H-pyrazole-5-carboxamide

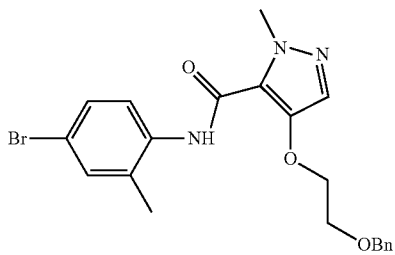 [SMILES: Cc1cc(Br)ccc1NC(=O)c1c(OCCOCc2ccccc2)cnn1C]

To a stirred solution of 4-bromo-2-methylaniline (6.2 g, 33.59 mmol, 1.1 equiv) and Et$_3$N (4.6 g, 45.80 mmol, 1.5 equiv) in DCM (200 mL) was added 4-(2-(benzyloxy)ethoxy)-1-methyl-1H-pyrazole-5-carbonyl chloride (9 g, 30.54 mmol, 1 equiv) in portions at 0° C. The resulting mixture was stirred for 1 h at room temperature and then quenched with water. The resulting mixture was extracted with CH$_2$Cl$_2$ and the combined organic layers were concentrated under reduced pressure. The crude product was recrystallized from MeOH (50 mL) to afford (13 g, 95.82%) of the title compound as a white solid. LC-MS: (ES, m/z): [M+H]$^+$ 444, 446

Step 9: Synthesis of N-(4-bromo-2-methylphenyl)-4-(2-hydroxyethoxy)-1-methyl-1H-pyrazole-5-carboxamide

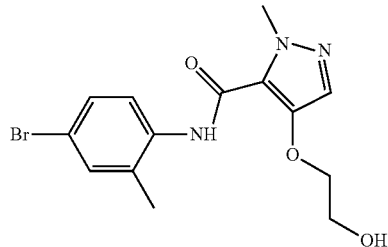 [SMILES: Cc1cc(Br)ccc1NC(=O)c1c(OCCO)cnn1C]

To a stirred solution of 4-(2-(benzyloxy)ethoxy)-N-(4-bromo-2-methylphenyl)-1-methyl-1H-pyrazole-5-carboxamide (13 g, 29.26 mmol, 1 equiv) in DCM (130 mL) was added BCl$_3$ (44 mL, 561.38 mmol, 19.19 equiv) dropwise at 0° C. The resulting mixture was stirred for 5 h at room temperature. The reaction was quenched with NaHCO$_3$(aq.) (300 mL), extracted with CH$_2$Cl$_2$, dried over anhydrous sodium sulfate, and filtered. The combined organic layers were concentrated to give 10.5 g (crude) of the title compound as a yellow solid. LC-MS: (ES, m/z): [M+H]$^+$ 354, 356.

Step 10: Synthesis of 2-((5-((4-bromo-2-methylphenyl)carbamoyl)-1-methyl-1H-pyrazol-4-yl)oxy)ethyl methanesulfonate

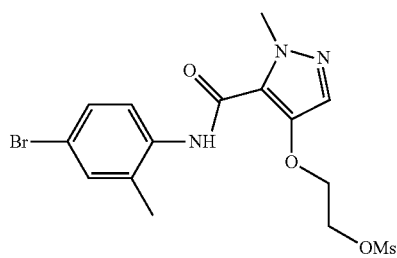 [SMILES: Cc1cc(Br)ccc1NC(=O)c1c(OCCOS(C)(=O)=O)cnn1C]

To a stirred solution of N-(4-bromo-2-methylphenyl)-4-(2-hydroxyethoxy)-1-methyl-1H-pyrazole-5-carboxamide (10.5 g, 29.64 mmol, 1 equiv) and Et$_3$N (9.0 g, 88.93 mmol, 3 equiv) in DCM (100 mL) was added MsCl (6.8 g, 59.29 mmol, 2 equiv) dropwise at 0° C. The resulting mixture was stirred for 5 h at room temperature. The reaction mixture was quenched with water and the resulting mixture was extracted with CH$_2$Cl$_2$. The combined organic layers were washed with water, dried over anhydrous Na$_2$SO$_4$. After filtration, the filtrate was concentrated under reduced pressure to give (13.4 g, 104.57%) of the title compound as a yellow solid. LC-MS: (ES, m/z): [M+H]$^+$ 432, 434.

Step 11: Synthesis of 7-(4-bromo-2-methylphenyl)-1-methyl-6,7-dihydro-1H-pyrazolo[3,4-f][1,4]-oxazepin-8 (5H)-one

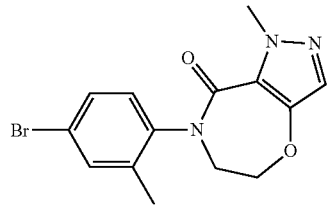 [SMILES: Cc1cc(Br)ccc1N1CCOc2cnn(C)c2C1=O]

To a stirred solution of 2-((5-((4-bromo-2-methylphenyl)carbamoyl)-1-methyl-1H-pyrazol-4-yl)-oxy)ethyl methanesulfonate (13.4 g, 31.00 mmol, 1 equiv) in DMF (200 mL, 2584.35 mmol, 83.37 equiv) were added NaH (1.86 g, 77.51 mmol, 2.50 equiv) in portions at 0° C. The resulting mixture was stirred for 3 h at room temperature. The reaction was quenched with sat. NH$_4$Cl (aq.) and the resulting mixture was extracted with EtOAc. The combined organic layers were concentrated under reduced pressure. The residue was purified by silica gel column chromatography with PE/EtOAc (5/1) as eluent to afford (8 g, 76.77%) of the title compound as a yellow solid. LC-MS: (ES, m/z): [M+H]$^+$ 336, 338.

Step 12: Synthesis of 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one

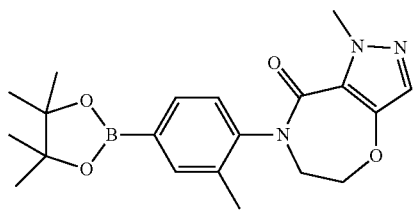 [SMILES: Cc1cc(B2OC(C)(C)C(C)(C)O2)ccc1N1CCOc2cnn(C)c2C1=O]

To a stirred mixture of 7-(4-bromo-2-methylphenyl)-1-methyl-6,7-dihydro-1H-pyrazolo[3,4-f]-[1,4]oxazepin-8 (5H)-one (8 g, 23.80 mmol, 1 equiv) and B$_2$Pin$_2$ (7.3 g, 28.56 mmol, 1.2 equiv) in dioxane (160 mL) were added KOAc (4.7 g, 47.59 mmol, 2 equiv) and Pd(dppf)Cl$_2$ (1.7 g, 2.38 mmol, 0.1 equiv). The resulting mixture was stirred for overnight at 80° C. under nitrogen atmosphere and the mixture was concentrated under reduced pressure. The residue was purified by silica gel column chromatography with PE/EtOAc (3/1) as eluent to afford (7.1 g, 77.85%) of the title compound as a white solid. LC-MS: (ES, m/z): [M+H]$^+$ 384.

Step 13: Synthesis of 1-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

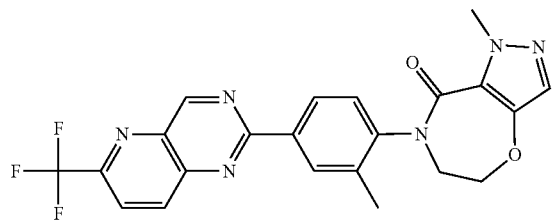 [SMILES: Cc1cc(-c2ncc3nc(C(F)(F)F)ccc3n2)ccc1N1CCOc2cnn(C)c2C1=O]

To a stirred solution of 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one (140 mg, 0.37 mmol, 1 equiv) and 2-chloro-6-(trifluoromethyl)pyrido[3,2-d]pyrimidine (140 mg, 0.60 mmol, 1.64 equiv) in t-BuOH (3 mL) were added H$_2$O (0.33 mL), K$_2$CO$_3$ (151.5 mg, 1.10 mmol, 3 equiv) and AMPhosPdCl$_2$ (77.4 mg, 0.11 mmol, 0.3 equiv). The resulting mixture was stirred for overnight at 80° C. under nitrogen atmosphere and then diluted with water. The resulting mixture was extracted with EtOAc and the combined organic layers were concentrated under reduced pressure. The residue was purified by Prep-TLC (CH$_2$Cl$_2$/MeOH=50/1) to afford (33.5 mg, 20.18%) of the title compound as a yellow solid. LC-MS: (ES, m/z): [M+H]$^+$ 455; $^1$H-NMR: (300 MHz, CD$_3$Cl, ppm): δ 2.44 (s, 3H), 4.00-4.02 (m, 2H), 4.18 (s, 3H), 4.53-4.55 (m, 2H), 7.26-7.36 (m, 2H), 8.14-8.17 (d, 1H), 8.61 (d, 1H), 8.66 (s, 1H), 9.83 (s, 1H).

Example 2

Synthesis of 3-methyl-5-(2-methyl-4-(6-(trifluoromethyl)quinazolin-2-yl)phenyl)-6,7-dihydropyrazolo[1,5-a]pyrazin-4 (5H)-one

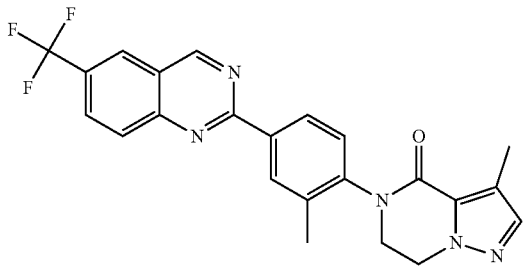

Step 1: Synthesis of 6-(trifluoromethyl)quinazoline-2,4(1H,3H)-dione

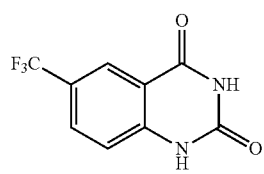 [SMILES: O=c1[nH]c(=O)c2cc(C(F)(F)F)ccc2[nH]1]

To a stirred solution of 2-amino-5-(trifluoromethyl)benzonitrile (30 g, 161.17 mmol, 1 equiv) in DMF (900 mL) was added DBU (73.6 g, 483.46 mmol, 3.00 equiv). The resulting mixture was stirred overnight at 100° C. under carbon dioxide atmosphere and then diluted with water. The reaction mixture was acidified to pH 5 with HCl (aq.), filtered, and the filter cake was washed with water. The resulting solid was dried in an oven under reduced pressure to give (32 g, 86.27%) of the title compound as a light yellow solid. LC-MS: (ES, m/z): $[M+H]^+$ 230

Step 2: Synthesis of 2,4-dichloro-6-(trifluoromethyl)quinazoline

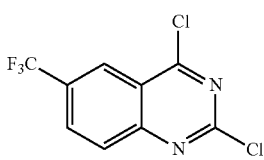

Into a 1 L 3-necked round-bottom flask were added 6-(trifluoromethyl)quinazoline-2,4(1H,3H)-dione (1:1) (57.8 g, 256.36 mmol, 1 equiv), $PCl_5$ (266.9 g, 1281.80 mmol, 5.00 equiv) and $POCl_3$ (295 mL). The resulting mixture was stirred for overnight at 120° C. and then concentrated under reduced pressure. The residue was quenched with water/ice at 0° C. and the resulting mixture was extracted with MTBE. The combined organic layers were dried over anhydrous $Na_2SO_4$. After filtration, the filtrate was concentrated under reduced pressure. The residue was purified by silica gel column chromatography with PE as eluent to afford (50.0 g, 74.79%) of the title compound as a light yellow solid. GC-MS: (ES, m/z): [M]266

Step 3: Synthesis of 2-chloro-6-(trifluoromethyl)quinazoline

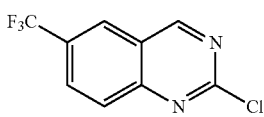 [SMILES: FC(F)(F)c1ccc2nc(Cl)ncc2c1]

To a stirred solution of 2,4-dichloro-6-(trifluoromethyl) quinazoline (58 g, 218.05 mmol, 1 equiv) and tributylstannane (74.7 g, 256.64 mmol, 1.10 equiv) in THF (623 mL) were added $Pd(pph_3)_4$ (27.0 g, 23.33 mmol, 0.1 equiv) under nitrogen atmosphere. The resulting mixture was stirred overnight at room temperature under nitrogen atmosphere. The resulting mixture was concentrated under reduced pressure and the residue was purified by silica gel column chromatography with PE/EtOAc (10/1) as eluent to afford the title compound (28 g, 55.36%) as a yellow solid. LC-MS: (ES, m/z): $[M+H]^+$ 233.

Step 4: Synthesis of ethyl 1-(2-(benzyloxy)ethyl)-4-methyl-1H-pyrazole-5-carboxylate

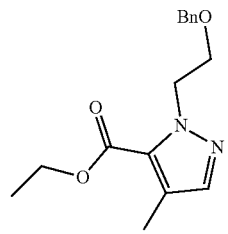 [SMILES: CCOC(=O)c1c(C)cnn1CCOCc1ccccc1]

Into a 50-mL 3-necked round-bottom flask purged under nitrogen atmosphere, was placed ethyl 4-methyl-1H-pyrazole-5-carboxylate (2 g, 12.97 mmol, 1 equiv), 2-(benzyloxy)ethan-1-ol (2.0 g, 13.14 mmol, 1.01 equiv), DIAD (3.9 g, 19.46 mmol, 1.5 equiv), and $PPh_3$ (5.1 g, 19.46 mmol, 1.5 equiv) in THF (20 mL). The resulting solution was stirred for overnight at room temperature. After concentrating the reaction mixture under vacuum, the residue was applied onto a silica gel column and eluted with ethyl acetate/petroleum ether (1/50) to give (3 g, 80.20%) of the title compound as colorless oil. LC-MS: (ES, m/z): $[M+H]^+$ 288

Step 5: Synthesis of 1-(2-(benzyloxy)ethyl)-4-methyl-1H-pyrazole-5-carboxylic acid

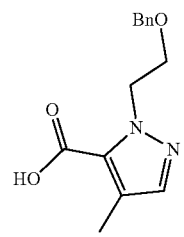 [SMILES: Cc1cnn(CCOCc2ccccc2)c1C(=O)O]

Into a 50-mL 3-necked round-bottom flask, was placed ethyl 1-(2-(benzyloxy)ethyl)-4-methyl-1H-pyrazole-5-carboxylate (2.9 g, 10.06 mmol, 1 equiv), NaOH (4M, 2 equiv), and EtOH (15 mL). The resulting solution was stirred for 2 h at 50° C. and then diluted with $H_2O$. The resulting mixture was concentrated to remove EtOH. The pH value of the solution was adjusted to 4 with HCl (1 mol/L). The resulting solution was extracted with ethyl acetate, dried over anhydrous sodium sulfate, and concentrated to give (2.1 g, 80.22%) of the title compound as a white solid. LC-MS: (ES, m/z): $[M+H]^+$ 260

Step 6: Synthesis of 1-(2-(benzyloxy)ethyl)-N-(4-bromo-2-methylphenyl)-4-methyl-1H-pyrazole-5-carboxamide

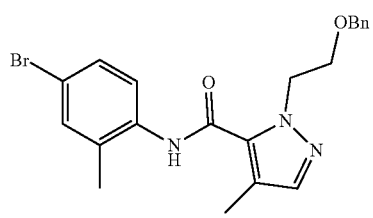

Into a 50-mL 3-necked round-bottom flask, was placed 1-(2-(benzyloxy)ethyl)-4-methyl-1H-pyrazole-5-carboxylic acid (1.2 g, 4.61 mmol, 1 equiv), 4-bromo-2-methylaniline (1.3 g, 6.99 mmol, 1.52 equiv), HATU (2.6 g, 6.92 mmol, 1.5 equiv), DIEA (1.2 g, 9.22 mmol, 2 equiv), and DMF (15 mL). The resulting solution was stirred for overnight at room temperature. The resulting solution was diluted with EtOAc and washed with H$_2$O. The resulting mixture was concentrated under vacuum and the residue was applied onto a silica gel column and eluted with ethyl acetate/petroleum ether (1/10) to give (1.6 g, 81.03%) of the title compound as a white solid. LC-MS: (ES, m/z): [M+H]$^+$ 428, 430

Step 7: Synthesis of N-(4-bromo-2-methylphenyl)-1-(2-hydroxyethyl)-4-methyl-1H-pyrazole-5-carboxamide

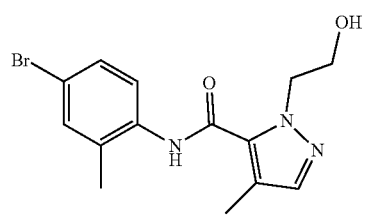 [SMILES: Cc1cc(Br)ccc1NC(=O)c1c(C)cnn1CCO]

Into a 50-mL 3-necked round-bottom flask under nitrogen atmosphere, was placed 1-(2-(benzyloxy)ethyl)-N-(4-bromo-2-methylphenyl)-4-methyl-1H-pyrazole-5-carboxamide (1 g, 1 equiv), and BCl$_3$ (1 mol/mL, 5 mL) was added dropwise at 0° C. The resulting solution was stirred for 1 h at 0° C. and then quenched with NaHCO$_3$. The resulting solution was extracted with ethyl acetate and the organic layers were combined. The organic layer was washed with H$_2$O, dried over anhydrous sodium sulfate and concentrated to give (512 mg, 67.65%) of the title compound as a white solid. LC-MS: (ES, m/z): [M+H]$^+$ 338, 340.

Step 8: Synthesis of 2-(5-((4-bromo-2-methylphenyl)carbamoyl)-4-methyl-1H-pyrazol-1-yl)ethyl methanesulfonate

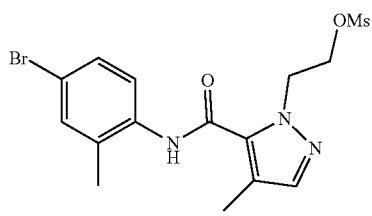 [SMILES: Cc1cc(Br)ccc1NC(=O)c1c(C)cnn1CCOS(C)(=O)=O]

Into a 25-mL 3-necked round-bottom flask, was placed N-(4-bromo-2-methylphenyl)-1-(2-hydroxyethyl)-4-methyl-1H-pyrazole-5-carboxamide (312 mg, 0.92 mmol, 1 equiv), DCM (5 mL), and MsCl (158.5 mg, 1.38 mmol, 1.5 equiv) was added dropwise at 0° C. The resulting solution was stirred for 1 h at RT and then quenched with water. The resulting solution was extracted with dichloromethane and the organic layers combined. The resulting mixture was washed with H$_2$O, dried, filtered and concentrated to give (416 mg) of the title compound as a crude product. LC-MS: (ES, m/z): [M+H]$^+$ 416, 418.

Step 9: Synthesis of 5-(4-bromo-2-methylphenyl)-3-methyl-6,7-dihydropyrazolo[1,5-a]pyrazin-4 (5H)-one

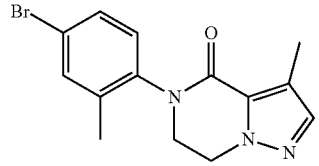

Into a 25-mL 3-necked round-bottom flask under N$_2$ atmosphere, was placed 2-(5-((4-bromo-2-methylphenyl)carbamoyl)-4-methyl-1H-pyrazol-1-yl)ethyl methanesulfonate (416 mg, 1.00 mmol, 1 equiv), DMF (5 mL, 64.61 mmol, 64.65 equiv), and NaH (36.0 mg, 1.50 mmol, 1.5 equiv) was added in portions at 0° C. The resulting solution was stirred for 1 h at 0° C. The reaction mixture was then quenched by added to 20 mL of NH$_4$Cl and extracted with ethyl acetate. The organic layer was washed with H$_2$O and then concentrated. The residue was applied onto a prep-TLC with ethyl acetate/petroleum ether (1/5) to give (300 mg, 93.76%) of the title compound as a white solid. LC-MS: (ES, m/z): [M+H]$^+$ 320, 322

Step 10: Synthesis of 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one

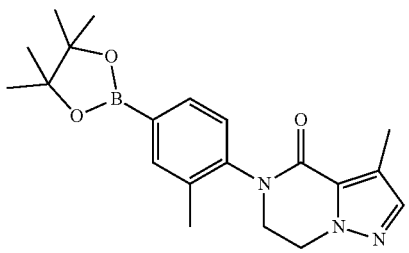 [SMILES: Cc1cc(B2OC(C)(C)C(C)(C)O2)ccc1N1CCn2ncc(C)c2C1=O]

Into a 8-mL sealed tube purged under nitrogen atmosphere, was placed 5-(4-bromo-2-methylphenyl)-3-methyl-6,7-dihydropyrazolo[1,5-a]pyrazin-4 (5H)-one (280 mg, 0.87 mmol, 1 equiv), 4,4,5,5-tetramethyl-2-(4,4,5,5-tetramethyl-1,3,2-dioxaborolan-2-yl)-1,3,2-dioxaborolane (333.1 mg, 1.31 mmol, 1.5 equiv), Pd(dppf)Cl$_2$ (96.0 mg, 0.13 mmol, 0.15 equiv), and KOAc (171.6 mg, 1.75 mmol, 2 equiv), in dioxane (3 mL). The resulting solution was stirred for overnight at 80° C. The resulting mixture was concentrated under vacuum and the residue was applied onto a silica gel column and eluted with ethyl acetate/petroleum ether (1/5) to give (204 mg, 63.52%) of the title compound as a white solid. LC-MS: (ES, m/z): [M+H]$^+$ 367.

Step 11: Synthesis of 2-methyl-5-(2-methyl-4-(6-(trifluoromethyl)quinazolin-2-yl)phenyl)-6,7-dihydropyrazolo[1,5-a]pyrazin-4 (5H)-one

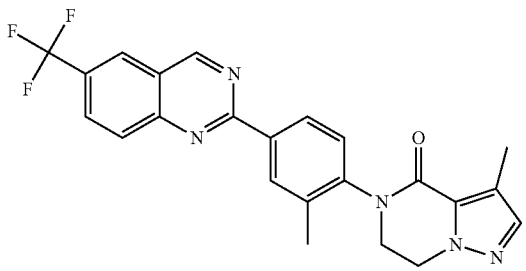

Into a 50-mL 3-necked round-bottom flask under nitrogen atmosphere, was placed 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one (180 mg, 0.49 mmol, 1 equiv), 2-chloro-6-(trifluoromethyl)-quinazoline (114.0 mg, 0.49 mmol, 1.00 equiv), Pd(PPh$_3$)$_4$ (85.0 mg, 0.07 mmol, 0.15 equiv), and K$_2$CO$_3$ (203.2 mg, 1.47 mmol, 3.00 equiv) in toluene (5.4 mL) and EtOH (2.7 mL). The resulting solution was stirred for overnight at 80° C. The resulting solution was diluted with H$_2$O, extracted with ethyl acetate, and the organic layers were combined. The residue was applied onto a silica gel column and eluted with ethyl acetate/petroleum ether (1/2) to give (31.8 mg, 14.83%) of the title compound as a light yellow solid. LC-MS: (ES, m/z): [M+H]$^+$ 438;

$^1$H-NMR: (300 MHz, DMSO-d6, ppm): δ 9.89 (s, 1H), 8.71 (s, 1H), 8.54 (d, 1H), 8.47 (d, 1H), 8.27 (t, 2H), 7.54 (d, 1H), 7.46 (s, 1H), 4.51 (t, 2H), 4.29 (m, 1H), 3.91 (m, 1H), 2.33 (s, 3H), 2.24 (s, 3H).

Example 3

Synthesis of 5-(2,5-dimethyl-4-(6-(trifluoromethyl) quinazolin-2-yl)phenyl)-3-methyl-6,7-dihydropyrazolo[1,5-a]pyrazin-4 (5H)-one

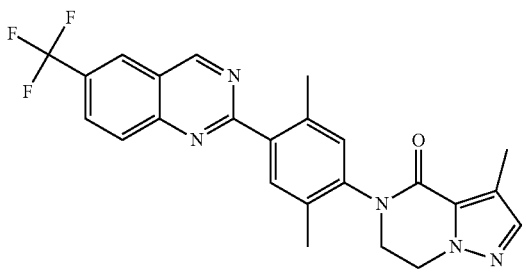

Step 1: Synthesis of 1-(2-(benzyloxy)ethyl)-4-methyl-1H-pyrazole-5-carbonyl chloride

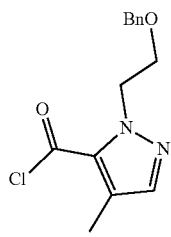 [SMILES: Cc1cnn(CCOCc2ccccc2)c1C(=O)Cl]

Into a 250-mL 3-necked round-bottom flask under N$_2$ atmosphere, was placed 1-(2-(benzyloxy)ethyl)-4-methyl-1H-pyrazole-5-carboxylic acid (6.4 g, 24.59 mmol, 1 equiv), prepared as described in Example 2 above, DCM (60 mL, 943.80 mmol, 38.39 equiv), DMF (0.2 g, 2.74 mmol, 0.11 equiv.), and (COCl)$_2$ (3.4 g, 27.05 mmol, 1.1 equiv) was added dropwise to the above solution at 0° C. The resulting solution was stirred for 1 h at RT and then concentrated under vacuum to give 6.9 g of the title compound as a crude product.

Step 2: Synthesis of 1-(2-(benzyloxy)ethyl)-N-(4-bromo-2,5-dimethylphenyl)-4-methyl-1H-pyrazole-5-carboxamide

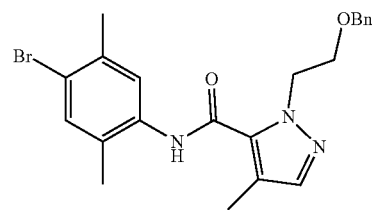

Into a 100 mL 3-necked round-bottom flask was added 4-bromo-2,5-dimethylaniline (3.3 g, 16.50 mmol, 1 equiv), DCM (50 mL), and Et$_3$N (3.3 g, 32.61 mmol, 1.98 equiv). To the above mixture 1-(2-(benzyloxy)ethyl)-4-methyl-1H-pyrazole-5-carbonyl chloride (4.6 g, 16.50 mmol, 1 equiv) in 20 mL of DCM was added dropwise at 0° C. The resulting mixture was stirred for additional 1 h at room temperature. The reaction mixture was quenched with water and the aqueous layer was extracted with CH$_2$Cl$_2$. The combined organic layer was dried over anhydrous sodium sulfate and concentrated under vacuum. The crude product was re-crystallized from MeOH (50 mL) to afford (5.4 g, 73.97%) of the title compound as a white solid. LC-MS: (ES, m/z): [M+H]$^+$ 442.

Step 3: Synthesis of N-(4-bromo-2,5-dimethylphenyl)-1-(2-hydroxyethyl)-4-methyl-1H-pyrazole-5-carboxamide

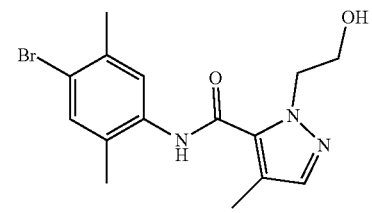 [SMILES: Cc1cc(NC(=O)c2c(C)cnn2CCO)c(C)cc1Br]

Into a 250-mL 3-necked round-bottom flask under nitrogen atmosphere was placed 1-(2-(benzyloxy)ethyl)-N-(4-bromo-2,5-dimethylphenyl)-4-methyl-1H-pyrazole-5-carboxamide (5.4 g, 1 equiv), DCM (50 mL), and BCl$_3$ (18.3 mL, 1M in DCM, 1.5 equiv) was added dropwise at 0° C. The resulting solution was stirred for 1 h at RT. After quenching with NaHCO$_3$(aq.), the reaction mixture was extracted with dichloromethane. The combined organic layer was washed with H$_2$O, dried over anhydrous sodium sulfate and concentrated under vacuum to give (4.1 g, 95.35%) of the title compound as a white solid. LC-MS: (ES, m/z): [M+H]+ 352.

Step 4: Synthesis of 2-(5-((4-bromo-2,5-dimethylphenyl)carbamoyl)-4-methyl-1H-pyrazol-1-yl)ethyl methanesulfonate

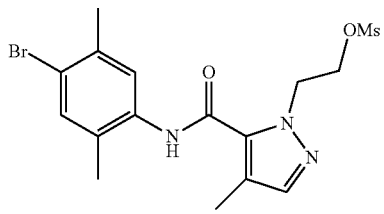 [SMILES: Cc1cc(NC(=O)c2c(C)cnn2CCOS(C)(=O)=O)c(C)cc1Br]

Into a 100-mL 3-necked round-bottom flask under nitrogen atmosphere, was placed N-(4-bromo-2,5-dimethylphenyl)-1-(2-hydroxyethyl)-4-methyl-1H-pyrazole-5-carboxamide (4.1 g, 11.64 mmol, 1 equiv), DCM (40 mL), Et₃N (2.4 g, 23.72 mmol, 2.04 equiv), and MsCl (2.0 g, 17.46 mmol, 1.50 equiv) was added dropwise to the above mixture at 0° C. The resulting solution was stirred for 1 h at RT. The reaction mixture was then quenched with water. The resulting solution was extracted with dichloromethane and the organic layers combined. The organic layer was washed with H₂O, dried over anhydrous sodium sulfate and concentrated under vacuum to give 4.75 g of the title compound as a crude product. LC-MS: (ES, m/z): [M+H]+ 430.

Step 5: Synthesis of 5-(4-bromo-2,5-dimethylphenyl)-3-methyl-6,7-dihydropyrazolo[1,5-a]pyrazin-4 (5H)-one

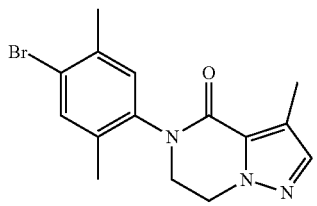

Into a 100-mL 3-necked round-bottom flask under nitrogen atmosphere, was added 2-(5-(((4-bromo-2,5-dimethylphenyl)carbamoyl)-4-methyl-1H-pyrazol-1-yl)ethyl methanesulfonate (4.75 g, 11.04 mmol, 1 equiv), and DMF (50 mL), and NaH (0.4 g, 16.67 mmol, 1.51 equiv) was added at 0° C. The resulting solution was stirred for 1 h at RT and then quenched with NH₄Cl (aq.). The resulting solution was extracted with ethyl acetate and the combined organic layer was washed with H₂O and concentrated. The residue was applied onto a silica gel column and eluted with ethyl acetate/petroleum ether (1:5) to give (3.1 g, 84.03%) of the title compound as a white solid. LC-MS: (ES, m/z): [M+H]+ 334.

Step 6: Synthesis of 5-(2,5-dimethyl-4-(4,4,5,5-tetramethyl-1,3,2-dioxaborolan-2-yl)phenyl)-3-methyl-6,7-dihydropyrazolo[1,5-a]pyrazin-4 (5H)-one

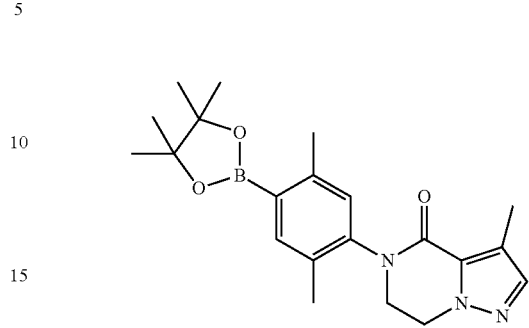

Into a 100-mL 3-necked round-bottom flask under nitrogen atmosphere, was placed 5-(4-bromo-2,5-dimethylphenyl)-3-methyl-6,7-dihydropyrazolo[1,5-a]pyrazin-4 (5H)-one (3.1 g, 9.28 mmol, 1 equiv), B₂Pin₂ (3.54 g, 13.92 mmol, 1.5 equiv), dioxane (30 mL), KOAc (1.8 g, 18.34 mmol, 1.98 equiv), and Pd(dppf)Cl₂ (2.0 g, 2.78 mmol, 0.3 equiv). The resulting solution was stirred overnight at 80° C. The resulting mixture was concentrated under vacuum. The residue was applied onto a silica gel column and eluted with ethyl acetate/petroleum ether (1:5) to give (3 g, 84.83%) of the title compound as a white solid. LC-MS: (ES, m/z): [M+H]+ 382

Step 7: Synthesis of 5-(2,5-dimethyl-4-(6-(trifluoromethyl)quinazolin-2-yl)phenyl)-3-methyl-6,7-dihydropyrazolo[1,5-a]pyrazin-4 (5H)-one

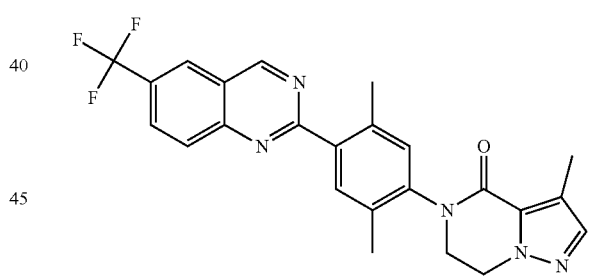

Into a 50-mL 3-necked round-bottom flask under nitrogen atmosphere, was placed 5-(2,5-dimethyl-4-(4,4,5,5-tetramethyl-1,3,2-dioxaborolan-2-yl)phenyl)-3-methyl-6,7-dihydropyrazolo[1,5-a]pyrazin-4 (5H)-one (1 g, 2.62 mmol, 1 equiv), 2-chloro-6-(trifluoromethyl)quinazoline (0.7 g, 2.89 mmol, 1.1 equiv), K₂CO₃ (1.1 g, 7.87 mmol, 3 equiv), toluene (14 mL), EtOH (7 mL), and Pd(PPh₃)₄ (0.5 g, 0.39 mmol, 0.15 equiv). The resulting solution was stirred for 12 at 80° C. The resulting mixture was diluted with and extracted with ethyl acetate. The combined organic layer was concentrated under reduced pressure. The residue was applied onto a silica gel column and eluted with ethyl acetate/petroleum ether (1:2) to give (307.1 mg, 25.94%) of the title compound as a white solid. LC-MS: (ES, m/z): [M+H]+ 452; ¹H-NMR: (300 MHz, DMSO-d6, ppm): δ 9.91 (s, 1H), 8.75 (s, 1H), 8.31 (d, 1H), 8.26 (d, 1H), 7.95 (s, 1H), 7.47 (s, 1H), 7.36 (s, 1H), 4.51-4.54 (t, 2H), 4.26-4.32 (m, 1H), 3.90-3.95 (m, 1H), 2.59 (s, 3H), 2.27 (s, 6H).

Example 4

Synthesis of 1-methyl-6-(2-methyl-4-(6-(trifluoromethyl)pyrido[3,2-d]pyrimidin-2-yl)phenyl)-1,4,5,6-tetrahydro-7H-pyrazolo[3,4-c]pyridin-7-one

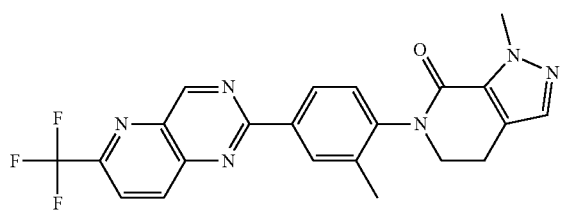

Step 1: Synthesis of methyl 4-allyl-1-methyl-1H-pyrazole-5-carboxylate

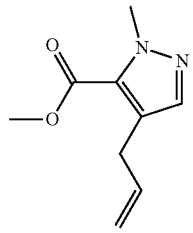

To a stirred solution of methyl 4-bromo-1-methyl-1H-pyrazole-5-carboxylate (100 g, 456.54 mmol, 1 equiv) and tributyl(prop-2-en-1-yl)stannane (166.3 g, 502.20 mmol, 1.1 equiv) in DMF (1000 mL) was added Pd(PPh$_3$)$_4$ (26.4 g, 22.83 mmol, 0.05 equiv). The resulting mixture was stirred overnight at 100° C. under nitrogen atmosphere and then was quenched with water. The resulting mixture was extracted with EtOAc. The combined organic layers were concentrated under reduced pressure. The residue was purified by silica gel column chromatography with PE/EtOAc (50/1) as eluent to afford (80 g, 97.24%) of the title compound as a yellow oil. LC-MS: (ES, m/z): [M+H]$^+$ 181.

Step 2. Synthesis of 4-allyl-1-methyl-1H-pyrazole-5-carboxylic acid

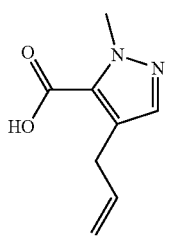

Into a 2-L 3-necked round-bottom flask, was placed methyl 4-allyl-1-methyl-1H-pyrazole-5-carboxylate (84 g, 466.13 mmol, 1 equiv), MeOH (840 mL, 20747.08 mmol, 44.51 equiv), NaOH (37.3 g, 932.57 mmol, 2.00 equiv). The resulting solution was stirred for 2 h at 50° C. and then diluted with H$_2$O. The resulting mixture was concentrated under vacuum to remove CH$_3$OH. The pH of the solution was adjusted to 5 with HCl (1 mol/L). The resulting solution was extracted with ethyl acetate and the organic layers combined and concentrated to give (61 g, 78.75%) of the title compound as a white solid. LC-MS: (ES, m/z): [M+H]$^+$ 167.

Step 3: Synthesis of 4-allyl-1-methyl-1H-pyrazole-5-carbonyl chloride

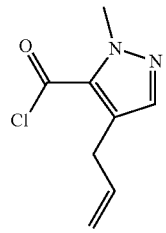

Into a 500-mL round-bottom flask was placed 4-allyl-1-methyl-1H-pyrazole-5-carboxylic acid (20 g, 120.35 mmol, 1 equiv) in DCM (200 mL, 3146.01 mmol, 26.14 equiv), and DMF (0.9 g, 12.04 mmol, 0.1 equiv). Oxalyl chloride (22.9 g, 180.42 mmol, 1.50 equiv) was added dropwise over 10 min at 0° C. The resulting reaction mixture was concentrated to give (21 g, 94.51%) of the title compound as a crude product.

Step 4: Synthesis of 4-allyl-N-(4-bromo-2-methylphenyl)-1-methyl-1H-pyrazole-5-carboxamide

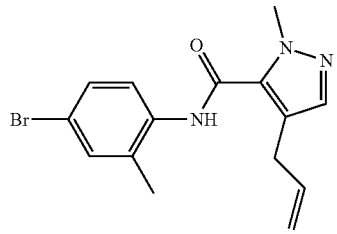 [SMILES: C=CCc1cnn(C)c1C(=O)Nc1ccc(Br)cc1C]

Into a 500-mL 3-necked round-bottom flask, was placed 4-bromo-2-methylaniline (25.4 g, 136.52 mmol, 1.20 equiv), Et$_3$N (17.3 g, 170.62 mmol, 1.5 equiv), and DCM. 4-Allyl-1-methyl-1H-pyrazole-5-carbonyl chloride (21 g, 113.75 mmol, 1 equiv) was added dropwise with stirring at 0° C. The resulting solution was stirred for 30 min at rt and then quenched with water. The resulting solution was extracted with DCM and the organic layers combined and concentrated. The crude product was purified by re-crystallization from CH$_3$OH to give (33 g, 86.81%) of the title compound as a white solid. LC-MS: (ES, m/z): [M+H]$^+$ 334.

Step 5: Synthesis of N-(4-bromo-2-methylphenyl)-4-(2,3-dihydroxypropyl)-1-methyl-1H-pyrazole-5-carboxamide

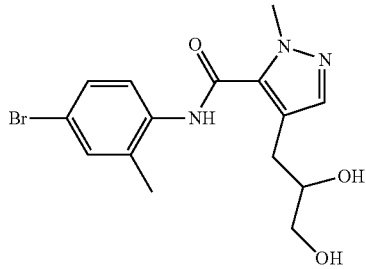 [SMILES: Cc1cc(Br)ccc1NC(=O)c1c(CC(O)CO)cnn1C]

Into a 500-mL 3-necked round-bottom flask was placed 4-allyl-N-(4-bromo-2-methylphenyl)-1-methyl-1H-pyrazole-5-carboxamide (21 g, 62.83 mmol, 1 equiv), NMO (22.1 g, 188.50 mmol, 3 equiv), THF (210 mL, 2.91 mmol, 0.05 equiv), H$_2$O (21 mL, 1165.68 mmol, 18.55 equiv), and OsO$_4$ (0.8 g, 3.15 mmol, 0.05 equiv). The resulting solution was stirred for 30 min at room temperature. The reaction mixture was quenched with 300 mL of NaS$_2$O$_4$. The resulting solution was extracted with ethyl acetate, water and then concentrated to give (37 g, 159.92%) of the title compound as a crude product. LC-MS: (ES, m/z): [M+H]$^+$ 368.

Step 6: Synthesis of N-(4-bromo-2-methylphenyl)-1-methyl-4-(2-oxoethyl)-1H-pyrazole-5-carboxamide

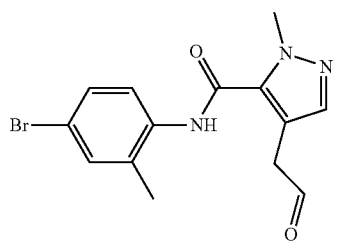 [SMILES: Cc1cc(Br)ccc1NC(=O)c1c(CC=O)cnn1C]

Into a 500-mL 3-necked round-bottom flask, was placed N-(4-bromo-2-methylphenyl)-4-(2,3-dihydroxypropyl)-1-methyl-1H-pyrazole-5-carboxamide (37 g, 100.48 mmol, 1 equiv), MeOH (370 mL), H$_2$O (37 mL), and NaIO$_4$ (43.0 g, 201.04 mmol, 2.00 equiv). The resulting solution was stirred for 30 min at room temperature, diluted with 370 mL of H$_2$O, and the resulting mixture was concentrated. The solids were filtered, washed with H$_2$O and dried to give 35 g (crude) of the title compound as a white solid. LC-MS: (ES, m/z): [M+H]$^+$ 336.

Step 7: Synthesis of N-(4-bromo-2-methylphenyl)-4-(2-hydroxyethyl)-1-methyl-1H-pyrazole-5-carboxamide

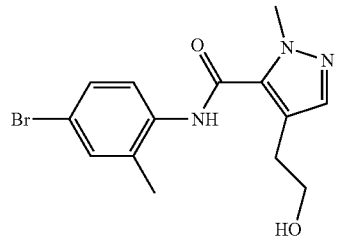 [SMILES: Cc1cc(Br)ccc1NC(=O)c1c(CCO)cnn1C]

Into a 1 L 3-necked round-bottom flask was placed N-(4-bromo-2-methylphenyl)-1-methyl-4-(2-oxoethyl)-1H-pyrazole-5-carboxamide (35 g, 104.11 mmol, 1 equiv) in MeOH (350 mL). NaBH$_4$ (4.7 g, 124.23 mmol, 1.19 equiv) was added in portions at 0° C. The resulting solution was stirred for 30 min at rt and then quenched with NH$_4$Cl solution (350 mL). The resulting mixture was concentrated and the solids were collected by filtration, washed with H$_2$O, dried to give (30 g, 85.20%) of the title compound as a white solid. LC-MS: (ES, m/z): [M+H]$^+$ 338.

Step 8: Synthesis of 2-(5-((4-bromo-2-methylphenyl)carbamoyl)-1-methyl-1H-pyrazol-4-yl)ethyl methanesulfonate

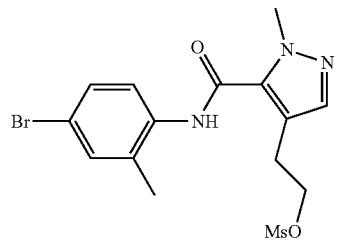 [SMILES: Cc1cc(Br)ccc1NC(=O)c1c(CCOS(C)(=O)=O)cnn1C]

Into a 1-L round-bottom flask, was placed N-(4-bromo-2-methylphenyl)-4-(2-hydroxyethyl)-1-methyl-1H-pyrazole-5-carboxamide (30 g, 88.70 mmol, 1 equiv), DCM (300 mL), and Et$_3$N (13.5 g, 133.41 mmol, 1.50 equiv). Methanesulfonyl chloride (15.2 g, 132.69 mmol, 1.50 equiv) was added dropwise with stirring at 0° C. The resulting solution was stirred for 30 min at rt and then quenched with water. The resulting solution was extracted with dichloromethane and concentrated to give (42 g, 113.74%) of the title compound as a white solid. LC-MS: (ES, m/z): [M+H]$^+$ 416.

Step 9: Synthesis of 6-(4-bromo-2-methylphenyl)-1-methyl-1,4,5,6-tetrahydro-7H-pyrazolo[3,4-c]pyridin-7-one

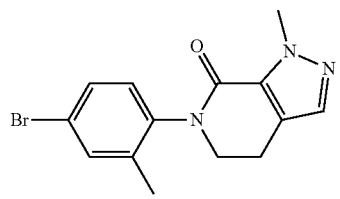 [SMILES: Cc1cc(Br)ccc1N1CCc2cnn(C)c2C1=O]

Into a 1 L 3-necked round-bottom flask was placed 2-(5-((4-bromo-2-methylphenyl)carbamoyl)-1-methyl-1H-pyrazol-4-yl)ethyl methanesulfonate (42 g, 100.89 mmol, 1 equiv), and DMF (420 mL, 5427.14 mmol, 53.79 equiv). NaH (3.6 g, 150.01 mmol, 1.49 equiv) was added in portions at 0° C. The resulting solution was stirred for 30 min at room temperature and then quenched with NH₄Cl. The solids were collected by filtration. The crude product was purified by re-crystallization from PE to give (23 g, 71.20%) of the title compound as a white solid. LC-MS: (ES, m/z): [M+H]⁺.

Step 10: Synthesis of 1-methyl-6-(2-methyl-4-(4,4,5,5-tetramethyl-1,3,2-dioxaborolan-2-yl)phenyl)-1,4,5,6-tetrahydro-7H-pyrazolo[3,4-c]pyridin-7-one

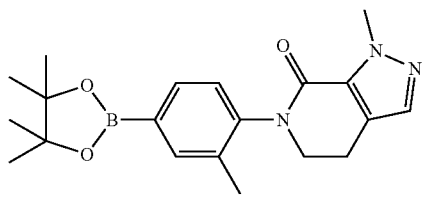 [SMILES: Cc1cc(B2OC(C)(C)C(C)(C)O2)ccc1N1CCc2cnn(C)c2C1=O]

Into a 500-mL 4-necked round-bottom flask under $N_2$ atmosphere, was placed $B_2Pin_2$ (23.8 g, 93.72 mmol, 1.50 equiv), 6-(4-bromo-2-methylphenyl)-1-methyl-1,4,5,6-tetrahydro-7H-pyrazolo[3,4-c]pyridin-7-one (20 g, 62.46 mmol, 1 equiv), Pd(dppf)Cl₂ (2.3 g, 3.12 mmol, 0.05 equiv), and KOAc (12.3 g, 124.93 mmol, 2 equiv) in dioxine (400 mL). The resulting solution was stirred overnight at 80° C. The resulting mixture was concentrated and the residue was applied onto a silica gel column and eluted with ethyl acetate/petroleum ether (1/5) to give (13 g, 56.67%) of the title compound as a white solid. LC-MS: (ES, m/z): [M+H]⁺ 368.

Step 11: Synthesis of 1-methyl-6-(2-methyl-4-(6-(trifluoromethyl)pyrido[3,2-d]pyrimidin-2-yl)phenyl)-1,4,5,6-tetrahydro-7H-pyrazolo[3,4-c]pyridin-7-one

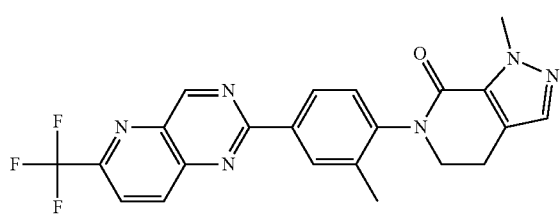

To a stirred mixture of 1-methyl-6-(2-methyl-4-(4,4,5,5-tetramethyl-1,3,2-dioxaborolan-2-yl)phenyl)-1,4,5,6-tetrahydro-7H-pyrazolo[3,4-c]pyridin-7-one (2 g, 5.45 mmol, 1 equiv) and 2-chloro-6-(trifluoromethyl)pyrido[3,2-d]pyrimidine (1.5 g, 6.53 mmol, 1.2 equiv), prepared as described in Example 1 above, in dioxane (200 mL) were added H₂O (40 mL), K₃PO₄ (2.3 g, 10.89 mmol, 2 equiv) and AMPhosPdCl₂ (1.2 g, 1.63 mmol, 0.3 equiv). The resulting mixture was stirred overnight at 50° C. under nitrogen atmosphere and then diluted with water. The organics were extracted with EtOAc and the combined organic layers were concentrated under reduced pressure. The residue was purified by silica gel column chromatography, eluted with PE/EtOAc (3/1) to give crude product which was re-crystallized from MeOH (50 mL) to afford (706.7 mg, 29.60%) of the title compound as a yellow solid. LC-MS: (ES, m/z): [M+H]⁺ 439; ¹H-NMR: (400 MHz, DMSO-d₆, ppm): δ 2.35 (s, 3H), 2.90-3.05 (m, 2H), 3.73-3.79 (m, 1H), 4.02-4.14 (m, 4H), 7.49 (s, 1H), 7.53-7.55 (d, 1H), 8.46-8.49 (m, 2H), 8.55 (s, 1H), 8.81 (d, 1H), 9.95 (s, 1H).

Example 5

Synthesis of 7-(2,5-dimethyl-4-(8-methyl-6-(trifluoromethyl)-1,5-naphthyridin-2-yl)phenyl)-1-methyl-6,7-dihydro-1H-pyrazolo[3,4-f][1,4]oxazepin-8 (5H)-one

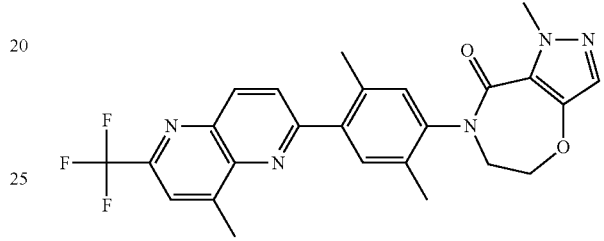

Step 1: Synthesis of 4-methyl-5-nitro-2-(trifluoromethyl)pyridine

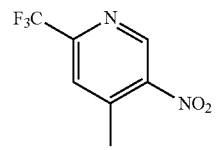

Into a 2 L 3-necked round-bottom flask under $N_2$ atmosphere, was placed 2-bromo-4-methyl-5-nitropyridine (100 g, 460.79 mmol, 1 equiv), methyl 2,2-difluoro-2-(fluorosulfonyl)acetate (177.0 g, 921.57 mmol, 2 equiv), and CuI (70.2 g, 368.60 mmol, 0.800 equiv) in DMF (1 L). The resulting solution was stirred for 14 h at 120° C. and then diluted with NH₄Cl (3 L), NH₄OH (0.5 L). The resulting solution was extracted with ethyl acetate and the combined organic layer was concentrated under reduced pressure. The residue was applied onto a silica gel column and eluted with petroleum ether to give (40 g, 41.94%) of the title compound as a red oil. GC-MS: (ES, m/z): [M]⁺206.

Step 2: Synthesis of 4-methyl-6-(trifluoromethyl)pyridin-3-amine

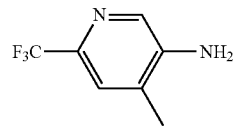

Into a 1 L 3-necked round-bottom flask was placed 4-methyl-5-nitro-2-(trifluoromethyl)pyridine (60 g, 291.26 mmol, 1 equiv), Fe (48.9 g, 873.79 mmol, 3 equiv), NH₄Cl (77.2 g, 1456.31 mmol, 5 equiv), and H₂O (500 mL). The resulting mixture was stirred for 2 at 80° C. The resulting solution was extracted with ethyl acetate. The residue was applied onto a silica gel column and eluted with ethyl acetate/petroleum ether (1/10) to give (27 g, 60.76%) of the title compound as a white solid. LC-MS: (ES, m/z): [M+H]⁺ 177.

Step 3: Synthesis of 2-bromo-4-methyl-6-(trifluoromethyl)pyridin-3-amine

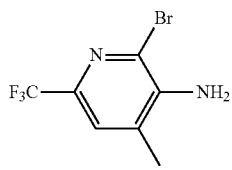

To a stirred solution 4-methyl-6-(trifluoromethyl)pyridin-3-amine (27 g, 153.41 mmol, 1 equiv) in DCM (270 mL) was added NBS (27.1 g, 153.41 mmol, 1 equiv) in portions at 0° C. under nitrogen atmosphere. The resulting mixture was stirred for 2 h at 0° C. under nitrogen atmosphere. The reaction mixture was quenched with water at room temperature and the resulting mixture was extracted with CH₂Cl₂. The combined organic layers were dried over anhydrous Na₂SO₄. After filtration, the filtrate was concentrated under reduced pressure. The residue was purified by silica gel column chromatography with PE/EtOAc (30/1) as eluent to afford (36.4 g, 96.45%) of the title compound as a red solid. LC-MS: (ES, m/z): [M+H]⁺ 255.

Step 4: Synthesis of ethyl 3-(3-amino-4-methyl-6-(trifluoromethyl)pyridin-2-yl)acrylate

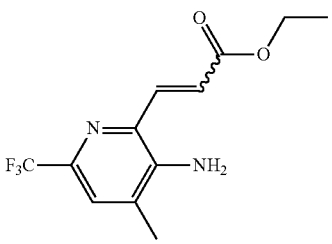 [SMILES: CCOC(=O)C=Cc1nc(C(F)(F)F)cc(C)c1N]

To a stirred mixture of 2-bromo-4-methyl-6-(trifluoromethyl)pyridin-3-amine (36 g, 141.16 mmol, 1 equiv) and ethyl prop-2-enoate (28.3 g, 282.67 mmol, 2.00 equiv) in DMF (720 mL) were added P(o-tol)₃ (8.6 g, 28.23 mmol, 0.2 equiv), Et₃N (42.9 g, 423.47 mmol, 3 equiv) and Pd(OAc)₂ (3.2 g, 14.12 mmol, 0.1 equiv). The resulting mixture was stirred overnight at 100° C. under nitrogen atmosphere. The reaction was quenched with water at room temperature. The resulting mixture was extracted with EtOAc and the combined organic layers were washed with NaCl (aq.). The resulting organic layer was concentrated under reduced pressure and the residue was purified by silica gel column chromatography, eluted with PE/EtOAc (20/1) to afford (23.9 g, 61.74%) of the title compound as a yellow solid. LC-MS: (ES, m/z): [M+H]⁺ 275.

Step 5: Synthesis of 8-methyl-6-(trifluoromethyl)-1,5-naphthyridin-2 (1H)-one

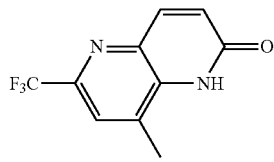

Into a 500 mL 3-necked round-bottom flask, was placed ethyl 3-(3-amino-4-methyl-6-(trifluoromethyl)pyridin-2-yl)acrylate (23.9 g, 87.23 mmol, 1 equiv), 1,4-dioxane (120 mL), and HCl (6M) (120 mL). The resulting solution was stirred overnight at 100° C. The resulting mixture was diluted with water and the solids were collected by filtration to give (18.8 g, 94.52%) of the title compound as a grey solid. LC-MS: (ES, m/z): [M+H]⁺ 229.

Step 6: Synthesis of 6-chloro-4-methyl-2-(trifluoromethyl)-1,5-naphthyridine

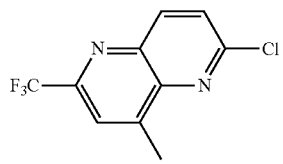 [SMILES: Cc1cc(C(F)(F)F)nc2ccc(Cl)nc12]

Into a 250-mL 3-necked round-bottom flask, was placed 8-methyl-6-(trifluoromethyl)-1,5-naphthyridin-2 (1H)-one (18.75 g, 82.24 mmol, 1 equiv), benzene phosphorus oxydichloride (95 mL). The resulting solution was heated to reflux for 3 h and then diluted with water. The solids were collected by filtration to give (15.7123 g, 77.67%) of the title compound as a grey solid. LC-MS: (ES, m/z): [M+H]⁺ 247.

Step 7. Synthesis of 4-(2-(benzyloxy)ethoxy)-N-(4-bromo-2,5-dimethylphenyl)-1-methyl-1H-pyrazole-5-carboxamide

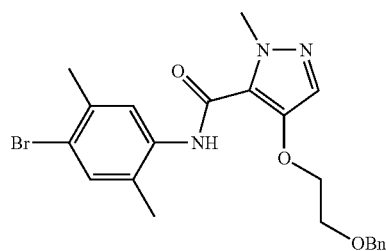 [SMILES: Cc1cc(NC(=O)c2c(OCCOCc3ccccc3)cnn2C)c(C)cc1Br]

Into a 100-mL 3-necked round-bottom flask under N₂ atmosphere, was placed 4-bromo-2,5-dimethylaniline (2.5 g, 12.72 mmol, 1.5 equiv), Et₃N (1.3 g, 12.72 mmol, 1.5 equiv), DCM (25 mL). 4-(2-(Benzyloxy)ethoxy)-1-methyl-1H-pyrazole-5-carbonyl chloride (2.5 g, 8.48 mmol, 1 equiv), prepared as described in Example 1, in 25 mL of DCM was added dropwise at 0° C. The resulting solution was stirred for 2 h at 0° C. The resulting mixture was concentrated under vacuum and the crude product was purified by re-crystallization from MeOH to give (3.78 g, 97.23%) of the title compound as a yellow solid. LC-MS: (ES, m/z): [M+H]⁺ 458.

Step 8: Synthesis of N-(4-bromo-2,5-dimethylphenyl)-4-(2-hydroxyethoxy)-1-methyl-1H-pyrazole-5-carboxamide

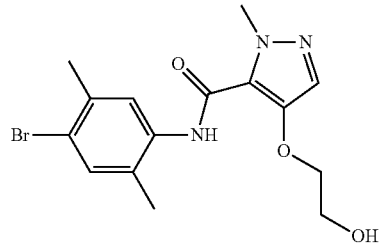 [SMILES: Cc1cc(NC(=O)c2c(OCCO)cnn2C)c(C)cc1Br]

Into a 100-mL 3-necked round-bottom flask under N₂ atmosphere, was placed 4-(2-(benzyloxy)-ethoxy)-N-(4-bromo-2,5-dimethylphenyl)-1-methyl-1H-pyrazole-5-carboxamide (3.78 g, 8.25 mmol, 1 equiv), DCM (40 mL), and BCl₃ (1.4 g, 12.07 mmol, 1.46 equiv) was added at 0° C. The resulting solution was stirred for 30 min at 0° C. and then quenched with 50 mL of NaHCO₃(aq.). The resulting solution was extracted with dichloromethane. The combined organic layer was dried over anhydrous sodium sulfate and concentrated under vacuum to give (3 g, 98.79%) of the title compound as a yellow solid. (ES, m/z): [M+H]⁺ 368

Step 9: Synthesis of 2-((5-((4-bromo-2,5-dimethylphenyl)carbamoyl)-1-methyl-1H-pyrazol-4-yl)oxy) ethyl methanesulfonate

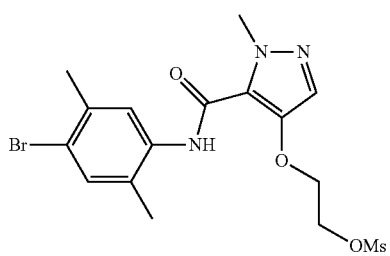 [SMILES: Cc1cc(NC(=O)c2c(OCCOS(C)(=O)=O)cnn2C)c(C)cc1Br]

Into a 100-mL 3-necked round-bottom flask under N₂ atmosphere, was placed N-(4-bromo-2,5-dimethylphenyl)-4-(2-hydroxyethoxy)-1-methyl-1H-pyrazole-5-carboxamide (3 g, 8.15 mmol, 1 equiv), Et₃N (1.2 g, 12.22 mmol, 1.5 equiv), DCM (30 mL), and MsCl (1.4 g, 12.22 mmol, 1.5 equiv) was added dropwise at 0° C. The resulting solution was stirred for 1 h at 0° C. The reaction was then quenched with water and the resulting solution was extracted with dichloromethane. The combined organic layer was dried over anhydrous sodium sulfate and concentrated to give (3.5 g, 96.25%) of the title compound as a yellow solid. LC-MS: (ES, m/z): [M+H]⁺ 446.

Step 10: Synthesis of 7-(4-bromo-2,5-dimethylphenyl)-1-methyl-6,7-dihydro-1H-pyrazolo[3,4-f][1,4]oxazepin-8 (5H)-one

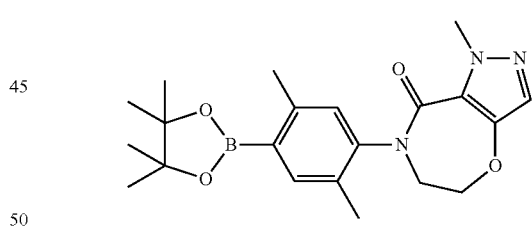

Into a 100-mL 3-necked round-bottom flask under N₂ atmosphere, was placed 2-((5-((4-bromo-2,5-dimethylphenyl)carbamoyl)-1-methyl-1H-pyrazol-4-yl)oxy)ethyl methanesulfonate (3.7 g, 8.29 mmol, 1 equiv), DMF (40 mL), and NaH (0.3 g, 12.50 mmol, 1.51 equiv) was added at 0° C. The resulting solution was stirred for 1 h at 0° C. and then quenched with NH₄Cl (aq.). The resulting solution was extracted with ethyl acetate. The combined organic layer was concentrated under reduced pressure. The residue was applied onto a silica gel column and eluted with ethyl acetate/petroleum ether (1:20) to give (2 g, 68.89%) of the title compound as a yellow solid. LC-MS: (ES, m/z): [M+H]⁺ 350.

Step 11: Synthesis of 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one Into a 50-mL 3-necked round-bottom flask under N₂ atmosphere, was placed 7-(4-bromo-2,5-dimethylphenyl)-1-methyl-6,7-dihydro-1H-pyrazolo[3,4-f][1,4]-oxazepin-8 (5H)-one (2 g, 5.71 mmol, 1 equiv), B₂Pin₂ (2.18 g, 8.60 mmol, 1.5 equiv), KOAc (1.7 g, 17.13 mmol, 3 equiv), dioxane (20 mL), and Pd(dppf)Cl₂ (0.6 g, 0.86 mmol, 0.15 equiv). The resulting solution was stirred for 12 h at 80° C. The resulting mixture was concentrated under vacuum. The residue was applied onto a silica gel column and eluted with ethyl acetate/petroleum ether (1:20) to give (2.2 g, 96.97%) of the title compound as a white solid. LC-MS: (ES, m/z): [M+H]⁺ 398.

Step 12: Synthesis of 7-(2,5-dimethyl-4-(8-methyl-6-(trifluoromethyl)-1,5-naphthyridin-2-yl)phenyl)-1-methyl-6,7-dihydro-1H-pyrazolo[3,4-f][1,4]oxazepin-8 (5H)-one

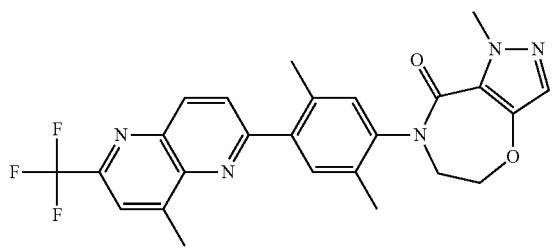 [SMILES: Cc1cc(N2CCOc3cnn(C)c3C2=O)c(C)cc1-c1ccc2nc(C(F)(F)F)cc(C)c2n1]

Into a 50-mL 3-necked round-bottom flask under N₂ atmosphere, was placed 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one (800 mg, 2.01 mmol, 1 equiv), 6-chloro-4-methyl-2-(trifluoromethyl)-1,5-naphthyridine (595.9 mg, 2.42 mmol, 1.2 equiv), Na₂CO₃ (640.3 mg, 6.04 mmol, 3 equiv), DME (14 mL), H₂O (3.5 mL), and Pd(PPh₃)₄ (349.0 mg, 0.30 mmol, 0.15 equiv). The resulting solution was stirred for 12 h at 80° C. The reaction was then quenched with water. The resulting solution was extracted with ethyl acetate and the combined organic layer was concentrated under reduced pressure. The residue was applied onto a silica gel column and eluted with dichloromethane/methanol (50:1) to give (529.9 mg, 54.65%) of the title compound as a yellow solid. LC-MS: (ES, m/z): [M+H]⁺ 482. ¹H-NMR: (300 MHz, DMSO-d₆, ppm): δ 8.65 (d, 1H), 8.17 (s, 1H), 8.16 (d, 1H), 7.58 (s, 1H), 7.37 (s, 1H), 7.29 (s, 1H), 4.46-4.58 (m, 2H), 3.98-4.02 (m, 5H), 2.89 (s, 3H), 2.51 (s, 3H), 2.25 (s, 3H).

Example 6

Synthesis of 3-methyl-5-(2-methyl-4-(6-(trifluoromethyl)-1,5-naphthyridin-2-yl)phenyl)-6,7-dihydropyrazolo[1,5-a]pyrazin-4 (5H)-one

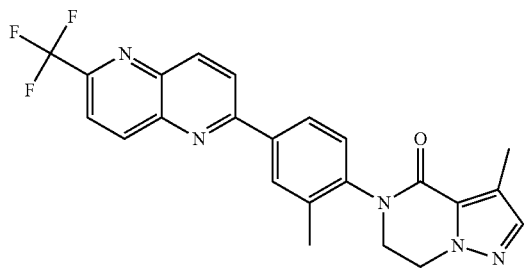

Step 1: Synthesis of 2-bromo-6-(trifluoromethyl)pyridin-3-amine

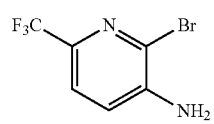

To a stirred solution of 6-(trifluoromethyl)pyridin-3-amine (5 g, 30.84 mmol, 1 equiv) in acetonitrile (200 mL) were added NBS (5.49 g, 30.84 mmol, 1 equiv) in portions at 0° C. under nitrogen atmosphere. The resulting mixture was stirred at 0° C. for 30 mins and then quenched with water. The resulting mixture was extracted with EtOAc. The combined organic layers were concentrated under reduced pressure. The residue was purified by silica gel column chromatography, eluted with EtOAc/PE (1/10) to afford (3.14 g, 42.24%) of the title compound as a yellow solid. LC-MS: (ES, m/z): [M+H]⁺ 241.

Step 2: Synthesis of ethyl 3-(3-amino-6-(trifluoromethyl)pyridin-2-yl)acrylate

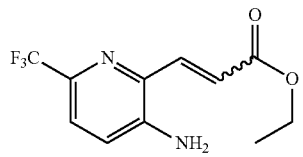

To a stirred solution of 2-bromo-6-(trifluoromethyl)pyridin-3-amine (3.14 g, 13.03 mmol, 1 equiv) and ethyl prop-2-enoate (2.61 g, 26.06 mmol, 2 equiv) in DMF (60 mL) were added Et₃N (3.95 g, 39.09 mmol, 3 equiv), P(o-tol)₃ (0.40 g, 1.30 mmol, 0.1 equiv) and Pd(OAc)₂ (0.15 g, 0.65 mmol, 0.05 equiv). The resulting mixture was stirred under nitrogen at 120° C. overnight. The reaction mixture was quenched with water and extracted with EtOAc. The combined organic layers were concentrated under reduced pressure. The residue was purified by silica gel column chromatography and eluted with EtOAc/PE (1/5) to afford (3.3 g, 97.34%) of the title compound as a yellow solid. LC-MS: (ES, m/z): [M+H]⁺ 261.

Step 3: Synthesis of 6-(trifluoromethyl)-1,5-naphthyridin-2 (1H)-one

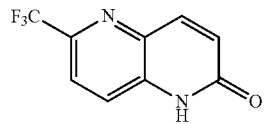 [SMILES: O=c1ccc2nc(C(F)(F)F)ccc2[nH]1]

To a stirred solution of ethyl 3-(3-amino-6-(trifluoromethyl)pyridin-2-yl)acrylate (1.5 g, 5.76 mmol, 1 equiv) in 1,4-dioxane (15 mL) was added HCl (30 mL). The resulting mixture was stirred at 100° C. overnight. The reaction mixture was basified to pH 8 with saturated NaHCO₃ and extracted with EtOAc. The combined organic layers were concentrated under reduced pressure to give the title compound (1.1 g, 89.11%) as a yellow solid. LC-MS: (ES, m/z): [M+H]⁺ 215.

Step 4: Synthesis of
2-chloro-6-(trifluoromethyl)-1,5-naphthyridine

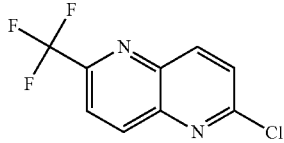 [SMILES: FC(F)(F)c1ccc2nc(Cl)ccc2n1]

A solution of 6-(trifluoromethyl)-1,5-naphthyridin-2 (1H)-one (1.18 g, 5.51 mmol, 1 equiv) in POCl₃ (12 mL, 128.74 mmol, 23.364 equiv) was stirred at 120° C. for 30 min. The reaction mixture was quenched with water/ice and then basified to pH 8 with saturated NaHCO₃. The resulting mixture was extracted with EtOAc. The combined organic layers were concentrated under reduced pressure to give (900 mg, 70.22%) of the title compound as a grey solid.

Step 5: Synthesis of 3-methyl-5-(2-methyl-4-(6-(trifluoromethyl)-1,5-naphthyridin-2-yl)phenyl)-6,7-dihydropyrazolo[1,5-a]pyrazin-4 (5H)-one

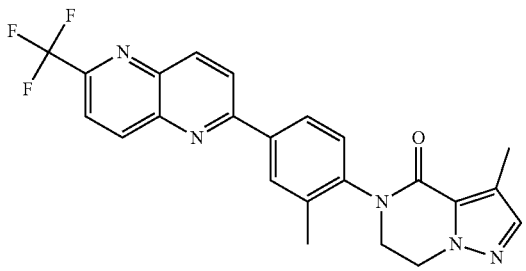 [SMILES: Cc1cc(-c2ccc3nc(C(F)(F)F)ccc3n2)ccc1N1CCn2ncc(C)c2C1=O]

Into a 25-mL 3-necked round-bottom flask under N₂ atmosphere, was placed 2-chloro-6-(trifluoromethyl)-1,5-naphthyridine (500 mg, 2.15 mmol, 1 equiv), 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one (789.5 mg, 2.15 mmol, 1.00 equiv), prepared as described in Example 2 above, Na₂CO₃ (683.5 mg, 6.45 mmol, 3 equiv), DME (10 mL, 103.32 mmol, 48.06 equiv), H₂O (2.5 mL, 138.77 mmol, 64.55 equiv), and Pd(PPh₃)₄ (372.6 mg, 0.32 mmol, 0.15 equiv). The resulting solution was stirred for 12 h at 80° C. The reaction was then quenched with water and the resulting solution was extracted with ethyl acetate. After concentration of the organic layer, the residue was applied onto a silica gel column and eluted with dichloromethane/methanol (20/1) to give (601.5 mg, 63.97%) of the title compound as a yellow solid. LC-MS: (ES, m/z): [M+H]⁺ 438; ¹H-NMR: (300 MHz, DMSO, ppm): δ 2.27 (s, 3H), 2.35 (s, 3H), 3.90-3.94 (m, 1H), 4.26-4.35 (m, 1H), 4.51-4.55 (t, 2H), 7.48 (s, 1H), 7.56 (d, 1H), 8.25 (dd, 2H), 8.33 (s, 1H), 8.61 (d, 1H), 8.69 (d, 1H), 8.79 (d, 1H).

Example 7

Synthesis of 5-(2-fluoro-5-methyl-4-(6-(trifluoromethyl)-1,5-naphthyridin-2-yl)phenyl)-3-methyl-6,7-dihydropyrazolo[1,5-a]pyrazin-4 (5H)-one

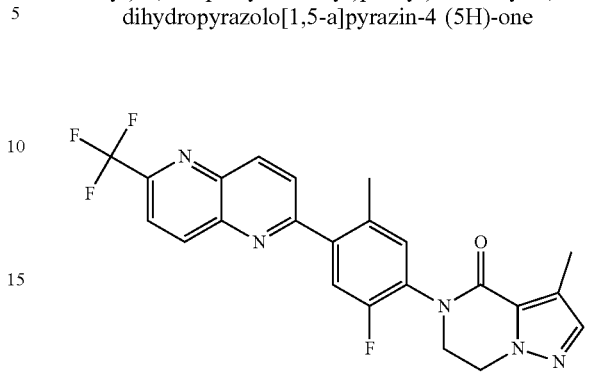

Step 1: Synthesis of ethyl 1-(2-(benzyloxy)ethyl)-4-methyl-1H-pyrazole-5-carboxylate

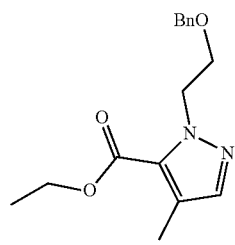 [SMILES: CCOC(=O)c1c(C)cnn1CCOCc1ccccc1]

To a stirred solution of ethyl 4-methyl-1H-pyrazole-5-carboxylate (50 g, 324.32 mmol, 1 equiv), DIAD (137.7 g, 681.07 mmol, 2.1 equiv) and 2-(benzyloxy)ethan-1-ol (49.4 g, 324.59 mmol, 1 equiv) in THF (500 mL) was added PPh₃ (221.2 g, 843.23 mmol, 2.6 equiv) in portions at 0° C. under nitrogen atmosphere. The resulting mixture was stirred overnight at room temperature. The residue was purified by silica gel column chromatography with PE/EtOAc (50/1) as eluent to afford the title compound (73 g, 78.06%) as a yellow oil. LC-MS: (ES, m/z): [M+H]⁺ 289. Ethyl 1-(2-(benzyloxy)ethyl)-4-methyl-1H-pyrazole-5-carboxylate was converted to 1-(2-(benzyloxy)ethyl)-4-methyl-1H-pyrazole-5-carboxylic acid as described in Example 2, Step 5 above.

Step 2: Synthesis of 1-(2-(benzyloxy)ethyl)-4-methyl-1H-pyrazole-5-carbonyl chloride

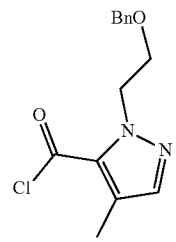 [SMILES: Cc1cnn(CCOCc2ccccc2)c1C(=O)Cl]

To a stirred solution of 1-(2-(benzyloxy)ethyl)-4-methyl-1H-pyrazole-5-carboxylic acid (15 g, 57.63 mmol, 1 equiv) and DMF (0.4 g, 5.76 mmol, 0.1 equiv) in DCM (300 mL) was added (COCl)$_2$ (11.0 g, 86.44 mmol, 1.5 equiv) dropwise at 0° C. The resulting mixture was stirred for 3 h at room temperature and then. concentrated under reduced pressure to give the title compound (17 g, crude) as a white solid.

Step 3: Synthesis of 1-(2-(benzyloxy)ethyl)-N-(4-bromo-2-fluoro-5-methylphenyl)-4-methyl-1H-pyrazole-5-carboxamide

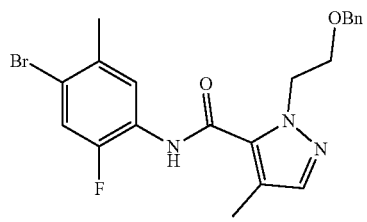 [SMILES: Cc1cc(NC(=O)c2c(C)cnn2CCOCc2ccccc2)c(F)cc1Br]

To a stirred solution of 4-bromo-2-fluoro-5-methylaniline (18.4 g, 90.41 mmol, 1.2 equiv) and Et$_3$N (15.2 g, 150.68 mmol, 2 equiv) in DCM (200 mL) was added 1-(2-(benzyloxy)ethyl)-4-methyl-1H-pyrazole-5-carbonyl chloride (21 g, 75.34 mmol, 1 equiv) dropwise at 0° C. under nitrogen atmosphere. The resulting mixture was stirred for 1 h at RT under nitrogen atmosphere and then diluted with water. The aqueous layer was extracted with CH$_2$Cl$_2$ and the organics were concentrated under reduced pressure. The crude product was re-crystallized from MeOH to afford (26 g, 77.32%) of the title compound as a white solid. LC-MS: (ES, m/z): [M+H]$^+$ 446.

Step 4: Synthesis of N-(4-bromo-2-fluoro-5-methylphenyl)-1-(2-hydroxyethyl)-4-methyl-1H-pyrazole-5-carboxamide

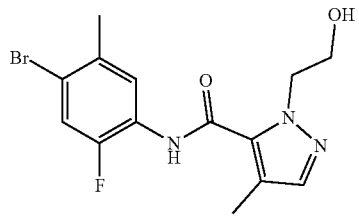 [SMILES: Cc1cc(NC(=O)c2c(C)cnn2CCO)c(F)cc1Br]

By proceeding analogously as described in Example 3, Step 3 above, but substituting 1-(2-(benzyloxy)ethyl)-N-(4-bromo-2-fluoro-5-methylphenyl)-4-methyl-1H-pyrazole-5-carboxamide (26 g, 58.25 mmol, 1 equiv) for 1-(2-(benzyloxy)ethyl)-N-(4-bromo-2,5-dimethylphenyl)-4-methyl-1H-pyrazole-5-carboxamide, (19.1 g, 95.82%) of the title compound was obtained as a white solid. LC-MS: (ES, m/z): [M+H]$^+$ 356.

Step 5: Synthesis of 2-(5-((4-bromo-2-fluoro-5-methylphenyl)carbamoyl)-4-methyl-1H-pyrazol-1-yl)ethyl methanesulfonate

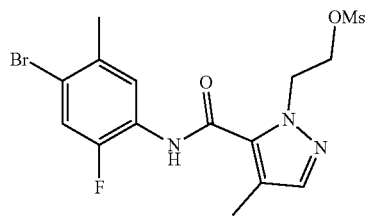 [SMILES: Cc1cc(NC(=O)c2c(C)cnn2CCOS(C)(=O)=O)c(F)cc1Br]

To a stirred solution of N-(4-bromo-2-fluoro-5-methylphenyl)-1-(2-hydroxyethyl)-4-methyl-1H-pyrazole-5-carboxamide (19.1 g, 53.62 mmol, 1 equiv) and Et$_3$N (10.9 g, 107.24 mmol, 2 equiv) in DCM (190 mL) was added MsCl (9.2 g, 80.43 mmol, 1.5 equiv) dropwise at 0° C. The resulting mixture was stirred for 30 min at room temperature and then diluted with water. The resulting mixture was extracted with CH$_2$Cl$_2$ and the combined organic layers were dried over anhydrous Na$_2$SO$_4$. After filtration, the filtrate was concentrated under reduced pressure. The crude product was re-crystallized from EA to afford (20.5 g, 88.03%) of the title compound as a white solid. LC-MS: (ES, m/z): [M+H]$^+$ 434.

Step 6: Synthesis of 5-(4-bromo-2-fluoro-5-methylphenyl)-3-methyl-6,7-dihydropyrazolo[1,5-a]pyrazin-4(5H)-one

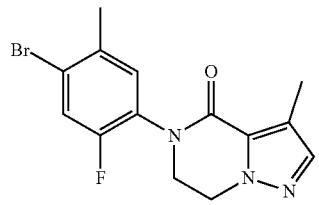 [SMILES: Cc1cc(N2CCn3ncc(C)c3C2=O)c(F)cc1Br]

To a stirred solution of 2-(5-((4-bromo-2-fluoro-5-methylphenyl)carbamoyl)-4-methyl-1H-pyrazol-1-yl)ethyl methanesulfonate (20.9 g, 48.13 mmol, 1 equiv) in DMF (209 mL) was added NaH (60%)(2.9 g, 72.19 mmol, 1.5 equiv) at 0° C. under nitrogen atmosphere. The resulting mixture was stirred for 0.5 h at 0° C. under nitrogen atmosphere. The reaction mixture was quenched by the addition of sat.NH$_4$Cl (aq.) (200 mL) at room temperature. The resulting mixture was extracted with EtOAc. The combined organic layers were dried over anhydrous Na$_2$SO$_4$. After filtration, the filtrate was concentrated under reduced pressure to give the title compound (16.2 g, 99.54%) as a white solid. LC-MS: (ES, m/z): [M+H]$^+$ 338.

Step 7: Synthesis of 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one

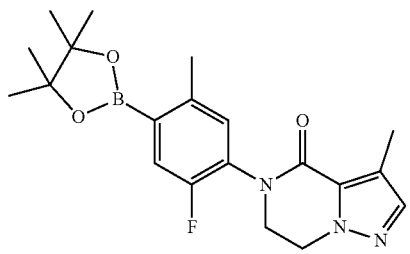 [SMILES: Cc1cc(N2CCn3ncc(C)c3C2=O)c(F)cc1B1OC(C)(C)C(C)(C)O1]

To a stirred solution of 5-(4-bromo-2-fluoro-5-methylphenyl)-3-methyl-6,7-dihydropyrazolo[1,5-a]pyrazin-4 (5H)-one (16.1 g, 47.61 mmol, 1 equiv) and $B_2Pin_2$ (18.1 g, 71.41 mmol, 1.5 equiv) in dioxane (161 mL) were added KOAc (9.3 g, 95.22 mmol, 2 equiv) and Pd(dppf)Cl$_2$ (3.5 g, 4.76 mmol, 0.1 equiv). The resulting mixture was stirred overnight at 80° C. under nitrogen atmosphere. The resulting mixture was concentrated under reduced pressure. The residue was purified by silica gel column chromatography with PE/EtOAc (5/1) as eluent to afford the title compound (15.8 g, 86.15%) as a white solid. LC-MS: (ES, m/z): [M+H]$^+$ 386.

Step 8: Synthesis of 5-(2-fluoro-5-methyl-4-(6-(trifluoromethyl)-1,5-naphthyridin-2-yl)phenyl)-3-methyl-6,7-dihydropyrazolo[1,5-a]pyrazin-4 (5H)-one

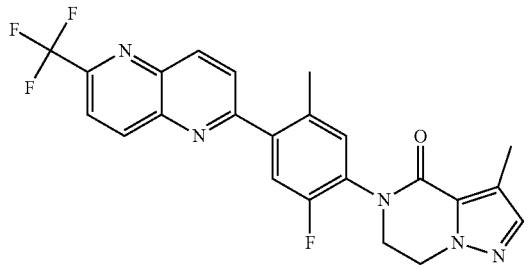

To a stirred solution of 2-chloro-6-(trifluoromethyl)-1,5-naphthyridine (500 mg, 2.15 mmol, 1 equiv) and 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one (828.2 mg, 2.15 mmol, 1 equiv) in DME (10 mL) and H$_2$O (2.5 mL) was added Na$_2$CO$_3$ (683.5 mg, 6.45 mmol, 3 equiv) and Pd(PPh$_3$)$_4$ (248.4 mg, 0.21 mmol, 0.1 equiv). The resulting mixture was stirred overnight at 80° C. under nitrogen atmosphere. The reaction mixture was diluted with water at room temperature and the resulting mixture was extracted with EtOAc. The combined organic layers were concentrated under reduced pressure and the residue was purified by silica gel column chromatography, eluted with PE/EtOAc (1/2) to afford the title compound (701.3 mg, 71.63%) as a grey solid. LC-MS: (ES, m/z): [M+H]$^+$ 456. $^1$H-NMR: (400 MHz, DMSO-d$_6$, ppm): (400 MHz, DMSO, ppm): δ 2.27 (s, 3H), 2.43 (s, 3H), 4.18 (t, 2H), 4.52 (t, 2H), 7.50 (s, 1H), 7.55 (d, 1H), 7.61 (d, 1H), 8.21 (d, 1H), 8.29 (d, 1H), 8.72 (d, 1H), 8.79 (d, 1H).

Example 8

Synthesis of 3-methyl-5-(2-methyl-4-(6-(trifluoromethyl)quinolin-2-yl)phenyl)-6,7-dihydropyrazolo-[1,5-a]pyrazin-4 (5H)-one

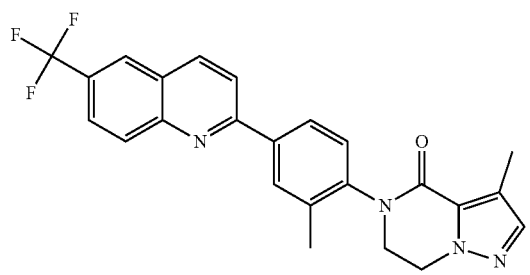 [SMILES: Cc1cc(-c2ccc3cc(C(F)(F)F)ccc3n2)ccc1N1CCn2ncc(C)c2C1=O]

Step 1: Synthesis of ethyl 3-(2-amino-5-(trifluoromethyl)phenyl)acrylate

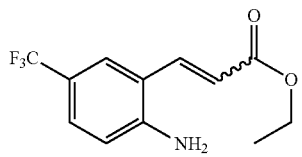 [SMILES: CCOC(=O)C=Cc1cc(C(F)(F)F)ccc1N]

Proceeding analogously as described in Example 6, Step 2 above but substituting 2-bromo-6-(trifluoromethyl)pyridin-3-amine with 2-bromo-4-trifluoromethylaniline provided (34 g, 92.27%) of the title compound as a yellow solid LC-MS: (ES, m/z): [M+H]$^+$ 260.

Step 2: Synthesis of 6-(trifluoromethyl)quinolin-2 (1H)-one

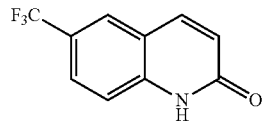 [SMILES: O=c1ccc2cc(C(F)(F)F)ccc2[nH]1]

Into a 2 L round-bottom flask, was placed ethyl 3-(2-amino-5-(trifluoromethyl)phenyl)-acrylate (34 g, 131.27 mmol, 1.00 equiv), dioxane (340 mL), and HCl (4M) (340 mL). The resulting solution was stirred for 12 h at 100° C. and then quenched with H$_2$O. The resulting solution was extracted with ethyl acetate. The combined organic layers were dried over anhydrous sodium sulfate and concentrated. The crude product was purified by re-crystallization from PE/EA (10/1) to give (27 g, 96.57%) of the title compound as a white solid. LC-MS: (ES, m/z): [M+H]$^+$ 214.

Step 3: Synthesis of 2-chloro-6-(trifluoromethyl)quinoline

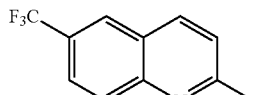

Into a 500-mL 3-necked round-bottom flask was placed 6-(trifluoromethyl)quinolin-2 (1H)-one (31 g, 145.54 mmol, 1.00 equiv), and POCl$_3$ (155 mL). The resulting solution was stirred for 3 h at 120° C. The resulting mixture was concentrated under vacuum. The residue was then quenched with water/ice and extracted with ethyl acetate. The mixture was dried over anhydrous sodium sulfate and concentrated to give (28 g, 83.28%) of the title compound as a tan solid. LC-MS: (ES, m/z): [M+H]$^+$ 232.

Step 4: Synthesis of 3-methyl-5-(2-methyl-4-(6-(trifluoromethyl)quinolin-2-yl)phenyl)-6,7-dihydropyrazolo[1,5-a]pyrazin-4 (5H)-one

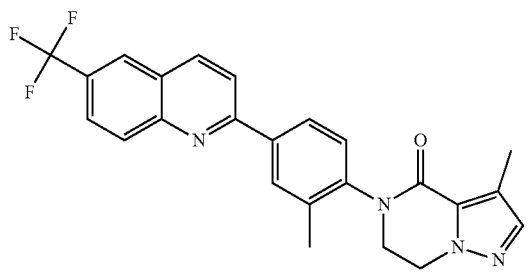

To a stirred mixture of 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one (1 g, 2.72 mmol, 1 equiv) and 2-chloro-6-(trifluoromethyl)quinoline (632 mg, 2.72 mmol, 1.00 equiv) in DME (12.64 mL) were added Na$_2$CO$_3$ (866.5 mg, 8.18 mmol, 3.00 equiv), Pd(PPh$_3$)$_4$ (314.4 mg, 0.27 mmol, 0.10 equiv) and H$_2$O (3.16 mL, 175.41 mmol, 64.42 equiv). The resulting solution was stirred for 3 h at 80° C. under nitrogen atmosphere. The reaction mixture was diluted with 50 mL of water and extracted with EtOAc. The combined organic layer was concentrated under reduced pressure. The residue was purified by silica gel column chromatography with PE/EtOAc (5/1) as eluent to afford the title compound (0.7792 g, 65.57%) as a white solid. LC-MS: (ES, m/z): [M+H]$^+$ 437. $^1$H-NMR: (400 MHz, DMSO-d$_6$, ppm): δ 2.26 (s, 3H), 2.35 (s, 3H), 3.90-3.94 (m, 1H), 4.26-4.33 (m, 1H), 4.51-4.54 (t, 2H), 7.48 (s, 1H), 7.54 (d, 1H), 8.02 (dd, 1H), 8.21 (dd, 1H), 8.27-8.29 (m, 2H), 8.35 (d, 1H), 8.54 (s, 1H), 8.69 (d, 1H).

Example 9

Synthesis of 3-methyl-5-(2-methyl-4-(8-methyl-6-(trifluoromethyl)quinazolin-2-yl)phenyl)-6,7-dihydropyrazolo[1,5-a]pyrazin-4 (5H)-one

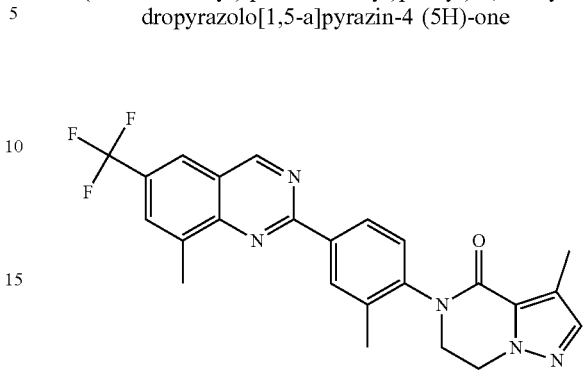

Step 1: Synthesis of 2-methyl-4-(trifluoromethyl)aniline

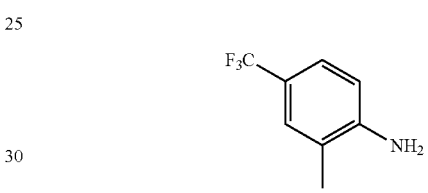

To a stirred mixture of 2-bromo-4-(trifluoromethyl)aniline (100 g, 416.63 mmol, 1 equiv) and trimethyl-1,3,5,2,4,6-trioxatriborinane (210.2 g, 1674.50 mmol, 4.02 equiv) in DMF were added Pd(PPh$_3$)$_4$ (24.2 g, 20.94 mmol, 0.05 equiv) and K$_2$CO$_3$ (144.4 g, 1044.82 mmol, 2.51 equiv). The resulting mixture was stirred overnight at 100° C. under nitrogen atmosphere. The reaction was diluted with water and extracted with EtOAc. The combined organic layer was concentrated under reduced pressure. The residue was purified by silica gel column chromatography with PE/EtOAc (10:1) as eluent to afford the title compound (60 g, 81.94%) as a white solid. LC-MS: (ES, m/z): [M+H]$^+$ 176.

Step 2: Synthesis of 2-bromo-6-methyl-4-(trifluoromethyl)aniline

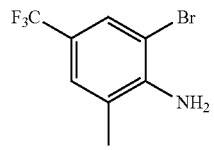

To a stirred solution of 2-methyl-4-(trifluoromethyl)aniline (60 g, 342.86 mol, 1 equiv) in DCM (1200 mL) was added NBS (60.7 g, 342.86 mmol, 1 equiv) in portions at 0° C. under nitrogen atmosphere. The resulting mixture was stirred for 2 h at 0° C. under nitrogen atmosphere. The reaction mixture was quenched with water at room temperature. The aqueous layer was extracted with DCM and the combined organic layers were concentrated under reduced pressure. The residue was purified by silica gel column chromatography with PE/EtOAc (30/1) as eluent to afford the title compound (49 g, 67.57%) as yellow oil. LC-MS: (ES, m/z): [M+H]+ 254.

Step 3: Synthesis of 2-amino-3-methyl-5-(trifluoromethyl)benzonitrile

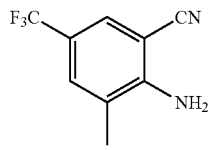

To a stirred solution of 2-bromo-6-methyl-4-(trifluoromethyl)aniline (49 g, 193.68 mol, 1 equiv) and Zn(CN)$_2$ (44.9 g, 141.34 mmol, 2.00 equiv) in DMF (1000 mL) was added Pd(PPh$_3$)$_4$ (11.2 g, 9.68 mmol, 0.05 equiv) at room temperature under nitrogen atmosphere. The resulting mixture was stirred overnight at 120° C. under nitrogen atmosphere. The reaction was quenched with water at room temperature and the aqueous layer was extracted with EtOAc. The combined organic layers were concentrated under reduced pressure. The residue was purified by silica gel column chromatography with PE/EtOAc (10/1) as eluent to afford the title compound (37.6 g, 97.16%) as a yellow solid. LC-MS: (ES, m/z): [M+H]+ 201.

Step 4: Synthesis of 8-methyl-6-(trifluoromethyl)quinazoline-2.4 (1H,3H)-dione

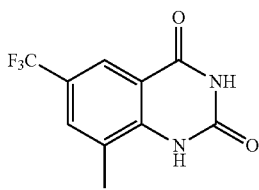 [SMILES: Cc1cc(C(F)(F)F)cc2c(=O)[nH]c(=O)[nH]c12]

To a stirred mixture of 2-amino-3-methyl-5-(trifluoromethyl)benzonitrile (37.6 g, 188.00 mmol, 1 equiv) in DMF (1200 mL) were added DBU (139.3 g, 564.00 mmol, 3.00 equiv). The resulting mixture was stirred overnight at 100° C. under CO$_2$ atmosphere. The reaction was quenched with water at room temperature. The mixture was acidified to pH5 with HCl (5M). The precipitated solids were collected by filtration and washed with water. The resulting solid was dried under infrared light to give the title compound (40 g, 87.20%) as a white solid. LC-MS: (ES, m/z): [M+H]+ 245.

Step 5: Synthesis of 2,4-dichloro-8-methyl-6-(trifluoromethyl)quinazoline

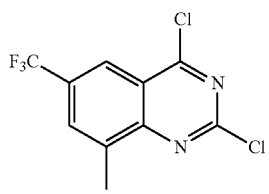 [SMILES: Cc1cc(C(F)(F)F)cc2c(Cl)nc(Cl)nc12]

To a stirred mixture of 8-methyl-6-(trifluoromethyl)quinazoline-2,4(1H,3H)-dione (29 g, 118.85 mmol, 1 equiv) in POCl$_3$ (150 mL) was added PCl$_5$ (123.6 g, 594.26 mmol, 5 equiv). The resulting mixture was stirred for 8 hours at 120° C. under nitrogen atmosphere. The resulting mixture was concentrated under vacuum and the residue was quenched with water/ice at room temperature. The aqueous layer was extracted with MTBE and the combined organic layers were washed with H$_2$O. The resulting organic phase was dried with anhydrous sodium sulfate and concentrated under reduced pressure. The residue was purified by silica gel column chromatography with PE/EtOAc (100/1) as eluent to afford the title compound (15.5 g, 46.57%) as a white solid. GC-MS: (ES, m/z): [M]+280.

Step 6: Synthesis of 2-chloro-8-methyl-6-(trifluoromethyl)quinazoline

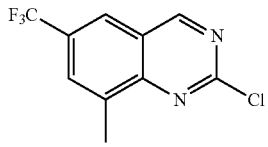 [SMILES: Cc1cc(C(F)(F)F)cc2cnc(Cl)nc12]

To a stirred mixture of 2,4-dichloro-8-methyl-6-(trifluoromethyl)quinazoline (34.8 g, 124.28 mmol, 1 equiv) in THF (350 mL) was added Bn$_3$SnH (39.9 g, 136.93 mmol, 1.10 equiv). Pd(PPh$_3$)$_4$ (14.4 g, 12.43 mmol, 0.10 equiv) was added at 0° C. under nitrogen atmosphere. The resulting mixture was stirred overnight at room temperature under nitrogen atmosphere. The reaction mixture was concentrated under reduced pressure and the residue was purified by silica gel column chromatography, eluted with PE/EtOAc (100/1) to afford the title compound (15.1308 g, 49.49%) as a light yellow solid. GC-MS: (ES, m/z): [M]+246.

Step 7: Synthesis of 3-methyl-5-(2-methyl-4-(8-methyl-6-(trifluoromethyl)quinazolin-2-yl)phenyl)-6,7-dihydropyrazolo[1,5-a]pyrazin-4 (5H)-one

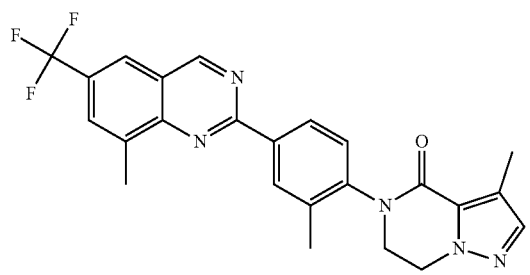 [SMILES: Cc1cc(-c2ncc3cc(C(F)(F)F)cc(C)c3n2)ccc1N1CCn2ncc(C)c2C1=O]

To a stirred solution of 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one (1.2 g, 3.27 mmol, 1 equiv) and 2-chloro-8-methyl-6-(trifluoromethyl)quinazoline (0.8 g, 3.27 mol, 1.00 equiv) in toluene (24 mL) was added EtOH (12 mL), K$_2$CO$_3$ (1.4 g, 9.80 mmol, 3 equiv) and Pd(PPh$_3$)$_4$ (0.4 g, 0.33 mmol, 0.1 equiv). The resulting mixture was stirred overnight at 80° C. under nitrogen atmosphere. The resulting mixture was diluted with and extracted with EtOAc. The combined organic layer was concentrated under reduced pressure. The residue was purified by silica gel column chromatography with PE/EtOAc (1/1) as eluent to the title compound (661 mg, 44.81%) as a white solid. LC-MS: (ES, m/z): [M+H]$^+$ 452. $^1$H-NMR: (300 MHz, DMSO-d$_6$, ppm): δ 2.21 (s, 3H), 2.36 (s, 3H), 2.88 (s, 3H), 3.90-3.93 (m, 1H), 4.27-4.33 (m, 1H), 4.53 (t, 2H), 7.48 (s, 1H), 7.56 (d, 1H), 8.17 (s, 1H), 8.50-8.60 (m, 3H), 9.86 (s, 1H).

Example 10

Synthesis of 6-(2,5-dimethyl-4-(6-(trifluoromethyl)-1,5-naphthyridin-2-yl)phenyl)-1-methyl-1,4,5,6-tetrahydro-7H-pyrazolo[3,4-c]pyridin-7-one

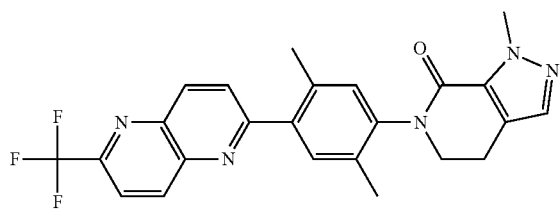

Step 1: Synthesis of methyl 4-allyl-1-methyl-1H-pyrazole-5-carboxylate

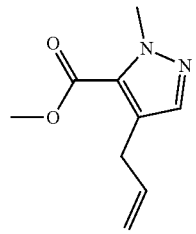

Into a 250-mL 3-necked round-bottom flask under N$_2$ atmosphere, was placed methyl 4-bromo-1-methyl-1H-pyrazole-5-carboxylate (5 g, 22.83 mmol, 1 equiv), tributyl(prop-2-en-1-yl)stannane (8.3 g, 25.07 mmol, 1.10 equiv), DMF (50 mL), Pd(PPh$_3$)$_4$ (2.6 g, 2.25 mmol, 0.10 equiv). The resulting solution was stirred overnight at 100° C. The reaction mixture was then quenched with water and extracted with ethyl acetate and the organic layers combined. The resulting mixture was concentrated and the residue was applied onto a silica gel column and eluted with ethyl acetate/petroleum ether (1:50) to give (3.2 g, 77.79%) of the title compound as yellow oil. LC-MS: (ES, m/z): [M+H]$^+$ 181.

Step 2: Synthesis of 4-allyl-1-methyl-1H-pyrazole-5-carboxylic acid

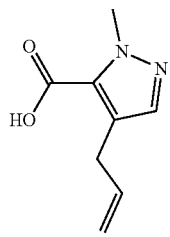

Into a 50-mL 3-necked round-bottom flask, was placed methyl 4-allyl-1-methyl-1H-pyrazole-5-carboxylate (3.2 g, 17.76 mmol, 1 equiv), THF (15 mL, 185.14 mmol, 10.43 equiv), and LiOH (0.9 g, 37.58 mmol, 2.12 equiv) in H$_2$O (7 mL). The resulting solution was stirred overnight at room temperature and then diluted with H$_2$O. The resulting mixture was concentrated and the resulting solution was extracted with ethyl acetate. The pH value of the aqueous layer was adjusted to 4 with HCl (1 mol/L) and the organics were extracted with ethyl acetate. The combined organic layer was dried over anhydrous sodium sulfate and concentrated under reduced pressure to give (2.1 g, 71.16%) of the title compound as a white solid. GC-MS: (ES, m/z): [M]$^+$ 166.

Step 3: Synthesis of 4-allyl-N-(4-bromo-2,5-dimethylphenyl)-1-methyl-1H-pyrazole-5-carboxamide

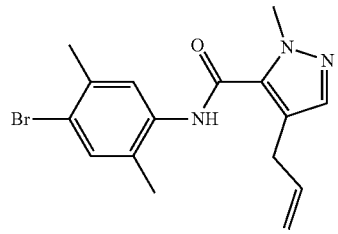 [SMILES: C=CCc1cnn(C)c1C(=O)Nc1cc(C)c(Br)cc1C]

Into a 25-mL 3-necked round-bottom flask under N$_2$ atmosphere, was placed 4-allyl-1-methyl-1H-pyrazole-5-carboxylic acid (0.843 g, 5.07 mmol, 1 equiv), 4-bromo-2,5-dimethylaniline (1.0 g, 5.00 mmol, 0.99 equiv), HATU (2.9 g, 7.63 mmol, 1.50 equiv), DIEA (1.3 g, 10.15 mmol, 2 equiv) and DMF (10 mL). The resulting solution was stirred overnight at room temperature. The reaction was then quenched with water and the resulting solution was extracted with ethyl acetate. The combined organic layer was concentrated under reduced pressure. The residue was applied onto a silica gel column and eluted with ethyl acetate/petroleum ether (1:10) to give 1.2 g (67.93%) of title compound as a white solid. LC-MS: (ES, m/z): [M+H]$^+$ 348.

Step 4: Synthesis of N-(4-bromo-2,5-dimethylphenyl)-4-(2,3-dihydroxypropyl)-1-methyl-1H-pyrazole-5-carboxamide

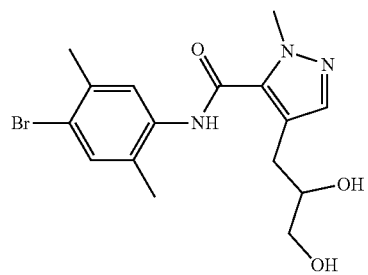 [SMILES: Cc1cc(NC(=O)c2c(CC(O)CO)cnn2C)c(C)cc1Br]

Into a 50-mL 3-necked round-bottom flask under N$_2$ atmosphere, was placed 4-allyl-N-(4-bromo-2,5-dimethylphenyl)-1-methyl-1H-pyrazole-5-carboxamide (1.2 g, 3.45 mmol, 1 equiv), THF (12 mL, 148.12 mmol, 42.98 equiv), NMO (1.2 g, 10.24 mmol, 2.97 equiv), H$_2$O (6 mL), and OsO₄ (43.8 mg, 0.17 mmol, 0.05 equiv). The resulting solution was stirred for 4 at room temperature and then quenched with 50 mL NaS₂O₈(aq.). The resulting solution was extracted with ethyl acetate. The combined organic layer was washed with H₂O, dried over anhydrous sodium sulfate and concentrated under vacuum to give 1.41 g of the title compound as a crude product. LC-MS: (ES, m/z): [M+H]⁺ 382.

Step 5: Synthesis of N-(4-bromo-2,5-dimethylphenyl)-1-methyl-4-(2-oxoethyl)-1H-pyrazole-5-carboxamide

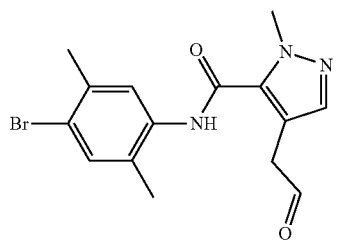 [SMILES: Cc1cc(NC(=O)c2c(CC=O)cnn2C)c(C)cc1Br]

Into a 50-mL 3-necked round-bottom flask purged was placed N-(4-bromo-2,5-dimethylphenyl)-4-(2,3-dihydroxypropyl)-1-methyl-1H-pyrazole-5-carboxamide (1.41 g, 3.69 mmol, 1 equiv), MeOH (15 mL), H₂O (1.5 mL), and NaIO₄ (1.6 g, 7.48 mmol, 2.03 equiv). The resulting solution was stirred for 2 h at room temperature and then quenched with H₂O. The resulting mixture was concentrated to remove MeOH and the resulting solution was extracted with ethyl acetate. The combined organic layer was washed with H₂O, dried over anhydrous sodium sulfate and concentrated under reduced pressure to give (1.2 g, 92.89%) the title compound as a solid. LC-MS: (ES, m/z): [M+H]⁺ 350.

Step 6: Synthesis of N-(4-bromo-2,5-dimethylphenyl)-4-(2-hydroxyethyl)-1-methyl-1H-pyrazole-5-carboxamide

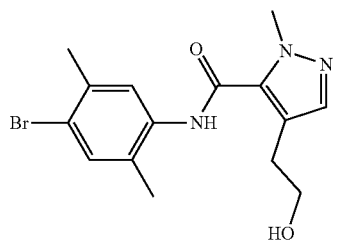 [SMILES: Cc1cc(NC(=O)c2c(CCO)cnn2C)c(C)cc1Br]

Into a 50-mL 3-necked round-bottom flask under N₂ atmosphere, was placed N-(4-bromo-2,5-dimethylphenyl)-1-methyl-4-(2-oxoethyl)-1H-pyrazole-5-carboxamide (1.2 g, 3.43 mmol, 1 equiv), MeOH (12 mL, 296.39 mmol, 86.50 equiv). NaBH₄ (0.2 g, 5.29 mmol, 1.54 equiv) was added at 0° C. The resulting solution was stirred for 2 h at RT and then quenched with NH₄Cl (aq.). The resulting solution was extracted with ethyl acetate. The combined organic layer was washed with H₂O, dried over anhydrous sodium sulfate and concentrated under reduced pressure to give (1.22 g) the title compound as crude product. LC-MS: (ES, m/z): [M+H]⁺ 352.

Step 7: Synthesis of 2-(5-((4-bromo-2,5-dimethylphenyl)carbamoyl)-1-methyl-1H-pyrazol-4-yl) ethyl methanesulfonate

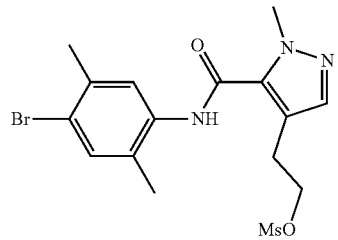 [SMILES: Cc1cc(NC(=O)c2c(CCOS(C)(=O)=O)cnn2C)c(C)cc1Br]

Into a 50-mL 3-necked round-bottom flask under N₂ atmosphere, was placed N-(4-bromo-2,5-dimethylphenyl)-4-(2-hydroxyethyl)-1-methyl-1H-pyrazole-5-carboxamide (1.3 g, 3.69 mmol, 1 equiv), DCM (15 mL), Et₃N (0.7 g, 6.92 mmol, 1.87 equiv). MsCl (0.6 g, 5.24 mmol, 1.42 equiv) was added dropwise at 0° C. The resulting solution was stirred for 2 h at room temperature. The reaction was then quenched with 50 mL of NaHCO₃(aqu.). The resulting solution was extracted with ethyl acetate and the organic layers combined. The resulting mixture was washed with H₂O, dried over anhydrous sodium sulfate and concentrated under vacuum to give 1.41 g of the title compound as a crude product. LC-MS: (ES, m/z): [M+H]⁺ 430.

Step 8: Synthesis of 6-(4-bromo-2,5-dimethylphenyl)-1-methyl-1,4,5,6-tetrahydro-7H-pyrazolo[3,4-c]pyridin-7-one

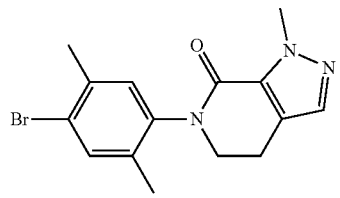 [SMILES: Cc1cc(N2CCc3cnn(C)c3C2=O)c(C)cc1Br]

Into a 50-mL 3-necked round-bottom flask under N₂ atmosphere, was placed 2-(5-((4-bromo-2,5-dimethylphenyl)carbamoyl)-1-methyl-1H-pyrazol-4-yl)ethyl methanesulfonate (1.41 g, 3.28 mmol, 1 equiv), DMF (15 mL). NaH (0.1 g, 4.17 mmol, 1.27 equiv) was added at 0° C. The resulting solution was stirred for 2 at room temperature. The reaction was then quenched by the addition of 50 mL of NH₄Cl (aq.). The resulting solution was extracted with ethyl acetate and the organic layers combined. The resulting mixture was washed with H₂O. The residue was applied onto a silica gel column and eluted with ethyl acetate/petroleum ether (1:5) to give (843 mg, 76.98%) of the title compound as a white solid. LC-MS (ES, m/z): [M+H]⁺ 334.

Step 9: Synthesis of 1-methyl-6-(2,5-dimethyl-4-(4,4,5,5-tetramethyl-1,3,2-dioxaborolan-2-yl)phenyl)-1,4,5,6-tetrahydro-7H-pyrazolo[3,4-c]pyridin-7-one

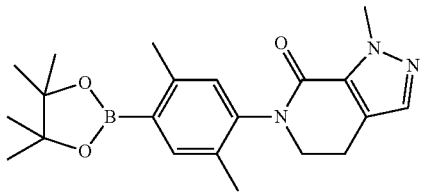 [SMILES: Cc1cc(N2CCc3cnn(C)c3C2=O)c(C)cc1B1OC(C)(C)C(C)(C)O1]

Into a 50-mL 3-necked round-bottom flask under N₂ atmosphere, was placed 6-(4-bromo-2,5-dimethylphenyl)-1-methyl-1,4,5,6-tetrahydro-7H-pyrazolo[3,4-c]pyridin-7-one (843 mg, 2.52 mmol, 1 equiv), dioxane (10 mL), KOAc (742.6 mg, 7.57 mmol, 3 equiv), and Pd(dppf)Cl₂ (553.7 mg, 0.76 mmol, 0.30 equiv). The resulting solution was stirred for overnight at 80° C. The resulting mixture was concentrated under vacuum. The residue was applied onto a silica gel column and eluted with ethyl acetate/petroleum ether (1:5) to give (520 mg, 54.07%) of the title compound as a white solid. LC-MS: (ES, m/z): [M+H]⁺ 382.

Step 10: Synthesis of 6-(2,5-dimethyl-4-(6-(trifluoromethyl)-1,5-naphthyridin-2-yl)phenyl)-1-methyl-1,4,5,6-tetrahydro-7H-pyrazolo[3,4-c]pyridin-7-one

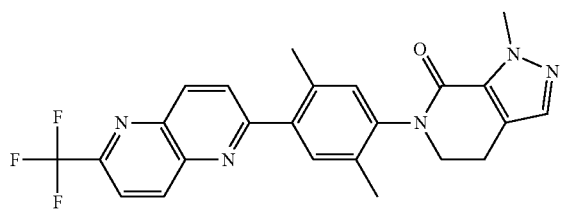 [SMILES: Cc1cc(N2CCc3cnn(C)c3C2=O)c(C)cc1-c1ccc2nc(C(F)(F)F)ccc2n1]

Proceeding analogously as described in Example 7, Step 8 above, but substituting 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4(5H)-one with 1-methyl-6-(2,5-dimethyl-4-(4,4,5,5-tetramethyl-1,3,2-dioxaborolan-2-yl)phenyl)-1,4,5,6-tetrahydro-7H-pyrazolo[3,4-c]pyridin-7-one gave (300 mg, 63.34%) of the title compound as a white solid. LC-MS: (ES, m/z): [M+H]⁺ 452; ¹H-NMR: (300 MHz, DMSO-d6, ppm): δ 8.77 (d, 1H), 8.69 (d, 1H), 8.27 (d, 1H), 8.17 (d, 1H), 7.55 (s, 1H), 7.48 (s, 1H), 7.34 (s, 1H), 4.01-4.09 (m, 4H), 3.71-3.79 (m, 1H), 2.90-3.04 (m, 2H), 2.40 (s, 3H), 2.25 (s, 3H).

Example 11

Synthesis of 6-(2-fluoro-5-methyl-4-(6-(trifluoromethyl)-1,5-naphthyridin-2-yl)phenyl)-1-methyl-1,4,5,6-tetrahydro-7H-pyrazolo[3,4-c]pyridin-7-one

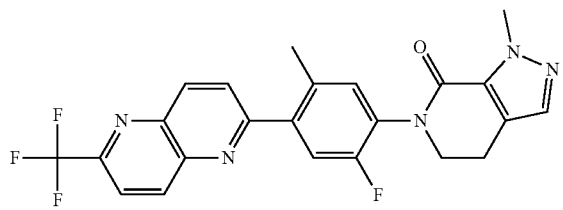

Step 1: Synthesis of 4-allyl-1-methyl-1H-pyrazole-5-carboxylic acid

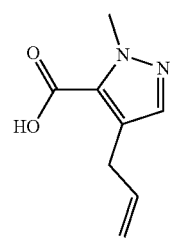

To a stirred solution of methyl 4-allyl-1-methyl-1H-pyrazole-5-carboxylate (5.5 g, 30.52 mmol, 1 equiv) in CH₃OH (55 mL) was added NaOH (2.45 g, 61.25 mmol, 2.01 equiv) at room temperature under nitrogen atmosphere. The resulting mixture was concentrated under reduced pressure. The residue was acidified to pH 6 with HCl (aq.). The resulting mixture was filtered and the filter cake was washed with water. The aqueous layer was extracted with EtOAc and the combined organic layers were dried over anhydrous Na₂SO₄. After filtration, the filtrate was concentrated under reduced pressure to give the title compound (4.5 g, 88.72%) as a white solid. LC-MS: (ES, m/z): [M+H]⁺ 167.

Methyl 4-allyl-1-methyl-1H-pyrazole-5-carboxylate was converted to 4-allyl-1-methyl-1H-pyrazole-5-carbonyl chloride as described in Example 4, Step 3 above.

Step 2: Synthesis of 4-allyl-N-(4-bromo-2-fluoro-5-methylphenyl)-1-methyl-1H-pyrazole-5-carboxamide

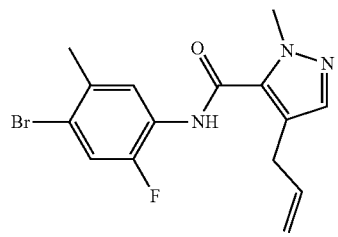 [SMILES: C=CCc1cnn(C)c1C(=O)Nc1cc(C)c(Br)cc1F]

Proceeding analogously as described in Example 4, Step 4, but substituting 4-bromo-2-methylaniline with 4-bromo-2-fluoro-5-methylaniline provided the title compound (68.49% yield) as a pink solid. LC-MS: (ES, m/z): [M+H]⁺ 352, 354.

Step 3: Synthesis of N-(4-bromo-2-fluoro-5-methylphenyl)-4-(2,3-dihydroxypropyl)-1-methyl-1H-pyrazole-5-carboxamide

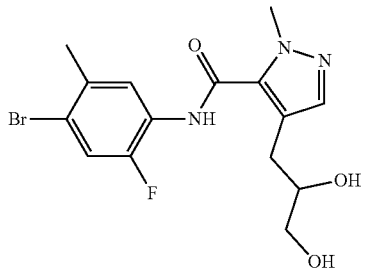 [SMILES: Cc1cc(NC(=O)c2c(CC(O)CO)cnn2C)c(F)cc1Br]

Into a 100 mL 3-necked round-bottom flask were added 4-allyl-N-(4-bromo-2-fluoro-5-methyl-phenyl)-1-methyl-1H-pyrazole-5-carboxamide (3.92 g, 11.13 mmol, 1 equiv), THF (39.2 mL), H₂O (3.92 mL), NMO (3.9 g, 33.39 mmol, 3.00 equiv) and OsO₄ (0.1 g, 0.39 mmol, 0.04 equiv). The resulting mixture was stirred for 4 h at room temperature and then quenched with Na₂S₂O₄ (aq.). The aqueous layer was extracted with EtOAc, and the resulting mixture was concentrated under reduced pressure to afford the title compound (4.5 g, 104.69%) as a white solid. The crude product was used in the next step directly without further purification. LC-MS: (ES, m/z): [M+H]⁺ 386, 388.

Step 4: Synthesis of N-(4-bromo-2-fluoro-5-methylphenyl)-4-(2-oxoethyl)-1-methyl-1H-pyrazole-5-carboxamide

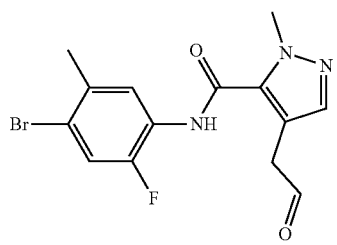

Into a 100 mL 3-necked round-bottom flask were added N-(4-bromo-2-fluoro-5-methylphenyl)-4-(2,3-dihydroxypropyl)-1-methyl-1H-pyrazole-5-carboxamide (4.5 g, 11.65 mmol, 1 equiv), MeOH (41 mL), H₂O (41 mL) and NaIO₄ (5.0 g, 23.38 mmol, 2.01 equiv). The resulting mixture was stirred for 3 h at room temperature and then diluted with water. The resulting mixture was concentrated under reduced pressure. The aqueous layer was extracted with EtOAc and the organic layer was concentrated to afford the title compound (2.83 g, 68.58%) as a yellow solid. The crude product was used in the next step directly without further purification. LC-MS: (ES, m/z): [M+H]⁺ 354, 356.

Step 5: Synthesis of N-(4-bromo-2-fluoro-5-methylphenyl)-4-(2-hydroxyethyl)-1-methyl-1H-pyrazole-5-carboxamide

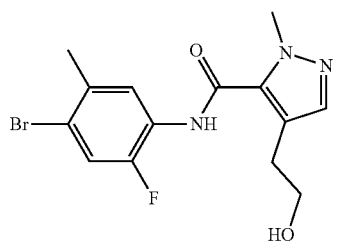 [SMILES: Cc1cc(NC(=O)c2c(CCO)cnn2C)c(F)cc1Br]

Into a 50 mL 3-necked round-bottom flask were added N-(4-bromo-2-fluoro-5-methylphenyl)-4-(2-oxoethyl)-1-methyl-1H-pyrazole-5-carboxamide (2.83 g, 7.99 mmol, 1 equiv), MeOH (28.3 mL) and NaBH₄ (0.4 g, 10.57 mmol, 1.32 equiv) was added at 0° C. The resulting mixture was stirred for 3 h at room temperature under nitrogen atmosphere. The reaction was quenched by the addition of sat. NH₄Cl (aq.) (40 mL) and the resulting mixture was concentrated under reduced pressure. The aqueous layer was extracted with EtOAc and the organic layer was concentrated under reduced pressure. The residue was purified by silica gel column chromatography with PE/EtOAc (1:1) as eluent to afford the title compound (1.3 g, 45.68%) as a yellow solid. LC-MS: (ES, m/z): [M+H]⁺ 356, 358.

Step 6. Synthesis of 2-(5-((4-bromo-2-fluoro-5-methylphenyl)carbamoyl)-1-methyl-1H-pyrazol-4-yl)ethyl methanesulfonate

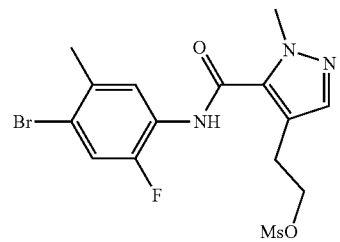 [SMILES: Cc1cc(NC(=O)c2c(CCOS(C)(=O)=O)cnn2C)c(F)cc1Br]

Into a 50 mL 3-necked round-bottom flask containing N-(4-bromo-2-fluoro-5-methylphenyl)-4-(2-hydroxyethyl)-1-methyl-1H-pyrazole-5-carboxamide (1.3 g, 3.65 mmol, 1 equiv), and DCM (26 mL), Et₃N (0.6 g, 5.47 mmol, 1.50 equiv) MsCl (0.6 g, 5.24 mmol, 1.44 equiv) was added at 0° C. The resulting mixture was stirred for 2 h at room temperature and then diluted with water. The aqueous layer was extracted with CH₂Cl₂ and the organic layer was concentrated under vacuum to afford the title compound (1.75 g, 110.41%) as a yellow solid. The crude product was used in the next step directly without further purification. LC-MS: (ES, m/z): [M+H]⁺ 434, 436.

Step 7: Synthesis of 6-(4-bromo-2-fluoro-5-methylphenyl)-1-methyl-1,4,5,6-tetrahydro-7H-pyrazolo[3,4-c]pyridin-7-one

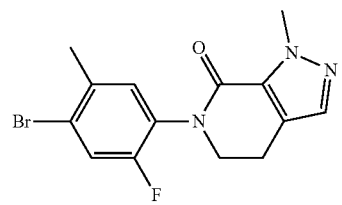 [SMILES: Cc1cc(N2CCc3cnn(C)c3C2=O)c(F)cc1Br]

Proceeding as described in Example 4, Step 9, but substituting 2-(5-((4-bromo-2-fluoro-5-methylphenyl)carbamoyl)-1-methyl-1H-pyrazol-4-yl)ethyl methanesulfonate for 2-(5-((4-bromo-2-methylphenyl)carbamoyl)-1-methyl-1H-pyrazol-4-yl)ethyl methanesulfonate the title compound was obtained (1.0 g, 73.38%) as a light yellow solid. LC-MS: (ES, m/z): [M+H]⁺ 338, 340.

Step 8: Synthesis of 6-(2-fluoro-5-methyl-4-(4,4,5,5-tetramethyl-1,3,2-dioxaborolan-2-yl)phenyl)-1-methyl-1,4,5,6-tetrahydro-7H-pyrazolo[3,4-c]pyridin-7-one

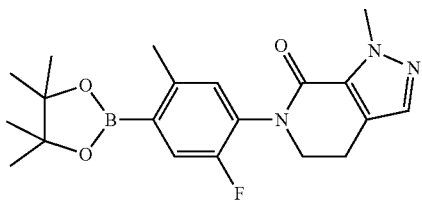 [SMILES: Cc1cc(N2CCc3cnn(C)c3C2=O)c(F)cc1B1OC(C)(C)C(C)(C)O1]

Proceeding as described in Example 4, Step 10 above, but substituting 6-(4-bromo-2-fluoro-5-methylphenyl)-1-methyl-1,4,5,6-tetrahydro-7H-pyrazolo[3,4-c]pyridin-7-one for 6-(4-bromo-2-methylphenyl)-1-methyl-1,4,5,6-tetrahydro-7H-pyrazolo[3,4-c]pyridin-7-one (1.01 g, 98.51%) of the title compound was obtained as a light yellow solid. LC-MS: (ES, m/z): [M+H]$^+$ 386.

Step 9: Synthesis of 6-(2-fluoro-5-methyl-4-(6-(trifluoromethyl)-1,5-naphthyridin-2-yl)phenyl)-1-methyl-1,4,5,6-tetrahydro-7H-pyrazolo[3,4-c]pyridin-7-one

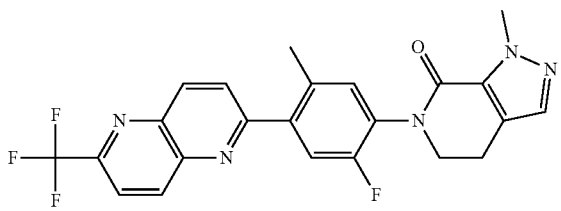

Into a 50 mL 3-necked round-bottom flask were added 6-(2-fluoro-5-methyl-4-(4,4,5,5-tetramethyl-1,3,2-dioxaborolan-2-yl)phenyl)-1-methyl-1,4,5,6-tetrahydro-7H-pyrazolo[3,4-c]pyridin-7-one (1 g, 2.60 mmol, 1 equiv), 2-chloro-6-(trifluoromethyl)-1,5-naphthyridine (0.6 g, 2.58 mmol, 0.99 equiv), Na$_2$CO$_3$ (0.8 g, 7.79 mmol, 3 equiv), DME (20 mL), H$_2$O (5 mL) and Pd(PPh$_3$)$_4$ (0.3 g, 0.26 mmol, 0.1 equiv). The resulting mixture was stirred for overnight at 80° C. under nitrogen atmosphere. The resulting mixture was concentrated under vacuum and the residue was purified by silica gel column chromatography, eluted with PE/EtOAc (1:1) to afford the title compound (596.1 mg, 50.43%) as a white solid. LC-MS: (ES, m/z): [M+H]$^+$ 456; $^1$H-NMR: (300 MHz, DMSO, ppm): δ 2.5 (s, 3H), 2.9 (t, 2H), 3.9 (t, 2H), 4.09 (s, 3H), 7.5 (m, 2H), 7.6 (m, 1H), 8.2 (d, 1H), 8.3 (d, 1H), 8.7 (d, 1H), 8.8 (d, 1H).

Example 12

Synthesis of 7-(2-fluoro-5-methyl-4-(6-(trifluoromethyl)-1,5-naphthyridin-2-yl)phenyl)-1-methyl-6,7-dihydro-1H-pyrazolo[3,4-f][1,4]oxazepin-8 (5H)-one

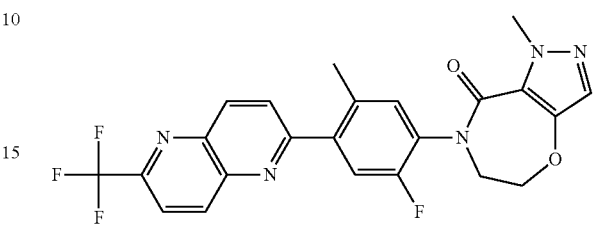

Step 1: Synthesis of 4-(2-(benzyloxy)ethoxy)-N-(4-bromo-2-fluoro-5-methylphenyl)-1-methyl-1H-pyrazole-5-carboxamide

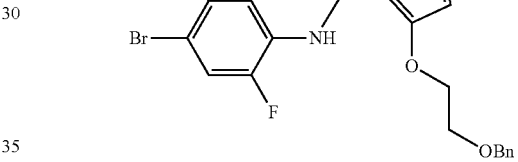

To a stirred solution of 4-(2-(benzyloxy)ethoxy)-1-methyl-1H-pyrazole-5-carbonyl chloride (0.9 g, 3.05 mmol, 1 equiv) and 4-bromo-2-fluoro-5-methylaniline (0.6 g, 3.05 mmol, 1 equiv) in DCM was added Et$_3$N (0.5 g, 4.58 mmol, 1.5 equiv) at 0° C. under nitrogen atmosphere. The resulting solution was stirred for 30 min. The reaction was quenched with water at room temperature. The aqueous layer was extracted with CH$_2$Cl$_2$ and the organic layer was concentrated under reduced pressure to give the title compound (1 g, 70.84%) as a white solid. LC-MS: (ES, m/z): [M+H]$^+$ 462.

Step 2. Synthesis of N-(4-bromo-2-fluoro-5-methylphenyl)-4-(2-hydroxyethoxy)-1-methyl-1H-pyrazole-5-carboxamide

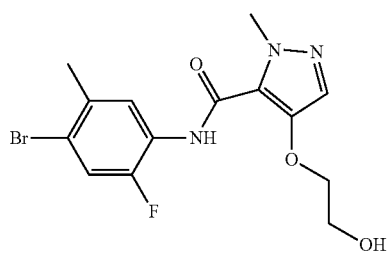 [SMILES: Cc1cc(NC(=O)c2c(OCCO)cnn2C)c(F)cc1Br]

To a stirred solution of 4-(2-(benzyloxy)ethoxy)-N-(4-bromo-2-fluoro-5-methylphenyl)-1-methyl-1H-pyrazole-5- carboxamide (1 g, 2.16 mmol, 1 equiv) in DCM was added BCl$_3$ (0.5 g, 4.27 mmol, 1.98 equiv) at 0° C. under nitrogen atmosphere. The resulting solution was stirred for 3 h. The reaction was quenched with water at room temperature. The aqueous layer was extracted with DCM and the resulting mixture was concentrated under reduced pressure to give the title compound (0.8 g, 99.37%) as a light yellow solid. LC-MS: (ES, m/z): [M+H]$^+$ 372.

Step 3: Synthesis of 2-((5-((4-bromo-2-fluoro-5-methylphenyl)carbamoyl)-1-methyl-1H-pyrazol-4-yl)oxy)ethyl methanesulfonate

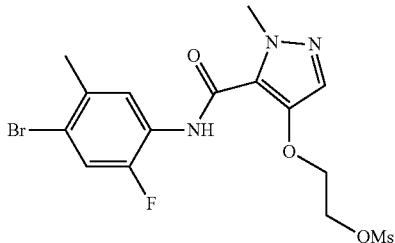 [SMILES: Cc1cc(NC(=O)c2c(OCCOS(C)(=O)=O)cnn2C)c(F)cc1Br]

To a stirred solution of N-(4-bromo-2-fluoro-5-methylphenyl)-4-(2-hydroxyethoxy)-1-methyl-1H-pyrazole-5-carboxamide (800 mg, 2.15 mmol, 1 equiv) in DCM was added Et$_3$N (327 mg, 3.23 mmol, 1.50 equiv) and MsCl (369 mg, 3.22 mmol, 1.50 equiv) was added at 0° C. under nitrogen atmosphere. The reaction mixture was quenched with water at room temperature. The aqueous layer was extracted with DCM and the combined organic layers were dried over anhydrous Na$_2$SO$_4$. After filtration, the filtrate was concentrated under reduced pressure to give the title compound (950 mg, 98.16%) as a white solid. LC-MS: (ES, m/z): [M+H]$^+$ 450.

Step 4: Synthesis of 7-(4-bromo-2-fluoro-5-methylphenyl)-1-methyl-6,7-dihydro-1H-pyrazolo[3,4-f][1,4]oxazepin-8 (5H)-one

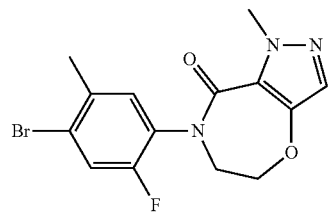 [SMILES: Cc1cc(N2CCOc3cnn(C)c3C2=O)c(F)cc1Br]

To a stirred solution of 2-((5-((4-bromo-2-fluoro-5-methylphenyl)carbamoyl)-1-methyl-1H-pyrazol-4-yl)oxy)ethyl methanesulfonate_(950 mg, 2.11 mmol, 1 equiv) in DMF (19 mL) was added NaH (127 mg, 5.29 mmol, 1.5 equiv) at 0° C. The reaction was quenched with NH$_4$Cl(aq.) at room temperature and the resulting mixture was extracted with EtOAc. The combined organic layers were concentrated under reduced pressure to give the title compound (618 mg, 82.70%) as a light yellow solid. LC-MS: (ES, m/z): [M+H]$^+$ 354.

Step 5: Synthesis of 1-methyl-7-(2-fluoro-5-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one

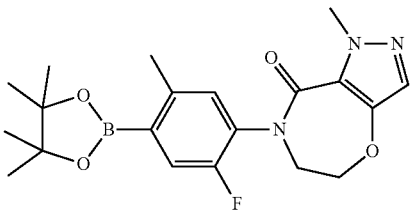 [SMILES: Cc1cc(N2CCOc3cnn(C)c3C2=O)c(F)cc1B1OC(C)(C)C(C)(C)O1]

To a stirred solution of 7-(4-bromo-2-fluoro-5-methylphenyl)-1-methyl-6,7-dihydro-1H-pyrazolo[3,4-f][1,4] oxazepin-8 (5H)-one (618 mg, 1.74 mmol, 1 equiv) in dioxane was added KOAc (342 mg, 3.48 mmol, 2.00 equiv), B2Pin2 (665 mg, 2.62 mmol, 1.50 equiv) and Pd(dppf)Cl$_2$ (128 mg, 0.17 mmol, 0.10 equiv) and the reaction mixture was heated at 80° C. under nitrogen atmosphere. The resulting mixture was concentrated under reduced pressure and the residue was purified by silica gel column chromatography with PE/EtOAc (10:1) as eluent to afford the title compound (714 mg, 101.98%) as a white solid. LC-MS: (ES, m/z): [M+H]$^+$ 402.

Step 6: Synthesis of 7-(2-fluoro-5-methyl-4-(6-(trifluoromethyl)-1,5-naphthyridin-2-yl)phenyl)-1-methyl-6,7-dihydro-1H-pyrazolo[3,4-f][1,4]oxazepin-8 (5H)-one To a stirred solution of 1-methyl-7-(2-fluoro-5-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one (714 mg, 1.78 mmol, 1 equiv) and 2-chloro-6-(trifluoromethyl)-1,5-naphthyridine (415 mg, 1.78 mmol, 1.00 equiv) in DME (14.3 mL) were added Pd(PPh$_3$)$_4$ (205.8 mg, 0.18 mmol, 0.10 equiv), Na$_2$CO$_3$ (566 mg, 5.34 mmol, 3.00 equiv) and H$_2$O (3.6 mL) at 80° C. under nitrogen atmosphere. The reaction was quenched by the addition of water at room temperature. The aqueous layer was extracted with EtOAc and the combined organic layers were concentrated under reduced pressure. The residue was purified by silica gel column chromatography, with PE/EtOAc (5/1) as eluent to afford the title compound (0.4245 g, 50.60%) as a white solid. LC-MS: (ES, m/z): [M+H]$^+$ 472; $^1$H-NMR: (300 MHz, CDCl$_3$, ppm): δ 2.43 (s, 3H), 4.00 (t, 2H), 4.16 (s, 3H), 4.51-4.53 (t, 2H), 7.26-7.32 (m, 2H), 7.40-7.44 (d, 1H), 7.87-7.90 (d, 1H), 8.02-8.04 (d, 1H), 8.60-8.65 (m, 2H).

Example 13

Synthesis of 5-(2-fluoro-4-(6-(trifluoromethyl)quinazolin-2-yl)phenyl)-3-methyl-6,7-dihydropyrazolo[1,5-a]pyrazin-4(5H)-one

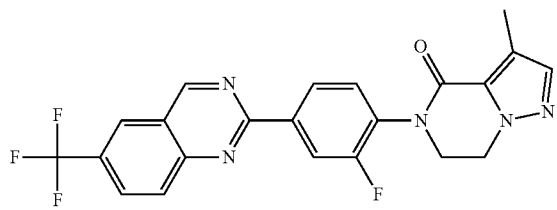 [SMILES: Cc1cnn2c1C(=O)N(c1ccc(-c3ncc4cc(C(F)(F)F)ccc4n3)cc1F)CC2]

Step 1: Synthesis of ethyl 1-(2-(benzyloxy)ethyl)-4-methyl-1H-pyrazole-5-carboxylate

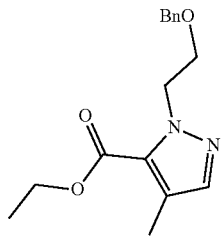 [SMILES: CCOC(=O)c1c(C)cnn1CCOCc1ccccc1]

To a stirred solution of ethyl 4-methyl-1H-pyrazole-5-carboxylate (50 g, 324.32 mmol, 1 equiv) and 2-(benzyloxy)ethan-1-ol (49.4 g, 324.59 mmol, 1.00 equiv) in THF (500 mL) were added DIAD (137.7 g, 681.07 mmol, 2.1 equiv) and PPh₃ (221.2 g, 843.23 mmol, 2.6 equiv) in portions at 0° C. under nitrogen atmosphere. The resulting mixture was stirred overnight at room temperature. The residue was purified by silica gel column chromatography with PE/EtOAc (50/1) as eluent to afford the title compound (73 g, 78.06%) as a yellow oil. LC-MS: (ES, m/z): [M+H]⁺ 289.

Step 2: Synthesis of 1-(2-(benzyloxy)ethyl)-4-methyl-1H-pyrazole-5-carboxylic acid

To a stirred solution of ethyl 1-(2-(benzyloxy)ethyl)-4-methyl-1H-pyrazole-5-carboxylate (36.7 g, 127.28 mmol, 1 equiv) in EtOH (367 mL) was added NaOH (4M) (63.64 mL, 2 equiv). The resulting mixture was stirred for 1 h at 40° C. and then quenched with water at room temperature. The reaction mixture was acidified to pH 4 with HCl (2M) (aq.) and the resulting mixture was extracted with EtOAc. The combined organic layers were dried over anhydrous Na₂SO₄. After filtration, the filtrate was concentrated under reduced pressure to give the title compound (30 g, 90.55%) as a white solid. LC-MS: (ES, m/z): [M+H]⁺ 261.

Step 3: Synthesis of 1-(2-(benzyloxy)ethyl)-4-methyl-1H-pyrazole-5-carbonyl chloride

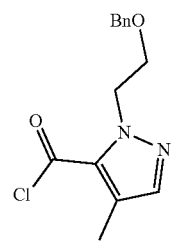 [SMILES: Cc1cnn(CCOCc2ccccc2)c1C(=O)Cl]

To a stirred solution of 1-(2-(benzyloxy)ethyl)-4-methyl-1H-pyrazole-5-carboxylic acid (15 g, 57.63 mmol, 1 equiv) and DMF (0.4 g, 5.76 mmol, 0.1 equiv) in DCM (300 mL) was added (COCl)₂ (11.0 g, 86.44 mmol, 1.5 equiv) dropwise at 0° C. The resulting mixture was stirred for 3 h at room temperature and then concentrated under reduced pressure to give the title compound (17 g, crude) as a white solid.

Step 4: Synthesis of 1-(2-(benzyloxy)ethyl)-N-(2-fluoro-4-bromophenyl)-4-methyl-1H-pyrazole-5-carboxamide

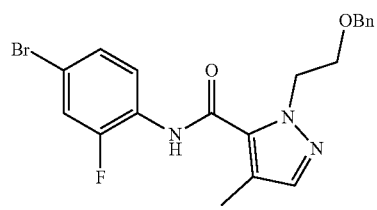 [SMILES: Cc1cnn(CCOCc2ccccc2)c1C(=O)Nc1ccc(Br)cc1F]

Into a 50-mL 3-necked round-bottom flask under N₂ atmosphere, was placed 1-(2-(benzyloxy)ethyl)-4-methyl-1H-pyrazole-5-carbonyl chloride (2 g, 7.18 mmol, 1 equiv), 4-bromo-2-fluoroaniline (1.6 g, 8.61 mmol, 1.2 equiv), Et₃N (1.1 g, 10.76 mmol, 1.5 equiv), and DCM (20 mL). The resulting solution was stirred for 2 h at 25° C. The reaction was then quenched with water and the resulting solution was extracted with dichloromethane. The organic layers were concentrated under vacuum. The crude product was purified by re-crystallization from CH₃OH to give (2.5 g, 80.60%) of the title compound as a white solid. LC-MS: (ES, m/z): [M+H]⁺ 432, 434.

Step 5: Synthesis of N-(4-bromo-2-fluorophenyl)-1-(2-hydroxyethyl)-4-methyl-1H-pyrazole-5-carboxamide

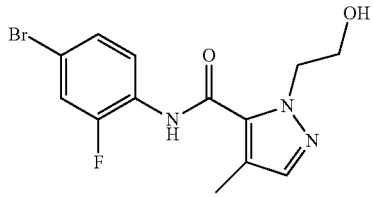 [SMILES: Cc1cnn(CCO)c1C(=O)Nc1ccc(Br)cc1F]

Into a 50-mL 3-necked round-bottom flask under N$_2$ atmosphere, was placed 1-(2-(benzyloxy)ethyl)-N-(2-fluoro-4-bromophenyl)-4-methyl-1H-pyrazole-5-carboxamide (2.5 g, 5.78 mmol, 1 equiv), DCM (25 mL), and BCl$_3$ (1M) (8.7 mL, 1.5 equiv) was added at 0° C. The resulting solution was stirred for 1 h at 0° C. The reaction was then quenched with NaHCO$_3$. The resulting solution was extracted with dichloromethane dried over anhydrous sodium sulfate and concentrated under vacuum to give (1.8 g, 94.85%) of the title compound as a white solid. LC-MS: (ES, m/z): [M+H]$^+$ 342, 344.

Step 6: Synthesis of 2-(5-((4-bromo-2-fluorophenyl)carbamoyl)-4-methyl-1H-pyrazol-1-yl)ethyl methanesulfonate

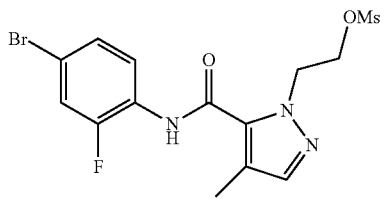 [SMILES: Cc1cnn(CCOS(C)(=O)=O)c1C(=O)Nc1ccc(Br)cc1F]

Into a 100-mL 3-necked round-bottom flask under N$_2$ atmosphere, was placed N-(4-bromo-2-fluorophenyl)-1-(2-hydroxyethyl)-4-methyl-1H-pyrazole-5-carboxamide (1.8 g, 5.26 mmol, 1 equiv), Et$_3$N (0.8 g, 7.89 mmol, 1.5 equiv), and DCM (40 mL), and MsCl (0.9 g, 7.89 mmol, 1.5 equiv) was added at 0° C. The resulting solution was stirred for 1 h at 0° C. The reaction mixture was then quenched with water and the resulting solution was extracted with dichloromethane dried over anhydrous sodium sulfate and concentrated to give (2.2 g, 99.51%) the title compound as a white solid. LC-MS: (ES, m/z): [M+H]$^+$ 420, 422.

Step 7: Synthesis of 5-(4-bromo-2-fluorophenyl)-3-methyl-6,7-dihydropyrazolo[1,5-a]pyrazin-4 (5H)-one

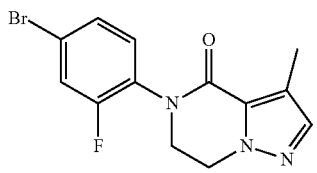 [SMILES: Cc1cnn2c1C(=O)N(c1ccc(Br)cc1F)CC2]

Into a 100-mL 3-necked round-bottom flask under N$_2$ atmosphere, was placed 2-(5-((4-bromo-2-fluorophenyl)carbamoyl)-4-methyl-1H-pyrazol-1-yl)ethyl methanesulfonate (2.2 g, 5.23 mmol, 1 equiv), DMF (45 mL), and NaH (0.33 g, 13.75 mmol, 2.63 equiv) was added at 0° C. The resulting solution was stirred for 1 h at 0° C. The reaction was then quenched with NH$_4$Cl, the resulting solution was extracted with ethyl acetate and the organic layer concentrated. The residue was applied onto a silica gel column and eluted with dichloromethane/methanol (50/1) to give (1.65 g, 97.23%) of the title compound as a yellow solid. LC-MS: (ES, m/z): [M+H]$^+$ 324, 326.

Step 8: Synthesis of 5-(2-fluoro-4-(4,4,5,5-tetramethyl-1,3,2-dioxaborolan-2-yl)phenyl)-3-methyl-6,7-dihydropyrazolo[1,5-a]pyrazin-4 (5H)-one

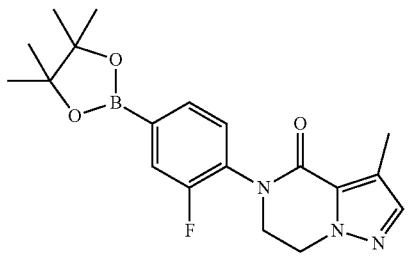 [SMILES: Cc1cnn2c1C(=O)N(c1ccc(B3OC(C)(C)C(C)(C)O3)cc1F)CC2]

Into a 50-mL 3-necked round-bottom flask under N$_2$ atmosphere, was placed 5-(4-bromo-2-fluorophenyl)-3-methyl-6,7-dihydropyrazolo[1,5-a]pyrazin-4 (5H)-one (1.65 g, 5.09 mmol, 1 equiv), B2Pin2 (1.9 g, 7.64 mmol, 1.5 equiv), KOAc (1.0 g, 10.18 mmol, 2 equiv), dioxane (20 mL), and Pd(dppf)Cl$_2$ (0.6 g, 0.76 mmol, 0.15 equiv). The resulting solution was stirred for 12 h at 80° C. The resulting mixture was concentrated and the residue was applied onto a silica gel column and eluted with ethyl acetate/petroleum ether (1/10) to give (1.85 g, 97.91%) the title compound as a yellow solid. LC-MS: (ES, m/z): [M+H]$^+$ 372.

Step 9: Synthesis of 5-(2-fluoro-4-(6-(trifluoromethyl)quinazolin-2-yl)phenyl)-3-methyl-6,7-dihydropyrazolo[1,5-a]pyrazin-4 (5H)-one

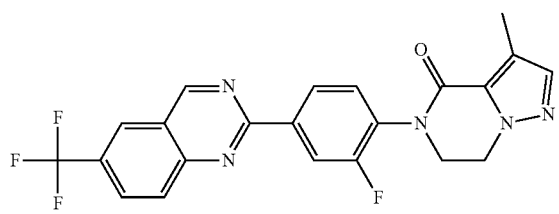 [SMILES: Cc1cnn2c1C(=O)N(c1ccc(-c3ncc4cc(C(F)(F)F)ccc4n3)cc1F)CC2]

Into a 50-mL 3-necked round-bottom flask under N$_2$ atmosphere, was placed 5-(2-fluoro-4-(4,4,5,5-tetramethyl-1,3,2-dioxaborolan-2-yl)phenyl)-3-methyl-6,7-dihydropyrazolo[1,5-a]pyrazin-4 (5H)-one (1 g, 2.69 mmol, 1 equiv), 2-chloro-6-(trifluoromethyl)quinazoline (0.8 g, 3.23 mmol, 1.2 equiv), K$_2$CO$_3$ (1.1 g, 8.08 mmol, 3 equiv), toluene (16 mL), EtOH (8 mL), and Pd(PPh$_3$)$_4$ (0.5 g, 0.40 mmol, 0.15 equiv). The resulting solution was stirred for 12 h at 80° C. The reaction was then quenched with water and the resulting solution was extracted with ethyl acetate. The organics were concentrated and the residue was applied onto a silica gel column and eluted with ethyl acetate/petroleum ether (1/5) to give (554.4 mg, (46.63%) of the title compound as a white solid. LC-MS: (ES, m/z): [M+H]⁺ 442. ¹H-NMR: (300 MHz, DMSO, ppm): δ 2.27 (s, 3H), 4.21-4.25 (dd, 2H), 4.51-4.55 (dd, 2H), 7.51 (s, 1H), 7.75 (t, 1H), 8.27-8.34 (m, 2H), 8.38-8.43 (dd, 1H), 8.49-8.52 (dd, 1H), 8.75 (s, 1H), 9.92 (s, 1H).

Example 14

Synthesis of 1-methyl-5-(2-methyl-4-(6-(trifluoromethyl)quinazolin-2-yl)phenyl)-4,5-dihydropyrrolo[3,4-c]pyrazol-6 (1H)-one

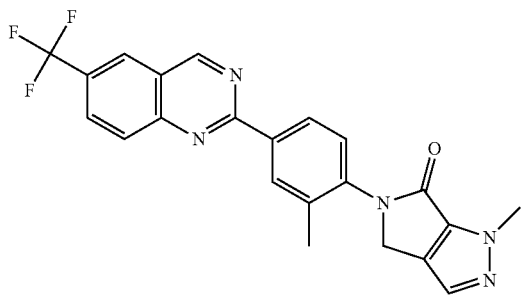 [SMILES: Cc1cc(-c2ncc3cc(C(F)(F)F)ccc3n2)ccc1N1Cc2cnn(C)c2C1=O]

Step 1: Synthesis of methyl 1-methyl-4-vinyl-1H-pyrazole-5-carboxylate

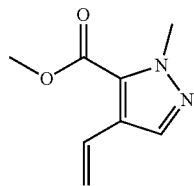

Into a 50-mL 3-necked round-bottom flask under N₂ atmosphere, was placed methyl 4-bromo-1-methyl-1H-pyrazole-5-carboxylate (1 g, 4.57 mmol, 1 equiv), tributyl(ethenyl)stannane (1.4 g, 4.41 mmol, 0.97 equiv), Pd(PPh₃)₄ (0.5 g, 0.43 mmol, 0.09 equiv) in DMF (10 mL). The resulting solution was stirred overnight at 100° C. The resulting solution was diluted with H₂O and extracted with ethyl acetate and the organic layer concentrated. The residue was applied onto a silica gel column and eluted with EA/PE (1:1) to give the title compound (580 mg 76.45%) as colorless oil. LC-MS: (ES, m/z): [M+H]⁺ 167.

Step 2: Synthesis of 1-methyl-4-vinyl-1H-pyrazole-5-carboxylic acid

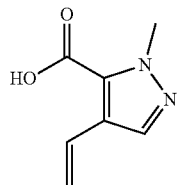

Into a 25-mL round-bottom flask, was placed methyl 1-methyl-4-vinyl-1H-pyrazole-5-carboxylate (560 mg, 3.37 mmol, 1 equiv), LiOH (96.8 mg, 4.04 mmol, 1.20 equiv), THF (5 mL, 61.71 mmol, 18.31 equiv), and H₂O (5 mL, 277.54 mmol, 82.36 equiv). The resulting solution was stirred overnight at room temperature and then diluted with H₂O. The resulting mixture was concentrated, extracted with ethyl acetate, dried over anhydrous sodium sulfate and concentrated to give (380 mg, 74.11%) the title compound as a white solid. LC-MS: (ES, m/z): [M+H]⁺ 153.

Step 3: Synthesis of 1-methyl-4-vinyl-1H-pyrazole-5-carbonyl chloride

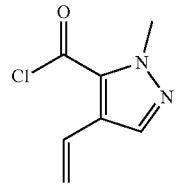

Into a 100 mL 3-necked round-bottom flask were added 1-methyl-4-vinyl-1H-pyrazole-5-carboxylic acid (1.92 g, 12.62 mmol, 1 equiv), DCM (40 mL), DMF (0.1 g, 1.26 mmol, 0.1 equiv) and (COCl)₂ (2.4 g, 18.91 mmol, 1.50 equiv) was added at 0° C. The resulting mixture was stirred for 2 h at room temperature and then concentrated under reduced pressure to afford the title compound (2.3 g, 106.84%) as a yellow solid. The crude product was used in the next step directly without further purification.

Step 4: Synthesis of N-(4-bromo-2-methylphenyl)-1-methyl-4-vinyl-1H-pyrazole-5-carboxamide

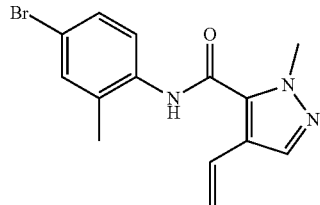 [SMILES: C=Cc1cnn(C)c1C(=O)Nc1ccc(Br)cc1C]

Into a 100 mL 3-necked round-bottom flask were added 4-bromo-2-methylaniline (2.4 g, 12.97 mmol, 1.02 equiv), DCM (40 mL), Et₃N (1.9 g, 18.78 mmol, 1.48 equiv) and 4-ethenyl-1-methyl-1H-pyrazole-5-carbonyl chloride (2.16 g, 12.66 mmol, 1 equiv) at 0° C. The resulting mixture was stirred for 2 h at room temperature and then diluted with water. The aqueous layer was extracted with CH₂Cl₂ and the organics were separated and concentrated under vacuum. The crude product was recrystallized from MeOH (20 mL) to give the title compound (3.8 g, 93.73%) as a light yellow solid. LC-MS: (ES, m/z): [M+H]⁺ 320, 322.

Step 5: Synthesis of N-(4-bromo-2-methylphenyl)-4-(1,2-dihydroxyethyl)-1-methyl-1H-pyrazole-5-carboxamide

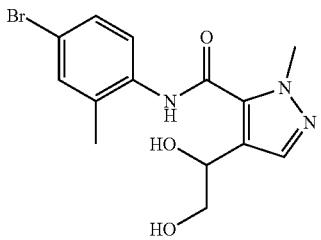 [SMILES: Cc1cc(Br)ccc1NC(=O)c1c(C(O)CO)cnn1C]

Into a 8 mL sealed tube were added N-(4-bromo-2-methylphenyl)-1-methyl-4-vinyl-1H-pyrazole-5-carboxamide (200 mg, 0.62 mmol, 1 equiv), NMO (219.5 mg, 1.87 mmol, 3.00 equiv), THF (2 mL), H$_2$O (0.2 mL) and OsO$_4$ (7.9 mg, 0.03 mmol, 0.05 equiv). The resulting mixture was stirred for 4 h at room temperature under nitrogen atmosphere. The reaction was quenched with Na$_2$S$_2$O$_4$ (aq.) at room temperature. The aqueous layer was extracted with EtOAc and the resulting mixture was concentrated under reduced pressure to afford the title compound (208 mg, 94.01%) as a yellow solid. LC-MS: (ES, m/z): [M+H]$^+$ 354, 356.

Step 6: Synthesis of N-(4-bromo-2-methylphenyl)-4-formyl-1-methyl-1H-pyrazole-5-carboxamide

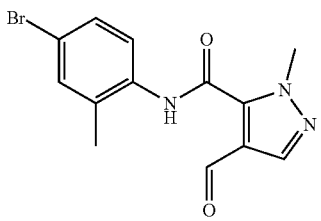 [SMILES: Cc1cc(Br)ccc1NC(=O)c1c(C=O)cnn1C]

Into a 8 mL sealed tube were added N-(4-bromo-2-methylphenyl)-4-(1,2-dihydroxyethyl)-1-methyl-1H-pyrazole-5-carboxamide (208 mg, 0.59 mmol, 1 equiv), MeOH (2 mL), H$_2$O (0.2 mL) and NaIO$_4$ (251.2 mg, 1.17 mmol, 2.00 equiv). The resulting mixture was stirred for 4 h at room temperature and then diluted with water. The aqueous layer was extracted with EtOAc and the resulting mixture was concentrated under vacuum to afford the title compound (180 mg, 95.15%) as a yellow solid. LC-MS: (ES, m/z): [M+H]$^+$ 322, 324.

Step 7: Synthesis of N-(4-bromo-2-methylphenyl)-4-(hydroxymethyl)-1-methyl-1H-pyrazole-5-carboxamide

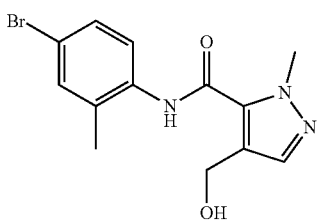 [SMILES: Cc1cc(Br)ccc1NC(=O)c1c(CO)cnn1C]

Into a 8 mL sealed tube were added N-(4-bromo-2-methylphenyl)-4-formyl-1-methyl-1H-pyrazole-5-carboxamide (180 mg, 0.56 mmol, 1 equiv), MeOH (1.8 mL) and NaBH$_4$ (25.4 mg, 0.67 mmol, 1.20 equiv) was added at 0° C. The resulting mixture was stirred for 4 h at room temperature under nitrogen atmosphere. The reaction was quenched with sat. NH$_4$Cl (aq.). The resulting mixture was concentrated under vacuum and the aqueous layer was extracted with EtOAc. The organic layer was concentrated under vacuum to the title compound (161 mg, 88.89%) as a white solid. LC-MS: (ES, m/z): [M+H]$^+$ 324, 326.

Step 8: Synthesis of (5-((4-bromo-2-methylphenyl)carbamoyl)-1-methyl-1H-pyrazol-4-yl)methyl methanesulfonate

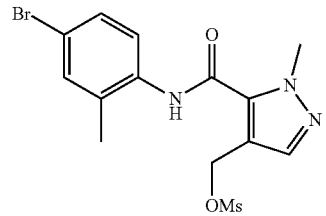 [SMILES: Cc1cc(Br)ccc1NC(=O)c1c(COS(C)(=O)=O)cnn1C]

Into a 8 mL sealed tube were added N-(4-bromo-2-methylphenyl)-4-(hydroxymethyl)-1-methyl-1H-pyrazole-5-carboxamide (161 mg, 0.50 mmol, 1 equiv), DCM (3.22 mL), and Et$_3$N (75.4 mg, 0.74 mmol, 1.50 equiv) and MsCl (87.6 mg, 0.76 mmol, 1.54 equiv) was added at 0° C. The resulting mixture was stirred for 2 h at room temperature and then diluted with water. The aqueous layer was extracted with CH$_2$Cl$_2$ and the organics were concentrated under reduced pressure to afford the title compound (230 mg, 115.13%) as a yellow solid. The crude product was used in the next step directly without further purification.

Step 9: Synthesis of 5-(4-bromo-2-methylphenyl)-1-methyl-4,5-dihydropyrrolo[3,4-c]pyrazol-6 (1H)-one

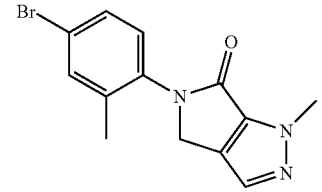 [SMILES: Cc1cc(Br)ccc1N1Cc2cnn(C)c2C1=O]

Into a 25 mL 3-necked round-bottom flask were added (5-((4-bromo-2-methylphenyl)carbamoyl)-1-methyl-1H-pyrazol-4-yl)methyl methanesulfonate (220 mg, 0.55 mmol, 1 equiv), and DMF (4.4 mL) and NaH (19.7 mg, 0.82 mmol, 1.50 equiv) was added at 0° C. in portions. The resulting mixture was stirred for 2 h at room temperature under nitrogen atmosphere. The reaction was quenched with sat. NH$_4$Cl (aq.). The aqueous layer was extracted with EtOAc and the organics were concentrated under reduced pressure. The residue was purified by Prep-TLC (PE/EtOAc 2:1) to afford the title compound (110 mg, 65.69%) as a yellow solid. LC-MS: (ES, m/z): [M+H]$^+$ 306, 308

105

Step 10: Synthesis of 1-methyl-5-(2-methyl-4-(4,4,5,5-tetramethyl-1,3,2-dioxaborolan-2-yl)phenyl)-4,5-dihydropyrrolo[3,4-c]pyrazol-6 (1H)-one

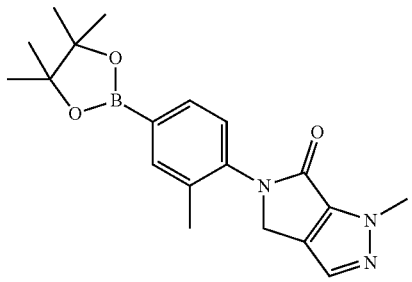

Into a 8 mL sealed tube were added 5-(4-bromo-2-methylphenyl)-1-methyl-4,5-dihydropyrrolo[3,4-c]pyrazol-6 (1H)-one (110 mg, 0.36 mmol, 1 equiv), 4,4,5,5-tetramethyl-2-(4,4,5,5-tetramethyl-1,3,2-dioxaborolan-2-yl)-1,3,2-dioxaborolane (100.4 mg, 0.40 mmol, 1.10 equiv), KOAc (70.5 mg, 0.72 mmol, 2 equiv), dioxane (2.2 mL) and Pd(dppf)Cl$_2$ (26.3 mg, 0.04 mmol, 0.1 equiv). The reaction mixture was stirred overnight at 80° C. under nitrogen atmosphere and concentrated under reduced pressure. The residue was purified by silica gel column chromatography, eluting with PE/EtOAc (1:1) to afford the title compound (120 mg, 94.55%) as a yellow solid. LC-MS: (ES, m/z): [M+H]$^+$ 354.

Step 11: Synthesis of 1-methyl-5-(2-methyl-4-(6-(trifluoromethyl)quinazolin-2-yl)phenyl)-4,5-dihydropyrrolo[3,4-c]pyrazol-6 (1H)-one

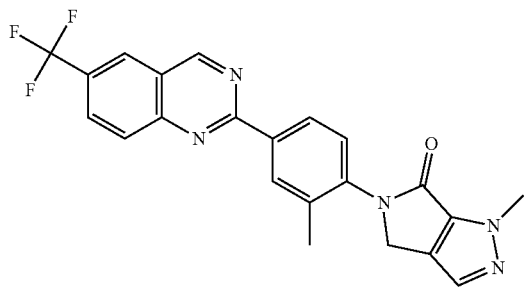 [SMILES: Cc1cc(-c2ncc3cc(C(F)(F)F)ccc3n2)ccc1N1Cc2cnn(C)c2C1=O]

Into a 8 mL sealed tube were added 1-methyl-5-(2-methyl-4-(4,4,5,5-tetramethyl-1,3,2-dioxaborolan-2-yl)phenyl)-4,5-dihydropyrrolo[3,4-c]pyrazol-6 (1H)-one (110 mg, 0.31 mmol, 1 equiv), 2-chloro-6-(trifluoromethyl)quinazoline (72.4 mg, 0.31 mmol, 1.00 equiv), K$_2$CO$_3$ (129.1 mg, 0.93 mmol, 3 equiv), toluene (2.2 mL), EtOH (1.1 mL) and Pd(PPh$_3$)$_4$ (36.0 mg, 0.03 mmol, 0.1 equiv). The resulting mixture was stirred overnight at 80° C. under nitrogen atmosphere, then concentrated under reduced pressure. The residue was purified by Prep-TLC (PE/EtOAc 1:1) to afford the title compound (57.8 mg, 43.84%) as a light yellow solid. LC-MS: (ES, m/z): [M+H]$^+$ 424; $^1$H-NMR: (300 MHz, DMSO-d$_6$, ppm): δ 2.35 (s, 3H), 4.01 (s, 3H), 4.73 (s, 2H), 7.59 (s, 1H), 7.62 (d, 1H), 8.28 (m, 2H), 8.49 (dd, 1H), 8.57 (s, 1H), 8.73 (s, 1H), 9.91 (s, 1H).

106

Example 15

Synthesis of 1-methyl-6-(2-methyl-4-(6-(trifluoromethyl)quinazolin-2-yl)phenyl)-1,4,5,6-tetrahydro-7H-pyrazolo[3,4-c]pyridin-7-one

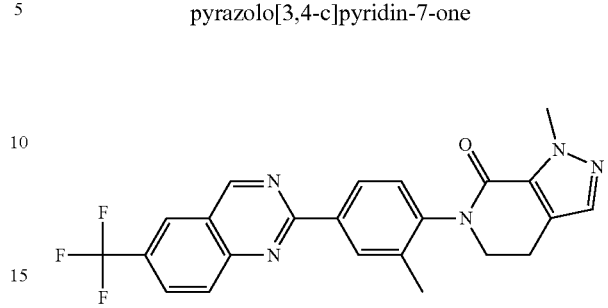

Into a 50-mL 3-necked round-bottom flask under N$_2$ atmosphere, was placed 1-methyl-6-(2-methyl-4-(4,4,5,5-tetramethyl-1,3,2-dioxaborolan-2-yl)phenyl)-1,4,5,6-tetrahydro-7H-pyrazolo[3,4-c]pyridin-7-one (1 g, 2.72 mmol, 1 equiv), 2-chloro-6-(trifluoromethyl)quinazoline (633.3 mg, 2.72 mmol, 1 equiv), K$_2$CO$_3$ (1128.9 mg, 8.17 mmol, 3.00 equiv), toluene (10 mL), EtOH (5 mL), and Pd(PPh$_3$)$_4$ (314.6 mg, 0.27 mmol, 0.1 equiv). The resulting solution was stirred overnight at 80° C., diluted with EtOAc and washed with H$_2$O. The organic layer was concentrated and the residue was applied onto a silica gel column and eluted with ethyl acetate/petroleum ether (1:2) to give (516.6 mg, 43.37%) of the title compound as a white solid. LC-MS: (ES, m/z): [M+H]$^+$ 438; $^1$H-NMR: (400 MHz, DMSO-d6, ppm): δ 9.90 (s, 1H), 8.72 (s, 1H), 8.54-8.55 (d, 1H), 8.47-8.49 (m, 1H), 8.25-8.30 (m, 2H), 7.48-7.53 (m, 2H), 4.05-4.12 (m, 4H), 3.72-3.78 (m, 1H), 2.91-3.05 (m, 2H), 2.34 (s, 3H).

Example 16

Synthesis of 3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one

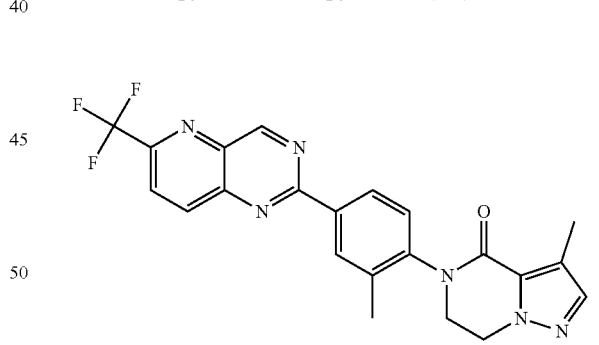

To a stirred solution of 2-chloro-6-(trifluoromethyl)quinazoline (1.5 g, 6.42 mmol, 1 equiv) and 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one (2.4 g, 6.42 mmol, 1 equiv) in t-BuOH (27 mL) and H$_2$O (3 mL) were added K$_2$CO$_3$ (2.7 g, 19.27 mmol, 3 equiv) and AMPhosPdCl$_2$ (1.4 g, 1.93 mmol, 0.3 equiv). The resulting mixture was stirred overnight at 80° C. under nitrogen atmosphere and then diluted with water. The resulting mixture was extracted with EtOAc and the combined organic layers were concentrated under reduced pressure. The residue was purified by silica gel column chromatography, by eluting with PE/EtOAc (1/2) to give crude product. The residue was purified by reverse flash chromatography with the following conditions: column, C18 gel; mobile phase, ACN and water (10 mmol/L NH₄HCO₃), 0% to 65% gradient in 40 min; detector, UV 254 nm to give the title compound (535.6 mg, 19.02%) as a yellow solid. LC-MS: (ES, m/z): [M+H]⁺ 439; ¹H-NMR: (300 MHz, DMSO-d₆, ppm): δ 2.26 (s, 3H), 2.36 (s, 3H), 3.91-3.95 (m, 1H), 4.28-4.36 (m, 1H), 4.51-4.55 (t, 2H), 7.48 (s, 1H), 7.57-7.60 (d, 1H), 8.46-8.57 (m, 3H), 8.81-8.84 (d, 1H), 9.97 (s, 1H).

Example 17

Synthesis of 3-methyl-5-(2-methyl-4-(8-methyl-6-(trifluoromethyl)-1,5-naphthyridin-2-yl)phenyl)-6,7-dihydropyrazolo[1,5-a]pyrazin-4 (5H)-one

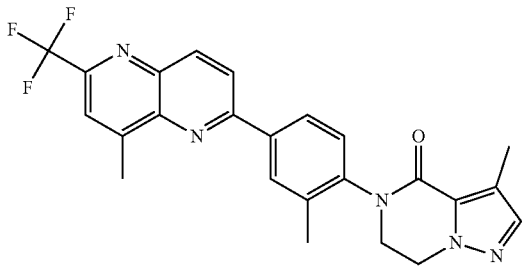 [SMILES: Cc1cc(-c2ccc3nc(C(F)(F)F)cc(C)c3n2)ccc1N1CCn2ncc(C)c2C1=O]

To a stirred solution of 6-chloro-4-methyl-2-(trifluoromethyl)-1,5-naphthyridine (500 mg, 2.03 mmol, 1 equiv) and 3-methyl-5-(2-methyl-4-(4,4,5,5-tetramethyl-1,3,2-dioxaborolan-2-yl)phenyl)-6,7-dihydropyrazolo[1,5-a]pyrazin-4 (5H)-one (744.6 mg, 2.03 mmol, 1.00 equiv) in DME (10 mL) and H₂O (2.5 mL) were added Na₂CO₃ (429.8 mg, 4.05 mmol, 2 equiv) and Pd(PPh₃)₄ (234.3 mg, 0.20 mmol, 0.1 equiv) at room temperature under nitrogen atmosphere. The resulting mixture was stirred overnight at 80° C. under nitrogen atmosphere. The reaction mixture was diluted with water at room temperature and extracted with EtOAc. The organic layer was concentrated under vacuum and the residue was purified by silica gel column chromatography by eluting with PE/EtOAc (1:2) to afford crude product. The crude product was re-crystallized from MeOH (10 mL) to afford the title compound (652 mg, 71.23%) as a white solid. LC-MS: (ES, m/z): [M+H]⁺ 452; 1H-NMR: (300 MHz, DMSO-d₆, ppm): δ 2.26 (s, 3H), 2.35 (s, 3H), 2.97 (s, 3H), 3.94-3.98 (m, 1H), 4.28-4.37 (m, 1H), 4.53 (t, 2H), 7.47 (s, 1H), 7.56 (d, 1H), 8.16 (s, 1H), 8.26-8.33 (m, 2H), 8.62 (q, 2H).

Example 18

Synthesis of 5-(2,5-dimethyl-4-(6-(trifluoromethyl)-1,5-naphthyridin-2-yl)phenyl)-3-methyl-6,7-dihydropyrazolo[1,5-a]pyrazin-4 (5H)-one

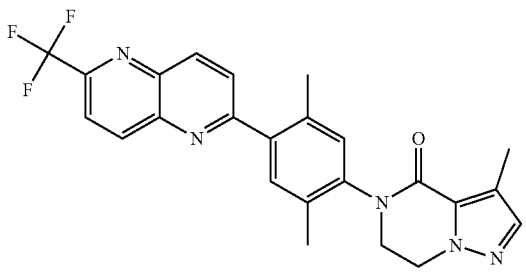 [SMILES: Cc1cc(N2CCn3ncc(C)c3C2=O)c(C)cc1-c1ccc2nc(C(F)(F)F)ccc2n1]

Proceeding as described in Example 5, Step 12 above, but substituting 6-chloro-4-methyl-2-(trifluoromethyl)-1,5-naphthyridine with 2-chloro-6-(trifluoromethyl)-1,5-naphthyridine and 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 5-(2,5-dimethyl-4-(4,4,5,5-tetramethyl-1,3,2-dioxaborolan-2-yl)phenyl)-3-methyl-6,7-dihydropyrazolo[1,5-a]pyrazin-4 (5H)-one gave crude product. Purification by silica gel column chromatography using ethyl acetate/petroleum ether (1/1) as eluent gave the title compound as a white solid in 51.79% yield. LC-MS: (ES, m/z): [M+H]⁺ 452; ¹H-NMR: (300 MHz, DMSO-d₆, ppm): δ 2.19 (s, 6H), 2.40 (s, 3H), 3.89-3.94 (m, 1H), 4.22-4.31 (m, 1H), 4.50-4.54 (t, 2H), 7.38 (s, 1H), 7.48 (s, 1H), 7.56 (s, 1H), 8.18 (d, 1H), 8.28 (d, 1H), 8.69 (d, 1H), 8.77 (d, 1H).

Example 19

Synthesis of 5-(2,5-dimethyl-4-(6-(trifluoromethyl)pyrido[3,2-d]pyrimidin-2-yl)phenyl)-3-methyl-6,7-dihydropyrazolo[1,5-a]pyrazin-4 (5H)-one

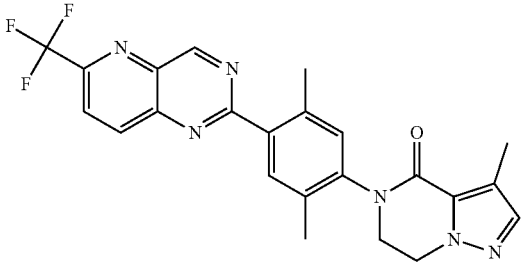

To a stirred solution of 5-(2,5-dimethyl-4-(4,4,5,5-tetramethyl-1,3,2-dioxaborolan-2-yl)phenyl)-3-methyl-6,7-dihydropyrazolo[1,5-a]pyrazin-4 (5H)-one (3.5 g, 9.18 mmol, 1 equiv) and 2-chloro-6-(trifluoromethyl)pyrido[3,2-d]pyrimidine (2.6 g, 11.02 mmol, 1.2 equiv) in dioxane (260 mL) were added K₃PO₄ (3.9 g, 18.36 mmol, 2 equiv), H₂O (50 mL) and AMPhosPdCl₂ (1.5 g, 2.12 mmol, 0.23 equiv). The resulting mixture was stirred overnight at 60° C. under nitrogen atmosphere. The resulting mixture was diluted with water and the aqueous layer was extracted with EtOAc. The combined organic layer was concentrated under reduced pressure. The residue was purified by silica gel column chromatography, by eluting with PE/EtOAc (3/1). The crude product was re-crystallized from MeOH to afford the title compound (501.0 mg, 12.06%) as a yellow solid. LC-MS: (ES, m/z): [M+H]⁺ 453; ¹H-NMR: (300 MHz, DMSO-d₆, ppm): δ 2.26 (s, 3H), 2.28 (s, 3H), 2.62 (s, 3H), 3.91-3.95 (m, 1H), 4.24-4.33 (m, 1H), 4.52 (t, 2H), 7.39 (s, 1H), 7.48 (s, 1H), 8.01 (s, 1H), 8.49 (d, 1H), 8.82 (d, 1H), 9.98 (s, 1H).

Example 20

Synthesis of 5-(2,5-dimethyl-4-(8-methyl-6-(trifluoromethyl)-1,5-naphthyridin-2-yl)phenyl)-3-methyl-6,7-dihydropyrazolo[1,5-a]pyrazin-4 (5H)-one

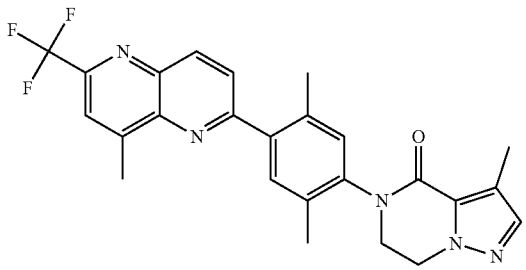 [SMILES: Cc1cc(N2CCn3ncc(C)c3C2=O)c(C)cc1-c1ccc2nc(C(F)(F)F)cc(C)c2n1]

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 5-(2,5-dimethyl-4-(4,4,5,5-tetramethyl-1,3,2-dioxaborolan-2-yl)phenyl)-3-methyl-6,7-dihydropyrazolo[1,5-a]pyrazin-4 (5H)-one gave crude product. Purification by silica gel column chromatography using ethyl acetate/petroleum ether (1:1) as eluent gave the title compound as a yellow solid in 53.48% yield. LC-MS: (ES, m/z): [M+H]$^+$ 466; $^1$H-NMR: (300 MHz, DMSO-$d_6$, ppm): δ 2.26 (s, 6H), 2.46 (s, 3H), 2.89 (s, 3H), 3.91-3.95 (m, 1H), 4.23-4.31 (m, 1H), 4.51-4.55 (m, 2H), 7.38 (s, 1H), 7.49 (s, 1H), 7.60 (s, 1H), 8.16-8.19 (m, 2H), 8.64 (d, 1H).

Example 21

Synthesis of 5-(2-fluoro-5-methyl-4-(6-(trifluoromethyl)pyrido[3,2-d]pyrimidin-2-yl)phenyl)-3-methyl-6,7-dihydropyrazolo[1,5-a]pyrazin-4 (5H)-one

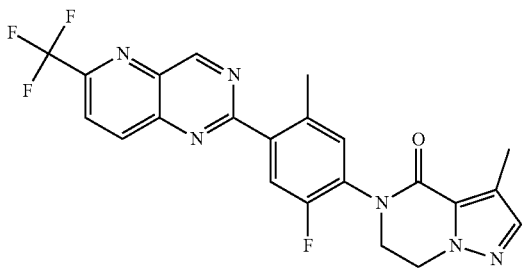 [SMILES: Cc1cc(N2CCn3ncc(C)c3C2=O)c(F)cc1-c1ncc2nc(C(F)(F)F)ccc2n1]

Proceeding as described in Example 19 above but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one (2 g, 5.19 mmol, 1 equiv) in dioxane (150 mL) gave the title compound as a yellow solid after purification by silica gel column chromatography, using PE/EtOAc (1:1) as an eluent. LC-MS: (ES, m/z): [M+H]$^+$ 457; $^1$H-NMR: (300 MHz, DMSO, ppm) δ 10.00 (s, 1H), 8.85 (d, 1H), 8.52 (d, 1H), 7.97 (d, 1H), 7.57 (d, 1H), 7.50 (d, 1H), 4.52 (t, 2H), 4.21 (t, 2H), 2.66 (s, 3H), 2.26 (s, 3H).

Example 22

Synthesis of 5-(2-fluoro-5-methyl-4-(8-methyl-6-(trifluoromethyl)-1,5-naphthyridin-2-yl)phenyl)-3-methyl-6,7-dihydropyrazolo[1,5-a]pyrazin-4 (5H)-one

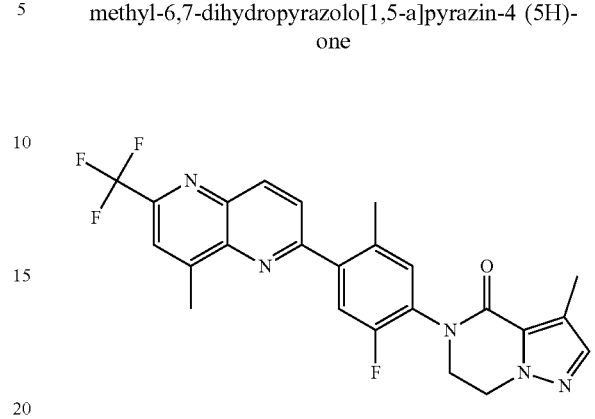

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one and 2-chloro-6-trifluoromethyl)-1,5-naphthyridine 6-chloro-4-methyl-2-(trifluoromethyl)-1,5-naphthyridine gave crude product. Purification by silica gel column chromatography using ethyl acetate/petroleum ether (1:5) as eluent gave the title compound as a yellow solid in 59.39% yield. LC-MS: (ES, m/z): [M+H]$^+$ 470; $^1$H-NMR: (400 MHz, DMSO-$d_6$, ppm): δ 2.27 (s, 3H), 2.49 (s, 3H), 2.91 (s, 3H), 4.19 (t, 2H), 4.52 (t, 2H), 7.50 (s, 1H), 7.56 (d, 1H), 7.66 (d, 1H), 8.12-8.23 (m, 2H), 8.67 (d, 1H).

Example 23

Synthesis of 5-(2,5-dimethyl-4-(6-(trifluoromethyl)quinolin-2-yl)phenyl)-3-methyl-6,7-dihydropyrazolo[1,5-a]pyrazin-4 (5H)-one

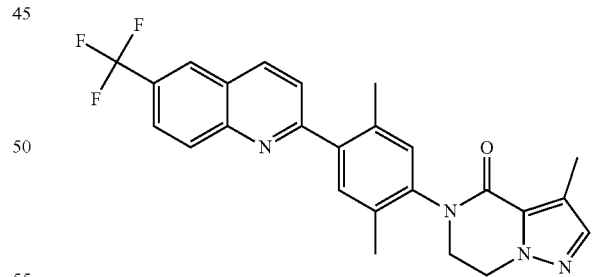

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 5-(2,5-dimethyl-4-(4,4,5,5-tetramethyl-1,3,2-dioxaborolan-2-yl)phenyl)-3-methyl-6,7-dihydropyrazolo[1,5-a]pyrazin-4 (5H)-one and 6-chloro-4-methyl-2-(trifluoromethyl)-1,5-naphthyridine with 2-chloro-6-(trifluoromethyl)quinoline gave crude product. Purification by silica gel column chromatography using ethyl acetate/petroleum ether (1:1) as eluent, followed by recrystallization from methanol gave the title compound as a yellow solid in 63.90% yield. LC-MS: (ES, m/z): [M+H]+ 451; $^1$H-NMR: (300 MHz, DMSO, ppm): δ 2.25 (s, 3H), 2.26 (s, 3H), 2.38 (s, 3H), 3.89-3.95 (m, 1H), 4.21-4.30 (m, 1H), 4.52 (t, 2H), 7.35 (s, 1H), 7.47 (s, 1H), 7.51 (s, 1H), 7.92 (d, 1H), 8.05 (dd, 1H), 8.26 (d, 1H), 8.59 (s, 1H), 8.68 (d, 1H).

Example 24

Synthesis of 5-(2-fluoro-5-methyl-4-(6-(trifluoromethyl)quinolin-2-yl)phenyl)-3-methyl-6,7-dihydropyrazolo[1,5-a]pyrazin-4 (5H)-one

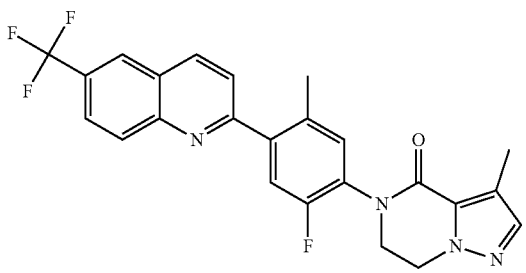 [SMILES: Cc1cc(N2CCn3ncc(C)c3C2=O)c(C)cc1-c1ccc2cc(C(F)(F)F)ccc2n1]

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one and 6-chloro-4-methyl-2-(trifluoromethyl)-1,5-naphthyridine with 2-chloro-6-(trifluoromethyl)quinoline gave crude product. Purification by silica gel column chromatography using ethyl acetate/petroleum ether (1:') as eluent, followed by recrystallization from PE/EtOAc gave the title compound as a white solid in 53.70% yield. LC-MS: (ES, m/z): [M+H]+ 455; $^1$H-NMR: (400 MHz, DMSO-d6, ppm): δ 2.27 (s, 3H), 2.41 (s, 3H), 4.18 (t, 2H), 4.52 (t, 2H), 7.49-7.57 (m, 3H), 7.95 (d, 1H), 8.06 (dd, 1H), 8.26 (d, 1H), 8.60 (s, 1H), 8.71 (d, 1H).

Example 25

Synthesis of 5-(2-fluoro-5-methyl-4-(6-(trifluoromethyl)quinazolin-2-yl)phenyl)-3-methyl-6,7-dihydropyrazolo[1,5-a]pyrazin-4 (5H)-one

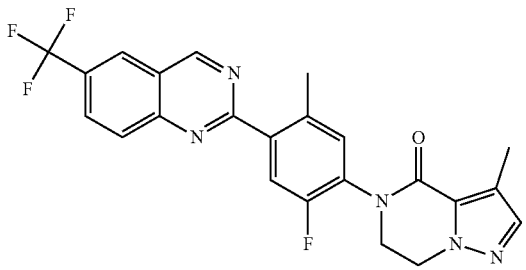 [SMILES: Cc1cc(N2CCn3ncc(C)c3C2=O)c(F)cc1-c1ncc2cc(C(F)(F)F)ccc2n1]

Proceeding as described in Example 2, Step 11 above, but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one gave the title compound. Recrystallization from methanol gave pure product as a white solid in 56.68% yield. LC-MS: (ES, m/z): [M+H]+ 456; $^1$H-NMR: (300 MHz, DMSO-d6, ppm): δ 2.27 (s, 3H), 2.73 (s, 3H), 4.20 (t, 2H), 4.52 (t, 2H), 7.50 (s, 1H), 7.55 (d, 1H), 7.94 (d, 1H), 8.27-8.35 (m, 2H), 8.78 (s, 1H), 9.94 (s, 1H).

Example 26

Synthesis of 5-(2-fluoro-5-methyl-4-(8-methyl-6-(trifluoromethyl)quinazolin-2-yl)phenyl)-3-methyl-6,7-dihydropyrazolo[1,5-a]pyrazin-4 (5H)-one

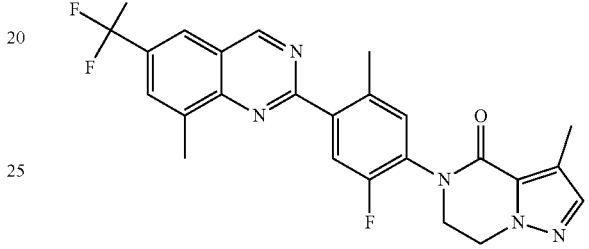

Proceeding as described in Example 2, Step 11 above but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 5-(2-fluoro-5-methyl-4-(4,4,5,5-tetramethyl-1,3,2-dioxaborolan-2-yl)phenyl)-3-methyl-6,7-dihydropyrazolo[1,5-a]pyrazin-4 (5H)-one and 2-chloro-6-(trifluoromethyl)-quinazoline with 2-chloro-8-methyl-6-(trifluoromethyl)-quinazoline gave the title compound as a white solid in 71.50% yield. LC-MS: (ES, m/z): [M+H]+ 470; $^1$H-NMR: (300 MHz, DMSO-d6, ppm): δ 2.27 (s, 3H), 2.71 (s, 3H), 2.82 (s, 3H), 4.20 (t, 2H), 4.52 (t, 2H), 7.49 (s, 1H), 7.56 (d, 1H), 8.05 (d, 1H), 8.20 (s, 1H), 8.56 (s, 1H), 9.88 (s, 1H).

Example 27

Synthesis of 1-methyl-6-(2-methyl-4-(6-(trifluoromethyl)-1,5-naphthyridin-2-yl)phenyl)-1,4,5,6-tetrahydro-7H-pyrazolo[3,4-c]pyridin-7-one

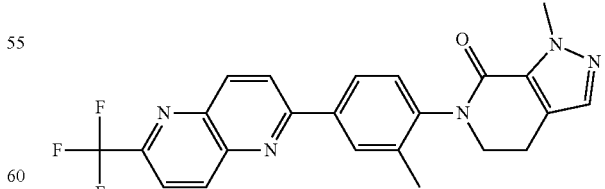

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 1-methyl-6-(2-methyl-4-(4,4,5,5-tetramethyl-1,3,2-dioxaborolan-2-yl)

phenyl)-1,4,5,6-tetrahydro-7H-pyrazolo[3,4-c]pyridin-7-one and 6-chloro-4-methyl-2-(trifluoromethyl)-1,5-naphthyridine with 2-chloro-6-(trifluoromethyl)-1,5-naphthyridine gave crude product. Purification by silica gel column chromatography using ethyl acetate/petroleum ether (1:5) as eluent gave the title compound as a white solid in 49% yield. LC-MS: (ES, m/z): [M+H]⁺ 438; ¹H-NMR: (400 MHz, DMSO, ppm): δ 2.34 (s, 3H), 2.91-3.05 (m, 2H), 3.72-3.77 (m, 1H), 4.05-4.12 (m, 4H), 7.49-7.54 (m, 2H), 8.24-8.26 (d, 2H), 8.33 (s, 1H), 8.60-8.62 (d, 1H), 8.68-8.80 (d, 1H), 8.79-8.80 (d, 1H).

Example 28

Synthesis of 1-methyl-6-(2-methyl-4-(8-methyl-6-(trifluoromethyl)-1,5-naphthyridin-2-yl)phenyl)-1,4,5,6-tetrahydro-7H-pyrazolo[3,4-c]pyridin-7-one

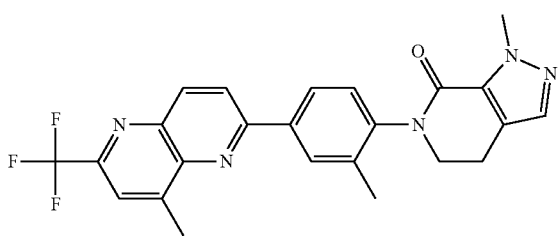 [SMILES: Cc1cc(-c2ccc3nc(C(F)(F)F)cc(C)c3n2)ccc1N1CCc2cnn(C)c2C1=O]

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 1-methyl-6-(2-methyl-4-(4,4,5,5-tetramethyl-1,3,2-dioxaborolan-2-yl)phenyl)-1,4,5,6-tetrahydro-7H-pyrazolo[3,4-c]pyridin-7-one gave crude product. Purification by silica gel column chromatography using ethyl acetate/petroleum ether (1:2) as eluent gave the title compound as a white solid in 72.20% yield. LC-MS: (ES, m/z): [M+H]⁺ 452; ¹H-NMR: (400 MHz, DMSO-d₆, ppm): δ 8.64 (d, 1H), 8.58 (d, 1H), 8.32 (s, 1H), 8.26 (dd, 1H), 8.15 (s, 1H), 7.52 (d, 1H), 7.48 (s, 1H), 4.05-4.12 (m, 4H), 3.72-3.78 (m, 1H), 2.90-3.03 (m, 5H), 2.34 (s, 3H).

Example 29

Synthesis of 1-methyl-7-(2-methyl-4-(6-(trifluoromethyl)quinazolin-2-yl)phenyl)-6,7-dihydro-1H-pyrazolo[3,4-f][1,4]oxazepin-8 (5H)-one

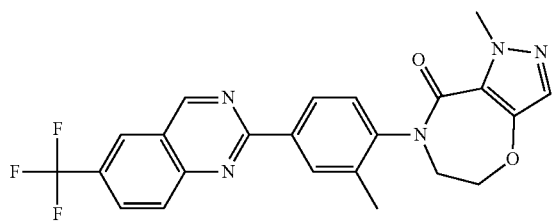 [SMILES: Cc1cc(-c2ncc3cc(C(F)(F)F)ccc3n2)ccc1N1CCOc2cnn(C)c2C1=O]

Proceeding as described in Example 2, Step 11 above but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one provide crude product. Purification of the crude product by silica gel column chromatography, by eluting with PE/EtOAc (3/1), followed by re-crystallized from PE/EtOAc (10/1, 50 mL) provided the title compound as an off-white solid in 48.59% yield. LC-MS: (ES, m/z): [M+H]⁺ 454; 1H-NMR: (300 MHz, DMSO, ppm): δ 2.34 (s, 3H), 3.97-4.05 (m, 5H), 4.46-4.58 (m, 2H), 7.37 (s, 1H), 7.48 (d, 1H), 8.25 (m, 2H), 8.48 (dd, 1H), 8.55 (d, 1H), 8.73 (s, 1H), 9.90 (s, 1H).

Example 30

Synthesis of 1-methyl-7-(2-methyl-4-(6-(trifluoromethyl)-1,5-naphthyridin-2-yl)phenyl)-6,7-dihydro-1H-pyrazolo[3,4-f][1,4]oxazepin-8 (5H)-one

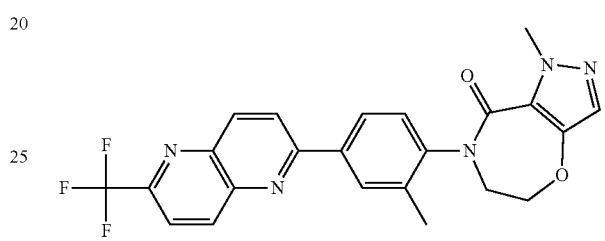

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one and 6-chloro-4-methyl-2-(trifluoromethyl)-1,5-naphthyridine with 2-chloro-6-(trifluoromethyl)-1,5-naphthyridine gave crude product. Purification by silica gel column chromatography using ethyl acetate/petroleum ether (1:3) as eluent, followed by recrystallization from PE/EtOAc (10:1) gave the title compound as an off-white solid in 69.10% yield. LC-MS: (ES, m/z): [M+H]⁺ 454; ¹H-NMR: (300 MHz, DMSO-d₆, ppm): δ 2.34 (s, 3H), 3.99-4.04 (m, 5H), 4.46-4.59 (m, 2H), 7.37 (s, 1H), 7.48 (d, 1H), 8.22-8.26 (m, 2H), 8.32 (d, 1H), 8.61 (d, 1H), 8.70 (d, 1H), 8.79 (d, 1H).

Example 31

Synthesis of 1-methyl-7-(2-methyl-4-(8-methyl-6-(trifluoromethyl)-1,5-naphthyridin-2-yl)phenyl)-6,7-dihydro-1H-pyrazolo[3,4-f][1,4]oxazepin-8 (5H)-one

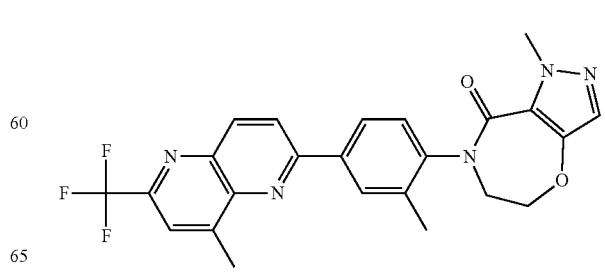

Proceeding as described in Example 5, Step 12 above, but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one gave crude product. Purification by silica gel column chromatography using ethyl acetate/petroleum ether (1:3) as eluent, followed by recrystallization from PE/EtOAc (10:1) gave the title compound as an off-white solid in 82% yield. LC-MS: (ES, m/z): [M+H]$^+$ 468; $^1$H-NMR: (300 MHz, DMSO-d6, ppm): δ 2.34 (s, 3H), 2.96 (s, 3H), 3.99-4.05 (m, 5H), 4.46-4.59 (m, 2H), 7.37 (s, 1H), 7.48 (d, 1H), 8.15 (d, 2H), 8.25 (dd, 1H), 8.31 (d, 1H), 8.57 (d, 1H), 8.64 (d, 1H).

Example 32

Synthesis of 7-(2,5-dimethyl-4-(6-(trifluoromethyl)-1,5-naphthyridin-2-yl)phenyl)-1-methyl-6,7-dihydro-1H-pyrazolo[3,4-f][1,4]oxazepin-8 (5H)-one

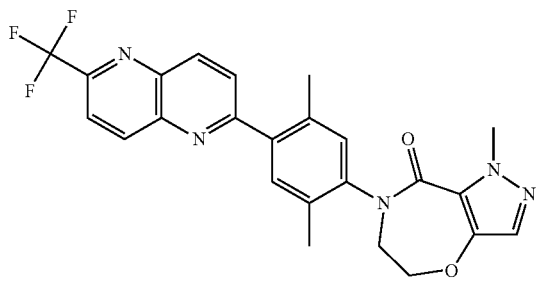 [SMILES: Cc1cc(N2CCOc3cnn(C)c3C2=O)c(C)cc1-c1ccc2nc(C(F)(F)F)ccc2n1]

Proceeding as described in Example 5, Step 12 above, but substituting 6-chloro-4-methyl-2-(trifluoromethyl)-1,5-naphthyridine with 6-chloro-2-(trifluoromethyl)-1,5-naphthyridine gave crude product. Purification by silica gel column chromatography using ethyl acetate/petroleum ether (1:10) as eluent gave the title compound as a white solid in 77.20% yield. LC-MS: (ES, m/z): [M+H]$^+$ 468; $^1$H-NMR: (300 MHz, DMSO, ppm): δ 2.24 (s, 3H), 2.40 (s, 3H), 3.97-4.01 (m, 5H), 4.46-4.58 (m, 2H), 7.29 (s, 1H), 7.36 (s, 1H), 7.54 (s, 1H), 8.16 (d, 1H), 8.27 (d, 1H), 8.69 (d, 1H), 8.77 (d, 1H).

Example 33

Synthesis of 7-(2-methyl-4-(6-(trifluoromethyl)quinazolin-2-yl)phenyl)-6,7-dihydro-H-pyrazolo[3,4-f][1,4]oxazepin-8 (5H)-one

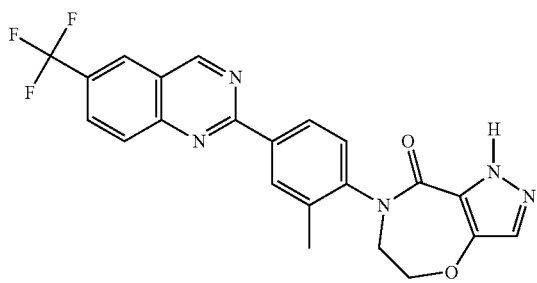 [SMILES: Cc1cc(-c2ncc3cc(C(F)(F)F)ccc3n2)ccc1N1CCOc2cn[nH]c2C1=O]

Step 1: Synthesis of methyl 4-bromo-1-(tetrahydro-2H-pyran-2-yl)-1H-pyrazole-5-carboxylate

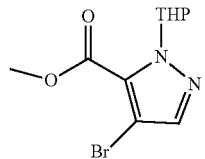

Into a 250-mL 3-necked round-bottom flask under N$_2$ atmosphere, was placed methyl 4-bromo-1H-pyrazole-5-carboxylate (7 g, 34.14 mmol, 1 equiv), 3,4-dihydro-2H-pyran (5.7 g, 68.29 mmol, 2 equiv), EA (70 mL), and PTSA (0.9 g, 5.12 mmol, 0.15 equiv). The resulting solution was stirred for 12 h at 80° C. and then quenched with water. The resulting solution was extracted with ethyl acetate. The residue was applied onto a silica gel column and eluted with ethyl acetate/petroleum ether (1:20) to give (7.1 g, 71.92%) of the title compound as a yellow liquid. LC-MS: (ES, m/z): [M+H]$^+$ 289

Step 2: Synthesis of 4-(2-(benzyloxy)ethoxy)-1-(tetrahydro-2H-pyran-2-yl)-1H-pyrazole-5-carboxylic acid

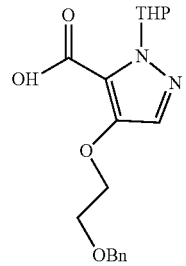

Into a 100-mL 3-necked round-bottom flask under N$_2$ atmosphere, was placed methyl 4-bromo-1-(tetrahydro-2H-pyran-2-yl)-1H-pyrazole-5-carboxylate (7 g, 24.21 mmol, 1 equiv), 2-(benzyloxy)ethan-1-ol (25 mL), Cs$_2$CO$_3$ (23.7 g, 72.63 mmol, 3 equiv), CuCl$_2$ (0.3 g, 2.42 mmol, 0.1 equiv). The resulting solution was stirred for 12 h at 130° C. The resulting solution was extracted with ethyl acetate and the pH value of the solution was adjusted to 5 with HOAc. The resulting solution was extracted with ethyl acetate and the organic layer was concentrated. The residue was applied onto a silica gel column and eluted with ethyl acetate/petroleum ether (1:1) to give (3.1 g, 36.97%) of the title compound as a yellow liquid. LC-MS: (ES, m/z): [M+H]$^+$ 347.

Step 3: Synthesis of 4-(2-(benzyloxy)ethoxy)-N-(4-bromo-2-methylphenyl)-1-(tetrahydro-2H-pyran-2-yl)-1H-pyrazole-5-carboxamide

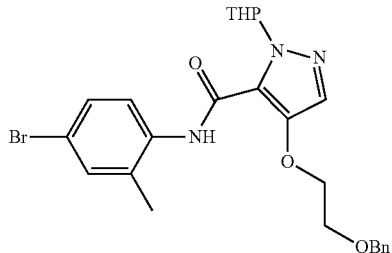

Into a 100-mL 3-necked round-bottom flask under N₂ atmosphere, was placed 4-(2-(benzyloxy)ethoxy)-1-(tetrahydro-2H-pyran-2-yl)-1H-pyrazole-5-carboxylic acid (3.07 g, 8.86 mmol, 1 equiv), 4-bromo-2-methylaniline (2.0 g, 10.64 mmol, 1.2 equiv), DIEA (2.3 g, 17.73 mmol, 2 equiv), DMF (30 mL), and HATU (5.1 g, 13.29 mmol, 1.5 equiv). The resulting solution was stirred for 12 h at 25° C. and then quenched with water. The resulting solution was extracted with ethyl acetate. The residue was applied onto a silica gel column and eluted with ethyl acetate/petroleum ether (1:5). The crude product was purified by re-crystallization from MeOH to give (2.88 g, 63.17%) of the title compound as a white solid. LC-MS: (ES, m/z): [M+H]⁺ 514.

Step 4: Synthesis of 4-(2-(benzyloxy)ethoxy)-N-(2-methyl-4-(4,4,5,5-tetramethyl-1,3,2-dioxaborolan-2-yl)phenyl)-1-(tetrahydro-2H-pyran-2-yl)-1H-pyrazole-5-carboxamide

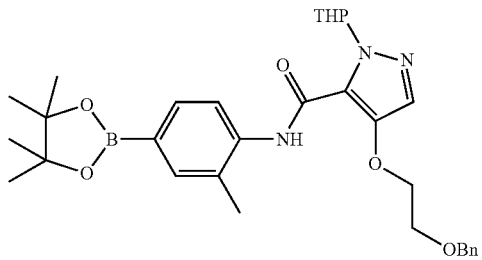

Into a 100-mL 3-necked round-bottom flask under N₂ atmosphere, was placed 4-(2-(benzyloxy)ethoxy)-N-(4-bromo-2-methylphenyl)-1-(tetrahydro-2H-pyran-2-yl)-1H-pyrazole-5-carboxamide (2.88 g, 5.60 mmol, 1 equiv), B₂Pin₂ (2.1 g, 8.27 mmol, 1.48 equiv), KOAc (1.1 g, 11.20 mmol, 2 equiv), dioxane (30 mL), and Pd(dppf)Cl₂ (0.6 g, 0.84 mmol, 0.15 equiv). The resulting solution was stirred for 12 h at 80° C. and the resulting mixture was concentrated. The residue was applied onto a silica gel column and eluted with ethyl acetate/petroleum ether (1:5) to give (2.5 g, 81.57%) of the title compound as a yellow solid. LC-MS: (ES, m/z): [M+H]⁺ 562.

Step 5: Synthesis of 4-(2-hydroxyethoxy)-N-(2-methyl-4-(4,4,5,5-tetramethyl-1,3,2-dioxaborolan-2-yl)phenyl)-1-(tetrahydro-2H-pyran-2-yl)-1H-pyrazole-5-carboxamide

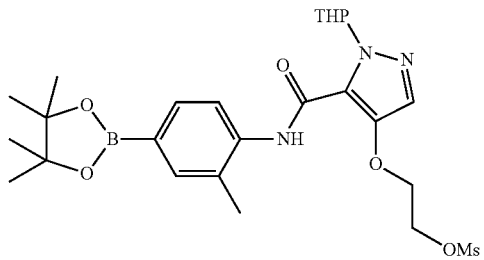

Into a 250-mL 3-necked round-bottom flask, was placed 4-(2-(benzyloxy)ethoxy)-N-(2-methyl-4-(4,4,5,5-tetramethyl-1,3,2-dioxaborolan-2-yl)phenyl)-1-(tetrahydro-2H-pyran-2-yl)-1H-pyrazole-5-carboxamide (2.46 g, 4.49 mmol, 1 equiv), MeOH (100 mL), and Pd/C (0.5 g), H₂₍g₎ passed through the reaction mixture. The resulting solution was stirred for 2 h at 70° C. under the atmosphere of H₂. The solids were filtered out and the filtrate was concentrated to give (1.7 g, 80.26%) of the title compound as a white solid. LC-0575-5: (ES, m/z): [M+H]⁺ 472.

Step 6: Synthesis of 2-((5-((2-methyl-4-(4,4,5,5-tetramethyl-1,3,2-dioxaborolan-2-yl)phenyl)carbamoyl)-1-(tetrahydro-2H-pyran-2-yl)-1H-pyrazol-4-yl)oxy)ethyl methanesulfonate Into a 100-mL 3-necked round-bottom flask under N₂ atmosphere, was placed 4-(2-hydroxyethoxy)-N-(2-methyl-4-(4,4,5,5-tetramethyl-1,3,2-dioxaborolan-2-yl)phenyl)-1-(tetrahydro-2H-pyran-2-yl)-1H-pyrazole-5-carboxamide (1.68 g, 3.56 mmol, 1 equiv), Et₃N (0.7 g, 7.13 mmol, 2 equiv), and DCM (40 mL), and MsCl (0.8 g, 7.13 mmol, 2 equiv) was added dropwise. The resulting solution was stirred for 1 h at 0° C. and then quenched with water. The resulting solution was extracted with dichloromethane and the organic layer was concentrated. The crude product was purified by re-crystallization from MeOH to give (1.85 g, 94.47%) of the title compound as a yellow solid. LC-MS: (ES, m/z): [M+H]⁺ 550.

Step 7: Synthesis of 7-(2-methyl-4-(4,4,5,5-tetramethyl-1,3,2-dioxaborolan-2-yl)phenyl)-1-(tetrahydro-2H-pyran-2-yl)-6,7-dihydro-1H-pyrazolo[3,4-f][1,4]oxazepin-8 (5H)-one

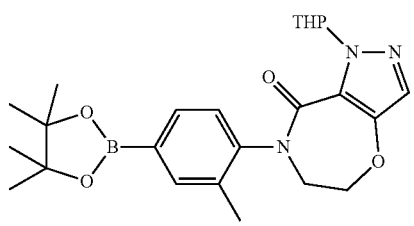

Into a 100-mL 3-necked round-bottom flask under N₂ atmosphere, was placed 2-((5-((2-methyl-4-(4,4,5,5-tetramethyl-1,3,2-dioxaborolan-2-yl)phenyl)carbamoyl)-1-(tetrahydro-2H-pyran-2-yl)-1H-pyrazol-4-yl)oxy)ethyl methanesulfonate (1.84 g, 3.35 mmol, 1 equiv) and DMF (40 mL), and NaH (60%) (0.27 g, 11.25 mmol, 3.36 equiv) was added at 0° C. The resulting solution was stirred for 1 h at 0° C. and then quenched with NH₄Cl(aq.). The resulting solution was extracted with ethyl acetate and the organic layer was concentrated. The residue was applied onto a silica gel column and eluted with dichloromethane/methanol (50:1) to give (1.45 g, 95.51%) of the title compound as a yellow solid. LC-MS: (ES, m/z): [M+H]⁺=454.

Step 8: Synthesis of 7-(2-methyl-4-(6-(trifluoromethyl)quinazolin-2-Yl)phenyl)-1-(tetrahydro-2H-pyran-2-yl)-6,7-dihydro-1H-pyrazolo[3,4-f][1,4]oxazepin-8 (5H)-one

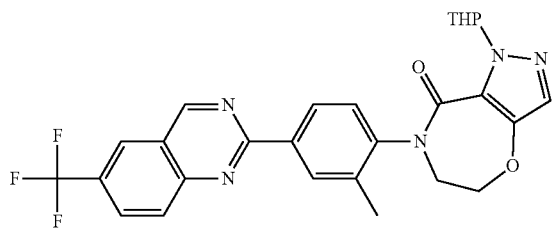

Into a 100-mL 3-necked round-bottom flask under N₂ atmosphere, was placed 7-(2-methyl-4-(4,4,5,5-tetramethyl-1,3,2-dioxaborolan-2-yl)phenyl)-1-(tetrahydro-2H-pyran-2-yl)-6,7-dihydro-1H-pyrazolo[3,4-f][1,4]oxazepin-8 (5H)-one (1.42 g, 3.13 mmol, 1 equiv), 2-chloro-6-(trifluoromethyl)quinazoline (0.9 g, 3.76 mmol, 1.2 equiv), K₂CO₃ (1.3 g, 9.40 mmol, 3 equiv), toluene (20 mL), EtOH (10 mL), and Pd(PPh₃)₄ (0.5 g, 0.47 mmol, 0.15 equiv). The resulting solution was stirred for 12 h at 80° C. and then concentrated under vacuum. The residue was applied onto a silica gel column and eluted with ethyl acetate/petroleum ether (1:1). The crude product was purified by re-crystallization from MeOH to give (1.4 g, 85.38%) of the title compound as a white solid. LC-MS: (ES, m/z): [M+H]⁺ 524.

Step 9: Synthesis of 7-(2-methyl-4-(6-(trifluoromethyl)quinazolin-2-yl)phenyl)-6,7-dihydro-1H-pyrazolo[3,4-f][1,4]oxazepin-8 (5H)-one

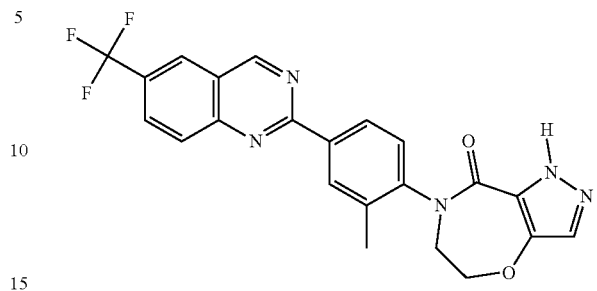

Into a 25-mL 3-necked round-bottom flask under N₂ atmosphere, was placed 7-(2-methyl-4-(6-(trifluoromethyl)quinazolin-2-yl)phenyl)-1-(tetrahydro-2H-pyran-2-yl)-6,7-dihydro-1H-pyrazolo[3,4-f][1,4]oxazepin-8 (5H)-one (1.4 g, 2.67 mmol, 1 equiv) in HCl/dioxane (10 mL). The resulting solution was stirred for 1 h at 25° C. and then quenched by the addition of 20 mL of NaHCO₃(aq.). The resulting solution was extracted with dichloromethane. The residue was applied onto a silica gel column and eluted with ethyl acetate/petroleum ether (1:1) to give (0.8 g, 68.08%) of the title compound as a white solid. LC-MS: (ES, m/z): [M+H]⁺ 440. ¹H-NMR: (300 MHz, DMSO-d6, ppm): δ 2.27 (s, 3H), 3.93-4.09 (m, 2H), 4.41-4.61 (m, 2H), 7.40 (s, 1H), 7.48 (d, 1H), 8.28 (t, 2H), 8.47 (dd, 2H), 8.54 (s, 1H), 8.73 (s, 1H), 9.90 (s, 1H), 13.13-13.20 (s, 1H).

Example 34

Synthesis 1-(2-hydroxyethyl)-7-(2-methyl-4-(6-(trifluoromethyl)quinazolin-2-yl)phenyl)-6,7-dihydro-1H-pyrazolo[3,4-f][1,4]oxazepin-8 (5H)-one

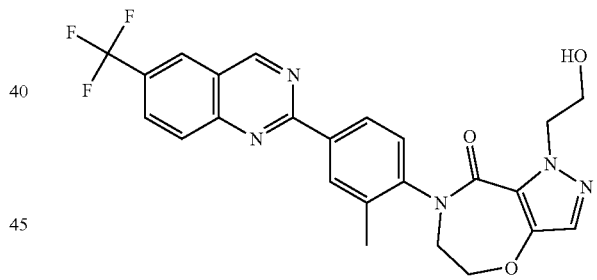

Step 1: Synthesis of 1-(2-(benzyloxy)ethyl)-7-(2-methyl-4-(6-(trifluoromethyl)quinazolin-2-yl)phenyl)-6,7-dihydro-1H-pyrazolo[3,4-f][1,4]oxazepin-8 (5H)-one

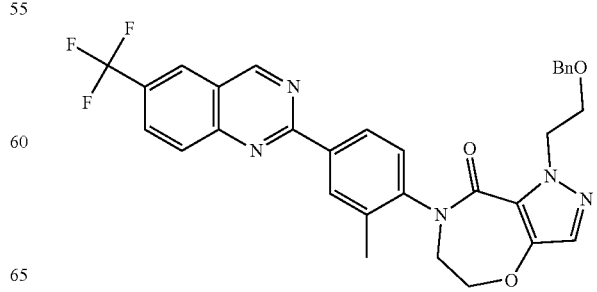

Into a 8-mL sealed tube under N$_2$ atmosphere, was placed 7-(2-methyl-4-(6-(trifluoromethyl)quinazolin-2-yl)phenyl)-6,7-dihydro-1H-pyrazolo[3,4-f][1,4]oxazepin-8 (5H)-one (200 mg, 0.46 mmol, 1 equiv), [(2-bromoethoxy)methyl]benzene (107.7 mg, 0.50 mmol, 1.1 equiv), and K$_2$CO$_3$ (125.8 mg, 0.91 mmol, 2 equiv) in DMF (2 mL). The resulting solution was stirred for 12 h at 80° C. and then quenched with water. The resulting solution was extracted with ethyl acetate and the organic layer was concentrated. The residue was applied onto Prep-TLC and eluted with ethyl acetate/petroleum ether (1:1) to give (100 mg, 38.30%) of the title compound as a yellow solid. LC-MS-PH: (ES, m/z): [M+H]$^+$ 574.

Step 2: Synthesis 1-(2-hydroxyethyl)-7-(2-methyl-4-(6-(trifluoromethyl)quinazolin-2-yl)phenyl)-6,7-dihydro-1H-pyrazolo[3,4-f][1,4]oxazepin-8 (5H)-one

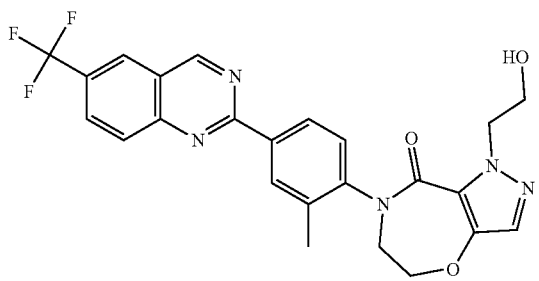 [SMILES: Cc1cc(-c2ncc3cc(C(F)(F)F)ccc3n2)ccc1N1CCOc2cnn(CCO)c2C1=O]

Into a 8-mL sealed tube under N$_2$ atmosphere, was placed 1-(2-(benzyloxy)ethyl)-7-(2-methyl-4-(6-(trifluoromethyl)quinazolin-2-yl)phenyl)-6,7-dihydro-1H-pyrazolo[3,4-f][1,4]oxazepin-8 (5H)-one (100 mg, 0.17 mmol, 1 equiv), DCM (2 mL), and BCl$_3$ (0.26 mL, 0.26 mmol, 1.5 equiv). The resulting solution was stirred for 1 hr at 0° C. The reaction was then quenched with 20 mL of NaHCO$_3$ and the resulting solution was extracted with ethyl acetate. The residue was applied onto Prep-TLC and eluted with dichloromethane/methanol (20:1) to give (48.2 mg, 57.19%) of the title compound as a white solid. LC-MS: (ES, m/z): [M+H]$^+$ 484. $^1$H-NMR-PH-IDE-0578-0: (300 MHz, DMSO-d6, ppm): δ 2.33 (s, 3H), 3.62-3.68 (m, 2H), 3.64 (q, 2H), 4.37-4.44 (m, 1H), 4.46-4.63 (m, 3H), 4.75-4.78 (m, 1H), 7.39 (s, 1H), 7.47 (d, 1H), 8.25 (s, 1H), 8.30 (d, 1H), 8.50 (s, 1H), 8.73 (s, 1H), 9.91 (s, 1H).

Example 35

Synthesis of 2-(7-(2-methyl-4-(6-(trifluoromethyl)quinazolin-2-yl)phenyl)-8-oxo-5,6,7,8-tetrahydro-2H-pyrazolo[3,4-f][1,4]oxazepin-2-yl)acetonitrile

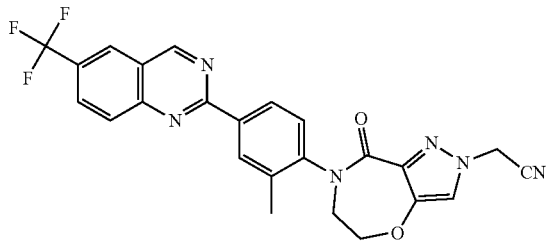 [SMILES: Cc1cc(-c2ncc3cc(C(F)(F)F)ccc3n2)ccc1N1CCOc2cn(CC#N)nc2C1=O]

To a stirred mixture of 7-(2-methyl-4-(6-(trifluoromethyl)quinazolin-2-yl)phenyl)-6,7-dihydro-1H-pyrazolo[3,4-f][1,4]oxazepin-8 (5H)-one (240 mg, 0.55 mmol, 1 equiv) and 2-bromoacetonitrile (131.0 mg, 1.09 mmol, 2 equiv) in DMF (4.8 mL) were added K$_2$CO$_3$ (226.5 mg, 1.64 mmol, 3 equiv). The resulting mixture was stirred for overnight at 80° C. in an oil bath. The reaction was quenched with water and extracted with EtOAc. The combined organic layers were concentrated under reduced pressure. The residue was purified by Prep-TLC (CH$_2$Cl$_2$/MeOH 30/1) to afford the title compound (50 mg, 19.13%) as a grey solid. LC-MS: (ES, m/z): [M+H]$^+$ 479. $^1$H-NMR: (400 MHz, DMSO-d6, ppm): δ 2.32 (s, 3H), 3.95-4.06 (m, 2H), 4.44-4.58 (m, 2H), 5.54 (s, 2H), 7.46 (d, 1H), 7.82 (s, 1H), 8.28 (s, 2H), 8.48 (d, 1H), 8.54 (s, 1H), 8.73 (s, 1H), 9.91 (s, 1H).

Example 36

Synthesis of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetonitrile

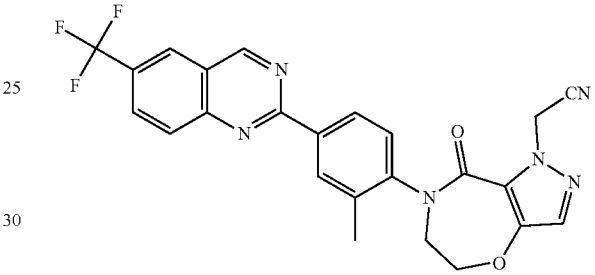

To a stirred mixture of 7-(2-methyl-4-(6-(trifluoromethyl)-quinazolin-2-yl)phenyl)-6,7-dihydro-1H-pyrazolo[3,4-f][1,4]oxazepin-8 (5H)-one (240 mg, 0.55 mmol, 1 equiv) and 2-bromoacetonitrile (131.0 mg, 1.09 mmol, 2 equiv) in DMF (4.8 mL) was added K$_2$CO$_3$ (226.5 mg, 1.64 mmol, 3 equiv). The resulting mixture was stirred overnight at 80° C. in an oil bath. The reaction was quenched with water and the resulting mixture was extracted with EtOAc. The combined organic layers were concentrated under reduced pressure. The residue was purified by Prep-TLC (CH$_2$Cl$_2$/MeOH 30/1) to afford the title compound (80 mg, 30.61%) as a yellow solid. LC-MS: (ES, m/z): [M+H]$^+$ 479. $^1$H-NMR: (300 MHz, DMSO-d6, ppm): δ 2.35 (s, 3H), 4.04-4.10 (m, 2H), 4.53-4.65 (m, 2H), 5.55-5.68 (m, 2H), 7.50 (d, 1H), 7.63 (s, 1H), 8.28 (s, 2H), 8.49 (dd, 1H), 8.55 (s, 1H), 8.73 (s, 1H), 9.91 (s, 1H).

Example 37

Synthesis of 2-(2-hydroxyethyl)-7-(2-methyl-4-(6-(trifluoromethyl)quinazolin-2-yl)phenyl)-6,7-dihydro-2H-pyrazolo[3,4-f][1,4]oxazepin-8 (5H)-one

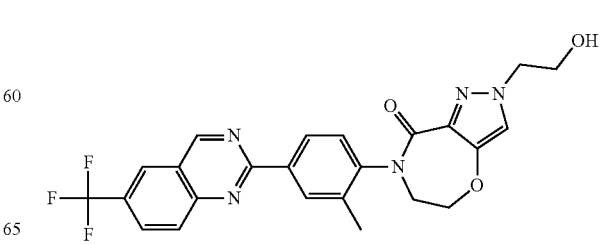

123

Step 1: Synthesis of 2-(2-(benzyloxy)ethyl)-7-(2-methyl-4-(6-(trifluoromethyl)quinazolin-2-yl)phenyl)-6,7-dihydro-2H-pyrazolo[3,4-f][1,4]oxazepin-8 (5H)-one

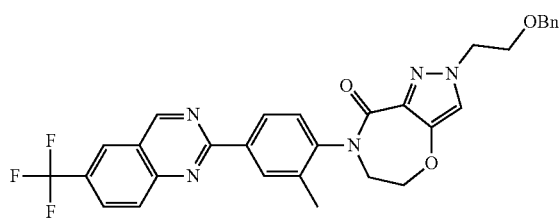 [SMILES: Cc1cc(-c2ncc3cc(C(F)(F)F)ccc3n2)ccc1N1CCOc2cn(CCOCc3ccccc3)nc2C1=O]

Into a 8-mL sealed tube under N₂ atmosphere, was placed 7-(2-methyl-4-(6-(trifluoromethyl)quinazolin-2-yl)phenyl)-6,7-dihydro-1H-pyrazolo[3,4-f][1,4]oxazepin-8 (5H)-one (200 mg, 0.46 mmol, 1 equiv), [(2-bromoethoxy)-methyl]benzene (107.7 mg, 0.50 mmol, 1.1 equiv), and K₂CO₃ (125.8 mg, 0.91 mmol, 2 equiv) in DMF (2 mL). The resulting solution was stirred for 12 h at 80° C. The reaction was then quenched with water. The resulting solution was extracted with ethyl acetate and the organic layer concentrated. The residue was applied onto Prep-TLC and eluted with ethyl acetate/petroleum ether (1:1) to give (100 mg, 38.30%) of the title compound as a yellow solid. LC-MS: (ES, m/z): [M+H]⁺ 574.

Step 2: Synthesis of 2-(2-hydroxyethyl)-7-(2-methyl-4-(6-(trifluoromethyl)quinazolin-2-yl)phenyl)-6,7-dihydro-2H-pyrazolo[3,4-f][1,4]oxazepin-8 (5H)-one

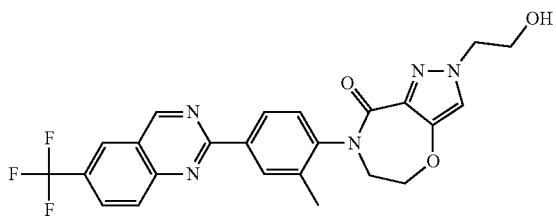 [SMILES: Cc1cc(-c2ncc3cc(C(F)(F)F)ccc3n2)ccc1N1CCOc2cn(CCO)nc2C1=O]

Into a 8-mL sealed tube under N₂ atmosphere, was placed 2-(2-(benzyloxy)ethyl)-7-(2-methyl-4-(6-(trifluoromethyl)quinazolin-2-yl)phenyl)-6,7-dihydro-2H-pyrazolo[3,4-f][1,4]oxazepin-8 (5H)-one (100 mg, 0.17 mmol, 1 equiv) in DCM (2 mL) and BCl₃ (30.3 mg, 0.26 mmol, 1.5 equiv) was added. The resulting solution was stirred for 1 h at 0° C. The reaction mixture was then quenched with NaHCO₃ and the resulting solution was extracted with ethyl acetate. The residue was applied onto Prep-TLC and eluted with dichloromethane/methanol (20:1) to give (19.7 mg, 23.37%) of the title compound as a yellow solid. LC-MS: (ES, m/z): [M+H]⁺ 484. ¹H-NMR: (300 MHz, DMSO-d6, ppm): δ 2.35 (s, 3H), 3.66-3.78 (m, 2H), 3.76-3.97 (m, 2H), 4.15-4.25 (m, 2H), 4.43-4.68 (m, 2H), 4.88-5.10 (m, 1H), 7.43 (d, 1H), 7.65 (s, 1H), 8.27 (s, 2H), 8.48 (d, 1H), 8.52 (s, 1H), 8.82 (s, 1H), 9.98 (s, 1H).

124

Example 38

Synthesis of 7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

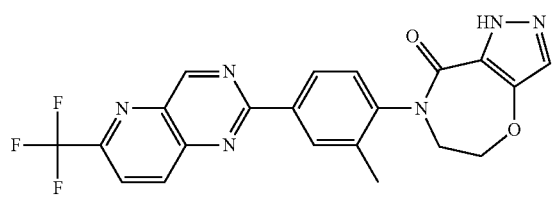 [SMILES: Cc1cc(-c2ncc3nc(C(F)(F)F)ccc3n2)ccc1N1CCOc2cn[nH]c2C1=O]

Step 1: Synthesis of 7-(2-methyl-4-(6-(trifluoromethyl)pyrido[3,2-d]pyrimidin-2-yl)phenyl)-1-(tetrahydro-2H-pyran-2-yl)-6,7-dihydro-1H-pyrazolo[3,4-f][1,4]oxazepin-8 (5H)-one

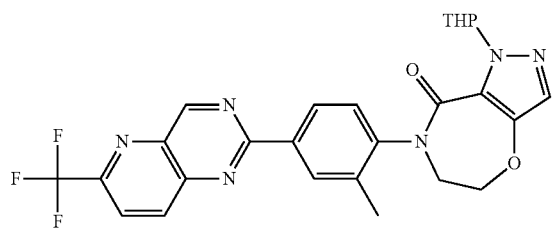

Proceeding analogously as described in Example 2, Step 11, but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 7-[2-methyl-4-(4,4,5,5-tetramethyl-1,3,2-dioxaborolan-2-yl)phenyl]-1-(oxan-2-yl)-1H,5H,6H,7H,8H-pyrazolo[3,4-f][1,4]oxazepin-8-one and 2-chloro-6-(trifluoromethyl)-quinazoline with 2-chloro-6-(trifluoromethyl)pyrido[3,2-d]pyrimidine gave (650 mg, 37.45%) of the title compound as a red solid.

Step 2: Synthesis of 7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

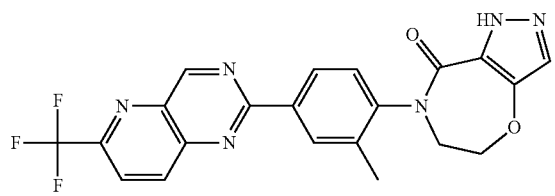 [SMILES: Cc1cc(-c2ncc3nc(C(F)(F)F)ccc3n2)ccc1N1CCOc2cn[nH]c2C1=O]

Into a 8-mL vial, was placed 7-(2-methyl-4-(6-(trifluoromethyl)pyrido[3,2-d]pyrimidin-2-yl)phenyl)-1-(tetrahydro-2H-pyran-2-yl)-6,7-dihydro-1H-pyrazolo[3,4-f][1,4]oxazepin-8 (5H)-one (600 mg, 1.14 mmol, 1 equiv), dioxane (1 mL), HCl (12M) (1 mL). The resulting solution was stirred for 2 h at room temperature. The reaction mixture was then quenched by the addition of solution of Na₂CO₃ and the resulting solution was extracted with ethyl acetate and concentrated under vacuum. The residue was applied onto a silica gel column with dichloromethane/methanol (30:1). The crude product (70 mg) was purified by Prep-HPLC under the following conditions (2 #SHIMADZU (HPLC-01)): Column, XBridge Prep OBD C18 Column, 30 150 mm 5 um; mobile phase, Water (0.05% NH$_3$H$_2$O) and ACN (42% PhaseB up to 52% in 7 min); Detector, UV) to give (13.9 mg, 2.76%) of the title compound as a white solid.

LC-MS: (ES, m/z): [M+H]$^+$ 441.2; $^1$H-NMR: (300 MHz, DMSO-d$_6$, ppm): δ 13.24 (s, 1H) 9.95 (s, 1H), 8.80 (d, 1H), 8.54 (s, 1H), 8.46 (dd, 2H), 7.49 (d, 1H), 7.40 (s, 1H), 4.54 (d, 1H), 4.45 (d, 1H), 3.99 (t, 2H), 2.32 (s, 3H).

Example 39

Synthesis of 7-(2-methyl-4-(6-(trifluoromethyl)-1,5-naphthyridin-2-yl)phenyl)-6,7-dihydro-3H-[1,2,3]triazolo[4,5-f][1,4]oxazepin-8 (5H)-one

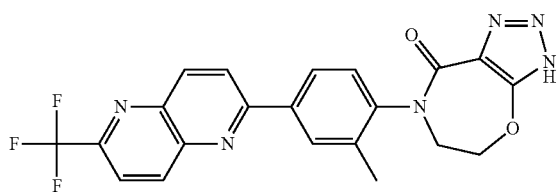 [SMILES: Cc1cc(-c2ccc3nc(C(F)(F)F)ccc3n2)ccc1N1CCOc2[nH]nnc2C1=O]

Step 1: Synthesis of ethyl 5-hydroxy-1-(4-methoxybenzyl)-1H-1,2,3-triazole-4-carboxylate

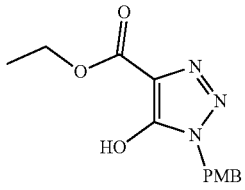

Into a 500-mL 3-necked round-bottom flask under N$_2$ atmosphere, were placed 1-(azidomethyl)-4-methoxybenzene (20 g, 122.56 mmol, 1 equiv), 1,3-diethyl propanedioate (29.4 g, 183.85 mmol, 1.5 equiv), EA (200 mL), and PTSA (3.2 g, 18.38 mmol, 0.15 equiv). The resulting solution was stirred for 12 h at 80° C. and then concentrated. The residue was applied onto a silica gel column and eluted with ethyl acetate/petroleum ether (1:20) to give (30 g, 88.28%) of the title compound as a yellow solid.

Step 2: Synthesis of 5-hydroxy-1-(4-methoxybenzyl)-1H-1,2,3-triazole-4-carboxylic acid

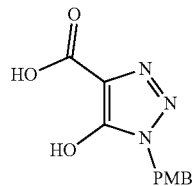

Into a 1000-mL 3-necked round-bottom under N$_2$ atmosphere, were placed ethyl 5-hydroxy-1-(4-methoxybenzyl)-1H-1,2,3-triazole-4-carboxylate (30 g, 108.19 mmol, 1 equiv), NaOH (4.8 g, 119.01 mmol, 1.1 equiv), H$_2$O (150 mL), and MeOH (300 mL). The resulting solution was stirred for 3 h at 25° C. and then concentrated under vacuum. After adding water, the pH value of the solution was adjusted to 5 with HCl. The resulting solution was extracted with ethyl acetate and concentrated to give (20 g, 74.17%) of the title compound as a yellow solid.

Step 3: Synthesis of N-(4-bromo-2-methylphenyl)-5-hydroxy-1-(4-methoxybenzyl)-1H-1,2,3-triazole-4-carboxamide

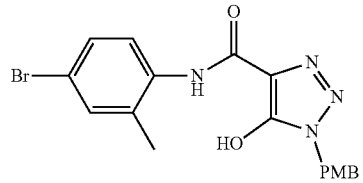

Into a 500-mL 3-necked round-bottom under N$_2$ atmosphere, were placed 5-hydroxy-1-(4-methoxybenzyl)-1H-1,2,3-triazole-4-carboxylic acid (20 g, 80.25 mmol, 1 equiv), 4-bromo-2-methylaniline (22.4 g, 120.37 mmol, 1.5 equiv), T$_3$P (38.3 g, 120.37 mmol, 1.5 equiv), DIEA (20.7 g, 160.50 mmol, 2 equiv), and THF (200 mL). The resulting solution was stirred for 12 h at 60° C. and then concentrated. The residue was applied onto a silica gel column and eluted with ethyl acetate/petroleum ether (1:20) to give (25 g, 74.66%) of the title compound as a yellow solid.

Step 4: Synthesis of 7-(4-bromo-2-methylphenyl)-3-(4-methoxybenzyl)-6,7-dihydro-3H-[1,2,3]triazolo[4,5-f][1,4]oxazepin-8 (5H)-one

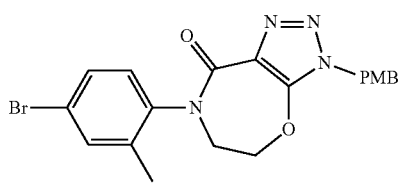

Into a 250-mL 3-necked round-bottom flask under N$_2$ atmosphere, were placed N-(4-bromo-2-methylphenyl)-5-hydroxy-1-(4-methoxy-benzyl)-1H-1,2,3-triazole-4-carboxamide (10 g, 23.97 mmol, 1 equiv), DMF (100 mL), 1,2-dibromoethane (5.4 g, 28.76 mmol, 1.2 equiv), and K$_2$CO$_3$ (6.6 g, 47.93 mmol, 2 equiv). The resulting solution was stirred for 12 h at 80° C. and then quenched with water. The resulting solution was extracted with ethyl acetate and then concentrated. The residue was applied onto a silica gel column and eluted with dichloromethane/methanol (30:1) to give (4 g, 37.65%) of the title compound as a yellow solid.

Step 5: Synthesis of 3-(4-methoxybenzyl)-7-(2-methyl-4-(4,4,5,5-tetramethyl-1,3,2-dioxaborolan-2-yl)phenyl)-6,7-dihydro-3H-[1,2,3]triazolo[4,5-f][1,4]oxazepin-8 (5H)-one

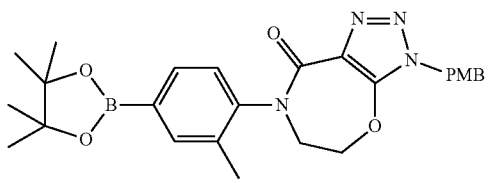

Proceeding analogously as described in Example 1, Step 12 but substituting 7-(4-bromo-2-methylphenyl)-1-methyl-6,7-dihydro-1H-pyrazolo[3,4-f]-[1,4]oxazepin-8 (5H)-one with 7-(4-bromo-2-methylphenyl)-3-(4-methoxybenzyl)-6,7-dihydro-3H-[1,2,3]triazolo[4,5-f][1,4]oxazepin-8 (5H)-one provided (2.6 g, 58.76%) of the title compound as a yellow solid.

Step 6: Synthesis of 3-(4-methoxybenzyl)-7-(2-methyl-4-(6-(trifluoromethyl)-1,5-naphthyridin-2-yl)phenyl)-6,7-dihydro-3H-[1,2,3]triazolo[4,5-f][1,4]oxazepin-8 (5H)-one

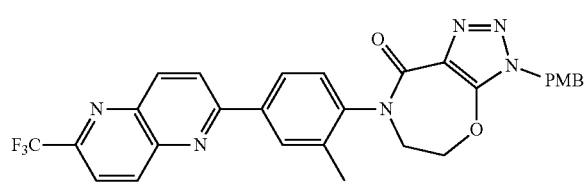

Proceeding analogously as described in Example 5, Step 12, but substituting 6-chloro-4-methyl-2-(trifluoromethyl)-1,5-naphthyridine with 2-chloro-6-(trifluoromethyl)-1,5-naphthyridine and 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 3-(4-methoxybenzyl)-7-(2-methyl-4-(4,4,5,5-tetramethyl-1,3,2-dioxaborolan-2-yl)phenyl)-6,7-dihydro-3H-[1,2,3]triazolo[4,5-f][1,4]oxazepin-8 (5H)-one provided crude product which was purified by re-crystallization from MeOH to give (450 mg, 65.27%) of the title compound as a yellow solid.

Step 7: Synthesis of 7-(2-methyl-4-(6-(trifluoromethyl)-1,5-naphthyridin-2-yl)phenyl)-6,7-dihydro-3H-[1,2,3]triazolo[4,5-f][1,4]oxazepin-8 (5H)-one

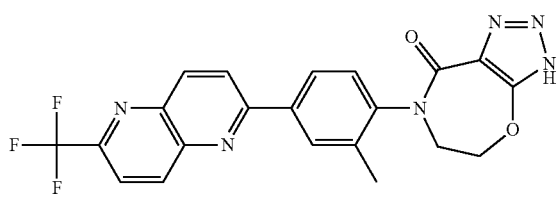 [SMILES: Cc1cc(-c2ccc3nc(C(F)(F)F)ccc3n2)ccc1N1CCOc2[nH]nnc2C1=O]

Into an 8-mL sealed tube under N₂ atmosphere, were placed 3-(4-methoxybenzyl)-7-(2-methyl-4-(6-(trifluoromethyl)-1,5-naphthyridin-2-yl)phenyl)-6,7-dihydro-3H-[1,2,3]triazolo[4,5-f][1,4]oxazepin-8 (5H)-one (400 mg, 0.71 mmol, 1 equiv) and TFA (4 mL). The resulting solution was stirred for 2 h at 80° C. and then concentrated. The crude product was purified by re-crystallization from MeOH to give (197.9 mg, 62.97%) of the title compound as a yellow solid. LC-MS: (ES, m/z): [M+H]⁺ 441.3H; ¹H NMR: (300 MHz, DMSO-d₆, ppm): δ 2.34 (s, 3H), 3.88-3.92 (m, 1H), 4.25-4.28 (m, 1H), 4.61-4.67 (m, 2H), 7.52 (d, 1H), 8.25 (d, 2H), 8.30 (s, 1H), 8.60 (d, 1H), 8.69 (d, 1H), 8.79 (d, 1H).

Example 40

Synthesis of 7-[2-methyl-4-[6-(trifluoromethyl)pyrido[3,2-d]pyrimidin-2-yl]phenyl]-1H,5H,6H,7H,8H-[1,2,3]triazolo[4,5-f][1,4]oxazepin-8-one

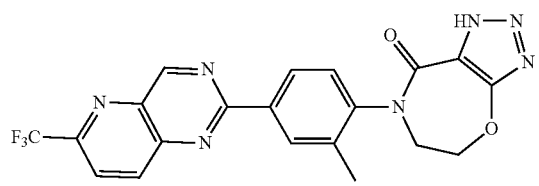 [SMILES: Cc1cc(-c2ncc3nc(C(F)(F)F)ccc3n2)ccc1N1CCOc2nn[nH]c2C1=O]

Step 1: Synthesis of 1-[(4-methoxyphenyl)methyl]-7-[2-methyl-4-[6-(trifluoromethyl)-pyrido-[3,2-d]pyrimidin-2-yl]phenyl]-1H,5H,6H,7H,8H-[1,2,3]triazolo[4,5-f][1,4]oxazepin-8-one

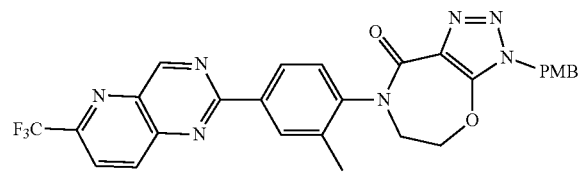

Proceeding analogously as described in Example 1, Step 13 but substituting 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one with 3-(4-methoxybenzyl)-7-(2-methyl-4-(4,4,5,5-tetramethyl-1,3,2-dioxaborolan-2-yl)phenyl)-6,7-dihydro-3H-[1,2,3]triazolo[4,5-f][1,4]oxazepin-8 (5H)-one provided (250 mg, 19.94%) of the title compound after silica gel column chromatograph with ethyl acetate/petroleum ether (1:1).

Step 2: Synthesis of 7-[2-methyl-4-[6-(trifluoromethyl)pyrido[3,2-d]pyrimidin-2-yl]phenyl]-1H,5H,6H,7H,8H-[1,2,3]triazolo[4,5-f][1,4]oxazepin-8-one

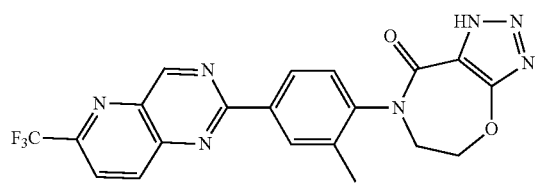 [SMILES: Cc1cc(-c2ncc3nc(C(F)(F)F)ccc3n2)ccc1N1CCOc2nn[nH]c2C1=O]

Proceeding analogously as described in Example 39, Step 7 but substituting 3-(4-methoxybenzyl)-7-(2-methyl-4-(6-(trifluoromethyl)-1,5-naphthyridin-2-yl)phenyl)-6,7-dihydro-3H-[1,2,3]triazolo[4,5-f][1,4]oxazepin-8 (5H)-one with 1-[(4-methoxyphenyl)-methyl]-7-[2-methyl-4-[6-(trifluoromethyl)pyrido[3,2-d]pyrimidin-2-yl]phenyl]-1H,5H,6H,7H,8H-[1,2,3]triazolo[4,5-f][1,4]oxazepin-8-one gave crude product. Purification by Prep-HPLC under following conditions: (2 #SHIMADZU (HPLC-01)): Column, XBridge Prep OBD Cis Column, 19*250 mm, 5 um; mobile phase, Water (10 mmol/L NH$_4$HCO$_3$+0.1% NH$_3$·H$_2$O) and ACN (25% PhaseB up to 37% in 8 min); Detector, UV; gave the title compound as a white solid. LC-MS: (ES, m/z): [M+H]$^+$ 442.1; $^1$H-NMR: (400 MHz, DMSO-d$_6$, ppm): δ 9.96 (s, 1H), 8.81-8.83 (d, 1H), 8.56 (s, 1H), 8.46-8.49 (m, 2H), 7.55 (d, 1H), 4.83-4.62 (m, 2H), 4.31 (s, 1H), 3.94-3.97 (m, 1H), 2.35 (s, 3H).

Example 41

Synthesis of 2-methyl-7-(2-methyl-4-(6-(trifluoromethyl)-1,5-naphthyridin-2-yl)-phenyl)-6,7-dihydro-2H-[1,2,3]triazolo[4,5-f][1,4]oxazepin-8 (5H)-one

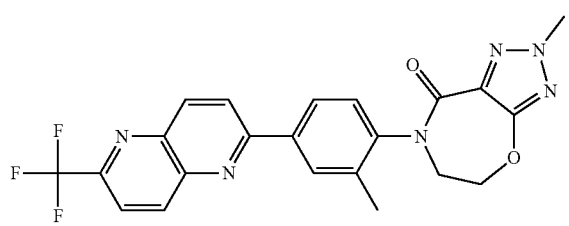 [SMILES: Cc1cc(-c2ccc3nc(C(F)(F)F)ccc3n2)ccc1N1CCOc2nn(C)nc2C1=O]

Step 1: Synthesis of 7-(4-bromo-2-methylphenyl)-2-methyl-6,7-dihydro-2H-[1,2,3]triazolo-[4,5-f][1,4]oxazepin-8 (5H)-one

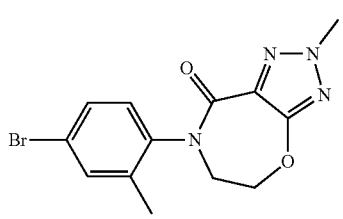 [SMILES: Cc1cc(Br)ccc1N1CCOc2nn(C)nc2C1=O]

To a stirred solution of 7-(4-bromo-2-methylphenyl)-3H,5H,6H,7H,8H-[1,2,3]triazolo-[4,5-f]-[1,4]oxazepin-8-one (6.2 g, 19.19 mmol, 1 equiv) in DMF (120 mL) were added K$_2$CO$_3$ (5.3 g, 38.37 mmol, 2 equiv) and MeI (3.0 g, 21.10 mmol, 1.1 equiv). The resulting mixture was stirred for overnight at 50° C. under nitrogen atmosphere. The reaction was quenched with water and extracted with EtOAc. The combined organic layers were concentrated under reduced pressure. The residue was purified by silica gel column chromatography using PE/EtOAc (1:1) as eluent to afford the title compound as a white solid.

Step 2: Synthesis of 2-methyl-7-(2-methyl-4-(4,4,5,5-tetramethyl-1,3,2-dioxaborolan-2-yl)phenyl)-6,7-dihydro-2H-[1,2,3]triazolo[4,5-f][1,4]oxazepin-8 (5H)-one

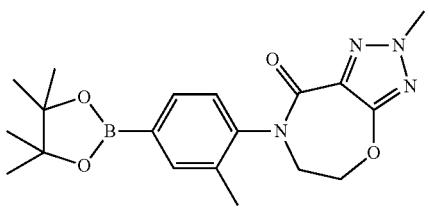

Proceeding analogously as described in Example 1, Step 12 but substituting 7-(4-bromo-2-methylphenyl)-1-methyl-6,7-dihydro-1H-pyrazolo[3,4-f]-[1,4]oxazepin-8 (5H)-one with 7-(4-bromo-2-methylphenyl)-2-methyl-6,7-dihydro-2H-[1,2,3]triazolo-[4,5-f][1,4]-oxazepin-8 (5H)-one provided crude product. Silica gel column with dichloromethane/ethyl acetate (1:2) afforded (1.1 g, 50.80%) of the title compound as a white solid.

Step 3: Synthesis of 2-methyl-7-(2-methyl-4-(6-(trifluoromethyl)-1,5-naphthyridin-2-yl)-phenyl)-6,7-dihydro-2H-[1,2,3]triazolo[4,5-f][1,4]oxazepin-8 (5H)-one

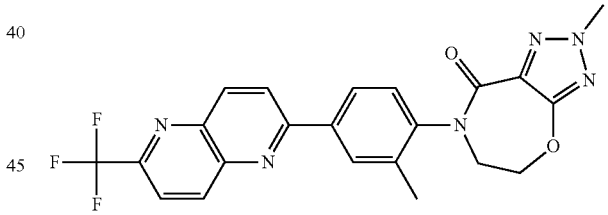

Proceeding analogously as described in Example 5, Step 12 but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 2-methyl-7-(2-methyl-4-(4,4,5,5-tetramethyl-1,3,2-dioxaborolan-2-yl)phenyl)-6,7-dihydro-2H-[1,2,3]triazolo[4,5-f][1,4]oxazepin-8 (5H)-one and 6-chloro-4-methyl-2-(trifluoromethyl)-1,5-naphthyridine with 2-chloro-6-(trifluoromethyl)-1,5-naphthyridine provided (58.3 mg, 19.72%) of the title compound as a white solid. LC-MS: (ES, m/z): [M+H]$^+$ 455.2; $^1$H-NMR: (300 MHz, DMSO-d$_6$, ppm): δ 8.79 (d, 1H), 8.70 (d, 1H), 8.67 (d, 1H), 8.30 (d, 1H), 8.25 (dd, 2H), 7.51 (d, 1H), 4.72 (t, 2H), 4.29 (d, 1H), 3.97 (s, 1H), 3.61 (s, 3H), 2.33 (s, 3H).

Example 42

Synthesis of 2-methyl-7-(2-methyl-4-(6-(trifluoromethyl)pyrido[3,2-d]pyrimidin-2-yl)phenyl)-6,7-dihydro-2H-[1,2,3]triazolo[4,5-f][1,4]oxazepin-8 (5H)-one

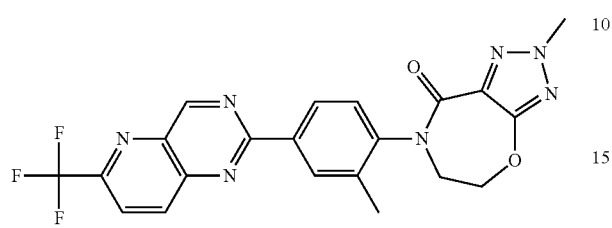

Into a 25-mL 3-necked round-bottom flask under N₂ atmosphere, were placed 2-methyl-7-[2-methyl-4-(4,4,5,5-tetramethyl-1,3,2-dioxaborolan-2-yl)phenyl]-2H,5H,6H,7H,8H-[1,2,3]triazolo[4,5-f][1,4]oxazepin-8-one (400 mg, 1.041 mmol, 1 equiv), 2-chloro-6-(trifluoromethyl)pyrido[3,2-d]pyrimidine (364.74 mg, 1.562 mmol, 1.5 equiv), K₂CO₃ (431.62 mg, 3.123 mmol, 3 equiv), t-BuOH (2.7 mL), H₂O (0.3 mL), and PdAMPHOS (368.56 mg, 0.521 mmol, 0.5 equiv). The resulting solution was stirred for 12 h at 80° C. The reaction mixture was then quenched with water. The resulting solution was extracted with ethyl acetate and the organic layer was separated and concentrated. The residue was applied onto Prep-TLC and eluted with dichloromethane/methanol (10:1). The crude product was purified by re-crystallization from MeOH. This resulted in 52.7 mg (11.12%) of the title compound as a yellow solid. LC-MS: (ES, m/z): [M+H]⁺ 456. ¹H-NMR: (300 MHz, DMSO-d₆, ppm): δ 2.34 (s, 3H), 3.61 (s, 3H), 3.94-3.98 (m, 1H), 4.29-4.32 (m, 1H), 4.69-4.73 (m, 2H), 7.54 (d, 1H), 8.47-8.51 (m, 3H), 8.83 (d, 1H), 9.97 (s, 1H).

Example 43

Synthesis of 2-methyl-7-(2-methyl-4-(6-(trifluoromethyl)quinazolin-2-yl)phenyl)-6,7-dihydro-2H-[1,2,3]triazolo[4,5-f][1,4]oxazepin-8 (5H)-one

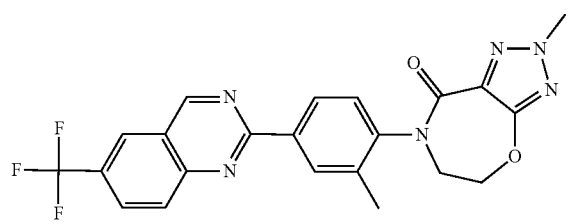 [SMILES: Cc1cc(-c2ncc3cc(C(F)(F)F)ccc3n2)ccc1N1CCOc2nn(C)nc2C1=O]

Into a 25-mL 3-necked round-bottom flask under N₂ atmosphere, were placed 2-methyl-7-[2-methyl-4-(4,4,5,5-tetramethyl-1,3,2-dioxaborolan-2-yl)phenyl]-2H,5H,6H,7H,8H-[1,2,3]triazolo[4,5-f][1,4]oxazepin-8-one (400 mg, 1.041 mmol, 1 equiv), 2-chloro-6-(trifluoromethyl)quinazoline (363.19 mg, 1.562 mmol, 1.5 equiv), K₂CO₃ (431.62 mg, 3.123 mmol, 3 equiv), toluene (3 mL), EtOH (1.5 mL), and Pd(PPh₃)₄ (180.44 mg, 0.156 mmol, 0.15 equiv). The resulting solution was stirred for 12 h at 80° C. The reaction was then quenched with water and extracted with ethyl acetate and the organic layer was concentrated under vacuum. The residue was applied onto Prep-TLC and eluted with dichloromethane/methanol (20:1). The crude product was purified by re-crystallization from MeOH to give the title compound (111.8 mg, 23.63%) as a white solid.

LC-MS: (ES, m/z): [M+H]⁺ 455. ¹H-NMR: (300 MHz, DMSO-d₆, ppm): δ 2.33 (s, 3H), 3.61 (s, 3H), 3.89 (m, 1H), 4.20-4.29 (m, 1H), 4.69-4.73 (m, 2H), 7.50 (d, 1H), 8.25 (m, 2H), 8.48 (d, 1H), 8.52 (s, 1H), 8.71 (s, 1H), 9.89 (s, 1H).

Example 44

Synthesis of 6-methyl-7-(2-methyl-4-(6-(trifluoromethyl)quinazolin-2-yl)phenyl)-6,7-dihydro-1H-pyrazolo[3,4-f][1,4]oxazepin-8 (5H)-one

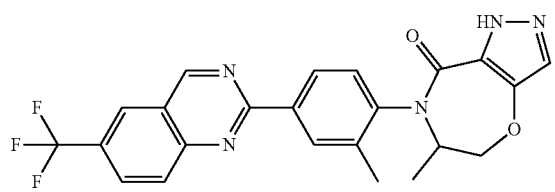 [SMILES: Cc1cc(-c2ncc3cc(C(F)(F)F)ccc3n2)ccc1N1C(=O)c2[nH]ncc2OCC1C]

Step 1: Synthesis of methyl 4-bromo-1-(tetrahydro-2H-pyran-2-yl)-1H-pyrazole-5-carboxylate

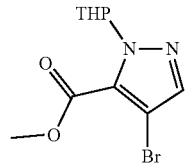

To a stirred solution/mixture of methyl 4-bromo-1H-pyrazole-5-carboxylate (100 g, 487.78 mmol, 1 equiv) and 3,4-dihydro-2H-pyran (53.3 g, 633.63 mmol, 1.30 equiv) in DCM (1000 mL) was added CF₃COOH (83.4 g, 731.43 mmol, 1.50 equiv) at room temperature under nitrogen atmosphere. The resulting mixture was stirred for 6 h at room temperature and then quenched with sat. NaHCO₃ (aq.). The aqueous layer was extracted with CH₂Cl₂ and the resulting mixture was washed with H₂O and was concentrated under reduced pressure. The residue was purified by silica gel column chromatography, eluting with PE/EtOAc (15:1) to afford the title compound (137 g, 97.14%) as a yellow liquid.

Step 2: Synthesis of 4-(benzyloxy)-1-(tetrahydro-2H-pyran-2-yl)-1H-pyrazole-5-carboxylic acid

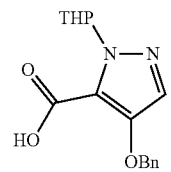

Into a 500-mL 3-necked round-bottom flask under N₂ atmosphere, were placed methyl 4-bromo-1-(tetrahydro-2H-pyran-2-yl)-1H-pyrazole-5-carboxylate (22 g, 76.09 mmol, 1 equiv), phenylmethanol (110 mL), Cs₂CO₃ (74.4 g, 228.35 mmol, 3.00 equiv), and CuCl₂ (1.0 g, 7.61 mmol, 0.1 equiv). The resulting solution was stirred overnight at 130° C. and then quenched with water. The resulting solution was extracted with ethyl acetate and the aqueous layers were combined. The pH value of the solution was adjusted to 4 with CH₃COOH (2 mol/L) and the resulting solution was extracted with ethyl acetate. The organics were removed and the residue was applied onto a silica gel column and eluted with ethyl acetate/petroleum ether (1:2) to give (5.1 g, 22.17%) of the title compound as a white solid.

Step 3: Synthesis of 4-(benzyloxy)-N-(4-bromo-2-methylphenyl)-1-(tetrahydro-2H-pyran-2-yl)-1H-pyrazole-5-carboxamide

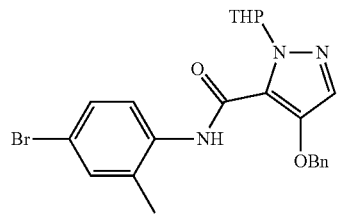

Into a 100-mL 3-necked round-bottom flask under N₂ atmosphere, were placed 4-(benzyloxy)-1-(tetrahydro-2H-pyran-2-yl)-1H-pyrazole-5-carboxylic acid (5.1 g, 16.87 mmol, 1 equiv), 4-bromo-2-methylaniline (3.1 g, 16.87 mmol, 1 equiv), HATU (9.6 g, 25.30 mmol, 1.5 equiv), DMF (50.0 mL), and DIEA (4.4 g, 33.74 mmol, 2 equiv). The resulting solution was stirred overnight at 40° C. and then quenched with water. The resulting solution was extracted with ethyl acetate and the organic layers were combined and then concentrated. The residue was applied onto a silica gel column and eluted with ethyl acetate/petroleum ether (1:5) to give (5.2 g, 65.54%) of the title compound as a white solid.

Step 4: Synthesis of N-(4-bromo-2-methylphenyl)-4-hydroxy-1-(tetrahydro-2H-pyran-2-yl)-1H-pyrazole-5-carboxamide

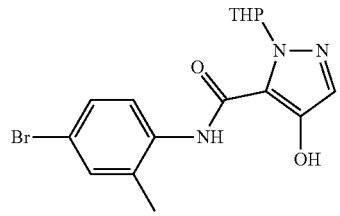

Into a 25-mL round-bottom flask purged and maintained under H₂ atmosphere, were placed 4-(benzyloxy)-N-(4-bromo-2-methylphenyl)-1-(tetrahydro-2H-pyran-2-yl)-1H-pyrazole-5-carboxamide (5.2 g, 10.4 mmol, 1 equiv), THF (100 mL), and Pd/C (520 mg). The resulting solution was stirred for 1 h at room temperature. Then the mixture was filtrated to remove Pd/C and the filtrate was concentrated to give the title compound (3.8 g, 90.48%) as a white solid.

Step 5: Synthesis of N-(4-bromo-2-methylphenyl)-4-(2-oxopropoxy)-1-(tetrahydro-2H-pyran-2-yl)-1H-pyrazole-5-carboxamide

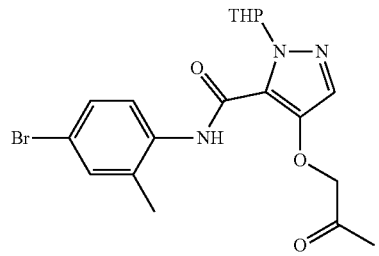

Into a 100-mL 3-necked round-bottom flask, were placed N-(4-bromo-2-methylphenyl)-4-hydroxy-1-(tetrahydro-2H-pyran-2-yl)-1H-pyrazole-5-carboxamide (3.8 g, 9.99 mmol, 1 equiv), 1-bromopropan-2-one (1.4 g, 10.2 mmol, 1 equiv), Na₂CO₃ (3.2 g, 30.19 mmol, 3.02 equiv), and DMF (40 mL). The resulting solution was stirred for 1 h at room temperature and then quenched with water. The resulting solution was extracted with ethyl acetate. The residue was applied onto a silica gel column and eluted with EA:PE (1:5) to give the title compound (3.3 g, 75.68%) as a solid.

Step 6: Synthesis of N-(4-bromo-2-methylphenyl)-4-(2-hydroxypropoxy)-1-(tetrahydro-2H-pyran-2-yl)-1H-pyrazole-5-carboxamide

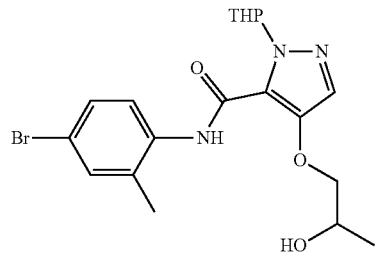

Into a 100-mL 3-necked round-bottom flask under N₂ atmosphere, were placed N-(4-bromo-2-methylphenyl)-4-(2-oxopropoxy)-1-(tetrahydro-2H-pyran-2-yl)-1H-pyrazole-5-carboxamide (3.1 g, 7.11 mmol, 1 equiv), and MeOH (30 mL, 740.97 mmol, 104.29 equiv), and NaBH₄ (0.3 g, 7.93 mmol, 1.12 equiv) was added at 0° C. The resulting solution was stirred for 2 h at room temperature and then quenched with NH₄Cl. The resulting solution was extracted with ethyl acetate, and the organic layer was dried over anhydrous sodium sulfate and concentrated under vacuum to give 3.1 g of the title compound as a crude product.

Step 7: Synthesis of 1-((5-((4-bromo-2-methylphenyl)carbamoyl)-1-(tetrahydro-2H-pyran-2-yl)-1H-pyrazol-4-yl)oxy)propan-2-yl methanesulfonate

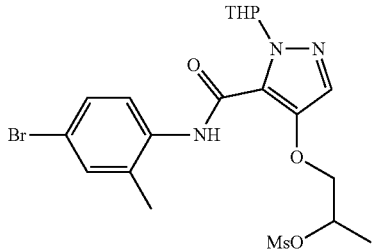

Into a 50-mL 3-necked round-bottom flask under N₂ atmosphere, were placed N-(4-bromo-2-methylphenyl)-4-(2-hydroxy-propoxy)-1-(tetrahydro-2H-pyran-2-yl)-1H-pyrazole-5-carboxamide (3 g, 6.84 mmol, 1 equiv), DCM (30 mL, 471.90 mmol, 68.95 equiv), and Et₃N (1.0 g, 9.88 mmol, 1.44 equiv), and MsCl (1.2 g, 10.27 mmol, 1.50 equiv) was added dropwise at 0° C. The resulting solution was stirred for 1 h at room temperature and then quenched with water. The resulting solution was extracted with dichloromethane, dried over anhydrous sodium sulfate, and concentrated under vacuum to give 3.7 g of the title compound as a crude product.

Step 8: Synthesis of 7-(4-bromo-2-methylphenyl)-6-methyl-1-(tetrahydro-2H-pyran-2-yl)-6,7-dihydro-1H-pyrazolo[3,4-f][1,4]oxazepin-8 (5H)-one

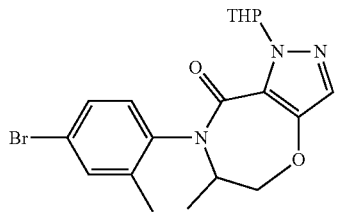

Into a 50-mL 3-necked round-bottom flask, were placed 1-((5-((4-bromo-2-methyl-phenyl)carbamoyl)-1-(tetrahydro-2H-pyran-2-yl)-1H-pyrazol-4-yl)oxy)propan-2-yl methanesulfonate (3.7 g, 7.16 mmol, 1 equiv), EtOH (40 mL), and t-BuOK (1.6 g, 14.26 mmol, 1.99 equiv). The resulting solution was stirred overnight at 50° C. The reaction was then quenched with NH₄Cl and the resulting mixture was concentrated to remove EtOH. The resulting solution was extracted with ethyl acetate and the organic layers was combined and concentrated. The residue was applied onto a silica gel column and eluted with ethyl acetate/petroleum ether (1:5) to give (2.1 g, 69.73%) of the title compound as a white solid.

Step 9: Synthesis of 6-methyl-7-(2-methyl-4-(4,4,5,5-tetramethyl-1,3,2-dioxaborolan-2-yl)phenyl)-1-(tetrahydro-2H-pyran-2-yl)-6,7-dihydro-1H-pyrazolo[3,4-f][1,4]oxazepin-8 (5H)-one

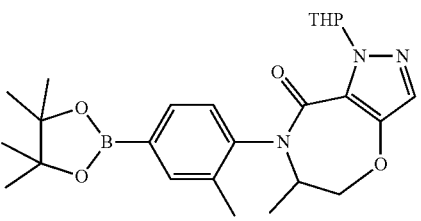

Proceeding as described in Example 5, Step 11 but substituting 7-(4-bromo-2,5-dimethylphenyl)-1-methyl-6,7-dihydro-1H-pyrazolo[3,4-f][1,4]-oxazepin-8 (5H)-one with 7-(4-bromo-2-methylphenyl)-6-methyl-1-(tetrahydro-2H-pyran-2-yl)-6,7-dihydro-1H-pyrazolo[3,4-f][1,4]oxazepin-8 (5H)-one provided crude product. Silica gel column with ethyl acetate/petroleum ether (1:2) afforded (1.3 g, 55.41%) of the title compound as a grey solid.

Step 10: Synthesis of 6-methyl-7-(2-methyl-4-(6-(trifluoromethyl)quinazolin-2-yl)phenyl)-1-(tetrahydro-2H-pyran-2-yl)-6,7-dihydro-1H-pyrazolo[3,4-f][1,4]oxazepin-8 (5H)-one

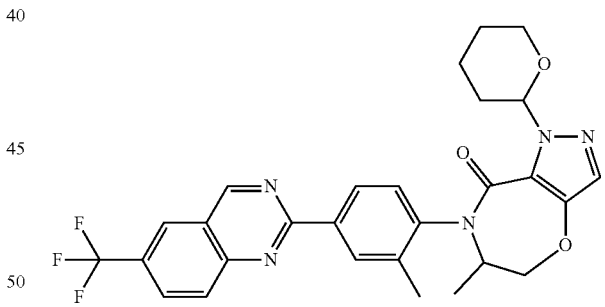

Proceeding as described in Example 2, Step 11 but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 6-methyl-7-(2-methyl-4-(4,4,5,5-tetramethyl-1,3,2-dioxaborolan-2-yl)phenyl)-1-(tetrahydro-2H-pyran-2-yl)-6,7-dihydro-1H-pyrazolo[3,4-f][1,4]oxazepin-8 (5H)-one provided crude product. Purification by prep-TLC with dichloromethane/methanol (20:1) as eluent gave (212 mg, 61.73%) the title compound as a white solid.

Step 11: Synthesis of 6-methyl-7-(2-methyl-4-(6-(trifluoromethyl)quinazolin-2-yl)phenyl)-6,7-dihydro-1H-pyrazolo[3,4-f][1,4]oxazepin-8 (5H)-one

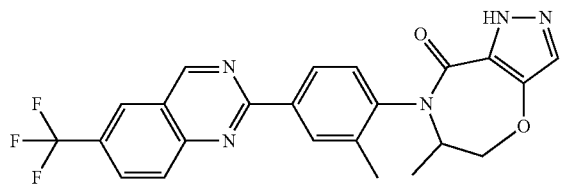 [SMILES: Cc1cc(-c2ncc3cc(C(F)(F)F)ccc3n2)ccc1N1C(=O)c2[nH]ncc2OCC1C]

Into a 8-mL sealed tube, were placed 6-methyl-7-(2-methyl-4-(6-(trifluoromethyl)-quinazolin-2-yl)phenyl)-1-(tetrahydro-2H-pyran-2-yl)-6,7-dihydro-1H-pyrazolo[3,4-f][1,4]oxazepin-8 (5H)-one (210 mg, 0.39 mmol, 1 equiv), dioxane (2 mL, 23.61 mmol, 60.43 equiv), and HCl (2 mL, 65.82 mmol, 168.49 equiv). The resulting solution was stirred for 2 h at room temperature and then quenched with NaHCO₃. The resulting solution was extracted with ethyl acetate. After removing the organics, the residue was applied onto a silica gel column and eluted with dichloromethane/methanol (20:1) to give (86 mg, 48.55%) of the title compound as a white solid. LC-MS: (ES, m/z): [M+H]⁺ 454.3; ¹H-NMR: (300 MHz, DMSO-d₆): δ 13.15-13.31 (m, 1H), 9.88 (s, 1H), 8.70 (s, 1H), 8.45-8.56 (m, 2H), 8.26 (t, 2H), 7.24-7.52 (m, 2H), 4.55-4.60 (m, 1H), 4.29-4.49 (m, 1H) 4.18-4.25 (m, 1H), 2.29 (s, 3H), 1.29-1.42 (m, 2H), 1.19-1.25 (m, 2H).

Example 45

Synthesis of 6-methyl-7-(2-methyl-4-(6-(trifluoromethyl)-1,5-naphthyridin-2-yl)phenyl)-6,7-dihydro-1H-pyrazolo[3,4-f][1,4]oxazepin-8 (5H)-one

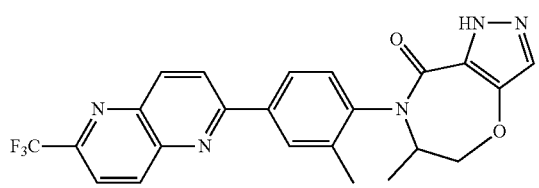 [SMILES: Cc1cc(-c2ccc3nc(C(F)(F)F)ccc3n2)ccc1N1C(=O)c2[nH]ncc2OCC1C]

Step 1: Synthesis of 6-methyl-7-(2-methyl-4-(6-(trifluoromethyl)quinazolin-2-yl)phenyl)-1-(tetrahydro-2H-pyran-2-yl)-6,7-dihydro-1H-pyrazolo[3,4-f][1,4]oxazepin-8 (5H)-one

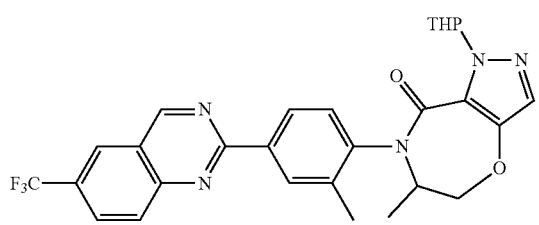

Proceeding as described in Example 2, Step 11 but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 6-methyl-7-(2-methyl-4-(4,4,5,5-tetramethyl-1,3-dioxolan-2-yl)phenyl)-1-(tetrahydro-2H-pyran-2-yl)-6,7-dihydro-1H-pyrazolo[3,4-f][1,4]oxazepin-8 (5H)-one provided crude product. Purification by pre-TLC by eluting with ethyl acetate/petroleum ether (1:2) provided the title compound (210 mg, 91.72%) as a white solid.

Step 2: Synthesis of 6-methyl-7-(2-methyl-4-(6-(trifluoromethyl)-1,5-naphthyridin-2-yl)phenyl)-6,7-dihydro-1H-pyrazolo[3,4-f][1,4]oxazepin-8 (5H)-one

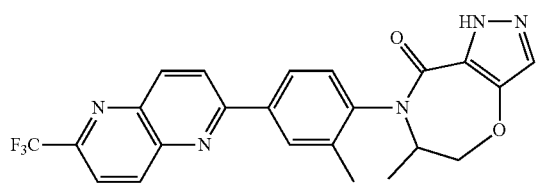 [SMILES: Cc1cc(-c2ccc3nc(C(F)(F)F)ccc3n2)ccc1N1C(=O)c2[nH]ncc2OCC1C]

Proceeding as described in Example 44, Step 11 but substituting 6-methyl-7-(2-methyl-4-(6-(trifluoromethyl)-quinazolin-2-yl)phenyl)-1-(tetrahydro-2H-pyran-2-yl)-6,7-dihydro-1H-pyrazolo[3,4-f][1,4]oxazepin-8 (5H)-one with 6-methyl-7-(2-methyl-4-(6-(trifluoromethyl)quinazolin-2-yl)phenyl)-1-(tetrahydro-2H-pyran-2-yl)-6,7-dihydro-1H-pyrazolo[3,4-f][1,4]oxazepin-8 (5H)-one provided the title compound (105 mg, 59.28%) as a white solid. LC-MS: (ES, m/z): [M+1]⁺ 454.3; ¹H-NMR: (300 MHz, DMSO-d6): δ 13.17 (d, 1H), 8.78 (d, 1H), 8.65 (d, 1H), 8.58-8.59 (m, 1H), 8.33 (s, 1H), 8.22-8.30 (m, 2H), 7.41-7.53 (m, 2H), 4.55-4.59 (m, 1H), 4.22-4.42 (m, 1H), 3.89-4.19 (m, 1H), 2.28 (d, 3H), 1.32-1.37 (d, 2H), 1.25 (d, 2H).

Example 46

Synthesis of 6-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

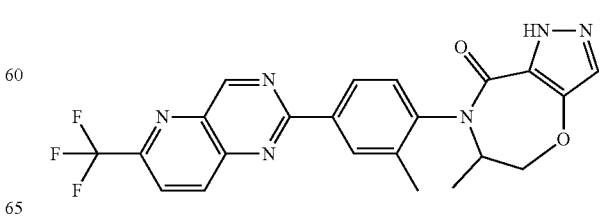

Step 1: Synthesis of 6-methyl-7-(2-methyl-4-(6-(trifluoromethyl)pyrido[3,2-d]pyrimidin-2-yl)phenyl)-1-(tetrahydro-2H-pyran-2-yl)-6,7-dihydro-1H-pyrazolo[3,4-f][1,4]oxazepin-8 (5H)-one

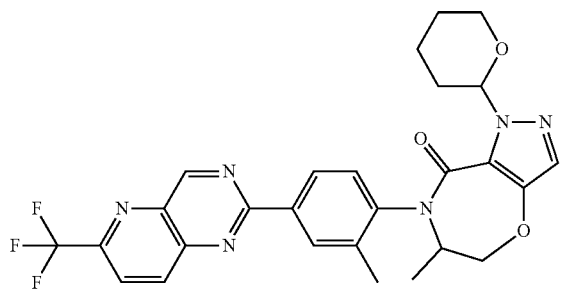 [SMILES: Cc1cc(-c2ncc3nc(C(F)(F)F)ccc3n2)ccc1N1C(=O)c2c(cnn2C2CCCCO2)OCC1C]

Proceeding as described in Example 2, Step 11 but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 6-methyl-7-(2-methyl-4-(4,4,5,5-tetramethyl-1,3,2-dioxaborolan-2-yl)phenyl)-1-(tetrahydro-2H-pyran-2-yl)-6,7-dihydro-1H-pyrazolo[3,4-f][1,4]oxazepin-8 (5H)-one provided crude product. Purification by pre-TLC by eluting silica gel column chromatography by eluting with ethyl acetate/petroleum ether (1:1) provided the title compound (110 mg, 19.18%) as a white solid.

Step 2: Synthesis of 6-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

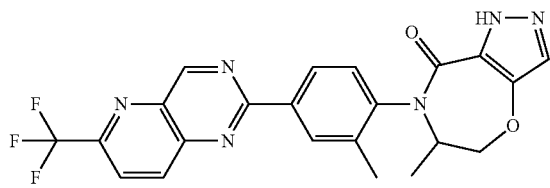

Proceeding as described in Example 44, Step 11 but substituting 6-methyl-7-(2-methyl-4-(6-(trifluoromethyl)-quinazolin-2-yl)phenyl)-1-(tetrahydro-2H-pyran-2-yl)-6,7-dihydro-1H-pyrazolo[3,4-f][1,4]oxazepin-8 (5H)-one with 6-methyl-7-(2-methyl-4-(6-(trifluoromethyl)-pyrido[3,2-d]pyrimidin-2-yl)phenyl)-1-(tetrahydro-2H-pyran-2-yl)-6,7-dihydro-1H-pyrazolo[3,4-f][1,4]oxazepin-8 (5H)-one provided the title compound (22.9 mg, 24.67%) as a white solid. LC-MS: (ES, m/z): [M+1]$^+$ 455.1; $^1$H-NMR: (300 MHz, DMSO-$d_6$): δ 13.18-13.25 (m, 1H), 9.98 (s, 1H), 8.83 (d, 1H), 8.47-8.44 (m, 3H), 7.44-7.58 (m, 2H), 4.61-4.63 (m, 1H), 4.26-4.59 (m, 1H), 3.93-4.23 (m, 1H), 2.32 (d, 3H), 1.22-1.32 (m, 3H).

Example 47

Synthesis of 2-methyl-7-(2-methyl-4-(6-(trifluoromethyl)pyrido[3,2-d]pyrimidin-2-yl)phenyl)-6,7-dihydro-2H-pyrazolo[3,4-f][1,4]oxazepin-8 (5H)-one

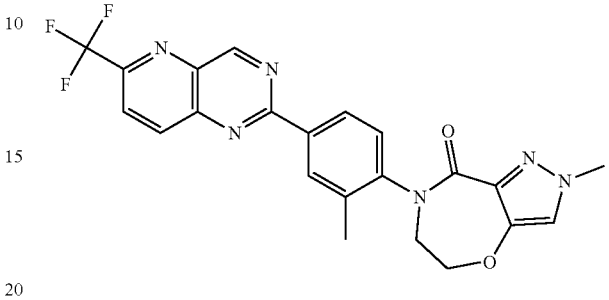

Proceeding as described in Example 1, Steps 6 to 13 but substituting 4-bromo-1-methyl-1H-pyrazole-5-carboxylic acid with methyl 4-bromo-1-methyl-1H-pyrazole-3-carboxylate provided the title compound as a white solid. LC-MS: (ES, m/z): [M+H]$^+$ 455.1; $^1$H-NMR: (300 MHz, DMSO-$d_6$, ppm): δ 2.30 (s, 3H), 3.86 (s, 3H), 3.96 (s, 2H), 4.39-4.50 (m, 2H), 7.46 (d, 1H), 7.64 (s, 1H), 8.45-8.49 (m, 2H), 8.54 (s, 1H), 8.82 (d, 1H), 9.96 (s, 1H).

Example 48

Synthesis of 2-methyl-7-(2-methyl-4-(6-(trifluoromethyl)-1,5-naphthyridin-2-yl)phenyl)-6,7-dihydro-2H-pyrazolo[3,4-f][1,4]oxazepin-8 (5H)-one

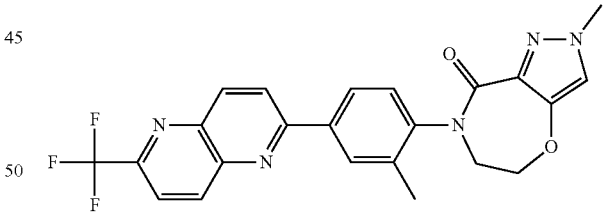

Proceeding as described in Example 5, Step 12 but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 2-methyl-7-[2-methyl-4-(4,4,5,5-tetramethyl-1,3,2-dioxaborolan-2-yl)phenyl]-2H,5H,6H,7H,8H-pyrazolo[3,4-f][1,4]oxazepin-8-one gave crude product. Purification by silica gel column with dichloromethane/methanol (10:1) as eluent, followed by re-crystallized from MeOH gave the title compound as a white solid. LC-MS: (ES, m/z): [M+H]$^+$ 454.1; $^1$H-NMR: (400 MHz, DMSO-$d_6$, ppm): δ 2.30 (s, 3H), 3.86 (s, 3H), 3.90-3.97 (m, 2H), 4.39-4.54 (m, 2H), 7.43 (d, 1H), 7.63 (s, 1H), 8.21-8.25 (m, 2H), 8.30 (s, 1H), 8.60 (d, 1H), 8.69 (d, 1H), 8.79 (d, 1H).

Example 49

Synthesis of 1-methyl-7-(2-methyl-4-(6-(trifluoromethyl)pyrido[3,2-d]pyrimidin-2-yl)phenyl)-5,6,7,8-tetrahydro-1H-pyrazolo[3,4-f][1,4]oxazepine

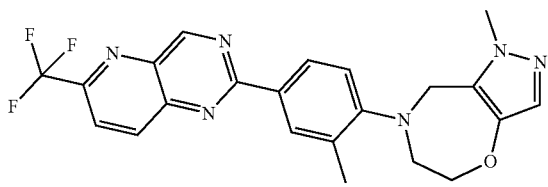 [SMILES: Cc1cc(-c2ncc3nc(C(F)(F)F)ccc3n2)ccc1N1CCOc2cnn(C)c2C1]

Step 1: Synthesis of 1-methyl-7-(2-methyl-4-(4,4,5,5-tetramethyl-1,3,2-dioxaborolan-2-yl)phenyl)-5,6,7,8-tetrahydro-1H-pyrazolo[3,4-f][1,4]oxazepine

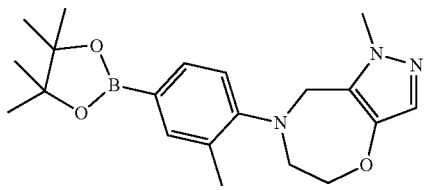 [SMILES: Cc1cc(B2OC(C)(C)C(C)(C)O2)ccc1N1CCOc2cnn(C)c2C1]

Into a 25-mL 3-necked round-bottom flask under $N_2$ atmosphere, were placed 1-methyl-7-(2-methyl-4-(4,4,5,5-tetramethyl-1,3,2-dioxaborolan-2-yl)phenyl)-6,7-dihydro-1H-pyrazolo[3,4-f][1,4]oxazepin-8 (5H)-one (500 mg, 1.305 mmol, 1 equiv) and THF (5 mL). LiAlH$_4$ (54.47 mg, 1.435 mmol, 1.10 equiv) was added in portions at 0° C. The resulting solution was stirred overnight at room temperature and then quenched with NaOH (1M). The pH value of the solution was adjusted to 5 with HCl (1M) and the resulting solution was extracted with ethyl acetate. The organic layers were combined and concentrated under vacuum. The residue was applied onto a silica gel column and eluted with ethyl acetate/petroleum ether (1:1) to give the title compound (63 mg, 13.08%) as a white solid.

Step 2: Synthesis of 1-methyl-7-(2-methyl-4-(6-(trifluoromethyl)pyrido[3,2-d]pyrimidin-2-yl)phenyl)-5,6,7,8-tetrahydro-1H-pyrazolo[3,4-f][1,4]oxazepine

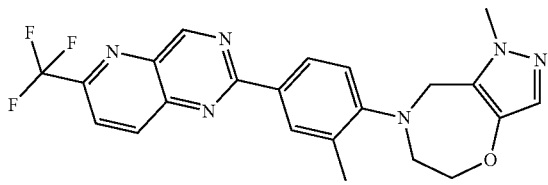 [SMILES: Cc1cc(-c2ncc3nc(C(F)(F)F)ccc3n2)ccc1N1CCOc2cnn(C)c2C1]

Into an 8-mL vial under $N_2$ atmosphere, were placed 1-methyl-7-(2-methyl-4-(4,4,5,5-tetramethyl-1,3,2-dioxaborolan-2-yl)phenyl)-5,6,7,8-tetrahydro-1H-pyrazolo[3,4-f][1,4]oxazepine (63 mg, 0.171 mmol, 1 equiv), 2-chloro-6-(trifluoromethyl)pyrido[3,2-d]pyrimidine (59.78 mg, 0.256 mmol, 1.5 equiv), K$_3$PO$_4$ (72.43 mg, 0.341 mmol, 2 equiv), dioxane (0.5 mL), H$_2$O (0.1 mL), and Pd(DtBPF)Cl$_2$ (11.12 mg, 0.017 mmol, 0.1 equiv). The resulting solution was stirred for overnight at 80° C. and then diluted with H$_2$O. The resulting solution was extracted with ethyl acetate and the organic layers were combined and concentrated in vacuum. The residue was applied onto a silica gel column and eluted with ethyl acetate/petroleum ether (1:1) to give the title compound (37.6 mg, 50.04%) as a yellow solid. LC-MS: (ES, m/z): [M+H]$^+$ 441; $^1$H-NMR: (300 MHz, DMSO-d$_6$ ppm): δ 9.88 (s, 1H), 8.73 (d, 1H), 8.45-8.40 (m, 3H), 7.27 (d, 1H), 7.14 (s, 1H), 4.34 (s, 2H), 4.10-4.07 (m, 2H), 3.75 (s, 3H), 3.49 (s, 2H), 2.44 (s, 3H).

Example 50

Synthesis of 1-methyl-7-(4-(6-(trifluoromethyl)pyrido[3,2-d]pyrimidin-2-yl)phenyl)-6,7-dihydro-1H-pyrazolo[3,4-f][1,4]oxazepin-8 (5H)-one

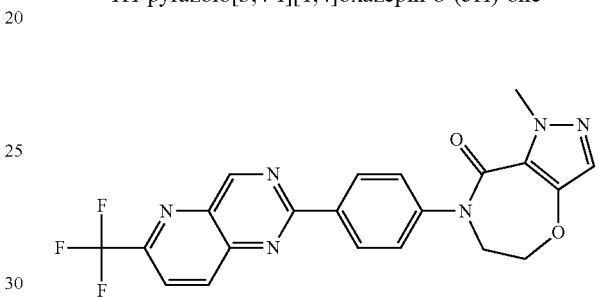

Step 1: Synthesis of 1-methyl-7-(4-(4,4,5,5-tetramethyl-1,3,2-dioxaborolan-2-yl)phenyl)-6,7-dihydro-1h-pyrazolo[3,4-f][1,4]oxazepin-8 (5 h)-one

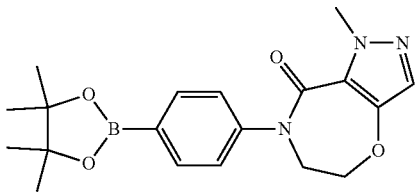 [SMILES: Cn1ncc2c1C(=O)N(c1ccc(B3OC(C)(C)C(C)(C)O3)cc1)CCO2]

Proceeding as described in Example 1, Steps 6 to 12 to but substituting 4-bromo-2-methylaniline with 4-bromoaniline in Step 8 provided the title compound as a white solid.

Step 2: Synthesis of 1-methyl-7-(4-(6-(trifluoromethyl)pyrido[3,2-d]pyrimidin-2-yl)phenyl)-6,7-dihydro-1H-pyrazolo[3,4-f][1,4]oxazepin-8 (5H)-one

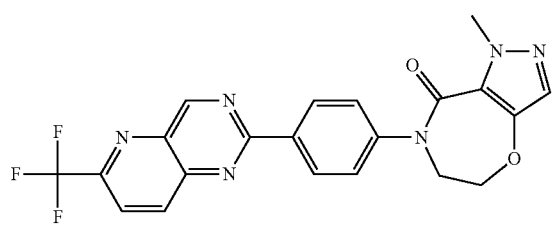 [SMILES: Cn1ncc2c1C(=O)N(c1ccc(-c3ncc4nc(C(F)(F)F)ccc4n3)cc1)CCO2]

To a stirred solution/mixture of 1-methyl-7-(4-(4,4,5,5-tetramethyl-1,3,2-dioxaborolan-2-yl)phenyl)-6,7-dihydro-1H-pyrazolo[3,4-f][1,4]oxazepin-8 (5H)-one (300 mg, 0.815 mmol, 1 equiv) and 2-chloro-6-(trifluoromethyl)pyrido[3,2-d]pyrimidine (209.32 mg, 0.896 mmol, 1.1 equiv) in dioxane (3 mL) were added K₃PO₄ (345.86 mg, 1.629 mmol, 2 equiv), H₂O (0.6 mL) and Pd(DtBPF)Cl₂ (106.19 mg, 0.163 mmol, 0.20 equiv) at room temperature under nitrogen atmosphere. The resulting mixture was stirred for 4 h at 100° C. under nitrogen atmosphere and then diluted with water. The aqueous layer was extracted with EtOAc and the resulting mixture was concentrated under vacuum. The residue was purified by Prep-TLC (CH₂Cl₂/MeOH 80:1) to afford the title compound (141.3 mg, 39.47%) as a white solid. LC-MS: (ES, m/z): [M+H]⁺ 441; ¹H-NMR: (300 MHz, DMSO-d₆, ppm): δ 9.96-9.96 (d, 1H), 8.81 (d, 1H), 8.63-8.67 (m, 2H), 8.47 (d, 1H), 7.59-7.64 (m, 2H), 7.36 (s, 1H), 4.51-4.53 (m, 2H), 4.14-4.15 (t, 2H), 4.02 (s, 3H).

Example 51

Synthesis of 7-(4-(6-fluoropyrido[3,2-d]pyrimidin-2-yl)-2-methylphenyl)-1-methyl-6,7-dihydro-1H-pyrazolo[3,4-f][1,4]oxazepin-8 (5H)-one

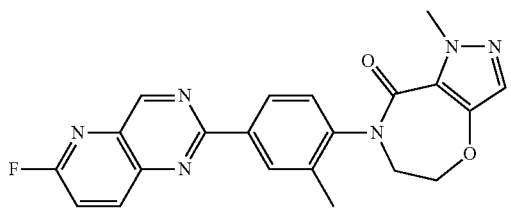 [SMILES: Cc1cc(-c2ncc3nc(F)ccc3n2)ccc1N1CCOc2cnn(C)c2C1=O]

Step 1: Synthesis of 2-bromo-6-fluoropyridin-3-amine

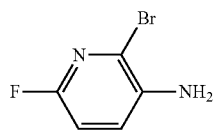

Into a 2000-mL 3-necked round-bottom flask under N₂ atmosphere, were placed 6-fluoropyridin-3-amine (24.5 g, 218.541 mmol, 1 equiv) and EA (1200 mL, 12258.087 mmol, 56.09 equiv) and NBS (40.84 g, 229.468 mmol, 1.05 equiv) was added at −10° C. The resulting solution was stirred for 1 h at −10° C. and then quenched with water. The resulting solution was extracted with ethyl acetate, dried over anhydrous sodium sulfate and concentrated to give the title compound (20 g, 47.91%) as a yellow solid.

Step 2: Synthesis of 3-amino-6-fluoropicolinonitrile

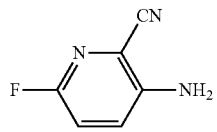

Into a 500-mL 3-necked round-bottom flask under N₂ atmosphere, were placed 2-bromo-6-fluoropyridin-3-amine (10 g, 52.355 mmol, 1 equiv), CuCN (14.07 g, 157.066 mmol, 3 equiv), and DMSO (200 mL). The resulting solution was stirred for 2 h at 120° C. and then quenched with water. The solids were filtered out and the resulting solution was extracted with ethyl acetate and the organic layer was concentrated. The residue was applied onto a silica gel column and eluted with ethyl acetate/petroleum ether (1:5) to give the title compound (7 g, 97.51%) of as yellow solid.

Step 3: Synthesis of 2-(aminomethyl)-6-fluoropyridin-3-amine

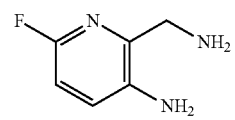

Into an 8-mL sealed tube under N₂ atmosphere, were placed 3-amino-6-fluoropicolinonitrile (200 mg), BH3-THF (1M) (3 ml), and THF (1 ml). The resulting solution was stirred for 30 min at 10° C. and then quenched with MeOH. The resulting mixture was concentrated and the residue was applied onto Prep-TLC and eluted with dichloromethane/methanol (10:1) to give the title compound (100 mg) as yellow solid.

Step 4: Synthesis of 7-(4-(6-fluoropyrido[3,2-d]pyrimidin-2-yl)-2-methylphenyl)-1-methyl-6,7-dihydro-1H-pyrazolo[3,4-f][1,4]oxazepin-8 (5H)-one

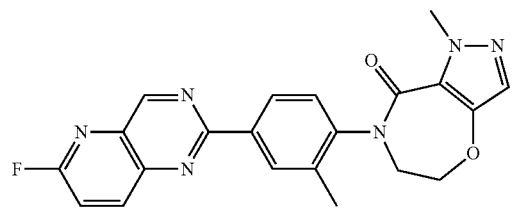 [SMILES: Cc1cc(-c2ncc3nc(F)ccc3n2)ccc1N1CCOc2cnn(C)c2C1=O]

Into a 20-mL sealed tube under N₂ atmosphere, were placed 3-methyl-4-[1-methyl-8-oxo-1H,5H,6H,7H,8H-pyrazolo[3,4-f][1,4]oxazepin-7-yl]benzaldehyde (200 mg, 0.701 mmol, 1 equiv), 2-(aminomethyl)-6-fluoropyridin-3-amine (98.95 mg, 0.701 mmol, 1 equiv), and MeOH (7 mL PhI(OAc)₂ (451.45 mg, 1.402 mmol, 2 equiv). The resulting solution was stirred for 1 h at 25° C. and then concentrated. The residue was applied onto Prep-TLC and eluted with dichloromethane/methanol (30:1) to give the title compound (144.8 mg, 51.08%) as a white solid. LC-MS: (ES, m/z): [M+H]⁺ 405; ¹H-NMR: (400 MHz, DMSO-d₆, ppm): δ 2.32 (s, 3H), 3.98 (s, 5H), 4.45-4.56 (m, 2H), 7.35 (s, 1H), 7.46 (d, 1H), 7.91 (d, 1H), 8.41 (d, 1H), 8.47 (s, 1H), 8.68-8.72 (m, 1H), 9.64 (s, 1H).

Example 52

Synthesis of 7-(4-(6-fluoro-1,5-naphthyridin-2-yl)-2-methylphenyl)-1-methyl-6,7-dihydro-1H-pyrazolo[3,4-f][1,4]oxazepin-8 (5H)-one

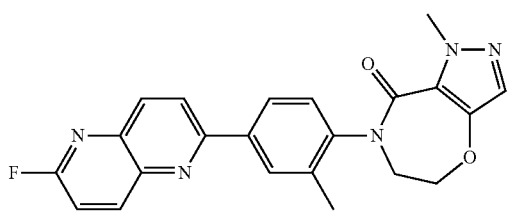

Step 1: Synthesis of ethyl (E)-3-(3-amino-6-fluoropyridin-2-yl)acrylate

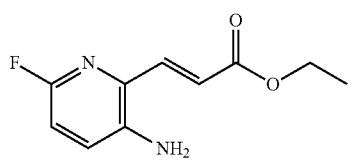

To a stirred mixture of 2-bromo-6-(trifluoromethyl)pyridin-3-amine (1.00 g, 4.149 mmol, 1.00 equiv) and ethyl prop-2-enoate (0.83 g, 8.298 mmol, 2.00 equiv) in DMF (20.00 mL) were added P(o-tol)$_3$ (0.25 g, 0.830 mmol, 0.20 equiv), Et$_3$N (1.26 g, 12.448 mmol, 3.00 equiv) and Pd(OAc)$_2$ (0.09 g, 0.415 mmol, 0.10 equiv). The resulting mixture was stirred for overnight at 100° C. under nitrogen atmosphere. The reaction mixture was quenched with water at room temperature. The resulting mixture was extracted with EtOAc and the combined organic layers was washed with NaCl (aq.) and then concentrated under reduced pressure. The residue was purified by silica gel column chromatography with PE/EtOAc (20:1) as eluent to afford the title compound (550 mg, 50.94%) as a yellow solid.

Step 2: Synthesis of 6-fluoro-1,5-naphthyridin-2 (1H)-one

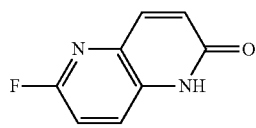 [SMILES: O=c1ccc2nc(F)ccc2[nH]1]

Into a 100 mL 3-necked round-bottom flask, were placed ethyl (E)-3-(3-amino-6-fluoropyridin-2-yl)acrylate (550.00 mg, 2.114 mmol, 1.00 equiv), dioxane (3.00 mL), and HCl (3.00 mL). The resulting solution was stirred overnight at 100° C. The resulting mixture was diluted with water and the solids were collected by filtration to give the title compound (400 mg, 88.37%) as a grey solid.

Step 3: Synthesis of 6-fluoro-1,5-naphthyridin-2-yl Trifluoromethanesulfonate

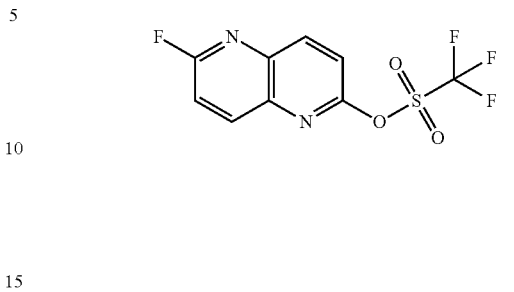

An ice water bath-cooled solution of 6-fluoro-1,5-naphthyridin-2 (1H)-one (350 mg, 2.132 mmol, 1 equiv) and TEA (431.54 mg, 4.265 mmol, 2 equiv) in DCM (17.5 mL) was mixed with a solution of trifluoromethanesulfonyl trifluoromethanesulfonate (721.92 mg, 2.559 mmol, 1.20 equiv) in DCM (4 mL) over 20 mins. The resulting mixture then was stirred for 2 h at 0° C. The reaction was quenched with sat. NaHCO$_3$ (aq.) at room temperature and the resulting mixture was extracted with CH$_2$Cl$_2$. The combined organic layers were dried over anhydrous Na$_2$SO$_4$. After filtration, the filtrate was concentrated under reduced pressure and the crude product was used in the next step directly without further purification.

Step 4: Synthesis of 7-(4-(6-fluoro-1,5-naphthyridin-2-yl)-2-methylphenyl)-1-methyl-6,7-dihydro-1H-pyrazolo[3,4-f][1,4]oxazepin-8 (5H)-one

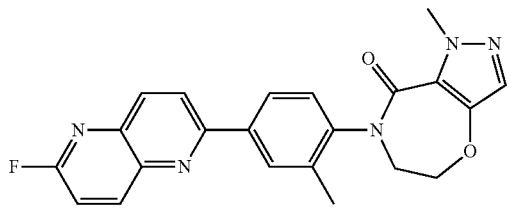

Proceeding as described in Example 5, Step 12 but substituting 7-(2,5-dimethyl-4-(4,4,5,5-tetramethyl-1,3,2-dioxaborolan-2-yl)phenyl)-1-methyl-6,7-dihydro-1H-pyrazolo[3,4-f][1,4]oxazepin-8 (5H)-one with 7-[2-methyl-4-(4,4,5,5-tetramethyl-1,3,2-dioxaborolan-2-yl)phenyl]-1H,5H,6H,7H,8H-pyrazolo[3,4-f][1,4]oxazepin-8-and 6-chloro-4-methyl-2-(trifluoromethyl)-1,5-naphthyridine with 6-fluoro-1,5-naphthyridin-2-yl trifluoromethanesulfonate gave crude product. The crude product was purified by silica gel column chromatography with PE/EtOAc (2:1) as eluent, followed by Prep-TLC (CH$_2$Cl$_2$/MeOH 40:1) and re-crystallization from MeOH (3 mL) to afford the title compound as a white solid. LC-MS: (ES, m/z): [M+H]$^+$ 404; $^1$H-NMR: (300 MHz, DMSO-d$_6$, ppm): δ 8.67 (t, 1H), 8.34-8.48 (m, 1H), 8.24 (d, 1H), 8.16 (dd, 1H), 7.63-7.67 (m, 1H), 7.45 (d, 1H), 7.37 (s, 1H), 4.45-4.58 (m, 2H), 4.0 (d, 5H), 2.32 (s, 3H).

Example 53

Synthesis of 7-(4-(6-fluoroquinazolin-2-yl)-2-methylphenyl)-1-methyl-6,7-dihydro-1H-pyrazolo[3,4-f][1,4]oxazepin-8 (5H)-one

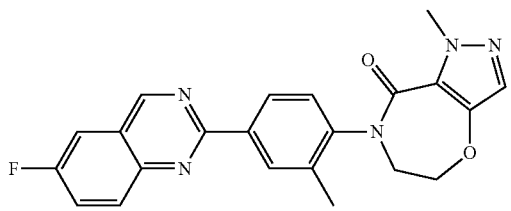 [SMILES: Cc1cc(-c2ncc3cc(F)ccc3n2)ccc1N1CCOc2cnn(C)c2C1=O]

Step 1: Synthesis of 6-fluoroquinazoline-2,4(1H,3H)-dione

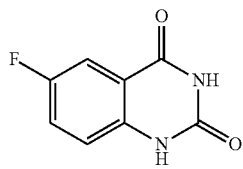

Into a 250-mL 3-necked round-bottom flask purged and maintained with $CO_2$, were placed 2-amino-5-fluorobenzonitrile (3 g, 22.038 mmol, 1 equiv), DMF (90 mL, 1162.958 mmol, 52.77 equiv), and DBU (10.06 g, 66.081 mmol, 3.00 equiv). The resulting solution was stirred for overnight at 100° C. and then diluted with $H_2O$. The pH value of the solution was adjusted to 5 with HCl (1 mol/L) and the resulting mixture was filtered, The solids were washed with $H_2O$ and dried to give (3.6 g, 90.68%) of the title compound as a yellow solid.

Step 2: Synthesis of 2,4-dichloro-6-fluoroquinazoline

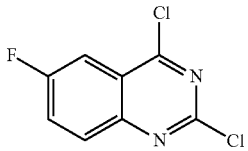 [SMILES: Fc1ccc2nc(Cl)nc(Cl)c2c1]

Into a 25-mL 3-necked round-bottom flask under $N_2$ atmosphere, were placed 6-fluoroquinazoline-2,4(1H,3H)-dione (3.6 g, 19.985 mmol, 1 equiv), $POCl_3$ (36.01 mL), and $PCl_5$ (20.81 g, 99.933 mmol, 5.00 equiv). The resulting solution was stirred overnight at 120° C. and then concentrated under vacuum. The resulting solution was diluted with of $H_2O$ and extracted with dichloromethane. The organic layers were combined, washed with $K_3PO_4$. The mixture was concentrated under vacuum to give the title compound (2.6 g, 72.22%) as a yellow solid.

Step 3: Synthesis of 2-chloro-6-fluoroquinazoline

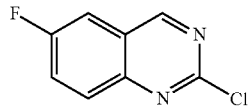

Into a 50-mL 3-necked round-bottom flask under $N_2$ atmosphere, were placed 2,4-dichloro-6-fluoroquinazoline (2.6 g, 11.980 mmol, 1 equiv), $Pd(PPh_3)_4$ (1.38 g, 1.198 mmol, 0.1 equiv), $PPh_3$ (4.71 g, 17.971 mmol, 1.5 equiv), THF (26.00 mL), and $Bu_3SnH$ (3.85 g, 13.179 mmol, 1.1 equiv). The resulting solution was stirred overnight at room temperature and then concentrated under vacuum. The residue was applied onto a silica gel column and eluted with ethyl acetate/petroleum ether (1:50) to give the title compound (1.2 g, 54.86%) as a white solid.

Step 4: Synthesis of 7-(4-(6-fluoroquinazolin-2-yl)-2-methylphenyl)-1-methyl-6,7-dihydro-1H-pyrazolo[3,4-f][1,4]oxazepin-8 (5H)-one

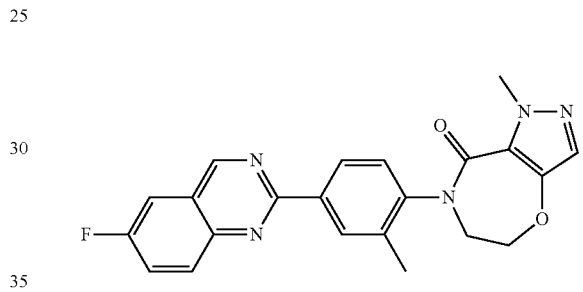

Proceeding as described in Example 50, Step 2, but substituting 2-chloro-6-(trifluoromethyl)pyrido[3,2-d]pyrimidine with 2-chloro-6-fluoroquinazoline (200 mg, 1.095 mmol, 1 equiv) and 1-methyl-7-(4-(4,4,5,5-tetramethyl-1,3,2-dioxaborolan-2-yl)phenyl)-6,7-dihydro-1H-pyrazolo[3,4-f][1,4]oxazepin-8 (5H)-one with 1-methyl-7-[2-methyl-4-(4,4,5,5-tetramethyl-1,3,2-dioxaborolan-2-yl)phenyl]-1H,5H,6H,7H,8H-pyrazolo[3,4-f][1,4]-oxazepin-8-one provided the title compound as a white solid. LC-MS: (ES, m/z): [M+H]+ 404.2; 1H-NMR: (400 MHz, DMSO-d6, ppm): δ 9.70 (s, 1H), 8.49 (d, 1H), 8.42 (m, 1H), 8.15-8.18 (m, 1H), 7.99-8.01 (m, 2H), 7.36 (s, 2H), 4.46-4.56 (m, 2H), 3.98-4.00 (m, 5H), 2.49-2.51 (m, 3H).

Example 54

Synthesis of 4-(2-methyl-4-(6-(trifluoromethyl)quinazolin-2-yl)phenyl)-3,4-dihydropyrido[2,3-f][1,4]oxazepin-5 (2H)-one

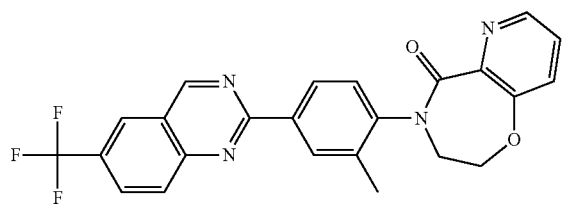 [SMILES: Cc1cc(-c2ncc3cc(C(F)(F)F)ccc3n2)ccc1N1CCOc2cccnc2C1=O]

Step 1: Synthesis of 3-(2-(benzyloxy)ethoxy)picolinic Acid

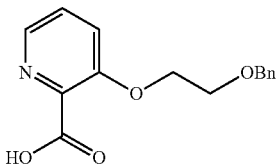 [SMILES: O=C(O)c1ncccc1OCCOCc1ccccc1]

To a stirred solution of methyl 3-bromopyridine-2-carboxylate (9.4 g, 43.512 mmol, 1 equiv) in 2-(benzyloxy)ethan-1-ol (50 mL) was added t-BuOLi (17.42 g, 217.558 mmol, 5 equiv) and Cu(OAc)$_2$ (1.58 g, 8.702 mmol, 0.2 equiv) in portions at room temperature under nitrogen atmosphere. The resulting mixture was stirred overnight at 130° C. under nitrogen atmosphere. The mixture was allowed to cool down to room temperature and then extracted with EtOAc. The aqueous layer was collected and acidified to pH 4 with HCl (aq.) and extracted with EtOAc. The organic layer was collected and concentrated and the residue was purified by silica gel column chromatography by eluting with CH$_2$Cl$_2$/MeOH (20:1) to afford the title compound (5 g, 42%) as a white solid.

Step 2: Synthesis of 3-(2-(benzyloxy)ethoxy)-N-(4-bromo-2-methylphenyl)picolinamide

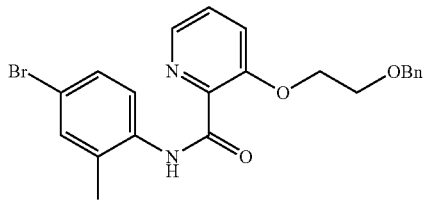 [SMILES: Cc1cc(Br)ccc1NC(=O)c1ncccc1OCCOCc1ccccc1]

To a stirred solution of 3-(2-(benzyloxy)ethoxy)picolinic acid (4.4 g, 16.100 mmol, 1 equiv) and 4-bromo-2-methylaniline (3.00 g, 16.100 mmol, 1 equiv) in DCM (44 mL, 692.122 mmol, 42.99 equiv) were added DIEA (4.16 g, 32.200 mmol, 2 equiv) and HATU (9.18 g, 24.150 mmol, 1.5 equiv) in portions at room temperature under nitrogen atmosphere. The resulting mixture was stirred for overnight at room temperature under nitrogen atmosphere and then extracted with EtOAc. After filtration, the filtrate was concentrated under reduced pressure. The residue was purified by silica gel column chromatography by eluting with CH$_2$Cl$_2$/MeOH (50:1) to afford the title compound (4.3 g, 61%) as a white solid.

Step 3: Synthesis of 4-(2-methyl-4-(4,4,5,5-tetramethyl-1,3,2-dioxaborolan-2-yl)phenyl)-3,4-dihydro-pyrido[2,3-f][1,4]oxazepin-5 (2H)-one

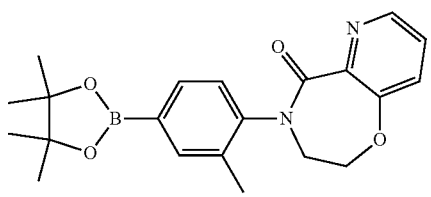 [SMILES: Cc1cc(B2OC(C)(C)C(C)(C)O2)ccc1N1CCOc2cccnc2C1=O]

Proceeding analogously as described in Example 1, Steps 9 to 12 but substituting 4-(2-(benzyloxy)ethoxy)-N-(4-bromo-2-methylphenyl)-1-methyl-1H-pyrazole-5-carboxamide with 3-(2-(benzyloxy)ethoxy)-N-(4-bromo-2-methylphenyl)picolinamide provided the title compound as a white solid.

Step 4: Synthesis of 4-(2-methyl-4-(6-(trifluoromethyl)quinazolin-2-yl)phenyl)-3,4-dihydropyrido[2,3-f][1,4]oxazepin-5 (2H)-one

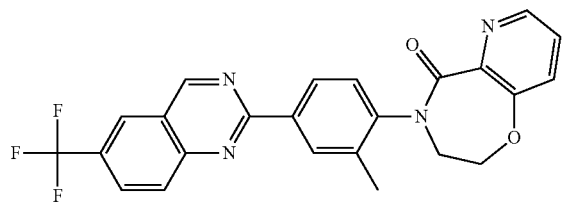 [SMILES: Cc1cc(-c2ncc3cc(C(F)(F)F)ccc3n2)ccc1N1CCOc2cccnc2C1=O]

Proceeding as described in Example 2, Step 11 but substituting 3-methyl-5-(2-methyl-4-(4,4,5,5-tetramethyl-1,3,2-dioxaborolan-2-yl)phenyl)-6,7-dihydro-pyrazolo[1,5-a]pyrazin-4 (5H)-one with 4-(2-methyl-4-(4,4,5,5-tetramethyl-1,3,2-dioxaborolan-2-yl)phenyl)-3,4-dihydropyrido[2,3-f][1,4]oxazepin-5 (2H)-one provided crude product. Purification by TLC with CH$_2$Cl$_2$/MeOH (20:1) as eluent gave the title compound as a white solid. LC-MS: (ES, m/z): [M+H]$^+$ 451.2; $^1$H-NMR: (400 MHz, DMSO-d$_6$, ppm): δ 9.92 (s, 1H), 8.74 (s, 1H), 8.59 (s, 1H), 8.52-8.51 (m, 2H), 8.30 (m, 2H), 7.68-7.65 (m, 2H), 7.62 (d, 1H), 4.47-4.45 (m, 2H), 3.94-3.92 (m, 2H), 2.38 (s, 3H).

Example 55

Synthesis of 8-(2-methyl-4-(6-(trifluoromethyl)quinazolin-2-yl)phenyl)-7,8-dihydropyrimido[4,5-f][1,4]oxazepin-9 (6H)-one

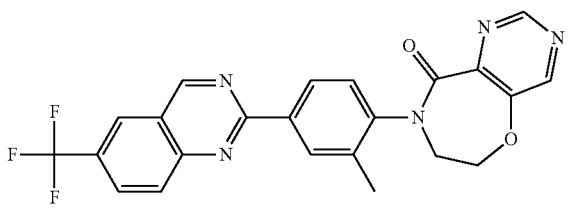

Step 1: Synthesis of 5-(2-(benzyloxy)ethoxy)pyrimidine-4-carboxylic acid

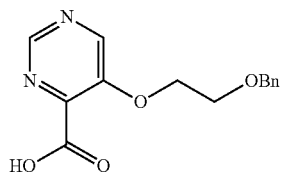 [SMILES: O=C(O)c1ncncc1OCCOCc1ccccc1]

To a stirred solution of 5-bromopyrimidine-4-carboxylic acid (4.3 g, 21.183 mmol, 1 equiv) and 2-(benzyloxy)ethan-1-ol (25 mL) were added $K_2CO_3$ (8.78 g, 63.548 mmol, 3 equiv) and $CuBr_2$ (0.95 g, 4.237 mmol, 0.2 equiv) at room temperature under nitrogen atmosphere. The resulting mixture was stirred for overnight at 100° C. under nitrogen atmosphere. The mixture was acidified to pH 5 with HCl (aq.) and extracted with EA. The residue was purified by silica gel column chromatography, eluted with $CH_2Cl_2$/ MeOH (10:1) to afford PH-IDE-0637-1 (1.0 g, 17%) as a white solid.

Step 2: Synthesis of 5-(2-(benzyloxy)ethoxy)-N-(4-bromo-2-methylphenyl)pyrimidine-4-carboxamide

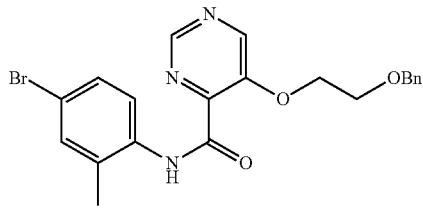 [SMILES: Cc1cc(Br)ccc1NC(=O)c1ncncc1OCCOCc1ccccc1]

Proceeding analogously as described in Example 54, Step 2 but substituting 3-(2-(benzyloxy)ethoxy)picolinic acid with 5-(2-(benzyloxy)ethoxy)pyrimidine-4-carboxylic acid and 4-bromo-2-methylaniline provided crude product. Purification by silica gel column chromatography, eluting with $CH_2Cl_2$/MeOH (10:1) provided the title compound as a white solid.

Step 3: Synthesis of 8-(2-methyl-4-(4,4,5,5-tetramethyl-1,3,2-dioxaborolan-2-yl)phenyl)-7,8-dihydropyrimido[4,5-f][1,4]oxazepin-9 (6H)-one

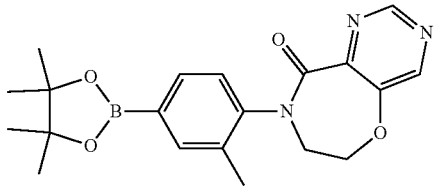 [SMILES: Cc1cc(B2OC(C)(C)C(C)(C)O2)ccc1N1CCOc2cncnc2C1=O]

Proceeding analogously as described in Example 1, Steps 9 to 12 but substituting 4-(2-(benzyloxy)ethoxy)-N-(4-bromo-2-methylphenyl)-1-methyl-1H-pyrazole-5-carboxamide with 5-(2-(benzyloxy)ethoxy)-N-(4-bromo-2-methylphenyl)pyrimidine-4-carboxamide to a stirred solution of 8-(4-bromo-2-methylphenyl)-7,8-dihydropyrimido[4,5-f][1, 4]oxazepin-9 (6H)-one provided the title compound as a white solid.

Step 4: Synthesis of 8-(2-methyl-4-(6-(trifluoromethyl)quinazolin-2-yl)phenyl)-7,8-dihydropyrimido [4,5-f][1,4]oxazepin-9 (6H)-one

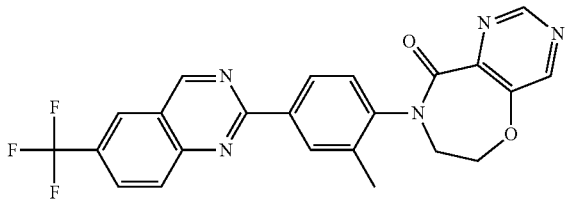 [SMILES: Cc1cc(-c2ncc3cc(C(F)(F)F)ccc3n2)ccc1N1CCOc2cncnc2C1=O]

Proceeding analogously as described in Example 50, Step 2, but substituting 1-methyl-7-(4-(4,4,5,5-tetramethyl-1,3,2-dioxaborolan-2-yl)phenyl)-6,7-dihydro-1H-pyrazolo[3,4-f] [1,4]oxazepin-8 (5H)-one with 8-(2-methyl-4-(4,4,5,5-tetramethyl-1,3,2-dioxaborolan-2-yl)phenyl)-7,8-dihydropyrimido[4,5-f][1,4]oxazepin-9 (6H)-one provided crude product. Purification by Prep-TLC ($CH_2Cl_2$/MeOH 20:1) provided the title compound as a white solid. LC-MS: (ES, m/z): [M+H]$^+$ 452.2; $^1$H-NMR: (400 MHz, DMSO-$d_6$, ppm): δ 9.92 (s, 1H), 9.10 (s, 1H), 8.81 (s, 1H), 8.74 (s, 1H), 8.59 (s, 1H), 8.52-8.51 (d, 1H), 8.30 (t, 2H), 7.57 (d, 1H), 4.66-4.62 (m, 2H), 4.08-4.04 (m, 2H), 2.36 (s, 3H).

Example 56

Synthesis of ethyl 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylate

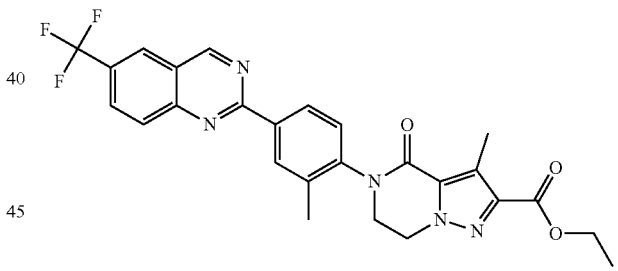

Step 1: Synthesis of 2-bromo-3-methyl-5-(2-methyl-4-(6-(trifluoromethyl)-quinazolin-2-yl)phenyl)-6,7-dihydropyrazolo[1,5-a]pyrazin-4 (5H)-one

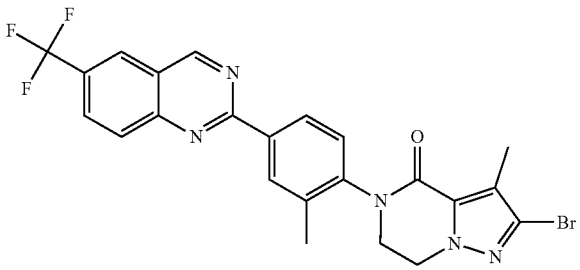 [SMILES: Cc1cc(-c2ncc3cc(C(F)(F)F)ccc3n2)ccc1N1CCn2nc(Br)c(C)c2C1=O]

To a stirred solution of 3-methyl-5-(2-methyl-4-(6-(trifluoromethyl)quinazolin-2-yl)phenyl)-6,7-dihydropyrazolo[1,5-a]pyrazin-4 (5H)-one (200 mg, 0.457 mmol, 1 equiv) in AcOH (2 mL) was added Br₂ (511 mg, 3.201 mmol, 7 equiv) dropwise at 0° C. under nitrogen atmosphere. The resulting mixture was stirred for overnight at 60° C. under nitrogen atmosphere. The resulting mixture was concentrated under reduced pressure and the resulting mixture was extracted with EtOAc and dried over anhydrous Na₂SO₄. After filtration, the filtrate was concentrated under reduced pressure to afford the title compound (127 mg, 54%) as a white solid.

Step 2: Synthesis of ethyl 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylate

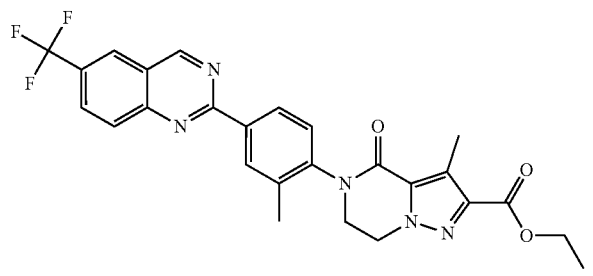 [SMILES: CCOC(=O)c1nn2c(c1C)C(=O)N(c1ccc(-c3ncc4cc(C(F)(F)F)ccc4n3)cc1C)CC2]

To a stirred solution of 2-bromo-3-methyl-5-(2-methyl-4-(6-(trifluoromethyl)-quinazolin-2-yl)-phenyl)-6,7-dihydropyrazolo[1,5-a]pyrazin-4 (5H)-one (3.1 g, 6.004 mmol, 1 equiv) and Pd(dppf)Cl₂ (0.88 g, 1.201 mmol, 0.2 equiv) in EtOH (31 mL) was added TEA (1.82 g, 18.012 mmol, 3 equiv) at room temperature under CO atmosphere. The resulting mixture was stirred for overnight at 80° C. under CO atmosphere and then concentrated under vacuum. The residue was purified by silica gel column chromatography but eluting with PE/EA (1:1) to afford the title compound (1.2 g, 39%) as a white solid. LC-MS: (ES, m/z): [M+H]⁺ 510.3; ¹H-NMR: (400 MHz, DMSO-d₆, ppm): δ 9.91 (s, 1H), 8.74 (s, 1H), 8.56 (s, 1H), 8.50 (d, 1H), 8.29 (t, 2H), 7.58-7.56 (d, 1H), 4.65 (t, 2H), 4.34-4.29 (m, 3H), 4.00-3.96 (m, 1H), 2.67 (s, 3H), 2.36 (s, 3H), 1.32 (t, 3H).

Example 57

Synthesis of 2-(hydroxymethyl)-3-methyl-5-(2-methyl-4-(6-(trifluoromethyl)-quinazolin-2-yl)phenyl)-6,7-dihydropyrazolo[1,5-a]pyrazin-4 (5H)-one

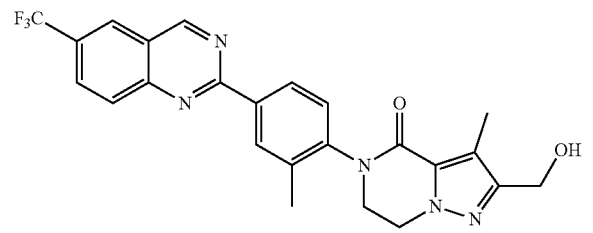 [SMILES: Cc1cc(-c2ncc3cc(C(F)(F)F)ccc3n2)ccc1N1CCn2nc(CO)c(C)c2C1=O]

Into a 25-mL 3-necked round-bottom flask under N₂ atmosphere, was placed ethyl 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylate (396 mg, 0.78 mmol, 1.00 equiv), oxolane (8 mg), and NaBHEt₃ (1 M) (3.11 mL, 4.00 mmol). The resulting solution was stirred for 3 h at −78° C. in a liquid nitrogen bath and then quenched with water/ice. The resulting solution was extracted with ethyl acetate, dried over anhydrous sodium sulfat, and concentrated. The residue was applied onto a silica gel column and eluted with ethyl acetate/petroleum ether (1/1) to give the title compound (12.0 mg) as a white solid. LC-MS: (ES, m/z): [M+H]⁺ 468.2; ¹H-NMR-PH-IDE-0645-0: (300 MHz, DMSO-d₆, ppm): δ 9.91 (s, 1H), 8.73 (s, 1H), 8.55 (s, 1H), 8.50 (d, 1H), 8.29 (s, 2H), 7.54 (d, 1H), 5.02 (t, 1H), 4.44 (m, 4H), 4.25 (m, 1H), 3.89 (m, 1H), 2.34 (s, 3H), 2.27 (s, 3H)

Example 58

Synthesis of 2-(1-hydroxyethyl)-3-methyl-5-(2-methyl-4-(6-(trifluoromethyl)-quinazolin-2-yl)phenyl)-6,7-dihydropyrazolo[1,5-a]pyrazin-4 (5H)-one

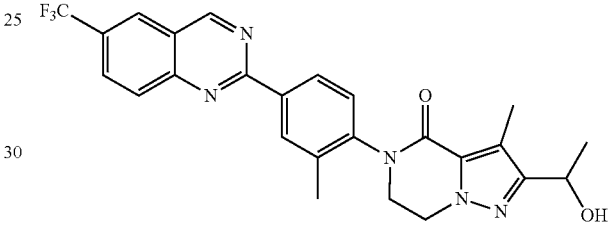

Step 1: Synthesis of 3-methyl-5-(2-methyl-4-(6-(trifluoromethyl)quinazolin-2-yl)phenyl)-2-vinyl-6,7-dihydropyrazolo[1,5-a]pyrazin-4 (5H)-one

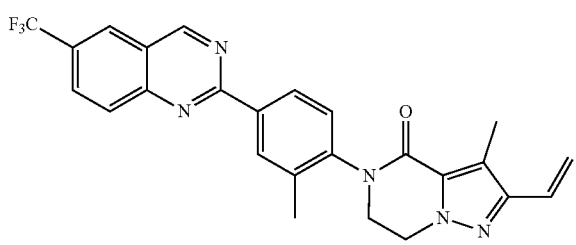 [SMILES: C=Cc1nn2c(c1C)C(=O)N(c1ccc(-c3ncc4cc(C(F)(F)F)ccc4n3)cc1C)CC2]

Into a 25-mL round-bottom flask under N₂ atmosphere, were placed 2-bromo-3-methyl-5-[2-methyl-4-[6-(trifluoromethyl)-quinazolin-2-yl]phenyl]-3H,3aH,4H,5H,6H,7H-pyrazolo[1,5-a]pyrazin-4-one (50 mg, 0.10 mmol, 1.00 equiv), tributyl(ethenyl)stannane (79 mg, 0.25 mmol, 2.50 equiv), tetrakis(triphenylphosphane) palladium (23 mg, 0.02 mmol, 0.20 equiv), and toluene (0.50 mL). The flask was wrapped with aluminum foil and the resulting solution was stirred for 12 h at 110° C. in an oil bath. The reaction was then quenched with water and the resulting solution was diluted with EA. The solids were filtered out and the resulting solution was extracted with ethyl acetate. The organic phase was dried over anhydrous sodium sulfate and after concentration, the residue was applied onto a silica gel column and eluted with ethyl acetate/petroleum ether (1/1) to give the title compound (38 mg) as a white solid.

Step 2: Synthesis of 2-(1,2-dihydroxyethyl)-3-methyl-5-(2-methyl-4-(6-(trifluoromethyl)-quinazolin-2-yl)phenyl)-6,7-dihydropyrazolo[1,5-a]pyrazin-4 (5H)-one

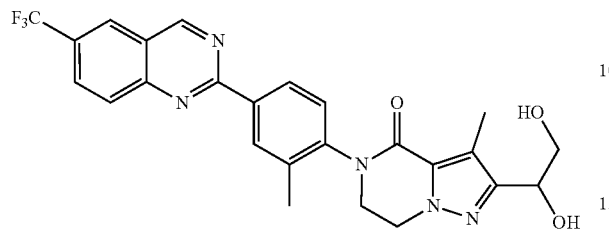

Into a 25-mL 3-necked round-bottom flask under N₂ atmosphere, were placed 3-methyl-5-(2-methyl-4-(6-(trifluoromethyl)-quinazolin-2-yl)-phenyl)-2-vinyl-6,7-dihydropyrazolo[1,5-a]pyrazin-4 (5H)-one (38.00 mg, 0.082 mmol, 1.00 equiv), THF (0.60 mL, 1.00 equiv), H₂O (0.20 mL), NMO (38.00 mg, 0.330 mmol, 4.00 equiv), and OsO₄ (8.00 mg, 0.033 mmol, 0.40 equiv) at 0° C. The resulting solution was stirred for 4 h at room temperature and then quenched with water. The resulting solution was extracted with ethyl acetate and the organic phase was washed with brine. The mixture was dried over anhydrous sodium sulfate and concentrated to give the title compound (36 mg, 80%) as a white solid.

Step 3: Synthesis of 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde

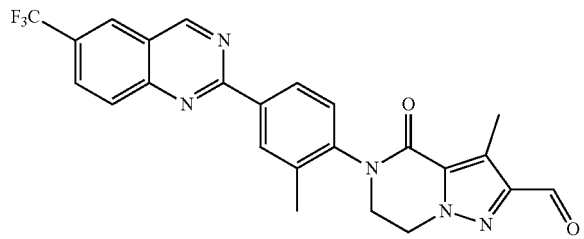 [SMILES: Cc1cc(-c2ncc3cc(C(F)(F)F)ccc3n2)ccc1N1CCn2nc(C=O)c(C)c2C1=O]

Into a 25-mL 3-necked round-bottom flask under N₂ atmosphere were placed 2-(1,2-dihydroxyethyl)-3-methyl-5-(2-methyl-4-(6-(trifluoromethyl)quinazolin-2-yl)phenyl)-6,7-dihydropyrazolo[1,5-a]pyrazin-4 (5H)-one (38.00 mg, 0.082 mmol, 1.00 equiv), dioxane (0.40 mL), H₂O (0.20 mL), and NaIO₄ (35.00 mg, 0.164 mmol, 2.0 equiv) at 0° C. The resulting solution was stirred for 1 h at room temperature and then quenched with water. The resulting solution was extracted with ethyl acetate and the organic phase was washed with brine. The organic layer was dried over anhydrous sodium sulfate, filtered and concentrated to give the title compound (28 mg, 90%) as a white solid.

Step 4: Synthesis of 2-(1-hydroxyethyl)-3-methyl-5-(2-methyl-4-(6-(trifluoromethyl)-quinazolin-2-yl)phenyl)-6,7-dihydropyrazolo[1,5-a]pyrazin-4 (5H)-one

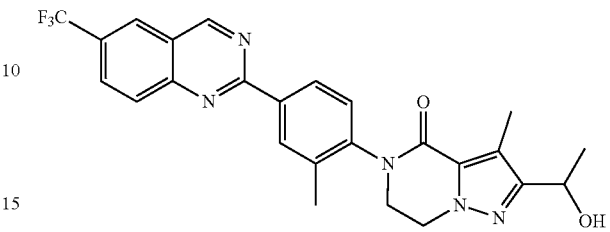

Into a 25-mL round-bottom flask purged and maintained with an inert atmosphere of nitrogen, were placed 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde (50 mg, 0.10 mmol, 1.00 equiv) and THF (0.5 mL) was added at 0° C. Chloro(methyl)magnesium (0.30 mL, 0.30 mmol, 3.00 equiv) was added and the resulting solution was stirred for 3 h at 0° C. in a water/ice bath. The reaction was then quenched with water/ice and extracted with ethyl acetate. The organic phase was dried over anhydrous sodium sulfate, filtered and concentrated. The residue was applied onto a silica gel column and eluted with ethyl acetate/petroleum ether (1/1) to give the title compound (24.2 mg) as a white solid. LC-MS: (ES, m/z): [M+H]⁺ 482; ¹H-NMR: (300 MHz, DMSO, ppm): δ 9.91 (s, 1H), 8.73 (s, 1H), 8.55 (d, 1H), 8.49 (dd, 1H), 8.28 (s, 2H), 7.53 (d, 1H), 5.02-4.84 (m, 2H), 4.80 (m, 2H), 4.44 (m, 1H), 3.88 (m, 1H), 2.34 (s, 3H), 2.27 (s, 3H), 1.43 (d, 3H).

Example 59

Synthesis of 2-(2-hydroxypropan-2-yl)-3-methyl-5-(2-methyl-4-(6-(trifluoromethyl)-quinazolin-2-yl)phenyl)-6,7-dihydropyrazolo[1,5-a]pyrazin-4 (5H)-one

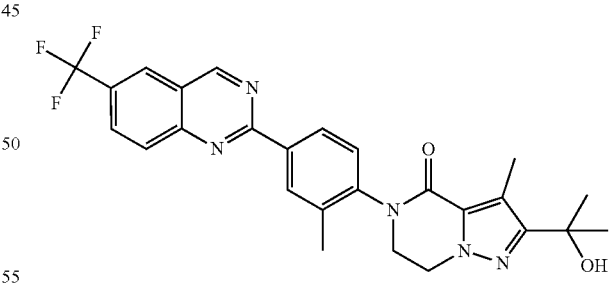

To a stirred solution of ethyl 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylate (200 mg, 0.393 mmol, 1 equiv) in THF (2 mL) was added TEA (119.17 mg, 1.178 mmol, 3 equiv). MeMgCl (0.39 mL, 1 mol/L, 1 equiv) was added dropwise at −78° C. with stirring for 30 min. After stirring for 2 h at room temperature under nitrogen atmosphere, the resulting mixture was extracted with EtOAc and the organic layer was concentrated. The residue was purified by Prep-TLC (CH₂Cl₂/MeOH 20:1) to afford the title compound (54.8 mg, 28%) as a white solid.

LC-MS: (ES, m/z): [M+H]⁺ 496.4; ¹H-NMR: (300 MHz, DMSO-d₆, ppm): δ 9.89 (s, 1H), 8.72 (s, 1H), 8.53 (s, 1H), 8.48 (d, 1H), 8.27 (s, 2H), 7.53 (d, 1H), 4.91 (s, 1H), 4.45-4.41 (m, 1H), 4.31-4.24 (m, 2H), 3.89-3.85 (m, 1H), 2.48 (s, 3H), 2.32 (s, 3H), 1.48 (s, 6H).

Example 60

Synthesis of 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylic acid

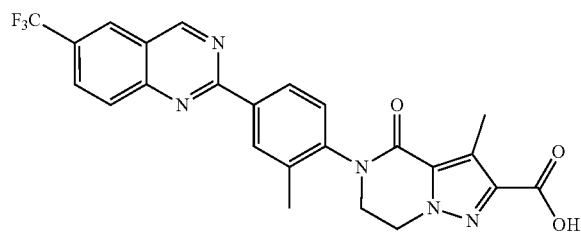 [SMILES: Cc1cc(-c2ncc3cc(C(F)(F)F)ccc3n2)ccc1N1CCn2nc(C(=O)O)c(C)c2C1=O]

Into a 8-ml sealed tube purged and maintained with an inert atmosphere of argon, were placed ethyl 3-methyl-5-[2-methyl-4-[6-(trifluoromethyl)quinazolin-2-yl]phenyl]-4H,5H,6H,7H-pyrazolo[1,5-a]pyrazine-2-carboxylate (200 mg, 0.404 mmol, 1 equiv), MeOH (2 ml), H₂O (0.3 ml), and NaOH (48.43 mg, 1.211 mmol, 3 equiv). The resulting solution was stirred for 1 h at 50° C. in an oil bath and then concentrated under vacuum. The pH value of the solution was adjusted to 3-4 with HCl (1.0 mol/l). The crude product was purified by re-crystallization from EA to give the title compound (140 mg, 73.46%) as a light-yellow solid. LC-MS: (ES, m/z): [M+H]⁺ 482.0; H-HNMR (300 MHz, DMSO, ppm): δ 2.34 (s, 3H), 2.49 (s, 3H), 3.93-3.97 (m, 1H), 4.30-4.34 (m, 1H), 4.60 (t, 2H), 7.55 (d, 1H), 8.28 (t, 2H), 8.48 (d, 1H), 8.55 (s, 1H), (m, 2H), 8.72 (s, 1H), 9.90 (s, 1H), 12.73 (bs, 1H).

Example 61

Synthesis of 3-methyl-5-(2-methyl-4-(6-(trifluoromethyl)quinazolin-2-yl)phenyl)-2-(morpholinomethyl)-6,7-dihydropyrazolo[1,5-a]pyrazin-4 (5H)-one

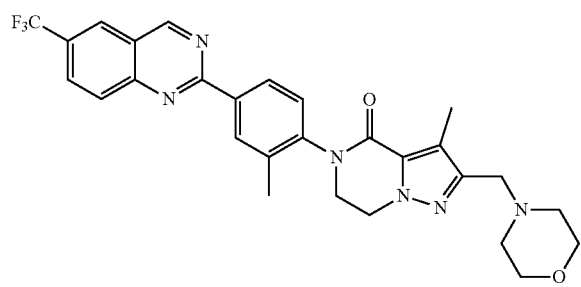 [SMILES: Cc1cc(-c2ncc3cc(C(F)(F)F)ccc3n2)ccc1N1CCn2nc(CN3CCOCC3)c(C)c2C1=O]

Into a 25-mL 3-necked round-bottom flask under N₂ atmosphere, were placed 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde (50 mg, 0.10 mmol, 1.00 equiv), oxolane (1 mL), morpholine (87 mg, 1.00 mmol, 10.00 equiv), acetic acid (3 mg), and NaBH₃CN (19 mg, 0.30 mmol, 3.00 equiv). The resulting solution was stirred for 3 h at room temperature and then quenched with water/ice. The resulting solution was extracted with ethyl acetate, dried over anhydrous sodium sulfate, filtered and the organ layer was concentrated. The residue was applied onto a silica gel column and eluted with ethyl acetate/hexane (1/1) to give the title compound (28.2 mg) as a white solid. LC-MS: (ES, m/z): [M+H]⁺ 537.2; ¹H-NMR: (400 MHz, DMSO-d₆, ppm δ 9.91 (s, 1H), 8.73 (s, 1H), 8.55 (s, 1H), 8.47 (d, 1H), 8.26 (s, 2H), 7.54 (d, 1H), 4.47 (m, 2H), 4.27 (m, 1H), 3.89 (m, 1H), 3.55 (m, 4H), 3.47 (s, 2H), 2.39 (d, 4H), 2.34 (s, 3H), 2.26 (s, 3H).

Example 62

Synthesis of (3-methyl-5-(2-methyl-4-(6-(trifluoromethyl)quinazolin-2-yl)phenyl)-4,5,6,7-tetrahydropyrazolo[1,5-a]pyrazin-2-yl)(morpholino)methanone

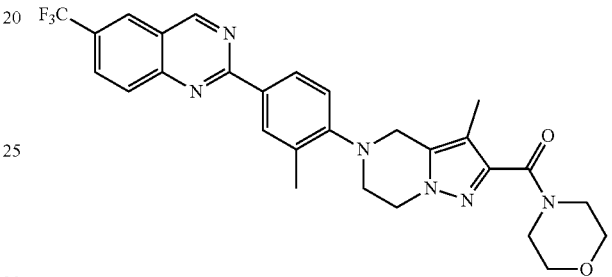

Into a 8-mL sealed tube purged and maintained under nitrogen atmosphere, were placed 3-methyl-5-(2-methyl-4-(6-(trifluoromethyl)quinazolin-2-yl)phenyl)-4,5,6,7-tetrahydropyrazolo[1,5-a]pyrazine-2-carboxylic acid (70 mg, 0.150 mmol, 1 equiv), morpholine (15.66 mg, 0.180 mmol, 1.20 equiv), DMF (1.0 mL), DIEA (38.71 mg, 0.299 mmol, 2 equiv), and HATU (85.41 mg, 0.225 mmol, 1.5 equiv). The resulting solution was stirred for 12 h at 25° C. and then quenched with water. The resulting solution was extracted with ethyl acetate and the organic layers combined and concentrated under vacuum to give the title compound (55 mg, 68.45%) as a light-yellow solid. LCMS: (ES, m/z) [M+H]⁺ 551.2; ¹H-NMR: (300 MHz, DMSO-d₆, ppm): δ 2.30 (s, 6H), 3.58-3.64 (m, 8H), 3.92-3.98 (m, 1H), 4.27-4.37 (m, 1H), 4.55 (d, 2H), 7.54 (d, 1H), 8.28 (t, 2H), 8.49 (d, 1H), 8.55 (s, 1H), 8.72 (s, 1H), 9.90 (s, 1H).

Example 63

Synthesis of 2-((dimethylamino)methyl)-3-methyl-5-(2-methyl-4-(6-(trifluoromethyl)-quinazolin-2-yl)phenyl)-6,7-dihydropyrazolo[1,5-a]pyrazin-4 (5H)-one

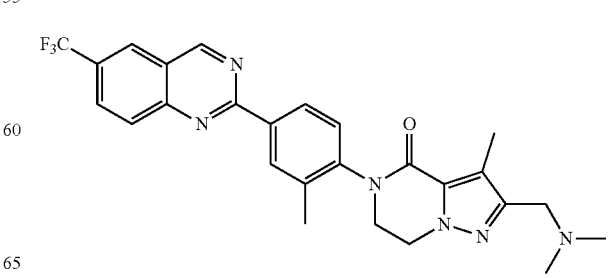

Into a 25-mL 3-necked round-bottom flask purged and maintained under nitrogen atmosphere, were placed 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde (50 mg, 0.10 mmol, 1.00 equiv), oxolane (1.50 mL), dimethylamine (0.50 mg, 10.0 mmol, 10.0 equiv), acetic acid (3 mg), and NaBH$_3$CN (19 mg, 3.00 mmol, 3.00 equiv). The resulting solution was stirred for 3 h at room temperature and then quenched with water/ice. The resulting solution was extracted with ethyl acetate. The combined organic phase was dried over anhydrous sodium sulfate, filtered and concentrated. The residue was applied onto a silica gel column and eluted with ethyl acetate/hexane (1/1) to give (39.2 mg) of the title compound as a white solid. LC-MS: (ES, m/z): [M+H]$^+$ 495.2; $^1$H-NMR: (400 MHz, DMSO-d$_6$, ppm): δ 9.91 (s, 1H), 8.73 (s, 1H), 8.55 (s, 1H), 8.48 (d, 1H), 8.29 (s, 2H), 7.54 (d, 1H), 4.47 (t, 2H), 4.27 (m, 1H), 3.92 (m, 1H), 3.40 (s, 2H), 2.35 (s, 3H), 2.25 (s, 3H), 2.17 (s, 6H).

Example 64

Synthesis of 3-bromo-5-(2-methyl-4-(6-(trifluoromethyl)quinazolin-2-yl)phenyl)-6,7-dihydropyrazolo[1,5-a]pyrazin-4 (5H)-one

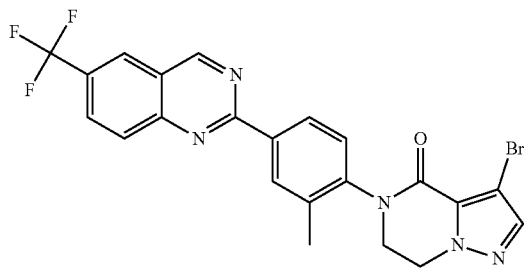

Step 1: Synthesis of methyl 1-(2-(benzyloxy)ethyl)-4-bromo-1H-pyrazole-5-carboxylate

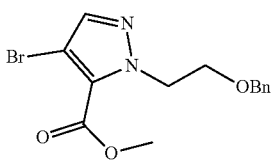 [SMILES: COC(=O)c1c(Br)cnn1CCOCc1ccccc1]

Into a 500-mL 3-necked round-bottom flask under N$_2$ atmosphere, were placed methyl 4-bromo-1H-pyrazole-5-carboxylate (20 g, 97.556 mmol, 1 equiv), 2-(benzyloxy)ethan-1-ol (29.69 g, 195.111 mmol, 2 equiv), DIAD (39.45 g, 195.111 mmol, 2 equiv), and THF (200 mL, 2468.598 mmol, 25.30 equiv), and PPh$_3$ (51.17 g, 195.111 mmol, 2 equiv) was added at 0° C. The resulting solution was stirred for 12 h at 25° C. and then concentrated. The residue was applied onto a silica gel column and eluted with dichloromethane/petroleum ether (1:10) to give the title compound (25 g, 75.55%) as a yellow liquid.

Step 2: Synthesis of 1-(2-(benzyloxy)ethyl)-4-bromo-1H-pyrazole-5-carboxylic acid

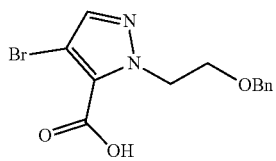 [SMILES: O=C(O)c1c(Br)cnn1CCOCc1ccccc1]

Into a 500-mL 3-necked round-bottom flask purged and maintained with an inert atmosphere of nitrogen, were placed methyl 1-(2-(benzyloxy)ethyl)-4-bromo-1H-pyrazole-5-carboxylate (25 g, 73.705 mmol, 1 equiv), EtOH (200 mL), H$_2$O (100 mL), and NaOH (8.84 g, 221.116 mmol, 3 equiv). The resulting solution was stirred for 12 h at 25° C. The pH value of the solution was adjusted to 5 with HCl and the resulting solution was extracted with ethyl acetate, dried over anhydrous sodium sulfate and concentrated to give the title compound (15 g, 62.59%) as a white solid.

Step 3: Synthesis of 3-bromo-5-(2-methyl-4-(4,4,5,5-tetramethyl-1,3,2-dioxaborolan-2-yl)phenyl)-6,7-dihydropyrazolo[1,5-a]pyrazin-4 (5H)-one

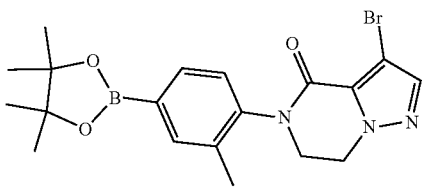 [SMILES: Cc1cc(B2OC(C)(C)C(C)(C)O2)ccc1N1CCn2ncc(Br)c2C1=O]

Proceeding analogously as described in Example 1, Steps 6 to 12, but substituting 4-bromo-1-methyl-1H-pyrazole-5-carboxylic acid with 1-(2-(benzyloxy)ethyl)-4-bromo-1H-pyrazole-5-carboxylic acid provided the title compound as a white solid.

Step 4: Synthesis of 3-bromo-5-(2-methyl-4-(6-(trifluoromethyl)quinazolin-2-yl)phenyl)-6,7-dihydropyrazolo[1,5-a]pyrazin-4 (5H)-one

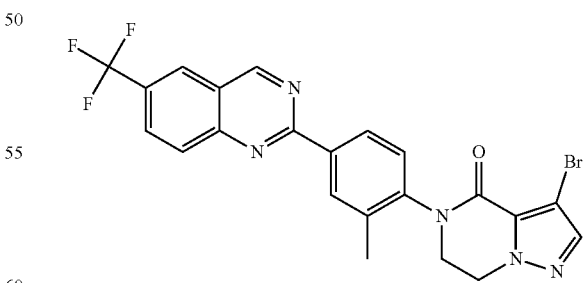

Proceeding analogously as described in Example 49, Step 2, but substituting 1-methyl-7-(2-methyl-4-(4,4,5,5-tetramethyl-1,3,2-dioxaborolan-2-yl)phenyl)-5,6,7,8-tetrahydro-1H-pyrazolo[3,4-f][1,4]oxazepane with 3-bromo-5-(2-methyl-4-(4,4,5,5-tetramethyl-1,3,2-dioxaborolan-2-yl)phenyl)-6,7-dihydropyrazolo[1,5-a]pyrazin-4 (5H)-one and 2-chloro-6-(trifluoromethyl)pyrido[3,2-d]pyrimidine with 2-chloro-6-(trifluoromethyl)quinazoline provided the title compound as a yellow solid. LC-MS: (ES, m/z): [M+H]+ 503.9; $^1$H-NMR: (300 MHz, DMSO, ppm): δ 9.90 (s, 1H), 8.72 (s, 1H), 8.54 (s, 1H), 8.48 (d, 1H), 8.28 (t, 2H), 7.79 (s, 1H), 7.56 (d, 1H), 4.60 (t, 2H), 4.40-4.29 (m, 1H), 3.95 (d, 1H), 2.34 (s, 3H).

Example 65

Synthesis of 5-(2-methyl-4-(6-(trifluoromethyl)quinazolin-2-yl)phenyl)-4-oxo-4,5,6,7-tetrahydropyrazolo[1,5-a]pyrazine-3-carboxylic acid

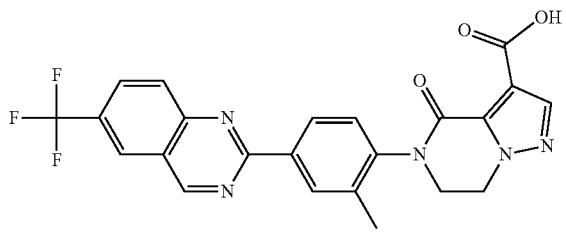 [SMILES: Cc1cc(-c2ncc3cc(C(F)(F)F)ccc3n2)ccc1N1CCn2ncc(C(=O)O)c2C1=O]

Step 1: Synthesis of ethyl 5-(2-methyl-4-(6-(trifluoromethyl)quinazolin-2-yl)phenyl)-4-oxo-4,5,6,7-tetrahydropyrazolo[1,5-a]pyrazine-3-carboxylate

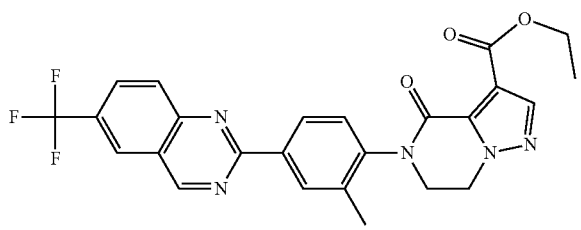 [SMILES: CCOC(=O)c1cnn2c1C(=O)N(c1ccc(-c3ncc4cc(C(F)(F)F)ccc4n3)cc1C)CC2]

Proceeding analogously as described in Example 56, Step 2, but substituting 2-bromo-3-methyl-5-(2-methyl-4-(6-(trifluoromethyl)quinazolin-2-yl)phenyl)-6,7-dihydropyrazolo-[1,5-a]pyrazin-4 (5H)-one with 3-bromo-5-(2-methyl-4-(6-(trifluoromethyl)-quinazolin-2-yl)phenyl)-6,7-dihydropyrazolo[1,5-a]pyrazin-4 (5H)-one provided the title compound as a light yellow solid.

Step 2: Synthesis of 5-(2-methyl-4-(6-(trifluoromethyl)quinazolin-2-yl)phenyl)-4-oxo-4,5,6,7-tetrahydropyrazolo[1,5-a]pyrazine-3-carboxylic acid

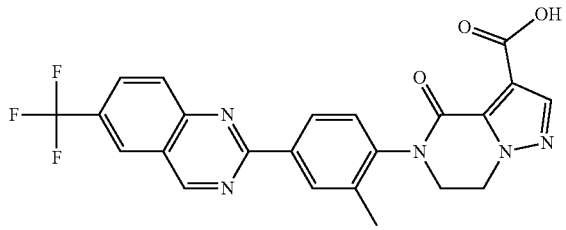 [SMILES: Cc1cc(-c2ncc3cc(C(F)(F)F)ccc3n2)ccc1N1CCn2ncc(C(=O)O)c2C1=O]

Proceeding analogously as described in Example 60 but substituting ethyl 3-methyl-5-[2-methyl-4-[6-(trifluoromethyl)quinazolin-2-yl]phenyl]-4H,5H,6H,7H-pyrazolo[1,5-a]pyrazine-2-carboxylate with ethyl 5-(2-methyl-4-(6-(trifluoromethyl)quinazolin-2-yl)phenyl)-4-oxo-4,5,6,7-tetrahydropyrazolo[1,5-a]pyrazine-3-carboxylate provided crude product. The crude product was purified by Prep-TLC (CH$_2$Cl$_2$/MeOH 1:1) to afford the title compound as a white solid. LC-MS: (ES, m/z): [M+H]+ 468.0; $^1$H-NMR: (300 MHz, DMSO-d$_6$, ppm): δ 14.00 (s, 1H), 9.91 (s, 1H), 8.73 (s, 1H), 8.59 (d, 1H), 8.52 (dd, 1H), 8.28 (t, 2H), 8.15 (s, 1H), 7.65 (d, 1H), 4.73 (dd, 2H), 4.45 (dt, 1H), 4.12 (dt, 1H), 2.41 (s, 3H).

Example 66

Synthesis of 5-(2-methyl-4-(6-(trifluoromethyl)quinazolin-2-yl)phenyl)-4-oxo-4,5,6,7-tetrahydropyrazolo[1,5-a]pyrazine-3-carboxamide

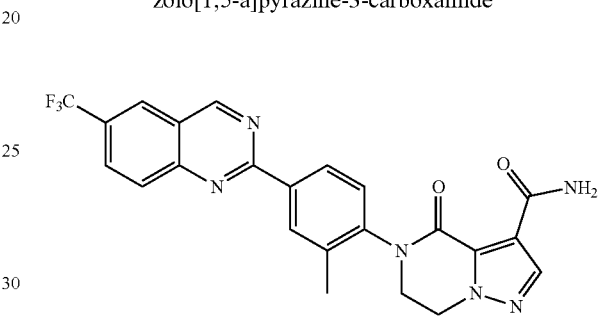

Proceeding analogously as described in Example 62 but substituting 3-methyl-5-(2-methyl-4-(6-(trifluoromethyl) quinazolin-2-yl)phenyl)-4,5,6,7-tetrahydropyrazolo[1,5-a] pyrazine-2-carboxylic acid with 5-(2-methyl-4-(6-(trifluoromethyl)quinazolin-2-yl)phenyl)-4-oxo-4,5,6,7-tetrahydropyrazolo[1,5-a]pyrazine-3-carboxylic acid and morpholine with NH$_4$Cl provided crude product. Purification by Prep-TLC (CH$_2$Cl$_2$/MeOH 12:1) provided the title compound as a light brown solid. LC-MS: (ES, m/z): [M+H]+ 467.2; $^1$H-NMR: (300 MHz, DMSO-d$_6$, ppm): δ 9.90 (s, 1H), 9.26 (s, 1H), 8.72 (s, 1H), 8.56 (s, 1H), 8.50 (d, 1H), 8.28 (s, 2H), 8.01 (s, 1H), 7.61 (d, 1H), 7.43 (s, 1H), 4.67 (t, 2H), 4.37 (dd, 1H), 4.09-3.97 (m, 1H), 3.04 (q, 1H), 2.37 (s, 3H).

Example 67

Synthesis of 5-(2-methyl-4-(6-(trifluoromethyl)quinazolin-2-yl)phenyl)-4-oxo-4,5,6,7-tetrahydropyrazolo[1,5-a]pyrazine-3-carbonitrile

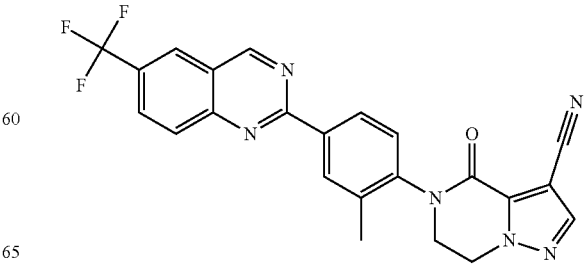

Into a 8-mL sealed tube under $N_2$ atmosphere, were placed 3-bromo-5-(2-methyl-4-(6-(trifluoromethyl)quinazolin-2-yl)phenyl)-6,7-dihydropyrazolo-[1,5-a]pyrazin-4 (5H)-one (150 mg, 0.299 mmol, 1 equiv), $Zn(CN)_2$ (70.14 mg, 0.597 mmol, 2 equiv), DMF (3 mL), and $Pd(PPh_3)_4$ (51.76 mg, 0.045 mmol, 0.15 equiv). The resulting solution was stirred for 12 h at 120° C. and then quenched with $NaHCO_3$. The resulting solution was extracted with ethyl acetate and the organic layer was concentrated. The residue was applied onto Prep-TLC and eluted with dichloromethane/methanol (40:1) to give the title compound (69.4 mg, 51.83%) as a yellow solid. LC-MS: (ES, m/z): $[M+H]^+$ 449.3; $^1$H-NMR: (400 MHz, DMSO-$d_6$, ppm): δ 2.38 (s, 3H), 4.01-4.04 (m, 1H), 4.37-4.44 (m, 1H), 4.68-4.71 (m, 2H), 7.59 (d, 1H), 8.29 (d, 3H), 8.50 (s, 1H), 8.55 (s, 1H), 8.73 (s, 1H), 9.91 (s, 1H).

Example 68

Synthesis of 5-(2-methyl-4-(6-(trifluoromethyl)quinazolin-2-yl)phenyl)-3-morpholino-6,7-dihydropyrazolo[1,5-a]pyrazin-4 (5H)-one

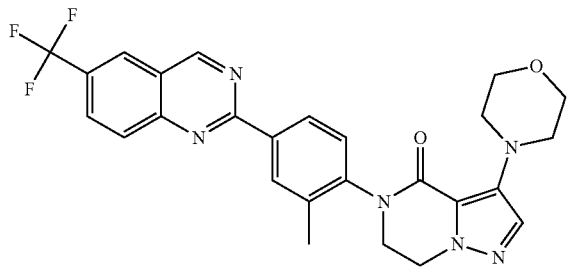 [SMILES: Cc1cc(-c2ncc3cc(C(F)(F)F)ccc3n2)ccc1N1CCn2ncc(N3CCOCC3)c2C1=O]

To a stirred solution/mixture of 3-bromo-5-(2-methyl-4-(6-(trifluoromethyl)-quinazolin-2-yl)phenyl)-6,7-dihydropyrazolo[1,5-a]pyrazin-4 (5H)-one (100 mg, 0.199 mmol, 1 equiv) and morpholine (86.72 mg, 0.995 mmol, 5.00 equiv) in dioxane (2 mL) was added t-BuONa (47.83 mg, 0.498 mmol, 2.5 equiv) at room temperature under nitrogen atmosphere. The resulting mixture was stirred for overnight at 50° C. and then diluted with water. The aqueous layer was extracted with EtOAc and the organic layer was concentrated. The residue was purified by Prep-TLC ($CH_2Cl_2$/ MeOH 80:1) to afford the title compound (51.5 mg, 50.87%) as a white solid. LC-MS: (ES, m/z): $[M+H]^+$ 509.2; $^1$H-NMR: (300 MHz, DMSO-$d_6$, ppm): δ 2.33 (s, 3H), 3.13 (d, 4H), 3.68 (t, 4H), 3.92 (s, 1H), 4.24 (s, 1H), 4.50 (t, 2H), 7.38 (s, 1H), 7.53 (d, 1H), 8.29 (s, 2H), 8.48 (d, 1H), 8.55 (s, 1H), 8.73 (s, 1H), 9.91 (s, 1H).

Example 69

Synthesis of 4-(5-(2-methyl-4-(6-(trifluoromethyl) quinazolin-2-yl)phenyl)-4-oxo-4,5,6,7-tetrahydropyazolo[1,5-a]pyrazin-3-yl)morpholin-3-one

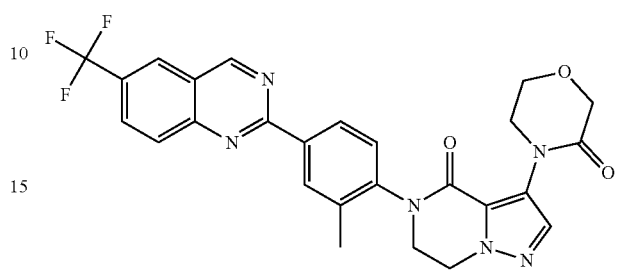

Into a 25-mL round-bottom flask, were placed 3-bromo-5-(2-methyl-4-(6-(trifluoro-methyl)quinazolin-2-yl)phenyl)-6,7-dihydropyrazolo[1,5-a]pyrazin-4 (5H)-one (150.00 mg, 0.299 mmol, 1.00 equiv), morpholin-3-one (36.23 mg, 0.358 mmol, 1.20 equiv), dioxane (2.00 mL), $K_2CO_3$ (82.54 mg, 0.597 mmol, 2.00 equiv), (1S,2S)-cyclohexane-1,2-diamine (6.82 mg, 0.060 mmol, 0.20 equiv), and CuI (5.69 mg, 0.030 mmol, 0.10 equiv). The resulting solution was stirred for 1 overnight at 110° C. and then quenched with water. The resulting solution was extracted with dichloromethane and the organic layer was concentrated. The residue was applied onto a Prep TLC and eluted with ethyl acetate/petroleum ether (1:1) to give the title compound (6.2 mg, 3.97%) as a white solid. LC-MS: (ES, m/z): 523.3; $^1$H-NMR: (300 MHz, DMSO-$d_6$, ppm): δ 2.36 (s, 3H), 3.72-3.75 (m, 2H), 3.91-3.94 (m, 3H), 4.17 (s, 2H), 4.33 (s, 1H), 4.60-4.63 (m, 2H), 7.58 (d, 1H), 7.71 (s, 1H), 8.30 (s, 2H), 8.51 (d, 1H), 8.56 (s, 1H), 8.74 (s, 1H), 9.92 (s, 1H).

Example 70

Synthesis of 5-(2-methyl-4-(6-(trifluoromethyl)quinazolin-2-yl)phenyl)-3-(morpholino-methyl)-6,7-dihydropyrazolo[1,5-a]pyrazin-4 (5H)-one

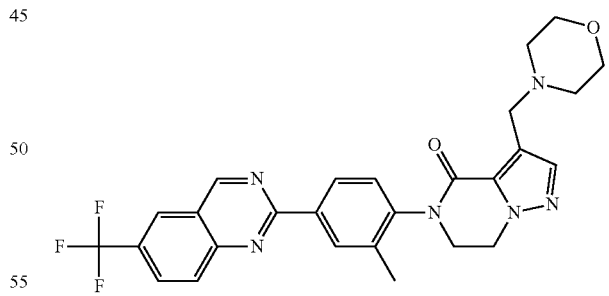

Proceeding analogously as described in Example 61, but substituting 3-methyl-5-(2-methyl-4-(6-(trifluoromethyl) quinazolin-2-yl)phenyl)-4-oxo-4,5,6,7-tetrahydropyrazolo [1,5-a]pyrazine-2-carbaldehyde with 5-(2-methyl-4-(6-(trifluoromethyl)quinazolin-2-yl)phenyl)-4-oxo-4,5,6,7-tetrahydropyrazolo[1,5-a]pyrazine-3-provided crude product. The crude product was purified by Prep-TLC ($CH_2Cl_2$/MeOH 40:1), followed by Prep-HPLC using the following conditions (Column: XSelect CSH Prep C18 OBD Column, 5 um, 19*150 mm; Mobile Phase A:Water (0.1% FA), Mobile Phase B: ACN; Flow rate: 20 mL/min; Gradient: 30% B to 37% B in 7 min; 254; 220 nm; Rt: 5.08 min) to afford the title compound as a white solid. LC-MS: (ES, m/z): [M−H]⁺523.4; ¹H-NMR (DMSO, 400 MHz, ppm): δ 9.89 (s, 1H), 8.72 (s, 1H), 8.54 (s, 1H), 8.50 (d, 1H), 88.27 (s, 2H), 7.56 (d, 2H), 4.67 (s, 2H), 3.98-4.56 (m, 3H), 3.70-3.95 (m, 5H), 2.40 (s, 4H), 2.32 (s, 3H).

Example 71

Synthesis of 7-(2-methyl-4-(6-(trifluoromethyl)quinazolin-2-yl)phenyl)-1-(2-morpholinoethyl)-6,7-dihydro-1H-pyrazolo[3,4-f][1,4]oxazepin-8 (5H)-one

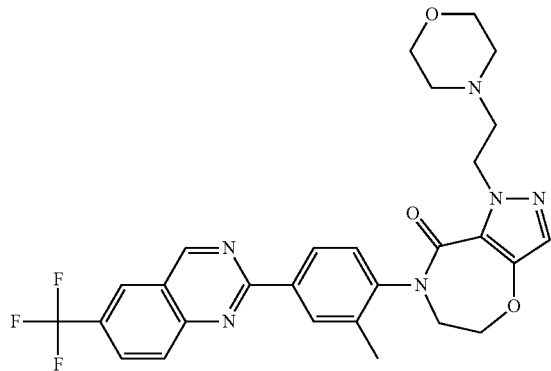 [SMILES: Cc1cc(-c2ncc3cc(C(F)(F)F)ccc3n2)ccc1N1CCOc2cnn(CCN3CCOCC3)c2C1=O]

Proceeding analogously as described in Example 64, Step 1, but substituting methyl 4-bromo-1H-pyrazole-5-carboxylate with 7-(2-methyl-4-(6-(trifluoromethyl)quinazolin-2-yl)phenyl)-6,7-dihydro-1H-pyrazolo[3,4-f][1,4]oxazepin-8 (5H)-one provided crude product. Purification by Prep-TLC (CH₂Cl₂/MeOH 60:1) gave the title compound as a white solid. LC-MS: (ES, m/z): [M+H]⁺ 553.2; ¹H-NMR: (300 MHz, CDCl₃, ppm): δ 9.56 (s, 1H), 8.62 (s, 1H), 8.57 (dd, 1H), 8.27 (s, 1H), 8.21 (d, 2H), 8.09 (dd, 1H), 7.30-7.43 (m, 2H), 4.73 (t, 2H), 4.49-4.53 (m, 2H), 3.99-4.03 (m, 2H), 3.68 (s, 4H), 2.81 (bs, 2H), 2.53 (bs, 4H), 2.41 (s, 3H).

Example 72

Synthesis of 1-(2-(4-hydroxypiperidin-1-yl)ethyl)-7-(2-methyl-4-(6-(trifluoromethyl)-quinazolin-2-yl)phenyl)-6,7-dihydro-1H-pyrazolo[3,4-f][1,4]oxazepin-8 (5H)-one

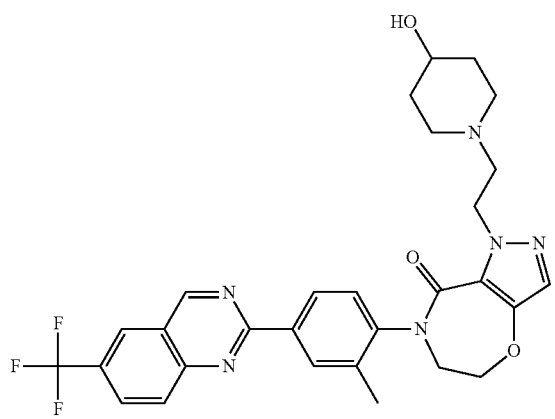 [SMILES: Cc1cc(-c2ncc3cc(C(F)(F)F)ccc3n2)ccc1N1CCOc2cnn(CCN3CCC(O)CC3)c2C1=O]

Step 1: Synthesis of 2-(4-(benzyloxy)piperidin-1-yl)ethan-1-ol

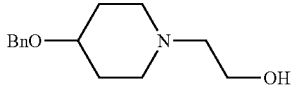

To a stirred solution/mixture of 4-(benzyloxy)piperidine (500 mg, 2.614 mmol, 1 equiv) and 2-bromoethan-1-ol (392.00 mg, 3.137 mmol, 1.20 equiv) in CH₃CN (0.4 mL) was added K₂CO₃ (1083.83 mg, 7.842 mmol, 3.00 equiv) at room temperature under nitrogen atmosphere. The resulting mixture was stirred for overnight at 90° C. and then quenched with sat. NH₄Cl (aq.). The aqueous layer was extracted with EtOAc and the organic layer was concentrated under vacuum. The residue was purified by reverse flash chromatography under following conditions: Column, C18 silica gel; mobile phase, MeOH in water, 10% to 50% gradient in 10 min; detector, UV 254 nm. The resulting mixture was concentrated and the residue was extracted with EtOAc. The combined organic layers were dried over anhydrous Na₂SO₄. After filtration, the filtrate was concentrated under reduced pressure to give the title compound (340 mg, 55.27%) as a yellow oil.

Step 2: Synthesis of 1-(2-(4-(benzyloxy)piperidin-1-yl)ethyl)-7-(2-methyl-4-(6-(trifluoro-methyl)quinazolin-2-yl)phenyl)-6,7-dihydro-1H-pyrazolo[3,4-f][1,4]oxazepin-8 (5H)-one

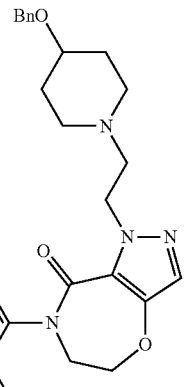

Proceeding analogously as described in example 64, Step 1, but substituting methyl 4-bromo-1 h-pyrazole-5-carboxylate with 7-(2-methyl-4-(6-(trifluoromethyl)quinazolin-2-yl)phenyl)-6,7-dihydro-1H-pyrazolo[3,4-f][1,4]oxazepin-8 (5H)-one and 2-(benzyloxy)ethan-1-ol with 2-(4-(benzyloxy)piperidin-1-yl)ethan-1-ol provided crude product. Purification by prep-TLC (CH₂Cl₂/MeOH 100:1) gave the title compound as a white solid.

Step 3: Synthesis of 1-(2-(4-hydroxypiperidin-1-yl)ethyl)-7-(2-methyl-4-(6-(trifluoromethyl)-quinazolin-2-yl)phenyl)-6,7-dihydro-1H-pyrazolo[3,4-f][1,4]oxazepin-8 (5H)-one

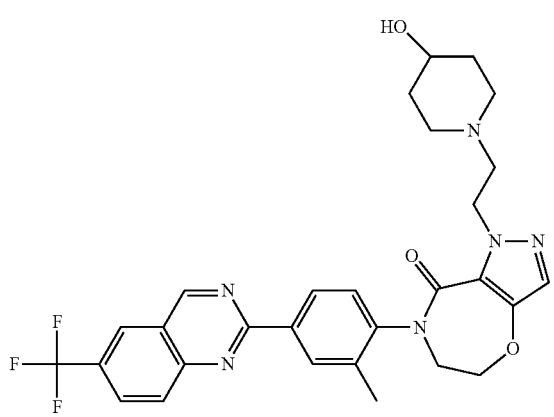 [SMILES: Cc1cc(-c2ncc3cc(C(F)(F)F)ccc3n2)ccc1N1CCOc2cnn(CCN3CCC(O)CC3)c2C1=O]

Proceeding analogously as described in Example 1, Step 9, but substituting 4-(2-(benzyloxy)ethoxy)-N-(4-bromo-2-methylphenyl)-1-methyl-1H-pyrazole-5-carboxamide with 1-(2-(4-(benzyloxy)piperidin-1-yl)ethyl)-7-(2-methyl-4-(6-(trifluoromethyl)quinazolin-2-yl)phenyl)-6,7-dihydro-1H-pyrazolo[3,4-f][1,4]oxazepin-8 (5H)-one gave crude product. Purification by prep-TLC (CH₂Cl₂/MeOH 50:1), followed by reverse flash chromatography under the following conditions: Column, C18 silica gel; mobile phase, MeOH in water, 10% to 50% gradient in 10 min; detector, UV 254 nm, provided the title compound as a white solid.

LC-MS: (ES, m/z): [M+H]⁺ 567.4; ¹H-NMR: (400 MHz, DMSO-d₆, ppm): δ 9.92 (s, 1H), 8.74 (s, 1H), 8.56 (s, 1H), 8.49 (d, 1H), 8.29 (m, 2H), 7.47-7.49 (d, 1H), 7.40 (s, 1H), 4.53 (s, 5H), 4.00 (s, 2H), 3.41 (s, 1H), 2.59-2.67 (m, 4H), 2.50 (s, 3H), 2.02 (s, 2H), 1.65 (d, 2H), 1.32 (d, 2H).

Example 73

Synthesis of 1-(2-(4,4-difluoropiperidin-1-yl)ethyl)-7-(2-methyl-4-(6-(trifluoromethyl)-quinazolin-2-yl)phenyl)-6,7-dihydro-1H-pyrazolo[3,4-f][1,4]oxazepin-8 (5H)-one

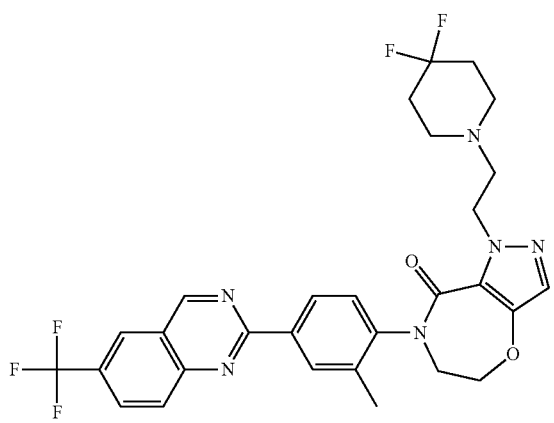 [SMILES: Cc1cc(-c2ncc3cc(C(F)(F)F)ccc3n2)ccc1N1CCOc2cnn(CCN3CCC(F)(F)CC3)c2C1=O]

Step 1: Synthesis of 2-(4,4-difluoropiperidin-1-yl)ethan-1-ol

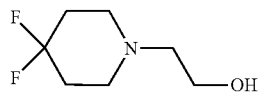

Proceeding analogously as described in Example 72, Step 1, but substituting 4-(benzyloxy)piperidine with 4,4-difluoropiperidine provided crude product which was used in the next step directly without further purification.

Step 2: Synthesis of 1-(2-(4,4-difluoropiperidin-1-yl)ethyl)-7-(2-methyl-4-(6-(trifluoromethyl)-quinazolin-2-yl)phenyl)-6,7-dihydro-1H-pyrazolo[3,4-f][1,4]oxazepin-8 (5H)-one

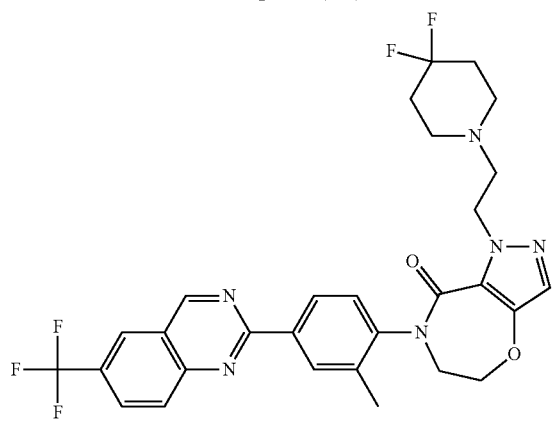

Proceeding analogously as described in Example 64, Step 1, but substituting 2-(benzyloxy)ethan-1-ol with 2-(4,4-difluoropiperidin-1-yl)ethan-1-ol and methyl 4-bromo-1H-pyrazole-5-carboxylate with 7-(2-methyl-4-(6-(trifluoromethyl)-quinazolin-2-yl)phenyl)-6,7-dihydro-1H-pyrazolo[3,4-f][1,4]oxazepin-8 (5H)-one provided crude product. Purification by Prep-TLC (CH₂Cl₂/MeOH 80:1) gave the title compound as a white solid. LC-MS: (ES, m/z): [M+H]⁺ 587.2; ¹H-NMR: (400 MHz, DMSO-d₆, ppm): δ 9.91 (s, 1H), 8.73 (s, 1H), 8.55 (s, 1H), 8.48 (dd, 1H), 8.29 (t, 2H), 7.46 (d, 1H), 7.42 (s, 1H), 4.47-4.59 (m, 4H), 4.00 (t, 2H), 2.71 (t, 2H), 2.50-2.51 (t, 4H), 2.34 (s, 3H), 1.85-1.92 (m, 4H).

Example 74

Synthesis of 1-(2-(dimethylamino)ethyl)-7-(2-methyl-4-(6-(trifluoromethyl)quinazolin-2-yl)phenyl)-6,7-dihydro-1H-pyrazolo[3,4-f][1,4]oxazepin-8 (5H)-one

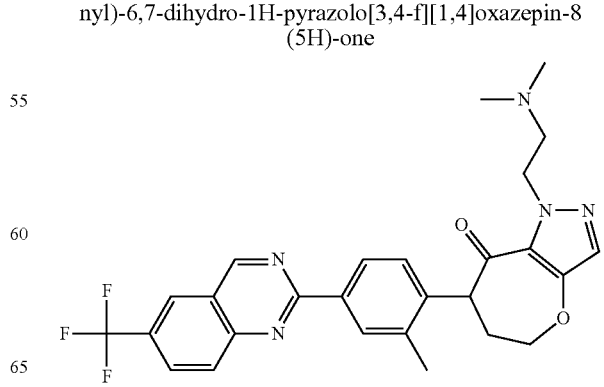

Proceeding analogously as described in Example 64, Step 1, but substituting 2-(benzyl-oxy)ethan-1-ol with 2-(dimethylamino)ethan-1-ol and methyl 4-bromo-1H-pyrazole-5-carboxylate with 7-(2-methyl-4-(6-(trifluoromethyl)quinazolin-2-yl)phenyl)-6,7-dihydro-1H-pyrazolo[3,4-f][1,4]oxazepin-8 (5H)-one gave crude product. Purification by Prep-TLC (CH$_2$Cl$_2$/MeOH 60:1) gave the title compound as a white solid. LC-MS: (ES, m/z): [M+H]$^+$ 511.2; $^1$H-NMR: (300 MHz, DMSO-d$_6$, ppm): δ 9.92 (s, 1H), 8.74 (s, 2H), 8.56 (d, 1H), 8.49 (dd, 1H), 8.30 (t, 2H), 7.49 (d, 1H), 7.40 (s, 1H), 4.47-4.61 (m, 4H), 4.00 (s, 2H), 2.50-2.60 (m, 2H), 2.34 (s, 3H), 2.16 (s, 6H).

Example 75

Synthesis of 7-[2-methyl-4-[6-(trifluoromethyl)quinazolin-2-yl]phenyl]-1-[(1H-1,2,3,4-tetrazol-5-yl)methyl]-1H,5H,6H,7H,8H-pyrazolo[3,4-f][1,4]oxazepin-8-one

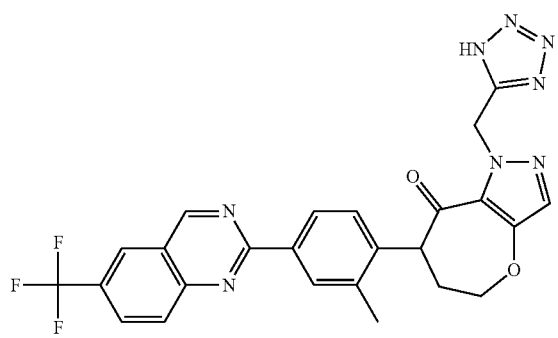

Step 1: Synthesis of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetamide

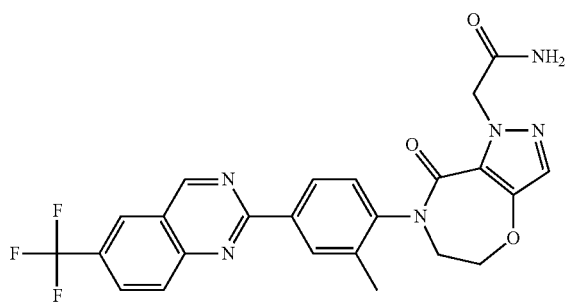

To a stirred solution of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetic acid (350.00 mg, 0.704 mmol, 1.00 equiv) and NH$_4$Cl (150.55 mg, 2.814 mmol, 4.00 equiv) in DMF (5.00 mL) were added DIEA (181.87 mg, 1.407 mmol, 2.00 equiv) and HATU (668.83 mg, 1.759 mmol, 2.50 equiv) at room temperature under nitrogen atmosphere. The resulting mixture was stirred overnight and then diluted with water. The aqueous layer was extracted with EtOAc and the organic layer was concentrated. The residue was purified by reverse flash chromatography with the following conditions: Column, C18 silica gel; mobile phase, MeOH in water, 10% to 50% gradient in 10 min; detector, UV 254 nm, to give the title compound (220 mg, 62.98%) as a white solid.

Step 2: Synthesis of 7-[2-methyl-4-[6-(trifluoromethyl)quinazolin-2-yl]phenyl]-1-[(1H-1,2,3,4-tetrazol-5-yl)methyl]-1H,5H,6H,7H,8H-pyrazolo[3,4-f][1,4]oxazepin-8-one

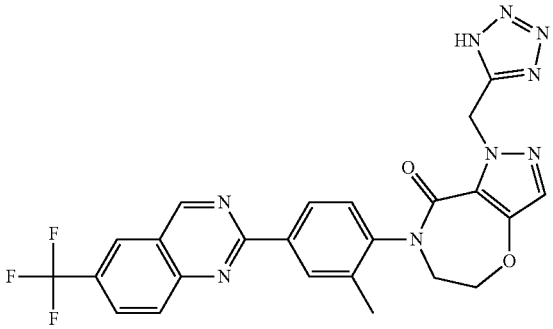 [SMILES: Cc1cc(-c2ncc3cc(C(F)(F)F)ccc3n2)ccc1C1CCOc2cnn(Cc3nnn[nH]3)c2C1=O]

A solution of SiCl$_4$ (102.67 mg, 0.604 mmol, 3 equiv) in dioxane (2 mL) was treated with NaN$_3$ (39.28 mg, 0.604 mmol, 3.00 equiv) for 2 h at room temperature under nitrogen atmosphere, followed by the addition of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetamide (100 mg, 0.201 mmol, 1 equiv). The resulting mixture was stirred for overnight at 100° C. The crude product (100 mg) was purified by Prep-HPLC with the following conditions (Column: XBridge Prep OBD C18 Column, 30×150 mm 5 um; Mobile Phase A: water (0.05% NH$_3$ in H$_2$O), Mobile Phase B: ACN; Flow rate:60 mL/min; Gradient:26% B to 38% B in 7 min; 254; 220 nm; RT:5.62 min.) to afford the title compound (46.9 mg, 44.65%) as a white solid. LC-MS: (ES, m/z): [M+H]$^+$ 522.2; $^1$H-NMR: (300 MHz, DMSO-d6, ppm): δ 9.90 (s, 1H), 8.73 (s, 1H), 8.52 (s, 1H), 8.52 (d, 1H), 8.28 (s, 2H), 7.43-7.45 (m, 2H), 5.97 (d, 1H), 5.79 (d, 1H), 4.55 (s, 2H), 3.93-3.99 (m, 2H), 2.22 (s, 3H).

Example 76

Synthesis of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetic acid

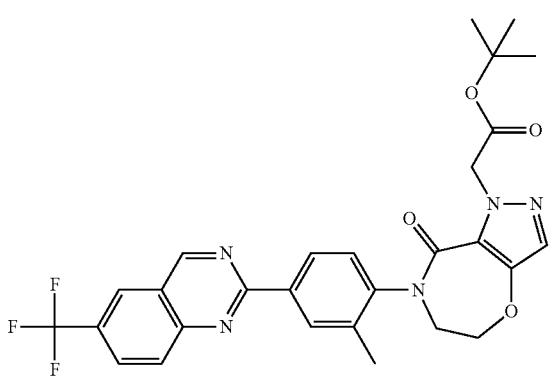 [SMILES: Cc1cc(-c2ncc3cc(C(F)(F)F)ccc3n2)ccc1N1CCOc2cnn(CC(=O)OC(C)(C)C)c2C1=O]

Step 1: Synthesis of tert-butyl 2-(7-(2-methyl-4-(6-(trifluoromethyl)quinazolin-2-yl)phenyl)-8-oxo-5,6,7,8-tetrahydro-H-pyrazolo[3,4-f][1,4]oxazepin-1-yl)acetate

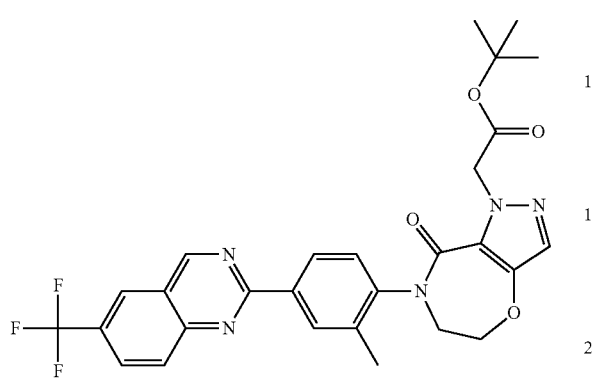

Proceeding analogously as described in Example 64, Step 1, but substituting 2-(benzyloxy)ethan-1-ol with tert-butyl 2-hydroxyacetate and methyl 4-bromo-1H-pyrazole-5-carboxylate with 7-(2-methyl-4-(6-(trifluoromethyl)quinazolin-2-yl)phenyl)-6,7-dihydro-1H-pyrazolo[3,4-f][1,4]oxazepin-8 (5H)-one provided crude product. Purification by silica gel column chromatography by eluting with PE/EtOAc (10:1) gave the title compound as a white solid.

Step 2: Synthesis of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetic acid

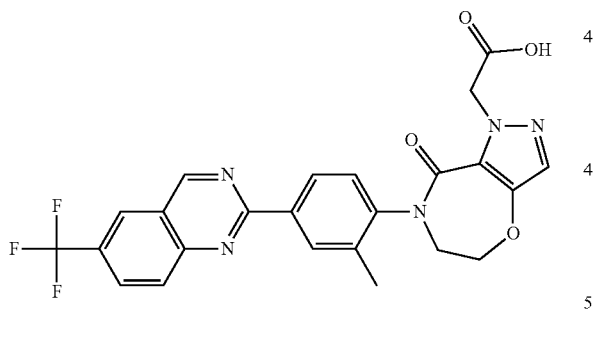

Proceeding analogously as described in Example 71, Step 2, but substituting 7-(2-methyl-4-(6-(trifluoromethyl)quinazolin-2-yl)phenyl)-1-(tetrahydro-2H-pyran-2-yl)-6,7-dihydro-1H-pyrazolo[3,4-f][1,4]oxazepin-8 (5H)-one with tert-butyl 2-(7-(2-methyl-4-(6-(trifluoromethyl)-quinazolin-2-yl)phenyl)-8-oxo-5,6,7,8-tetrahydro-1H-pyrazolo[3,4-f][1,4]oxazepin-1-yl)acetate gave crude product. Purification by reverse flash chromatography under the following conditions: Column, C18 silica gel; mobile phase, $(NH_4)_2CO_3$ in water, 10% to 50% gradient in 10 min; detector, UV 254 nm, gave the title compound. LC-MS: (ES, m/z): [M+H]⁺ 498.3; ¹H-NMR: (400 MHz, DMSO-d6, ppm): δ 9.90 (s, 1H), 8.72 (s, 1H), 8.53 (s, 1H), 8.47 (d, 1H), 8.27 (t, 2H), 7.43 (d, 1H), 7.34 (s, 1H), 5.02-5.06 (m, 1H), 4.91 (d, 1H), 4.53 (m, 2H), 3.96 (m, 2H), 2.29 (s, 3H).

Example 77

Synthesis of 2-((1H-tetrazol-5-yl)methyl)-7-(2-methyl-4-(6-(trifluoromethyl)-quinazolin-2-yl)phenyl)-6,7-dihydro-2H-pyrazolo[3,4-f][1,4]oxazepin-8 (5H)-one

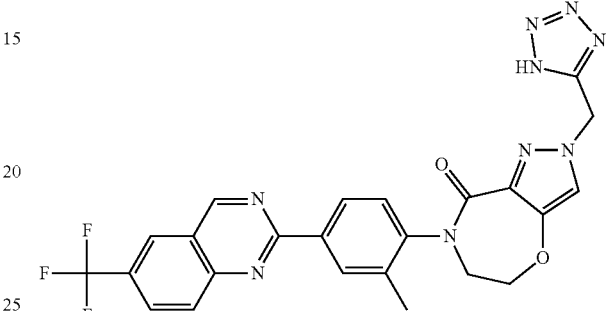

Step 1: Synthesis of 2-(7-(2-methyl-4-(6-(trifluoromethyl)quinazolin-2-yl)phenyl)-8-oxo-5,6,7,8-tetrahydro-2H-pyrazolo[3,4-f][1,4]oxazepin-2-yl)acetamide

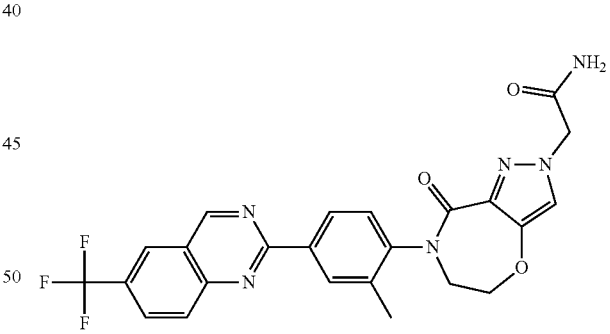

Proceeding analogously as described in Example 62, Step 1, but substituting 3-methyl-5-(2-methyl-4-(6-(trifluoromethyl)quinazolin-2-yl)phenyl)-4,5,6,7-tetrahydropyrazolo[1,5-a]pyrazine-2-carboxylic acid with 2-(7-(2-methyl-4-(6-(trifluoromethyl)-quinazolin-2-yl)phenyl)-8-oxo-5,6,7,8-tetrahydro-2H-pyrazolo[3,4-f][1,4]oxazepin-2-yl)acetic acid and morpholine with $NH_4Cl$ provided crude product. Purification by Prep-TLC ($CH_2Cl_2$/MeOH 10:1) gave the title compound as a white solid.

173

Step 2: Synthesis of 2-((1H-tetrazol-5-yl)methyl)-7-(2-methyl-4-(6-(trifluoromethyl)-quinazolin-2-yl)phenyl)-6,7-dihydro-2H-pyrazolo[3,4-f][1,4]oxazepin-8 (5H)-one

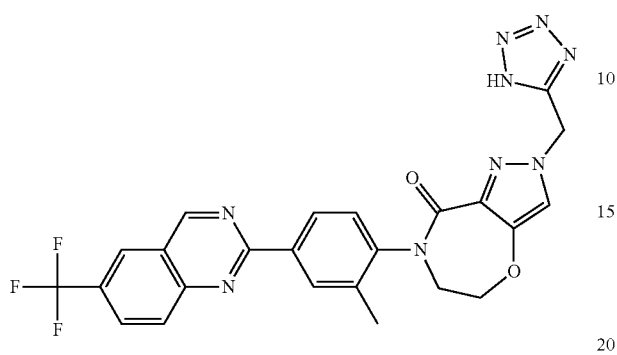

Proceeding analogously as described in Example 75, Step 2, but substituting of 2-(7-(2-methyl-4-(6-(trifluoromethyl)quinazolin-2-yl)phenyl)-8-oxo-5,6,7,8-tetrahydro-1H-pyrazolo[3,4-f][1,4]oxazepin-1-yl)acetamide with 2-(7-(2-methyl-4-(6-(trifluoromethyl)-quinazolin-2-yl)phenyl)-8-oxo-5,6,7,8-tetrahydro-2H-pyrazolo[3,4-f][1,4]oxazepin-2-yl)acetamide gave crude product which was purified by Prep-HPLC to afford the title compound as a white solid. LC-MS: (ES, m/z): [M+H]$^+$ 522.3; $^1$H-NMR: (400 MHz, DMSO-d$_6$, ppm): δ 9.91 (s, 1H), 8.73 (s, 1H), 8.53 (s, 1H), 8.47 (d, 1H), 8.29 (t, 2H), 7.57 (s, 1H), 7.44 (d, 1H), 5.44 (s, 2H), 4.52-4.44 (m, 2H), 4.02-3.91 (m, 2H), 2.30 (s, 3H).

Example 78

Synthesis of 2-(7-(2-methyl-4-(6-(trifluoromethyl)quinazolin-2-yl)phenyl)-8-oxo-5,6,7,8-tetrahydro-2H-pyrazolo[3,4-f][1,4]oxazepin-2-yl)acetic acid

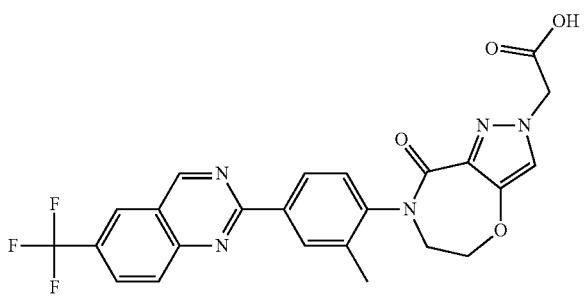 [SMILES: Cc1cc(-c2ncc3cc(C(F)(F)F)ccc3n2)ccc1N1CCOc2cn(CC(=O)O)nc2C1=O]

To tert-butyl 2-(7-(2-methyl-4-(6-(trifluoromethyl)quinazolin-2-yl)phenyl)-8-oxo-5,6,7,8-tetrahydro-2H-pyrazolo[3,4-f][1,4]oxazepin-2-yl)acetate (770 mg, 1.391 mmol, 1 equiv) was added hydrogen chloride in 1,4-dioxane solution (5 ml) and the solution was stirred for 1 h at room temperature. The resulting mixture was concentrated under reduced pressure and the crude product was purified by Prep-HPLC under the following conditions (CH$_3$CN: NH$_4$HCO$_3$, 40:60) to afford the title compound (660 mg, 95%) as a white solid. LC-MS: (ES, m/z): [M+H]$^+$ 498.2; $^1$H-NMR: (400 MHz, DMSO-d$_6$, ppm): δ 9.83 (s, 1H), 8.65 (s, 1H), 8.48 (s, 1H), 8.43 (d, 1H), 8.25 (s, 2H), 7.56 (s, 1H), 7.41 (d, 1H), 4.71 (s, 2H), 4.50-4.44 (m, 2H), 3.96-3.93 (m, 2H), 2.28 (s, 3H).

174

Example 79

Synthesis of 3-(hydroxymethyl)-5-(2-methyl-4-(6-(trifluoromethyl)quinazolin-2-yl)phenyl)-6,7-dihydropyrazolo[1,5-a]pyrazin-4 (5H)-one Step 1: Synthesis of 5-(2-methyl-4-(6-(trifluoromethyl)quinazolin-2-yl)phenyl)-4-oxo-4,5,6,7-tetrahydropyrazolo[1,5-a]pyrazine-3-carbaldehyde Proceeding analogously as described in Example 58, Steps 1-3, but substituting 2-bromo-3-methyl-5-[2-methyl-4-[6-(trifluoromethyl)-quinazolin-2-yl]phenyl]-3H,3aH,4H,5H,6H,7H-pyrazolo[1,5-a]pyrazin-4-one with 3-bromo-5-(2-methyl-4-(6-(trifluoromethyl)quinazolin-2-yl)phenyl)-6,7-dihydropyrazolo[1,5-a]pyrazin-4 (5H)-one provided the title compound as a yellow solid.

Step 2: Synthesis of 3-(hydroxymethyl)-5-(2-methyl-4-(6-(trifluoromethyl)quinazolin-2-yl)phenyl)-6,7-dihydropyrazolo[1,5-a]pyrazin-4 (5H)-one Into an 8-mL sealed tube purged under N$_2$ atmosphere, were placed 5-(2-methyl-4-(6-(trifluoromethyl)quinazolin-2-yl)phenyl)-4-oxo-4,5,6,7-tetrahydropyrazolo[1,5-a]pyrazine-3-carbaldehyde (100 mg, 0.222 mmol, 1 equiv), THF (2 mL), and 1-boranylpyrrolidine lithium (19.91 mg, 0.222 mmol, 1 equiv). The resulting solution was stirred for 12 h at −78° C. and then quenched with water. The resulting solution was extracted with ethyl acetate and the organic layer was concentrated. The residue was applied onto Prep-TLC and eluted with dichloromethane/methanol (15:1) to give in the title compound (40.7 mg, 40.52%) as a white solid. LC-MS: (ES, m/z): [M+H]$^+$ 454.3; $^1$H-NMR: (400 MHz, DMSO-d$_6$, ppm): δ 2.35 (s, 3H), 3.93-3.97 (m, 1H), 4.29-4.36 (m, 1H), 4.54-4.57 (m, 4H), 4.65 (s, 1H), 7.56 (d, 2H), 7.62 (s, 1H), 8.27 (t, 2H), 8.40 (d, 1H), 8.52 (s, 1H), 8.73 (s, 1H), 9.91 (s, 1H).

Example 80

Synthesis of (R)—N-(1-hydroxypropan-2-yl)-3-methyl-5-(2-methyl-4-(6-(trifluoromethyl)-quinazolin-2-yl)phenyl)-4-oxo-4,5,6,7-tetrahydropyrazolo[1,5-a]pyrazine-2-carboxamide

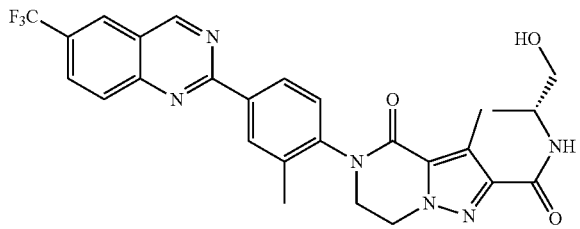 [SMILES: Cc1cc(-c2ncc3cc(C(F)(F)F)ccc3n2)ccc1N1CCn2nc(C(=O)N[C@H](C)CO)c(C)c2C1=O]

Into a 8-mL sealed tube under nitrogen atmosphere, were placed 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylic acid (40 mg, 0.083 mmol, 1 equiv), (2R)-2-aminopropan-1-ol (9.36 mg, 0.125 mmol, 1.50 equiv), DMF (1.2 mL), EDCI (19.11 mg, 0.100 mmol, 1.2 equiv), and HOBT (13.47 mg, 0.100 mmol, 1.2 equiv). The resulting solution was stirred for 12 h at room temperature and then quenched with water. The resulting solution was extracted with ethyl acetate and the organic layers combined and concentrated under vacuum. The residue was purified by Prep-TLC (CH$_2$Cl$_2$/MeOH 20:1) to afford the title compound (4.32 mg, 9.65%) as a white solid. LC-MS: (ES, m/z): [M+H]$^+$ 539.3; $^1$H-NMR: (400 MHz, DMSO, ppm): δ 9.91 (s, 1H), 8.73 (s, 1H), 8.56 (s, 1H), 8.50 (d, 1H), 8.29 (s, 2H), 7.73 (d, 1H), 7.57 (d, 1H), 4.80 (t, 1H), 4.59 (d, 2H), 4.33 (s, 1H), 3.98 (s, 2H), 3.43-3.33 (m, 2H), 2.36 (s, 3H), 1.13 (d, 3H).

Example 81

Synthesis of (S)-3-((1-hydroxypropan-2-yl)amino)-5-(2-methyl-4-(6-(trifluoromethyl)-quinazolin-2-yl)phenyl)-6,7-dihydropyrazolo[1,5-a]pyrazin-4 (5H)-one

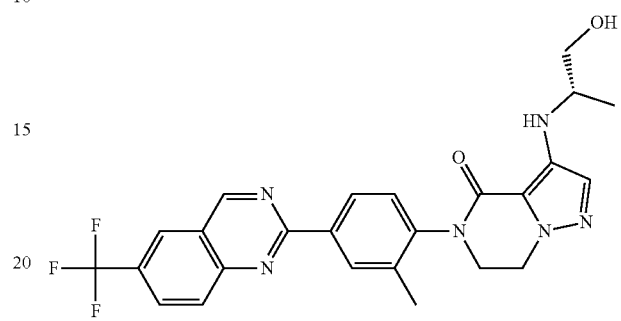

Into a 8-mL sealed tube under nitrogen atmosphere, were placed 3-bromo-5-(2-methyl-4-(6-(trifluoromethyl)quinazolin-2-yl)phenyl)-6,7-dihydropyrazolo[1,5-a]pyrazin-4 (5H)-one (100 mg, 0.199 mmol, 1 equiv), (2S)-2-aminopropan-1-ol (149.54 mg, 1.991 mmol, 10 equiv), picolinic acid (244.88 mg, 1.991 mmol, 10 equiv), K$_2$CO$_3$ (137.57 mg, 0.995 mmol, 5 equiv), CuSO$_4$ (317.76 mg, 1.991 mmol, 10 equiv), and DMF (2 mL). The resulting solution was stirred for 12 h at 110° C. and then quenched with water. The resulting solution was extracted with ethyl acetate and the organic layer was concentrated. The residue was applied onto Prep-TLC and eluted with dichloromethane/methanol (20:1) to give the title compound (36.1 mg, 36.52%) as a white solid. LC-MS: (ES, m/z): [M+H]$^+$ 497.4; $^1$H-NMR: (400 MHz, DMSO-d$_6$, ppm): δ 1.12 (s, 3H), 2.33 (s, 3H), 3.39 (s, 2H), 3.86-3.88 (m, 1H), 4.26 (s, 1H), 4.40 (s, 2H), 4.76 (s, 1H), 4.89 (d, 1H), 7.23 (s, 1H), 7.52 (d, 1H), 8.25 (t, 2H), 8.46 (d, 1H), 8.52 (s, 1H), 8.70 (s, 1H), 9.88 (s, 1H).

Example 82

Synthesis of 3-(hydroxymethyl)-1-methyl-7-(2-methyl-4-(6-(trifluoromethyl)-pyrido-[3,2-d]pyrimidin-2-yl)phenyl)-6,7-dihydro-1H-pyrazolo[3,4-f][1,4]oxazepin-8 (5H)-one

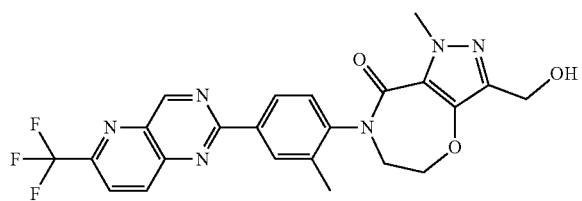 [SMILES: Cc1cc(-c2ncc3nc(C(F)(F)F)ccc3n2)ccc1N1CCOc2c(CO)nn(C)c2C1=O]

Step 1: Synthesis of 3-bromo-1-methyl-7-(2-methyl-4-(6-(trifluoromethyl)pyrido[3,2-d]-pyrimidin-2-yl)phenyl)-6,7-dihydro-1H-pyrazolo[3,4-f][1,4]oxazepin-8 (5H)-one

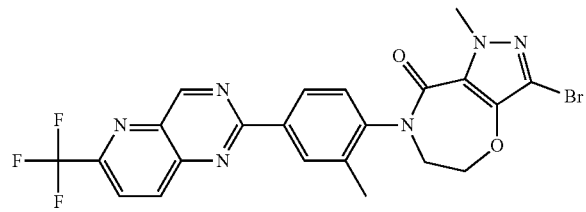 [SMILES: Cc1cc(-c2ncc3nc(C(F)(F)F)ccc3n2)ccc1N1CCOc2c(Br)nn(C)c2C1=O]

To a stirred solution of 1-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one (2.00 g, 4.401 mmol, 1.00 equiv) in EtOH (40.00 mL) and H₂O (8.00 mL) were added NaOAc (0.72 g, 8.803 mmol, 2 equiv) and Br₂ (1.41 g, 8.823 mmol, 2.00 equiv) at room temperature. The resulting mixture was stirred for overnight at 60° C. and then diluted with water. The resulting mixture was concentrated under vacuum and the aqueous layer was extracted with EtOAc. The organic layer was concentrated under vacuum and the residue was purified by silica gel column chromatography by eluting with PE/EtOAc (5:1) to the title compound (1.2 g, 51.12%) as a white solid.

Step 2: Synthesis of 1-methyl-7-(2-methyl-4-(6-(trifluoromethyl)pyrido[3,2-d]pyrimidin-2-yl)phenyl)-8-oxo-5,6,7,8-tetrahydro-1H-pyrazolo[3,4-f][1,4]oxazepine-3-carbaldehyde

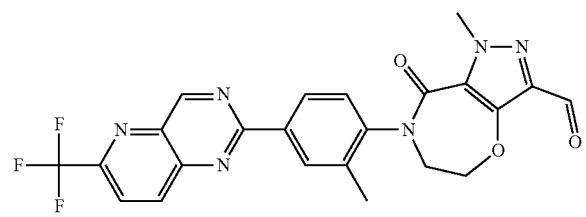 [SMILES: Cc1cc(-c2ncc3nc(C(F)(F)F)ccc3n2)ccc1N1CCOc2c(C=O)nn(C)c2C1=O]

Proceeding analogously as described in Example 58, Steps 1-3, but substituting 2-bromo-3-methyl-5-[2-methyl-4-[6-(trifluoromethyl)-quinazolin-2-yl]phenyl]-3H,3aH,4H,5H,6H,7H-pyrazolo[1,5-a]pyrazin-4-one with 3-bromo-1-methyl-7-(2-methyl-4-(6-(trifluoromethyl)-pyrido[3,2-d]pyrimidin-2-yl)phenyl)-6,7-dihydro-1H-pyrazolo[3,4-f][1,4]oxazepin-8 (5H)-one provided the title compound as a white solid.

Step 3: Synthesis of 3-(hydroxymethyl)-1-methyl-7-(2-methyl-4-(6-(trifluoromethyl)-pyrido-[3,2-d]pyrimidin-2-yl)phenyl)-6,7-dihydro-1H-pyrazolo[3,4-f][1,4]oxazepin-8 (5H)-one

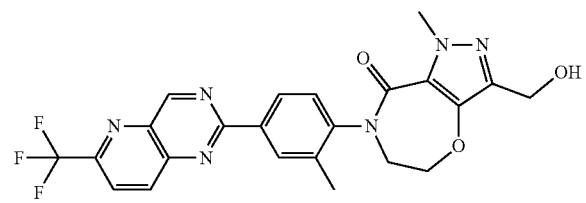 [SMILES: Cc1cc(-c2ncc3nc(C(F)(F)F)ccc3n2)ccc1N1CCOc2c(CO)nn(C)c2C1=O]

To a stirred solution of 1-methyl-7-(2-methyl-4-(6-(trifluoromethyl)pyrido[3,2-d]pyrimidin-2-yl)phenyl)-8-oxo-5,6,7,8-tetrahydro-1H-pyrazolo[3,4-f][1,4]oxazepine-3-carbaldehyde (100 mg, 0.207 mmol, 1 equiv) in THF (4 mL) was added NaBH₃CN (39.08 mg, 0.622 mmol, 3.00 equiv) at room temperature. The resulting mixture was stirred for 2 days at room temperature. The reaction was quenched with sat. NH₄Cl (aq.) at room temperature. The aqueous layer was extracted with EtOAc (4×510 mL). The residue was purified by Prep-TLC (CH₂Cl₂/MeOH 40:1) to afford the title compound (21.9 mg, 21.81%) as a white solid. LC-MS: (ES, m/z): [M+H]⁺ 485.3; ¹H-NMR: (300 MHz, DMSO-d₆, ppm): δ 9.95 (s, 1H), 8.81 (d, 1H), 8.54 (s, 1H), 8.44-8.49 (m, 2H), 7.49 (d, 1H), 4.97 (t, 1H), 4.44-4.60 (m, 2H), 4.36 (d, 2H), 3.97-3.99 (m, 5H), 2.32 (s, 3H).

Example 83

Synthesis of 3-(1-hydroxyethyl)-1-methyl-7-(2-methyl-4-(6-(trifluoromethyl)-pyrido[3,2-d]pyrimidin-2-yl)phenyl)-6,7-dihydro-1H-pyrazolo[3,4-f][1,4]oxazepin-8 (5H)-one

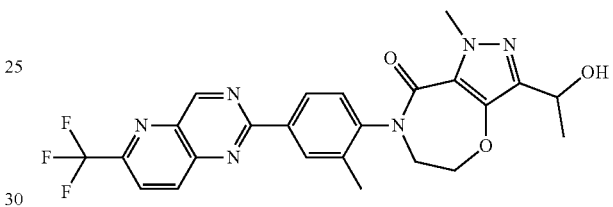

Into a 25-mL 3-necked round-bottom flask under N₂ atmosphere, were placed 1-methyl-7-(2-methyl-4-(6-(trifluoromethyl)pyrido[3,2-d]pyrimidin-2-yl)phenyl)-8-oxo-5,6,7,8-tetrahydro-1H-pyrazolo[3,4-f][1,4]oxazepine-3-carbaldehyde (50 mg, 0.11 mmol, 1.00 equiv), oxolane (0.50 mg), and chloro-(methyl)magnesium (0.33 mL, 0.30 mmol, 3.00 equiv). The resulting solution was stirred for 3 h at room temperature and then quenched with water/ice. The resulting solution was extracted with ethyl acetate and organic layer was dried over anhydrous sodium sulfate, filtered and concentrated. The residue was applied onto a silica gel column and eluted with ethyl acetate/petroleum ether (1/1) to give the title compound (21.0 mg) as a white solid. LC-MS (ES, m/z): [M+H]⁺ 499.2; ¹H-NMR (300 MHz, DMSO-d₆, ppm): δ 9.95 (s, 1H), 8.83 (d, 1H), 8.56 (s, 1H), 8.45-8.49 (m, 2H), 7.49 (d, 1H), 4.88-5.01 (m, 1H), 4.71-4.82 (m, 1H), 4.43-4.62 (m, 2H), 3.95 (s, 5H), 2.31 (s, 3H), 1.43 (d, 3H).

Example 84

Synthesis of 3-(2-hydroxypropan-2-yl)-1-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one

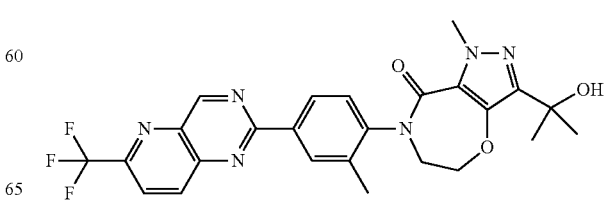

Proceeding analogously as described in Example 59, Step 1, but substituting ethyl 3-methyl-5-(2-methyl-4-(6-(trifluoromethyl)quinazolin-2-yl)phenyl)-4-oxo-4,5,6,7-tetrahydropyrazolo[1,5-a]pyrazine-2-carboxylate with ethyl 1-methyl-7-(2-methyl-4-(6-(trifluoromethyl)pyrido[3,2-d]pyrimidin-2-yl)phenyl)-8-oxo-5,6,7,8-tetrahydro-1H-pyrazolo[3,4-f][1,4]oxazepine-3-carboxylate provided crude product. Purification by prep-TLC (PE/EtOAc 60:1) gave the title compound as a white solid. LC-MS: (ES, m/z): [M+H]+ 513.3; $^1$H-NMR: (300 MHz, DMSO-d6, ppm): δ 9.95 (s, 1H), 8.81 (d, 1H), 8.54 (s, 1H), 8.45-8.50 (m, 2H), 7.49 (d, 1H), 4.73 (s, 1H), 4.52 (t, 2H), 3.95 (t, 5H), 2.32 (s, 3H), 1.48 (s, 6H).

Example 85

Synthesis of 3-((dimethylamino)methyl)-1-methyl-7-(2-methyl-4-(6-(trifluoromethyl)pyrido-[3,2-d]pyrimidin-2-yl)phenyl)-6,7-dihydro-1H-pyrazolo[3,4-f][1,4]oxazepin-8 (5H)-one

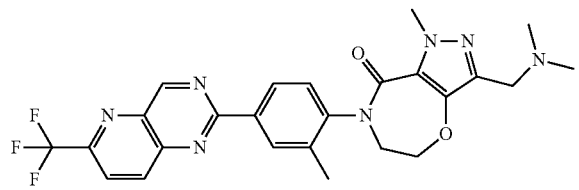 [SMILES: Cc1cc(-c2ncc3nc(C(F)(F)F)ccc3n2)ccc1N1CCOc2c(CN(C)C)nn(C)c2C1=O]

Proceeding as described in Example 63 but substituting 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde with 1-methyl-7-(2-methyl-4-(6-(trifluoromethyl)pyrido[3,2-d]pyrimidin-2-yl)phenyl)-8-oxo-5,6,7,8-tetrahydro-1H-pyrazolo[3,4-f][1,4]oxazepine-3-carbaldehyde gave crude product. Purification by Prep-TLC (CH$_2$Cl$_2$/MeOH 40:1) gave the title compound as a white solid. LC-MS: (ES, m/z): [M+H]+ 512.2; $^1$H-NMR: (300 MHz, DMSO-d$_6$, ppm): δ 9.95 (s, 1H), 8.81 (d, 1H), 8.54-8.54 (d, 1H), 8.44-8.49 (m, 2H), 7.48 (d, 1H), 4.45-4.56 (m, 2H), 3.97 (s, 5H), 3.28-3.33 (t, 2H), 2.32 (s, 3H), 2.14 (s, 6H).

Example 86

Synthesis of ethyl 1-methyl-7-(2-methyl-4-(6-(trifluoromethyl)pyrido[3,2-d]pyrimidin-2-yl)phenyl)-8-oxo-5,6,7,8-tetrahydro-1H-pyrazolo[3,4-f][1,4]oxazepine-3-carboxylate

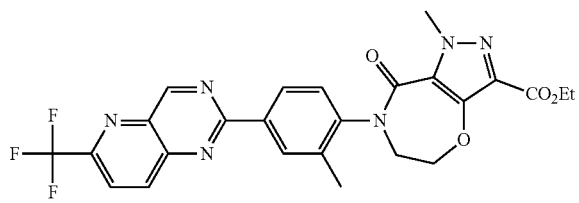 [SMILES: CCOC(=O)c1nn(C)c2c1OCCN(c1ccc(-c3ncc4nc(C(F)(F)F)ccc4n3)cc1C)C2=O]

Proceeding as described in Example 56, Step 2, but substituting 2-bromo-3-methyl-5-(2-methyl-4-(6-(trifluoromethyl)quinazolin-2-yl)phenyl)-6,7-dihydropyrazolo[1,5-a]pyrazin-4 (5H)-one with 3-bromo-1-methyl-7-(2-methyl-4-(6-(trifluoromethyl)pyrido[3,2-d]pyrimidin-2-yl)phenyl)-6,7-dihydro-1H-pyrazolo[3,4-f][1,4]oxazepin-8 (5H)-one provided crude product. Purification by Prep-TLC (CH$_2$Cl$_2$/MeOH 60:1) and a second Prep-HPLC under the following conditions (Column: XBridge Prep OBD C18 Column, 19*250 mm, 5 um; Mobile Phase A: water (0.05% NH$_3$—H$_2$O), Mobile Phase B: ACN; Flow rate: 20 mL/min; Gradient: 49 B to 49 B in 11.5 min; 254; 220 nm; RT:10.83 min) gave the title compound as a white solid. LC-MS: (ES, m/z): [M+H]+ 527.2; $^1$H-NMR: (300 MHz, DMSO-d6, ppm): δ 9.95 (s, 1H), 8.81 (d, 1H), 8.45-8.55 (m, 3H), 7.49 (d, 1H), 4.55-4.63 (m, 2H), 4.23-4.30 (m, 2H), 4.05 (d, 5H), 2.33 (s, 3H), 1.21-1.30 (m, 3H).

Example 87

Synthesis of 2-(hydroxymethyl)-3-methyl-5-(2-methyl-4-(6-(trifluoromethyl)-quinazolin-2-yl)phenyl)-6,7-dihydropyrazolo[1,5-a]pyrazin-4 (5H)-one

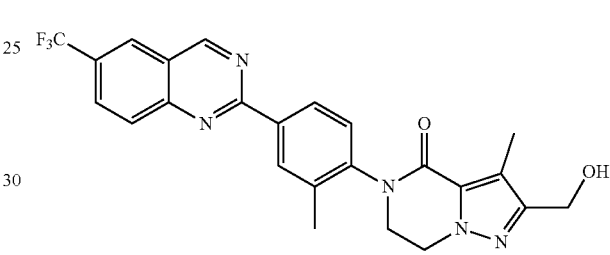

Step 1: Synthesis of 2-bromo-3-methyl-5-(2-methyl-4-(6-(trifluoromethyl)-1,5-naphthyridin-2-yl)phenyl)-6,7-dihydropyrazolo[1,5-a]pyrazin-4 (5H)-one

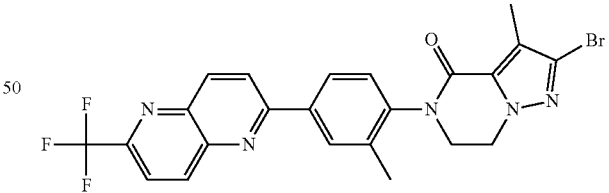

Proceeding analogously as described in Example 56, Step 1, but substituting 3-methyl-5-(2-methyl-4-(6-(trifluoromethyl)quinazolin-2-yl)phenyl)-6,7-dihydropyrazolo[1,5-a]pyrazin-4 (5H)-one with 3-methyl-5-(2-methyl-4-(6-(trifluoromethyl)-1,5-naphthyridin-2-yl)phenyl)-6,7-dihydropyrazolo[1,5-a]pyrazin-4 (5H)-one gave crude product. Purification by silica gel column chromatography (PE/EA 5:1) gave the title compound as a light-yellow solid.

181

Step 2: Synthesis of 2-(((tert-butyldimethylsilyl)oxy)methyl)-3-methyl-5-(2-methyl-4-(6-(trifluoromethyl)-1,5-naphthyridin-2-yl)phenyl)-6,7-dihydropyrazolo[1,5-a]pyrazin-4 (5H)-one

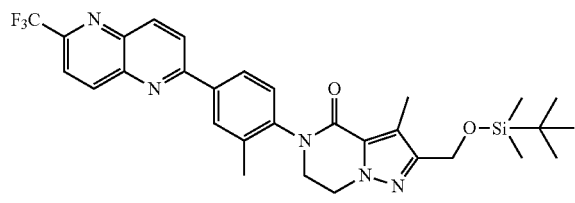 [SMILES: Cc1cc(-c2ccc3nc(C(F)(F)F)ccc3n2)ccc1N1CCn2nc(CO[Si](C)(C)C(C)(C)C)c(C)c2C1=O]

Into a 8-mL sealed tube under N₂ atmosphere, were placed 2-bromo-3-methyl-5-(2-methyl-4-(6-(trifluoromethyl)-1,5-naphthyridin-2-yl)phenyl)-6,7-dihydropyrazolo[1,5-a]pyrazin-4 (5H)-one (300 mg, 0.581 mmol, 1 equiv), Bu₃SnCH₃OTBS (380.00 mg, 0.872 mmol, 1.50 equiv), toluene (3.5 mL, 0.038 mmol, 0.07 equiv), and Pd(PPh₃)₄ (134.28 mg, 0.116 mmol, 0.2 equiv). The resulting solution was stirred for 12 h at 110° C. in an oil bath. The reaction mixture was then quenched with water and the resulting solution was extracted with ethyl acetate. The organic layers were combined and concentrated under reduced pressure. The residue was purified by Prep-TLC (PE/EtOAc 1:1) to afford the title compound (130 mg, 38.46%) as a white solid.

Step 3: Synthesis of 2-(hydroxymethyl)-3-methyl-5-(2-methyl-4-(6-(trifluoromethyl)-1,5-naphthyridin-2-yl)phenyl)-6,7-dihydropyrazolo[1,5-a]pyrazin-4 (5H)-one

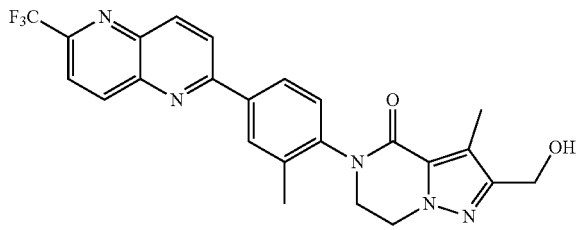 [SMILES: Cc1cc(-c2ccc3nc(C(F)(F)F)ccc3n2)ccc1N1CCn2nc(CO)c(C)c2C1=O]

Into an 8-mL sealed tube, were placed 2-(((tert-butyldimethylsilyl)oxy)methyl)-3-methyl-5-(2-methyl-4-(6-(trifluoromethyl)-1,5-naphthyridin-2-yl)phenyl)-6,7-dihydropyrazolo[1,5-a]pyrazin-4 (5H)-one (130 mg, 0.223 mmol, 1 equiv), THF (2.5 mL), and TBAF (175.29 mg, 0.670 mmol, 3.00 equiv). The resulting solution was stirred for 4 h at room temperature and then quenched with NH₄Cl. The resulting solution was extracted with ethyl acetate and the organic layers were combined and concentrated under vacuum. The residue was purified by Prep-TLC (hexane/EtOAc 1:1) to afford the title compound (51 mg, 48.82%) as a white solid. LC-MS: (ES, m/z): [M+H]⁺ 468.2; ¹H-NMR: (400 MHz; d₆-DMSO, ppm): δ 8.81 (d, 1H), 8.71 (d, 1H), 8.63 (d, 1H), 8.34 (s, 1H), 8.27 (dd, 2H), 7.57 (d, 1H), 5.00 (t, 1H), 4.48 (dd, 4H), 4.30 (dt, 1H), 3.92-3.98 (m, 1H), 2.35 (s, 3H), 2.28 (s, 3H).

182

Example 88

Synthesis of 2-(hydroxymethyl)-3-methyl-5-(2-methyl-4-(6-(trifluoromethyl)-pyrido-[3,2-d]pyrimidin-2-yl)phenyl)-6,7-dihydropyrazolo[1,5-a]pyrazin-4 (5H)-one

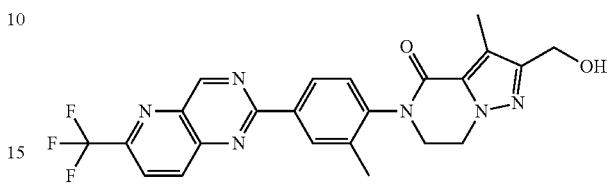

Step 1: Synthesis of 2-bromo-3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one

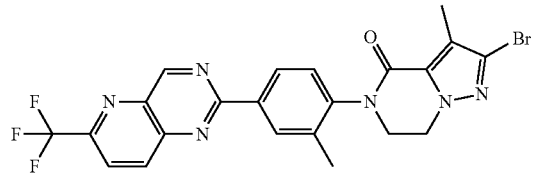 [SMILES: Cc1cc(-c2ncc3nc(C(F)(F)F)ccc3n2)ccc1N1CCn2nc(Br)c(C)c2C1=O]

Proceeding analogously as described in Example 56, Step 1, but substituting 3-methyl-5-(2-methyl-4-(6-(trifluoromethyl)quinazolin-2-yl)phenyl)-6,7-dihydropyrazolo[1,5-a]pyrazin-4 (5H)-one with 3-methyl-5-(2-methyl-4-(6-(trifluoromethyl)-pyrido[3,2-d]pyrimidin-2-yl)phenyl)-6,7-dihydropyrazolo[1,5-a]pyrazin-4 (5H)-one provided crude product. Purification by prep-TLC (CH₂Cl₂/MeOH 60:1) provided the title compound as a white solid.

Step 2: Synthesis of 2-(((tert-butyldimethylsilyl)oxy)methyl)-3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one

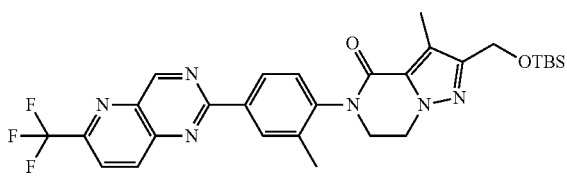 [SMILES: Cc1cc(-c2ncc3nc(C(F)(F)F)ccc3n2)ccc1N1CCn2nc(CO[Si](C)(C)C(C)(C)C)c(C)c2C1=O]

Proceeding analogously as described in Example 87, Step 2, but substituting 2-bromo-3-methyl-5-(2-methyl-4-(6-(trifluoromethyl)-1,5-naphthyridin-2-yl)phenyl)-6,7-dihydropyrazolo-[1,5-a]pyrazin-4 (5H)-one with 2-bromo-3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one provided crude product. Purification by Prep-TLC (CH₂Cl₂/MeOH 100:1) gave the title compound as a white solid.

Step 3: Synthesis of 2-(hydroxymethyl)-3-methyl-5-(2-methyl-4-(6-(trifluoromethyl)-pyrido-[3,2-d]pyrimidin-2-yl)phenyl)-6,7-dihydropyrazolo[1,5-a]pyrazin-4 (5H)-one

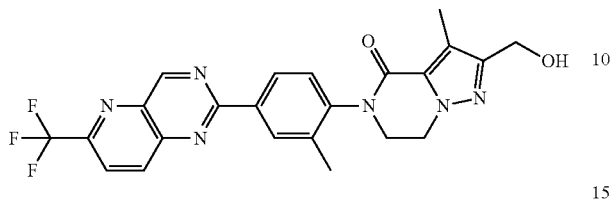

Proceeding analogously as described in Example 87, Step 3, but substituting 2-(((tert-butyldimethylsilyl)oxy)methyl)-3-methyl-5-(2-methyl-4-(6-(trifluoromethyl)quinazolin-2-yl)phenyl)-6,7-dihydropyrazolo[1,5-a]pyrazin-4 (5H)-one with 2-(((tert-butyldimethyl-silyl)oxy)methyl)-3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one gave the title compound as a crude product. Purification by Prep-TLC (EtOAc) gave the title compound as a white solid. LC-MS: (ES, m/z): [M+H]$^+$ 469.2; $^1$H-NMR: (400 MHz, CDCl$_3$, ppm): δ 9.81 (s, 1H), 8.65 (s, 1H), 8.57-8.60 (m, 2H), 8.14 (d, 1H), 7.40 (d, 1H), 4.74 (s, 2H), 4.53 (t, 2H), 4.22-4.29 (m, 1H), 3.91-3.97 (m, 1H), 2.40-2.43 (d, 6H).

Example 89

Synthesis of 2-(2-hydroxyethoxy)-3-methyl-5-(2-methyl-4-(6-(trifluoromethyl)quinazolin-2-yl)phenyl)-6,7-dihydropyrazolo[1,5-a]pyrazin-4 (5H)-one

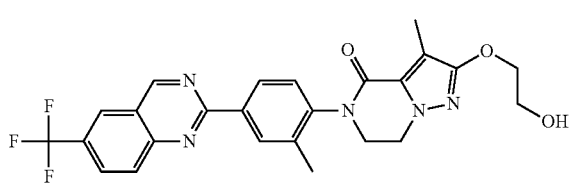 [SMILES: Cc1cc(-c2ncc3cc(C(F)(F)F)ccc3n2)ccc1N1CCn2nc(OCCO)c(C)c2C1=O]

Into a 5-mL sealed tube under N$_2$ atmosphere, were placed 2-bromo-3-methyl-5-(2-methyl-4-(6-(trifluoromethyl)quinazolin-2-yl)phenyl)-6,7-dihydropyrazolo[1,5-a]pyrazin-4 (5H)-one (200.00 mg, 0.387 mmol, 1.00 equiv), ethane-1,2-diol (3.00 mL), t-BuOLi (93.03 mg, 1.162 mmol, 3.00 equiv), and Cu(OAC)$_2$ (14.07 mg, 0.077 mmol, 0.20 equiv). The final reaction mixture was irradiated with microwave radiation for 2 h at 150° C. and then quenched with water. The resulting solution was extracted with ethyl acetate and the organic layers were combined and concentrated. The residue was applied onto a Prep TLC with ethyl acetate/petroleum ether (1:1) to give the title compound (41.8 mg, 21.69%) as a white solid. LC-MS: (ES, m/z): [M+H]$^+$ 498.3; $^1$H-NMR: (300 MHz, DMSO-d$_6$, ppm): δ 2.11 (s, 3H), 2.34 (s, 3H), 3.70-3.72 (m, 2H), 3.73-3.75 (m, 1H), 4.18-4.35 (m, 5H), 4.83-4.86 (m, 1H), 7.56 (d, 1H), 8.29 (s, 2H), 8.50 (d, 1H), 8.56 (s, 1H), 8.74 (s, 1H), 9.92 (s, 1H).

Example 90

Synthesis of 7-((benzyloxy)methyl)-3-methyl-5-(2-methyl-4-(6-(trifluoromethyl)-quinazolin-2-yl)phenyl)-6,7-dihydropyrazolo[1,5-a]pyrazin-4 (5H)-one

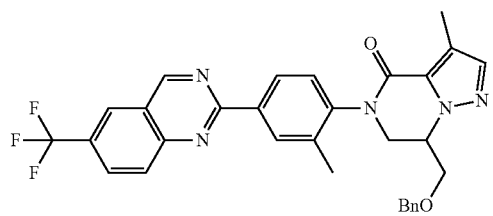 [SMILES: Cc1cc(-c2ncc3cc(C(F)(F)F)ccc3n2)ccc1N1CC(COCc2ccccc2)n2ncc(C)c2C1=O]

Step 1: Synthesis of 1-(1,3-bis(benzyloxy)propan-2-yl)-4-methyl-1H-pyrazole-5-carboxylic acid

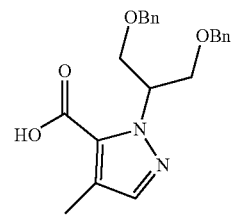 [SMILES: Cc1cnn(C(COCc2ccccc2)COCc2ccccc2)c1C(=O)O]

Proceeding analogously as described in Example 64, Steps 1 and 2, but substituting methyl 4-bromo-1H-pyrazole-5-carboxylate with ethyl 4-methyl-1H-pyrazole-5-carboxylate and 2-(benzyloxy)ethan-1-ol with 1,3-bis(benzyloxy)propan-2-ol gave crude product. Purification by silica gel column with ethyl acetate/petroleum ether (1:20) gave the title compound as a light brown liquid.

Step 2: Synthesis of 1-(1,3-bis(benzyloxy)propan-2-yl)-4-methyl-1H-pyrazole-5-carbonyl chloride

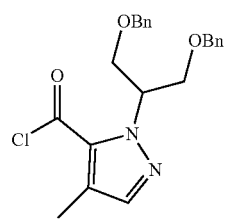 [SMILES: Cc1cnn(C(COCc2ccccc2)COCc2ccccc2)c1C(=O)Cl]

Proceeding analogously as described in Example 1, Step 7, but substituting 4-(2-(benzyloxy)ethoxy)-1-methyl-1H-pyrazole-5-carboxylic acid with 1-(1,3-bis(benzyloxy)propan-2-yl)-4-methyl-1H-pyrazole-5-carboxylic acid gave the title compound as a brown solid.

185

Step 3: Synthesis of 1-(1,3-bis(benzyloxy)propan-2-yl)-4-methyl-N-(2-methyl-4-(6-(trifluoromethyl)quinazolin-2-yl)phenyl)-1H-pyrazole-5-carboxamide

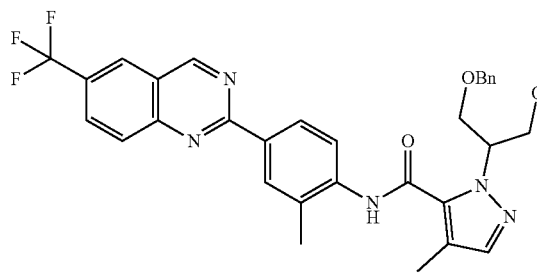

Proceeding analogously as described in Example 1, Step 8, but substituting 4-(2-(benzyloxy)ethoxy)-1-methyl-1H-pyrazole-5-carbonyl chloride with 1-(1,3-bis(benzyloxy)propan-2-yl)-4-methyl-1H-pyrazole-5-carbonyl chloride and 4-bromo-2-methylaniline with 2-methyl-4-[6-(trifluoromethyl)quinazolin-2-yl]aniline gave crude product. The crude product was applied onto a silica gel column and eluted with ethyl acetate/petroleum ether (1:2) to give the title compound as a brown solid.

Step 4: Synthesis of 7-((benzyloxy)methyl)-3-methyl-5-(2-methyl-4-(6-(trifluoromethyl)-quinazolin-2-yl)phenyl)-6,7-dihydropyrazolo[1,5-a]pyrazin-4 (5H)-one

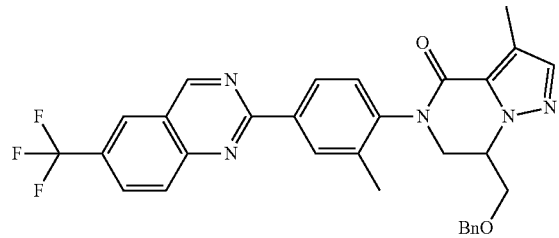 [SMILES: Cc1cc(-c2ncc3cc(C(F)(F)F)ccc3n2)ccc1N1CC(COCc2ccccc2)n2ncc(C)c2C1=O]

Proceeding analogously as described in Example 1, Steps 9-11, but substituting 4-(2-(benzyloxy)ethoxy)-N-(4-bromo-2-methylphenyl)-1-methyl-1H-pyrazole-5-carboxamide with (1,3-bis(benzyloxy)propan-2-yl)-4-methyl-N-(2-methyl-4-(6-(trifluoromethyl)-quinazolin-2-yl)phenyl)-1H-pyrazole-5-carboxamide gave crude product. The crude product was applied onto a Prep TLC and eluted with ethyl acetate/petroleum ether (1:1) to give the title compound as a white solid. LC-MS: (ES, m/z): [M+H]⁺ 558.3; ¹H-NMR: (400 MHz, DMSO-d₆, ppm): δ 2.19-2.34 (m, 6H), 3.79-3.89 (m, 2H), 3.95-4.04 (m, 1H), 4.09-4024 (m, 1H), 4.45-4.63 (m, 3H), 4.82-4.95 (m, 1H), 7.20-7.43 (m, 5H), 7.54 (s, 1H) 7.58 (d, 1H), 8.28 (t, 2H), 8.42-8.60 (m, 2H), 8.55 (s, 1H), 8.74 (s, 1H), 9.91 (s, 1H).

Example 91

Synthesis of 3-methyl-5-(2-methyl-4-(6-(trifluoromethyl)quinazolin-2-yl)phenyl)-2-((2-methylmorpholino)methyl)-6,7-dihydropyrazolo[1,5-a]pyrazin-4 (5H)-one

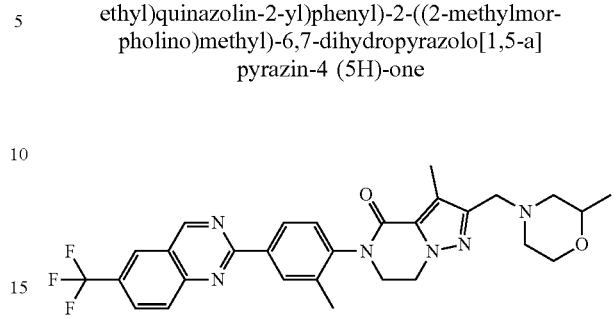

Proceeding analogously as described in Example 61 but substituting morpholine with 2-methylmorpholine provided crude product. Purification by Prep-TLC (CH₂Cl₂/MeOH 40:1), followed by reverse flash chromatography [column, C18 silica gel; mobile phase, MeOH in water, 10% to 50% gradient in 10 min; detector, UV 254 nm] gave the title compound as a white solid. LC-MS: (ES, m/z): [M+H]⁺ 551.3; ¹H-NMR: (300 MHz, DMSO-d6, ppm): δ 9.90 (s, 1H), 8.71 (s, 1H), 8.53 (s, 1H), 8.48 (d, 1H), 8.27 (m, 2H), 7.54 (d, 1H), 4.46 (d, 2H), 4.25-4.32 (m, 1H), 3.84-3.94 (m, 1H), 3.67-3.77 (m, 1H), 3.45 (s, 4H), 2.57-2.75 (m, 2H), 2.33 (s, 3H), 2.25 (s, 3H), 1.97-2.11 (m, 1H), 1.68-1.81 (m, 1H), 1.02 (d, 3H).

Example 92

Synthesis of 2-(1-hydroxyethyl)-5-(2-methyl-4-(6-(trifluoromethyl)quinazolin-2-yl)phenyl)-6,7-dihydropyrazolo[1,5-a]pyrazin-4 (5H)-one

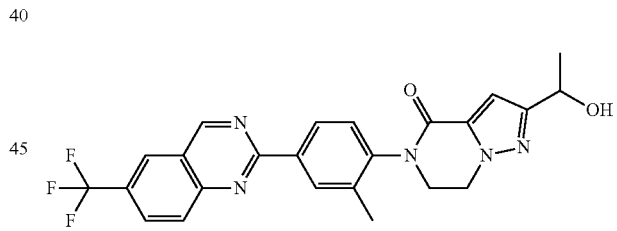

Step 1: Synthesis of diethyl 1-(2-(benzyloxy)ethyl)-1H-pyrazole-3,5-dicarboxylate

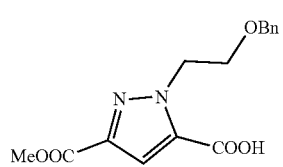

Proceeding analogously as described in Example 64, Steps 1 and 2, but substituting methyl 4-bromo-1H-pyrazole-5-carboxylate with diethyl 1H-pyrazole-3,5-dicarboxylate provided the title compound as a yellow solid.

Step 2: Synthesis of 5-(4-bromo-2-methylphenyl)-4-oxo-4,5,6,7-tetrahydropyrazolo[1,5-a]pyrazine-2-carboxylic acid

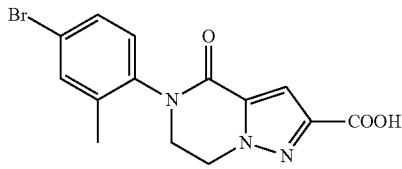 [SMILES: Cc1cc(Br)ccc1N1CCn2nc(C(=O)O)cc2C1=O]

Proceeding analogously as described in Example 1, Steps 7-11, but substituting 4-(2-(benzyloxy)ethoxy)-1-methyl-1H-pyrazole-5-carboxylic acid with 1-(2-(benzyloxy)ethyl)-3-(methoxycarbonyl)-1H-pyrazole-5-carboxylic acid provided the title compound as a yellow solid.

Step 3: Synthesis of 5-(4-bromo-2-methylphenyl)-4-oxo-4,5,6,7-tetrahydropyrazolo[1,5-a]pyrazine-2-carbonyl chloride

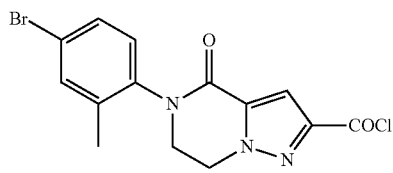 [SMILES: Cc1cc(Br)ccc1N1CCn2nc(C(=O)Cl)cc2C1=O]

Proceeding analogously as described in Example 1, Step 7, but substituting 4-(2-(benzyloxy)ethoxy)-1-methyl-1H-pyrazole-5-carboxylic acid with 5-(4-bromo-2-methylphenyl)-4-oxo-4,5,6,7-tetrahydropyrazolo[1,5-a]pyrazine-2-carboxylic gave the title compound as a yellow liquid.

Step 4: Synthesis of 5-(4-bromo-2-methylphenyl)-N-methoxy-N-methyl-4-oxo-4,5,6,7-tetrahydropyrazolo[1,5-a]pyrazine-2-carboxamide

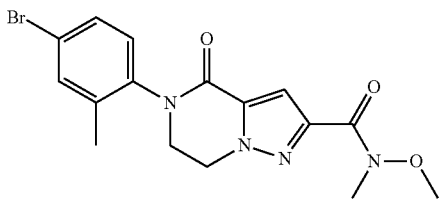 [SMILES: CON(C)C(=O)c1cc2n(n1)CCN(c1ccc(Br)cc1C)C2=O]

Into a 100-mL 3-necked round-bottom flask under $N_2$ atmosphere, were placed 5-(4-bromo-2-methylphenyl)-4-oxo-4,5,6,7-tetrahydropyrazolo[1,5-a]pyrazine-2-carbonyl chloride (2.50 g, 6.782 mmol, 1.00 equiv), $Et_3N$ (1.03 g, 10.173 mmol, 1.50 equiv), DCM (50 ml), and methoxy(methyl)amine (0.50 g, 8.138 mmol, 1.20 equiv). The resulting solution was stirred for 1 h at 0° C. and then concentrated. The residue was applied onto a silica gel column and eluted with dichloromethane/methanol (80:1) to give the title compound (1.3 g, 48.74%) as a yellow solid.

Step 5: Synthesis of N-methoxy-N-methyl-5-(2-methyl-4-(4,4,5,5-tetramethyl-1,3,2-dioxaborolan-2-yl)phenyl)-4-oxo-4,5,6,7-tetrahydropyrazolo[1,5-a]pyrazine-2-carboxamide

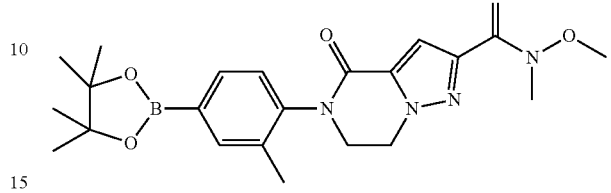

Proceeding analogously as described in Example 1, Step 12, but substituting 7-(4-bromo-2-methylphenyl)-1-methyl-6,7-dihydro-1H-pyrazolo[3,4-f]-[1,4]oxazepin-8 (5H)-one with 5-(4-bromo-2-methylphenyl)-N-methoxy-N-methyl-4-oxo-4,5,6,7-tetrahydropyrazolo[1,5-a]pyrazine-2-carboxamide gave crude product. Purification by silica gel column with ethyl acetate/petroleum ether (1:1) gave the title compound as a yellow liquid.

Step 6: Synthesis of N-methoxy-N-methyl-5-(2-methyl-4-(6-(trifluoromethyl)quinazolin-2-yl)phenyl)-4-oxo-4,5,6,7-tetrahydropyrazolo[1,5-a]pyrazine-2-carboxamide

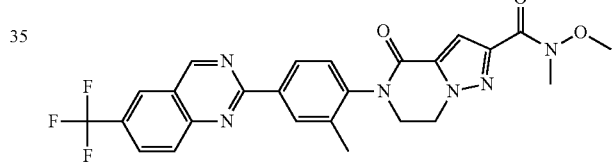

Proceeding analogously as described in Example 49, Step 2, but substituting 1-methyl-7-(2-methyl-4-(4,4,5,5-tetramethyl-1,3,2-dioxaborolan-2-yl)phenyl)-5,6,7,8-tetrahydro-1H-pyrazolo[3,4-f][1,4]oxazepane N-methoxy-N-methyl-5-(2-methyl-4-(4,4,5,5-tetramethyl-1,3,2-dioxaborolan-2-yl)phenyl)-4-oxo-4,5,6,7-tetrahydropyrazolo[1,5-a]pyrazine-2-carboxamide and $K_3PO_4$ with $K_2CO_3$ gave crude product. Purification by silica gel column with ethyl acetate/petroleum ether (2:1) as eluent gave the title compound as a yellow solid.

Step 7: Synthesis of 2-acetyl-5-(2-methyl-4-(6-(trifluoromethyl)quinazolin-2-yl)phenyl)-6,7-dihydropyrazolo[1,5-a]pyrazin-4 (5H)-one

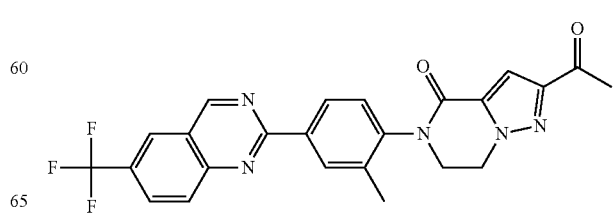

Proceeding analogously as described in Example 58, Step 4, but substituting 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde with N-methoxy-N-methyl-5-(2-methyl-4-(6-(trifluoromethyl)quinazolin-2-yl)phenyl)-4-oxo-4,5,6,7-tetrahydropyrazolo[1,5-a]pyrazine-2-carboxamide gave crude product. Purification by Prep-TLC with dichloromethane/methanol (30:1) gave the title compound as a yellow solid.

Step 8: Synthesis of 2-(1-hydroxyethyl)-5-(2-methyl-4-(6-(trifluoromethyl)quinazolin-2-yl)phenyl)-6,7-dihydropyrazolo[1,5-a]pyrazin-4 (5H)-one

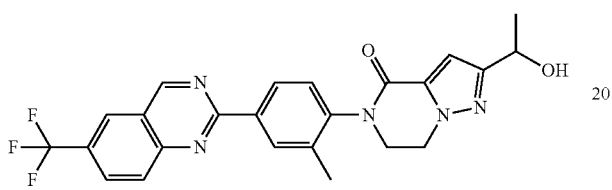

Proceeding analogously as described in Example 79, Step 2, but substituting 5-(2-methyl-4-(6-(trifluoromethyl)quinazolin-2-yl)phenyl)-4-oxo-4,5,6,7-tetrahydropyrazolo[1,5-a]pyrazine-3-carbaldehyde with 2-acetyl-5-(2-methyl-4-(6-(trifluoromethyl)-quinazolin-2-yl)phenyl)-6,7-dihydropyrazolo[1,5-a]pyrazin-4 (5H)-one gave crude product. Purification by Prep-TLC with dichloromethane/methanol (40:1) gave the title compound as a white solid.

LC-MS: (ES, m/z): [M+H]$^+$ 468.3; $^1$H-NMR: (300 MHz, DMSO-d$_6$, ppm): δ 1.40 (d, 3H), 2.64 (s, 3H), 3.97-3.98 (m, 1H), 4.25-4.35 (m, 1H), 4.51-4.55 (m, 2H), 4.76-4.78 (m, 1H), 5.20 (d, 1H), 6.76 (s, 1H), 7.57 (d, 1H), 8.28 (t, 2H), 8.50 (d, 1H), 8.55 (s, 1H), 8.73 (s, 1H), 9.91 (s, 1H).

Example 93

Synthesis of 8-methyl-2-(2-methyl-4-(6-(trifluoromethyl)quinazolin-2-yl)phenyl)-3,4-dihydro-2H-pyrazolo[1,5-e][1,2,5]thiadiazine 1,1-dioxide

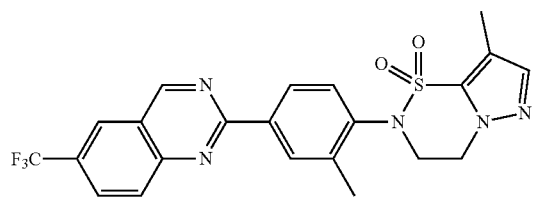 [SMILES: Cc1cc(-c2ncc3cc(C(F)(F)F)ccc3n2)ccc1N1CCn2ncc(C)c2S1(=O)=O]

Step 1: Synthesis of 5-iodo-4-methyl-1H-pyrazole

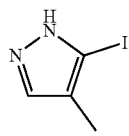

Into a 250-mL 3-necked round-bottom flask under N$_2$ atmosphere, were placed 4-methyl-1H-pyrazole (5.00 g, 60.897 mmol, 1.00 equiv), DMF (100.00 mL), and NIS (14.39 g, 63.942 mmol, 1.05 equiv). The resulting solution was stirred for 1 h at 25° C. and then quenched with water. The resulting solution was extracted with ethyl acetate and the organic layer was separated and concentrated in vacuum. The residue was by Flash chromatography to give the title compound (4 g, 31.58%) as a white solid.

Step 2: Synthesis of 5-(benzylthio)-4-methyl-1H-pyrazole

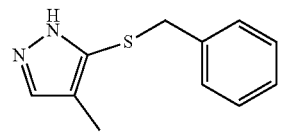

Into a 100-mL 3-necked round-bottom flask under N$_2$ atmosphere, were placed 5-iodo-4-methyl-1H-pyrazole (2.00 g, 9.615 mmol, 1.00 equiv), CuSO$_4$ (3.07 g, 19.231 mmol, 2.00 equiv), K$_2$CO$_3$ (2.66 g, 19.231 mmol, 2.00 equiv), DMF (50.00 mL), (2.37 g, 19.231 mmol, 2.00 equiv), and picolinic acid (5.96 g, 48.076 mmol, 5.00 equiv). The resulting solution was stirred for 12 h at 110° C. The reaction was then quenched by the addition of water. The resulting solution was extracted with ethyl acetate and the organic layer was separated and concentrated. The residue was applied onto a silica gel column with dichloro-methane/methanol (50:1) to give (2.5 g, 127.27%) of the title compound as a yellow solid.

Step 3: Synthesis of 1-(2-(benzyloxy)ethyl)-5-(benzylthio)-4-methyl-1H-pyrazole

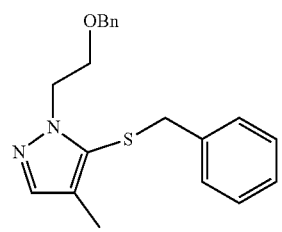 [SMILES: Cc1cnn(CCOCc2ccccc2)c1SCc1ccccc1]

Into a 100-mL 3-necked round-bottom flask under N$_2$ atmosphere, were placed 5-(benzylthio)-4-methyl-1H-pyrazole (2.30 g, 11.259 mmol, 1.00 equiv), 2-(benzyloxy)ethan-1-ol (3.43 g, 22.517 mmol, 2.00 equiv), DIAD (4.55 g, 22.517 mmol, 2.00 equiv), THF (50.00 mL), and PPh$_3$ (5.91 g, 22.517 mmol, 2.00 equiv). The resulting solution was stirred for 1 h at 0° C. and then concentrated. The residue was applied onto a silica gel column and eluted with ethyl acetate/petroleum ether (1:50) to give the title compound (1.2 g, 31.49%) as a yellow liquid.

Step 4: Synthesis of 1-(2-(benzyloxy)ethyl)-4-methyl-1H-pyrazole-5-sulfonyl chloride

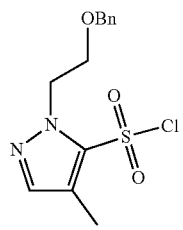 [SMILES: Cc1cnn(CCOCc2ccccc2)c1S(=O)(=O)Cl]

Into a 100-mL 3-necked round-bottom flask under N₂ atmosphere, were placed 1-(2-(benzyloxy)ethyl)-5-(benzylthio)-4-methyl-1H-pyrazole (1.20 g, 3.545 mmol, 1.00 equiv), MeCN (40.00 mL), AcOH (0.50 mL), H₂O (1.00 mL), and DCDMH (1.39 g, 7.091 mmol, 2.00 equiv). The resulting solution was stirred for 12 h at 25° C. and then concentrated to give the title compound (2.5 g, 116.88%) as a yellow liquid.

Step 5: Synthesis of 1-(2-(benzyloxy)ethyl)-4-methyl-N-(2-methyl-4-(6-(trifluoromethyl)-quinazolin-2-yl)phenyl)-1H-pyrazole-5-sulfonamide

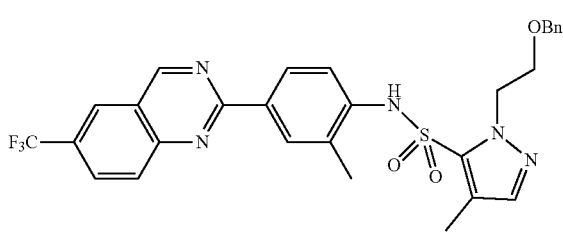 [SMILES: Cc1cc(-c2ncc3cc(C(F)(F)F)ccc3n2)ccc1NS(=O)(=O)c1c(C)cnn1CCOCc1ccccc1]

Into a 100-mL 3-necked round-bottom flask under N₂ atmosphere, were placed 1-(2-(benzyloxy)ethyl)-4-methyl-1H-pyrazole-5-sulfonyl chloride (2.50 g, 7.942 mmol, 1.00 equiv), 2-methyl-4-[6-(trifluoromethyl)quinazolin-2-yl]aniline (3.61 g, 11.913 mmol, 1.50 equiv), and pyridine (50.00 mL). The resulting solution was stirred for 12 h at 25° C. and then concentrated. The residue was purified by Flash chromatography to give (200 mg, 4.33%) of the title compound as a yellow solid.

Step 6: Synthesis of 1-(2-hydroxyethyl)-4-methyl-N-(2-methyl-4-(6-(trifluoromethyl)-quinazolin-2-yl)phenyl)-1H-pyrazole-5-sulfonamide

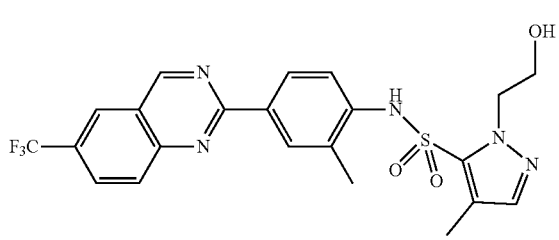 [SMILES: Cc1cc(-c2ncc3cc(C(F)(F)F)ccc3n2)ccc1NS(=O)(=O)c1c(C)cnn1CCO]

Into an 8-mL sealed tube purged and maintained under nitrogen atmosphere, were placed 1-(2-(benzyloxy)ethyl)-4-methyl-N-(2-methyl-4-(6-(trifluoromethyl)quinazolin-2-yl)phenyl)-1H-pyrazole-5-sulfonamide (190.00 mg, 0.327 mmol, 1.00 equiv), DCM (5.00 mL), and BCl₃ (1M) (0.33 mL). The resulting solution was stirred for 1 h at 0° C. and then quenched with NaHCO₃. The resulting solution was extracted with ethyl acetate and the organic layer was separated and concentrated. The residue was applied onto Prep-TLC and eluted with dichloromethane/methanol (20:1) to give the title compound (100 mg, 62.28%) as a yellow solid.

Step 7: Synthesis of 8-methyl-2-(2-methyl-4-(6-(trifluoromethyl)quinazolin-2-yl)phenyl)-3,4-dihydro-2H-pyrazolo[1,5-e][1,2,5]thiadiazine 1,1-dioxide

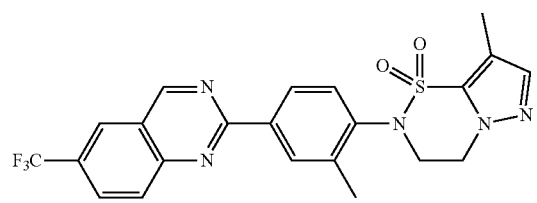 [SMILES: Cc1cc(-c2ncc3cc(C(F)(F)F)ccc3n2)ccc1N1CCn2ncc(C)c2S1(=O)=O]

Into a 20-mL sealed tube under nitrogen atmosphere, were placed 1-(2-hydroxyethyl)-4-methyl-N-(2-methyl-4-(6-(trifluoromethyl)quinazolin-2-yl)phenyl)-1H-pyrazole-5-sulfonamide (90.00 mg, 0.183 mmol, 1.00 equiv), THF (9.00 mL), PPh₃ (96.06 mg, 0.366 mmol, 2.00 equiv), and DIAD (74.06 mg, 0.366 mmol, 2.00 equiv). The resulting solution was stirred for 1 h at 0° C. and then concentrated. The residue was applied onto Prep-TLC and eluted with dichloromethane/methanol (30:1) to give the title compound (44.2 mg, 50.98%) as a white solid. LC-MS: (ES, m/z): [M+H]⁺ 474.3; ¹H-NMR: (400 MHz, DMSO-d₆, ppm): δ 2.25 (s, 3H), 2.66 (s, 3H), 4.18-4.21 (m, 1H), 4.35-4.50 (m, 3H), 7.24 (d, 1H), 7.64 (s, 1H), 8.27 (t, 1H), 8.42 (d, 1H), 8.59 (s, 1H), 8.72 (s, 1H), 9.90 (s, 1H).

Example 94

Synthesis of 5-(5-(2-methyl-4-(6-(trifluoromethyl)quinazolin-2-yl)phenyl)-4-oxo-4,5,6,7-tetrahydropyrazolo[1,5-a]pyrazin-3-yl)imidazolidine-2,4-dione

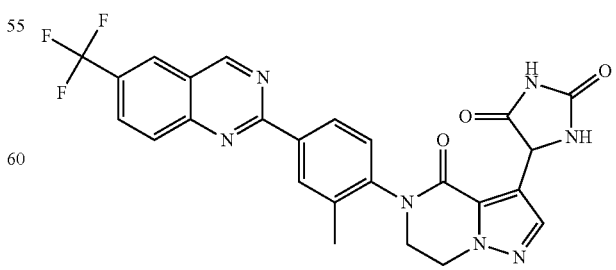

Step 1: Synthesis of 5-(2-methyl-4-(6-(trifluoromethyl)quinazolin-2-yl)phenyl)-4-oxo-4,5,6,7-tetrahydropyrazolo[1,5-a]pyrazine-3-carbaldehyde

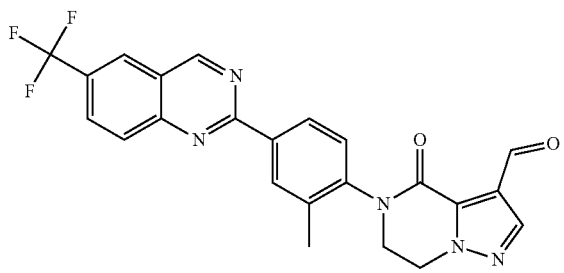 [SMILES: Cc1cc(-c2ncc3cc(C(F)(F)F)ccc3n2)ccc1N1CCn2ncc(C=O)c2C1=O]

Proceeding analogously as described in Example 58, Steps 1-3, but substituting 2-bromo-3-methyl-5-[2-methyl-4-[6-(trifluoromethyl)-quinazolin-2-yl]phenyl]-3H,3aH,4H,5H,6H,7H-pyrazolo[1,5-a]pyrazin-4-one with 3-bromo-5-(2-methyl-4-(6-(trifluoromethyl)quinazolin-2-yl)phenyl)-6,7-dihydropyrazolo[1,5-a]pyrazin-4 (5H)-one gave crude product. Purification by silica gel column with ethyl acetate/petroleum ether (1:5) gave the title compound as a yellow solid.

Step 2: Synthesis of 5-(5-(2-methyl-4-(6-(trifluoromethyl)quinazolin-2-yl)phenyl)-4-oxo-4,5,6,7-tetrahydropyrazolo[1,5-a]pyrazin-3-yl)imidazolidine-2,4-dione

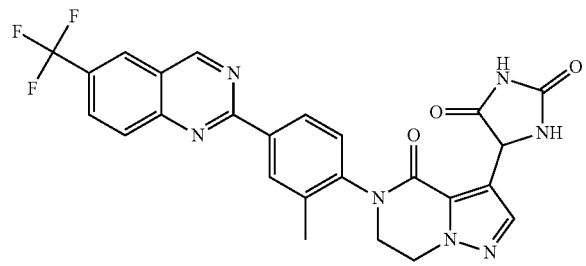 [SMILES: Cc1cc(-c2ncc3cc(C(F)(F)F)ccc3n2)ccc1N1CCn2ncc(C3NC(=O)NC3=O)c2C1=O]

Into a 8-mL sealed tube under $N_2$ atmosphere, were placed 5-(2-methyl-4-(6-(trifluoromethyl)quinazolin-2-yl)phenyl)-4-oxo-4,5,6,7-tetrahydropyrazolo[1,5-a]pyrazine-3-carbaldehyde (100 mg, 0.229 mmol, 1 equiv), KCN (29.78 mg, 0.457 mmol, 2 equiv), $(NH_4)_2CO_3$ (131.81 mg, 1.372 mmol, 6 equiv), and EtOH (50%) (2 mL). The resulting solution was stirred for 6 h at 60° C. and then quenched with $NaHCO_3$. The resulting solution was extracted with ethyl acetate and organic layer was concentrated. The residue was applied onto Prep-TLC with chloroform/methanol (10:1) to give the title compound (16.9 mg, 14.18%) as a white solid. LC-MS: (ES, m/z): [M+H]⁺ 522.3; ¹H-NMR: (400 MHz, DMSO-d₆, ppm): δ 2.34 (d, 3H), 3.90-4.10 (m, 1H), 4.20-4.40 (m, 1H), 4.53-4.68 (m, 2H), 5.52 (d, 1H), 7.58 (t, 1H), 7.68 (d, 1H), 8.09 (s, 1H), 8.28 (t, 2H), 8.50 (d, 1H), 8.56 (s, 1H), 8.73 (s, TH), 9.91 (s, TH), 10.71 (s, TH).

Example 95

Synthesis of (R)-3-methyl-5-(2-methyl-4-(6-(trifluoromethyl)quinazolin-2-yl)phenyl)-2-((2-methylmorpholino)methyl)-6,7-dihydropyrazolo[1,5-a]pyrazin-4 (5H)-one

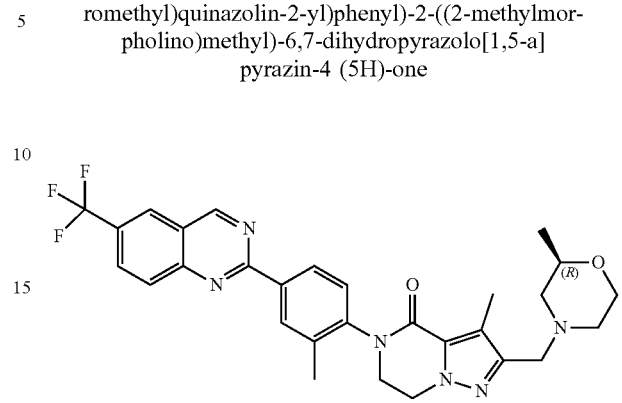

Proceeding analogously as described in Example 61 but substituting morpholine with (2R)-2-methylmorpholine gave crude product. Purification by Prep-TLC ($CH_2Cl_2$/MeOH 40:1) gave the title compound as a white solid. LC-MS: (ES, m/z): [M+H]⁺ 551.3; ¹H-NMR: (400 MHz, DMSO-D₆, ppm): δ 9.91 (s, 1H), 8.74 (s, 1H), 8.55 (s, 1H), 8.50 (d, 1H), 8.29 (t, 2H), 7.54-7.56 (d, 1H), 4.50 (bs, 2H), 4.26-4.33 (m, 1H), 3.90-3.93 (m, 1H), 3.74 (bs, 1H), 3.48 (bs, 4H), 2.67-2.77 (m, 2H), 2.35 (s, 3H), 2.27 (s, 3H), 1.99-2.07 (bs, 1H), 1.76-1.82 (bs, 1H), 1.05 (d, 3H).

Example 96

Synthesis of (S)-3-methyl-5-(2-methyl-4-(6-(trifluoromethyl)quinazolin-2-yl)phenyl)-2-((2-methylmorpholino)methyl)-6,7-dihydropyrazolo[1,5-a]pyrazin-4 (5H)-one

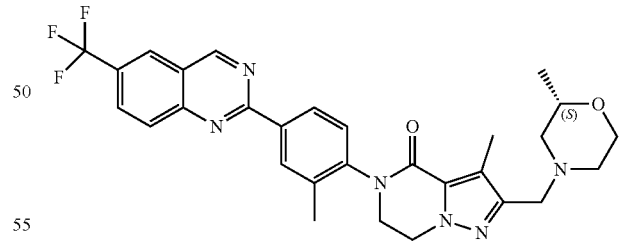

Proceeding analogously as described in Example 61 but substituting morpholine with (2S)-2-methylmorpholine gave crude product. Purification by prep-tlc ($CH_2Cl_2$/MeOH 30:1) gave the title compound as a white solid. LC-MS: (ES, m/z): [M+H]⁺ 551.4; ¹H-NMR: (400 MHz, DMSO-d₆, ppm): δ 9.90 (s, 1H), 8.72 (s, 1H), 8.55 (s, 1H), 8.48 (d, 1H), 8.50 (m, 2H), 8.28 (s, 2H), 7.54 (d, 1H), 4.49 (t, 2H), 4.28-4.32 (m, 1H), 3.89-3.93 (m, 1H), 3.74 (d, 1H), 3.46 (s, 4H), 2.68 (d, 2H), 2.35 (s, 3H), 2.26 (s, 3H), 2.06 (t, 1H), 1.76 (t, 1H), 1.04 (d, 3H).

Example 97

Synthesis of (3-methyl-5-(2-methyl-4-(6-(trifluoromethyl)quinazolin-2-yl)phenyl)-4-oxo-4,5,6,7-tetrahydropyrazolo[1,5-a]pyrazin-2-yl)methyl dihydrogen phosphate

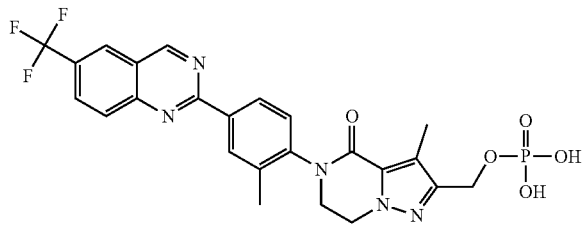 [SMILES: Cc1cc(-c2ncc3cc(C(F)(F)F)ccc3n2)ccc1N1CCn2nc(COP(=O)(O)O)c(C)c2C1=O]

Step 1: Synthesis of 2-(chloromethyl)-3-methyl-5-(2-methyl-4-(6-(trifluoromethyl)quinazolin-2-yl)phenyl)-6,7-dihydropyrazolo[1,5-a]pyrazin-4 (5H)-one

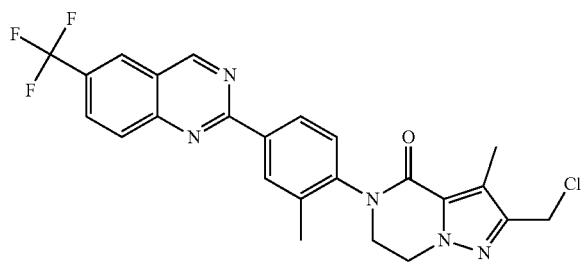 [SMILES: Cc1cc(-c2ncc3cc(C(F)(F)F)ccc3n2)ccc1N1CCn2nc(CCl)c(C)c2C1=O]

To a stirred solution/mixture of 2-(hydroxymethyl)-3-methyl-5-(2-methyl-4-(6-(trifluoromethyl)quinazolin-2-yl)phenyl)-6,7-dihydropyrazolo[1,5-a]pyrazin-4 (5H)-one (170.00 mg, 0.364 mmol, 1.00 equiv) and TEA (110.40 mg, 1.091 mmol, 3 eq) in DCM (5 mL) and in a 8 mL vial, MsCl (124.98 mg, 1.091 mmol, 3.00 equiv) was added dropwise at degrees C. The resulting mixture was stirred overnight at RT under nitrogen atmosphere. The resulting mixture was diluted with water (20 mL) and extracted with EtOAc (4×20 mL). The EA phase was concentrated under vacuum. The residue was purified by Prep-TLC (CH$_2$Cl$_2$:MeOH=50:1) gave the title compound (50 mg, 96.2%) as a white solid.

Step 2: Synthesis of di-tert-butyl ((3-methyl-5-(2-methyl-4-(6-(trifluoromethyl)quinazolin-2-yl)phenyl)-4-oxo-4,5,6,7-tetrahydropyrazolo[1,5-a]pyrazin-2-yl)methyl) phosphate

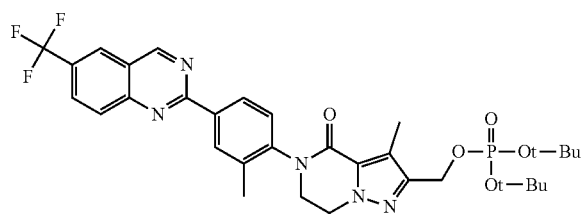

To a stirred solution of 2-(chloromethyl)-3-methyl-5-[2-methyl-4-[6-(trifluoromethyl)quinazolin-2-yl]phenyl]-4H,5H,6H,7H-pyrazolo[1,5-a]pyrazin-4-one (220.00 mg, 0.453 mmol, 1.00 equiv) in DMF (8.00 mL) in a 20 mL vial, di-tert-butyl potassium phosphate (1124.22 mg, 4.528 mmol, 10.00 equiv) at room temperature. The resulting mixture was stirred for 3 days at 50 degrees C. under nitrogen atmosphere. The resulting mixture was diluted with water (30 mL). The aqueous layer was extracted with EtOAc (4×30 mL).

The resulting mixture was concentrated under vacuum. The residue was purified by Prep-TLC (CH$_2$Cl$_2$:MeOH=120:1) to afford di-tert-butyl (3-methyl-5-[2-methyl-4-[6-(trifluoromethyl)quinazolin-2-yl]phenyl]-4-oxo-4H,5H,6H,7H-pyrazolo[1,5-a]pyrazin-2-yl)methyl phosphate (150 mg, 50.22%) as a white solid.

Step 3: Synthesis of (3-methyl-5-(2-methyl-4-(6-(trifluoromethyl)quinazolin-2-yl)phenyl)-4-oxo-4,5,6,7-tetrahydropyrazolo[1,5-a]pyrazin-2-yl)methyl dihydrogen phosphate

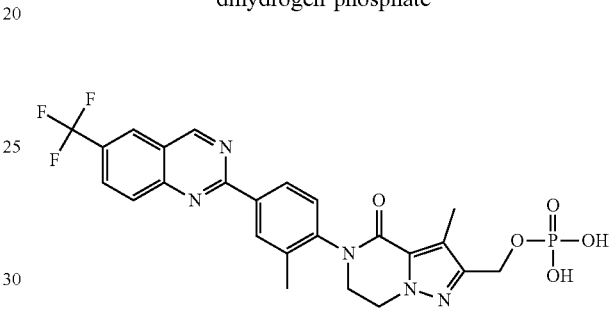

To a stirred solution of di-tert-butyl (3-methyl-5-[2-methyl-4-[6-(trifluoromethyl) quinazolin-2-yl]phenyl]-4-oxo-4H,5H,6H,7H-pyrazolo[1,5-a]pyrazin-2-yl)methyl phosphate (140.00 mg, 0.212 mmol, 1 equiv) in DCM (4.00 mL) in an 8 mL vial, TFA (2.00 mL) was added at 0° C. The resulting mixture was stirred for 1 h at room temperature and then concentrated under reduced pressure. The resulting mixture was diluted with CH$_2$Cl$_2$ (5 mL) and then concentrated under reduced pressure. The resulting mixture was diluted with DMF (4 mL) and then concentrated under reduced pressure. The residue was purified by reverse flash chromatography with the following conditions (C18 silica gel; mobile phase, MeOH in water, 10% to 50% gradient in 10 min; detector, UV 254 nm) gave the title compound (31.1 mg) as a white solid. LC-MS: (ES, m/z): [M+H]$^+$ 548.3; $^1$H-NMR: (400 MHz, DMSO-d$_6$, ppm): δ 9.90 (s, 1H), 8.72 (s, 1H), 8.55 (s, 2H), 8.48 (d, 1H), 8.28 (t, 1H), 7.55 (d, 1H), 4.85 (d, 2H), 4.52 (t, 2H), 4.27-4.34 (m, 1H), 3.91-3.94 (m, 1H), 2.34 (s, 3H), 2.27 (s, 3H).

Example 98

Synthesis of 3-methyl-5-(2-methyl-4-(6-(trifluoromethyl)quinazolin-2-yl)phenyl)-2-((4-oxopiperidin-1-yl)methyl)-6,7-dihydropyrazolo[1,5-a]pyrazin-4 (5H)-one

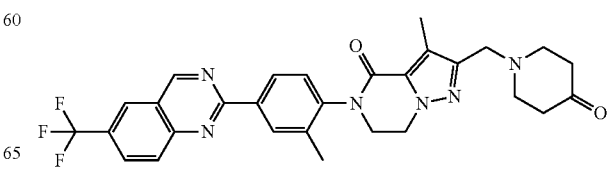

Proceeding analogously as described in Example 61, but substituting morpholine with piperidin-4-one hydrochloride gave crude product. Purification by reverse flash chromatography (conditions: column, c18 silica gel; mobile phase, meoh in water, 10% to 50% gradient in 10 min; detector, uv 254 nm) gave the title compound as a white solid. LC-MS: (ES, m/z): [M+H]$^+$ 549.4; $^1$H-NMR: (400 MHz, DMSO-d6, ppm): δ 9.90 (s, 1H), 8.72 (s, 1H), 8.49-8.55 (m, 2H), 8.28 (s, 2H), 7.55 (d, 1H), 4.49 (s, 2H), 4.29 (s, 1H), 3.92 (s, 1H), 3.62 (s, 2H), 2.72 (s, 4H), 2.30-2.50 (m, 10H).

Example 99

Synthesis of 2-((4-fluoropiperidin-1-yl)methyl)-3-methyl-5-(2-methyl-4-(6-(trifluoromethyl)-quinazolin-2-yl)phenyl)-6,7-dihydropyrazolo[1,5-a]pyrazin-4 (5H)-one

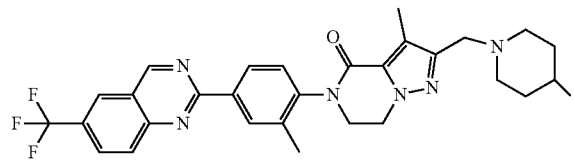

Proceeding analogously as described in Example 61, but substituting morpholine with 4-fluoropiperidine gave crude product. Purification by Prep-TLC (CH$_2$Cl$_2$/MeOH 40:1) gave the title compound as a white solid. LC-MS: [M+H]$^+$ 553.4; $^1$H-NMR: (300 MHz, DMSO-d$_6$, ppm): δ 9.91 (s, 1H), 8.74 (s, 1H), 8.55 (s, 1H), 8.49 (d, 1H), 8.29 (m, 2H), 7.56 (d, 1H), 4.47-4.51 (m, 3H), 4.28-4.32 (m, 1H), 3.89-3.93 (m, 1H), 3.48 (bs, 2H), 2.50-2.51 (s, 2H), 2.26-2.34 (m, 8H), 1.60-1.88 (m, 4H).

Example 100

Synthesis of 2-((4-hydroxypiperidin-1-yl)methyl)-3-methyl-5-(2-methyl-4-(6-(trifluoromethyl)-quinazolin-2-yl)phenyl)-6,7-dihydropyrazolo[1,5-a]pyrazin-4 (5H)-one

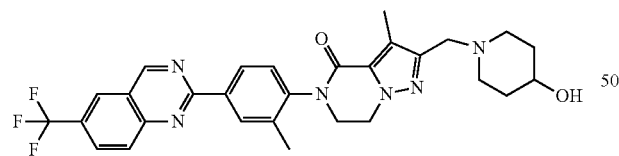

Proceeding analogously as described in Example 61, but substituting morpholine with 4-hydroxypiperidine gave crude product. The crude product was purified by reverse flash chromatography (Conditions: column, C18 silica gel; mobile phase, MeOH in water, 10% to 50% gradient in 10 min; detector, UV 254 nm) to give the title compound as a white solid.

LC-MS: (ES, m/z): [M+H]$^+$ 551.4; $^1$H-NMR: (400 MHz, DMSO-d$_6$, ppm): δ 9.91 (s, 1H), 8.74 (s, 1H), 8.55 (s, 1H), 8.48 (d, 1H) (d, 1H), 8.29 (t, 2H), 7.55 (d, 1H), 4.55 (s, 1H), 4.47-4.50 (m, 2H), 4.26-4.33 (m, 1H), 3.90-3.93 (m, 1H), 3.43 (s, 3H), 2.64-2.72 (m, 2H), 2.35 (s, 3H), 2.25 (s, 3H), 2.05 (s, 2H), 1.71 (d, 2H), 1.36 (d, 2H).

Example 101

Synthesis of 2-((1,1-dioxidothiomorpholino)methyl)-3-methyl-5-(2-methyl-4-(6-(trifluoromethyl)quinazolin-2-yl)phenyl)-6,7-dihydropyrazolo[1,5-a]pyrazin-4 (5H)-one

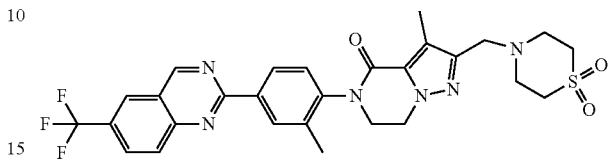

Into a 8 mL vial were added 3-methyl-5-[2-methyl-4-[6-(trifluoromethyl)quinazolin-2-yl]phenyl]-4-oxo-4H,5H,6H,7H-pyrazolo[1,5-a]pyrazine-2-carbaldehyde (50.00 mg, 0.107 mmol, 1.00 equiv) and THF (1.00 mL) at room temperature. Thiomorpholine-1,1-dione (72.61 mg, 0.537 mmol, 5.00 equiv) was added at room temperature and the resulting mixture was stirred overnight. To the above mixture was added acetic acid (0.01 mL) at room temperature and NaBH$_3$CN (13.50 mg, 0.215 mmol, 2 equiv) at 0° C. The residue was purified by Prep-TLC (CH$_2$Cl$_2$/MeOH 40:1) to afford the title compound (20.7 mg, 16.48%) as a white solid. LC-MS: (ES, m/z): [M+H]$^+$ 585.4; $^1$H-NMR: (300 MHz, DMSO-d$_6$, ppm): δ 9.92 (s, 1H), 8.74 (s, 1H), 8.55 (s, 1H), 8.49 (d, 1H), 8.29 (t, 2H), 7.56 (d, 1H), 4.49-4.53 (m, 3H), 4.28-4.32 (m, 1H), 3.89-3.93 (m, 2H), 3.10-3.12 (m, 4H), 2.93 (s, 4H), 2.36 (m, 3H), 2.29 (m, 3H), 2.08 (m, 1H)

Example 102

Synthesis of 2-((2-oxa-7-azaspiro[3.5]nonan-7-yl)methyl)-3-methyl-5-(2-methyl-4-(6-(trifluoromethyl)quinazolin-2-yl)phenyl)-6,7-dihydropyrazolo[1,5-a]pyrazin-4 (5H)-one

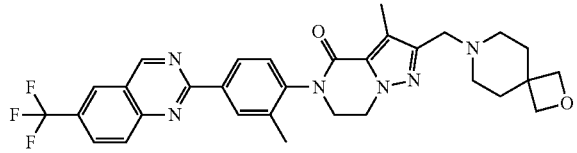 [SMILES: Cc1cc(-c2ncc3cc(C(F)(F)F)ccc3n2)ccc1N1CCn2nc(CN3CCC4(CC3)COC4)c(C)c2C1=O]

Proceeding analogously as described in Example 61, but substituting morpholine with 2-oxa-7-azaspiro[3.5]nonane gave crude product. Purification by reverse flash chromatography (Conditions: column, C18 silica gel; mobile phase, MeOH in water, 10% to 50% gradient in 10 min; detector, UV 254 nm) gave the title compound as a white solid. LC-MS: (ES, m/z): [M+H]$^+$ 577.4; $^1$H-NMR: (300 MHz, CDCl$_3$, ppm): δ 9.59 (s, 1H), 8.65 (s, 1H), 8.58 (d, 1H), 8.29 (s, 1H), 8.23 (d, 1H), 8.11 (d, 1H), 7.41 (d, 1H), 4.54 (t, 2H), 4.44 (s, 4H), 4.26 (m, 1H), 3.55 (s, 2H), 2.45 (s, 9H), 1.95 (s, 4H), 1.65 (s, 2H)

Example 103

Synthesis of 3-methyl-5-(2-methyl-4-(6-(trifluoromethyl)quinazolin-2-yl)phenyl)-2-((4-methyl-piperazin-1-yl)methyl)-6,7-dihydropyrazolo[1,5-a]pyrazin-4 (5H)-one

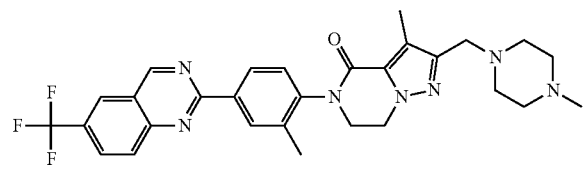 [SMILES: Cc1cc(-c2ncc3cc(C(F)(F)F)ccc3n2)ccc1N1CCn2nc(CN3CCN(C)CC3)c(C)c2C1=O]

Proceeding analogously as described in Example 61, but substituting morpholine with 1-methylpiperazine gave crude product. Purification by Prep-TLC (CH$_2$Cl$_2$/MeOH 40:1) gave the title compound as a white solid. LC-MS: (ES, m/z): [M+H]$^+$ 550; $^1$H-NMR: (300 MHz, DMSO-d$_6$, ppm): δ 9.91 (s, 1H), 8.73 (s, 1H), 8.55 (s, 1H), 8.50 (d, 1H), 8.28 (t, 2H), 7.56 (d, 1H), 4.48 (t, 2H), 4.28-4.32 (m, 1H), 3.88-3.92 (m, 1H), 3.45 (s, 2H), 3.32-3.34 (s, 1H), 2.34 (s, 7H), 2.30 (s, 6H), 2.25 (s, 3H).

Example 104

Synthesis of 3-methyl-2-((4-methyl-3-oxopiperazin-1-yl)methyl)-5-(2-methyl-4-(6-(trifluoro-methyl)quinazolin-2-yl)phenyl)-6,7-dihydropyrazolo[1,5-a]pyrazin-4 (5H)-one

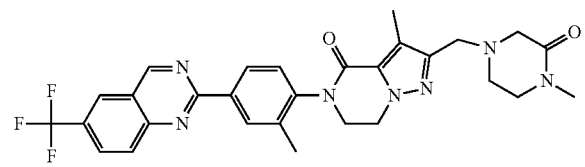 [SMILES: Cc1cc(-c2ncc3cc(C(F)(F)F)ccc3n2)ccc1N1CCn2nc(CN3CCN(C)C(=O)C3)c(C)c2C1=O]

Proceeding analogously as described in Example 61, but substituting morpholine with 1-methylpiperazin-2-one gave crude product. Purification by Prep TLC (CH$_2$Cl$_2$/MeOH 40:1) gave the title compound as a white solid. LC-MS: (ES, m/z): [M+H]$^+$ 564.4; $^1$H-NMR: (300 MHz, DMSO-d$_6$, ppm): δ 9.91 (s, 1H), 8.74 (s, 1H), 8.55 (s, 1H), 8.50 (s, 1H), 8.50 (d, 1H), 8.29 (t, 2H), 7.56 (d, 1H), 4.50-4.51 (m, 2H), 4.27-4.36 (m, 1H), 3.90-3.94 (m, 1H), 3.58-3.62 (m, 2H), 3.28-3.35 (d, 2H), 3.05 (s, 2H), 2.86 (s, 3H), 2.82 (s, 1H), 2.50 (s, 1H), 2.35 (s, 3H), 2.27 (s, 3H)

Example 105

Synthesis of 3-methyl-5-(2-methyl-4-(6-(trifluoromethyl)pyrido[3,2-d]pyrimidin-2-yl)phenyl)-2-(morpholinomethyl)-6,7-dihydropyrazolo[1,5-a]pyrazin-4 (5H)-one

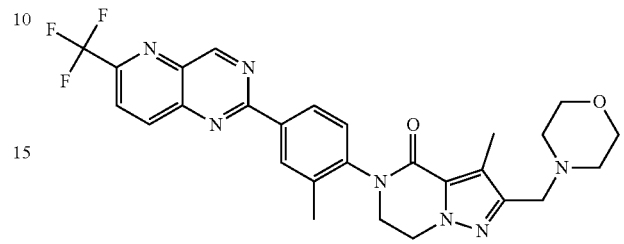

Step 1: Synthesis of 3-methyl-5-(2-methyl-4-(6-(trifluoromethyl)pyrido[3,2-d]pyrimidin-2-yl)phenyl)-4-oxo-4,5,6,7-tetrahydropyrazolo[1,5-a]pyrazine-2-carbaldehyde

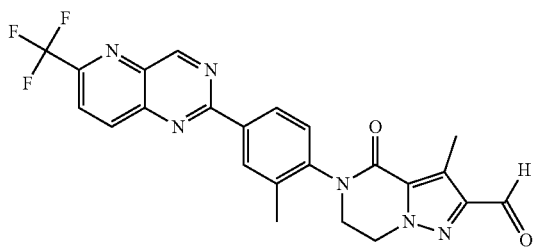 [SMILES: Cc1cc(-c2ncc3nc(C(F)(F)F)ccc3n2)ccc1N1CCn2nc(C=O)c(C)c2C1=O]

Proceeding analogously as described in Example 58, Steps 1 to 3, but substituting 2-bromo-3-methyl-5-[2-methyl-4-[6-(trifluoromethyl)-quinazolin-2-yl]phenyl]-3H,3aH,4H,5H,6H,7H-pyrazolo[1,5-a]pyrazin-4-one with 2-bromo-3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one provided crude product. Purification by Prep-TLC (CH$_2$Cl$_2$/MeOH 60:1) gave the title compound as a solid.

Step 2: Synthesis of 3-methyl-5-(2-methyl-4-(6-(trifluoromethyl)pyrido[3,2-d]pyrimidin-2-yl)phenyl)-2-(morpholinomethyl)-6,7-dihydropyrazolo[1,5-a]pyrazin-4 (5H)-one

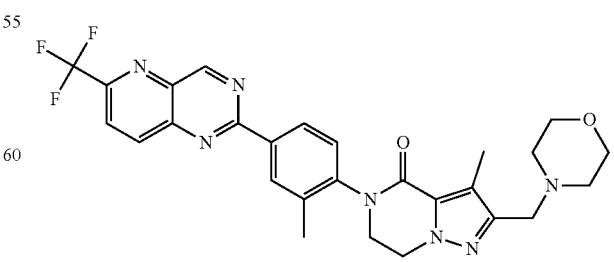

Proceeding analogously as described in Example 61, but substituting 3-methyl-5-(2-methyl-4-(6-(trifluoromethyl)

quinazolin-2-yl)phenyl)-4-oxo-4,5,6,7-tetrahydropyrazolo[1,5-a]pyrazine-2-carbaldehyde with 3-methyl-5-(2-methyl-4-(6-(trifluoromethyl)pyrido[3,2-d]pyrimidin-2-yl)phenyl)-4-oxo-4,5,6,7-tetrahydropyrazolo[1,5-a]pyrazine-2-carbaldehyde provided crude product. Purification by reverse flash chromatography (Conditions: column, C18 silica gel; mobile phase, MeOH in water, 10% to 50% gradient in 10 min; detector, UV 254 nm) provided the title compound as a white solid. LC-MS: (ES, m/z): [M+H]$^+$ 538.4; $^1$H-NMR: (400 MHz, DMSO-d$_6$, ppm): δ 9.97 (s, 1H), 8.82 (d, 1H), 8.57 (s, 1H), 8.50 (t, 2H), 7.58 (d, 1H), 4.50 (t, 2H), 4.27-4.32 (m, 1H), 3.90-3.93 (m, 1H), 3.56 (t, 4H), 3.34 (s, 2H), 2.31-2.39 (m, 4H), 2.26 (s, 3H).

Example 106

Synthesis of 3-methyl-5-(2-methyl-4-(6-(trifluoromethyl)-1,5-naphthyridin-2-yl)phenyl)-2-(morpholinomethyl)-6,7-dihydropyrazolo[1,5-a]pyrazin-4 (5H)-one

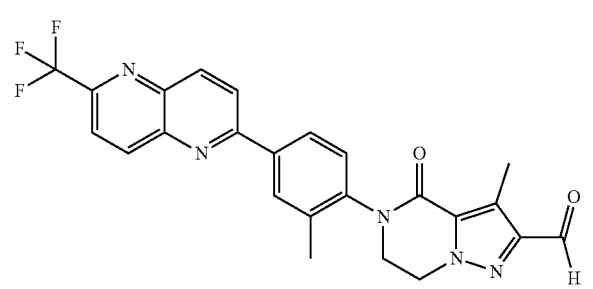 [SMILES: Cc1cc(-c2ccc3nc(C(F)(F)F)ccc3n2)ccc1N1CCn2nc(C=O)c(C)c2C1=O]

Step 1: Synthesis of 3-methyl-5-(2-methyl-4-(6-(trifluoromethyl)-1,5-naphthyridin-2-yl)phenyl)-4-oxo-4,5,6,7-tetrahydropyrazolo[1,5-a]pyrazine-2-carbaldehyde

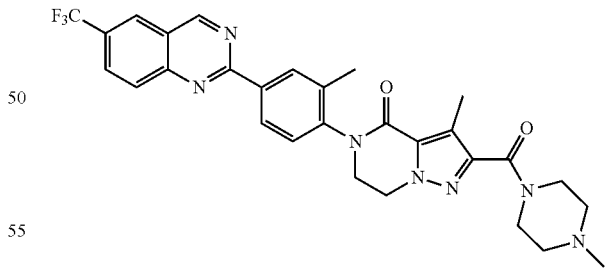

Proceeding analogously as described in Example 58, Steps 1-3, but substituting 2-bromo-3-methyl-5-[2-methyl-4-[6-(trifluoromethyl)-quinazolin-2-yl]phenyl]-3H,3aH,4H,5H,6H,7H-pyrazolo[1,5-a]pyrazin-4-one with 2-bromo-3-methyl-5-(2-methyl-4-(6-(trifluoromethyl)-1,5-naphthyridin-2-yl)phenyl)-6,7-dihydropyrazolo[1,5-a]pyrazin-4 (5H)-one gave the title compound as a white solid.

Step 2: Synthesis of 3-methyl-5-(2-methyl-4-(6-(trifluoromethyl)-1,5-naphthyridin-2-yl)phenyl)-2-(morpholinomethyl)-6,7-dihydropyrazolo[1,5-a]pyrazin-4 (5H)-one

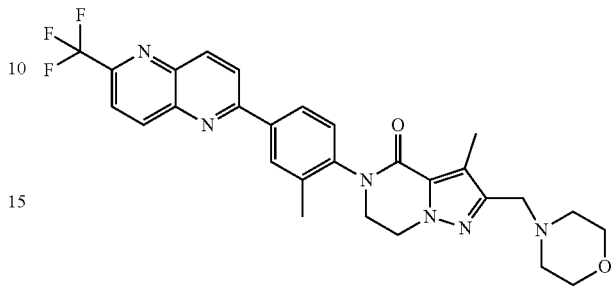

Proceeding analogously as in Example 61, but substituting 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde with 3-methyl-5-(2-methyl-4-(6-(trifluoromethyl)-1,5-naphthyridin-2-yl)phenyl)-4-oxo-4,5,6,7-tetrahydropyrazolo[1,5-a]pyrazine-2-carbaldehyde gave crude product. Purification by Prep-TLC (CH$_2$Cl$_2$/MeOH 40:1) gave the title compound as a white solid. LC-MS: [M+H]$^+$ 537; $^1$H-NMR: (300 MHz, DMSO-d$_6$, ppm): δ 8.80 (d, 1H), 8.69 (d, 1H), 8.62 (d, 1H), 8.26 (d, 1H), 8.24-8.27 (m, 2H), 7.55 (s, 1H), 4.47-4.51 (m, 2H), 4.28-4.32 (m, 1H), 3.88-3.92 (m, 1H), 3.31-3.57 (m, 6H), 2.08-2.52 (m, 10H).

Example 107

Synthesis of 3-methyl-5-(2-methyl-4-(6-(trifluoromethyl)quinazolin-2-yl)phenyl)-2-(4-methylpiperazine-1-carbonyl)-6,7-dihydropyrazolo[1,5-a]pyrazin-4 (5H)-one Proceeding analogously as described in Example 62, Step 1, but substituting morpholine1-provided crude product. Purification by Prep-TLC (CH$_2$Cl$_2$/MeOH 30:1) gave the title compound as a white solid. LC-MS: (ES, m/z): [M+H]$^+$ 564.4; $^1$H-NMR: (400 MHz, DMSO-d$_6$, ppm): δ 9.91 (s, 1H), 8.74 (s, 1H), 8.56 (s, 1H), 8.49 (d, 1H), 8.26 (t, 2H), 7.56 (d, 1H), 4.56-4.59 (m, 2H), 4.31-4.38 (m, 1H), 3.93-3.98 (m, 1H), 3.62-3.65 (m, 4H), 2.45-2.50 (m, 7H), 2.36 (s, 3H), 2.23 (s, 3H).

Example 108

Synthesis of 2-((4,4-difluoropiperidin-1-yl)methyl)-3-methyl-5-(2-methyl-4-(6-(trifluoro-methyl)quinazolin-2-yl)phenyl)-6,7-dihydropyrazolo[1,5-a]pyrazin-4 (5H)-one

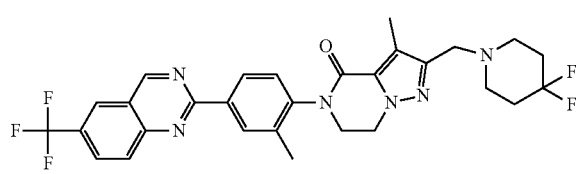 [SMILES: Cc1cc(-c2ncc3cc(C(F)(F)F)ccc3n2)ccc1N1CCn2nc(CN3CCC(F)(F)CC3)c(C)c2C1=O]

Proceeding analogously as described in Example 61, but substituting morpholine with 4,4-difluoropiperidine provided crude product. Purification by Prep-TLC (CH$_2$Cl$_2$/MeOH 40:1) gave the title compound as a white solid. LC-MS: (ES, m/z): [M−H]$^+$571.4; $^1$H-NMR: (300 MHz, DMSO-d$_6$, ppm): δ 9.91 (s, 1H), 8.73 (s, 1H), 8.55 (s, 1H), 8.48 (d, 1H), 8.28 (t, 1H), 7.55 (d, 1H), 4.49 (t, 2H), 4.30-4.34 (m, 1H), 4.25-4.28 (m, 1H), 3.88-3.94 (m, 1H), 3.55 (s, 1H), 3.31-3.33 (s, 4H), 2.35 (s, 3H), 2.27 (s, 3H), 1.90-1.99 (m, 4H).

Example 109

Synthesis of 2-((2-hydroxy-2-azaspiro[3.3]heptan-2-yl)methyl)-3-methyl-5-(2-methyl-4-(6-(trifluoromethyl)pyrido[3,2-d]pyrimidin-2-yl)phenyl)-6,7-dihydropyrazolo[1,5-a]pyrazin-4 (5H)-one

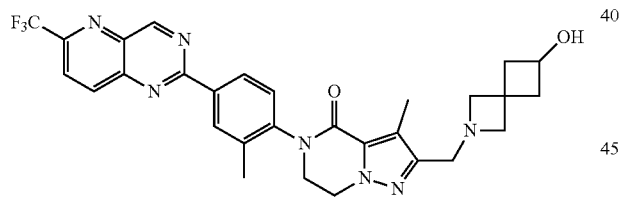

Proceeding analogously as described in Example 61, but substituting morpholine with 2-azaspiro[3.3]heptan-6-ol (182.35 mg, 1.611 mmol, 5 equiv) gave crude product. Purification by Prep-HPLC with the following conditions (Column: XBridge Prep OBD C18 Column, 30×150 mm 5 um; Mobile Phase A: water (0.05% NH$_3$—H$_2$O), Mobile Phase B: ACN; Flow rate:60 mL/min; Gradient:41% B to 56% B in 7 min; 254; 220 nm; RT: 6.25 min) gave the title compound as a white solid. LC-MS: (ES, m/z): [M+H]$^+$ 563.4; $^1$H-NMR: (400 MHz, DMSO-d$_6$, ppm): δ 9.91 (s, 1H), 8.74 (s, 1H), 8.55 (s, 1H), 8.49 (d, 1H), 8.30 (t, 2H), 7.55 (d, 1H), 4.94 (d, 1H), 4.47 (t, 2H), 4.26-4.31 (m, 1H), 3.88-3.94 (m, 2H), 3.46 (s, 2H), 3.11 (s, 2H), 3.07 (s, 2H), 2.28-2.32 (m, 5H), 2.22 (s, 3H), 1.87 (t, 2H).

Example 110

Synthesis of 2-((2-oxa-6-azaspiro[3.5]nonan-6-yl)methyl)-3-methyl-5-(2-methyl-4-(6-(trifluoromethyl)quinazolin-2-yl)phenyl)-6,7-dihydropyrazolo[1,5-a]pyrazin-4 (5H)-one

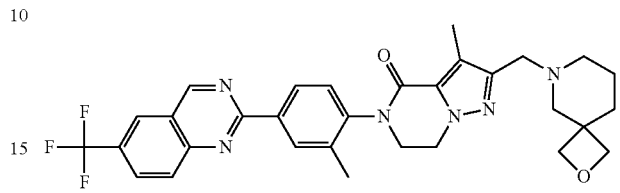

Proceeding analogously as described in Example 61, but substituting morpholine with 2-oxa-6-azaspiro[3.5]nonane oxalic acid gave crude product. Purification by Prep-HPLC (Conditions: (2 #SHIMADZU (HPLC-01)): Column, XBridge Prep OBD C18 Column, 19*250 mm, 5 um; mobile phase, and (60% PhaseB up to 70% in 8 min); Detector, UV) gave the title compound as a white solid. LC-MS: (ES, m/z): [M+H]$^+$ 577.3; $^1$H-NMR: (300 MHz, DMSO-d$_6$, ppm): δ 1.40 (s, 2H), 1.61 (s, 2H), 2.25-2.35 (m, 8H), 2.49 (s, 2H), 3.47 (s, 2H), 3.88-3.92 (m, 1H), 4.16-4.34 (m, 5H), 4.48 (s, 2H), 7.55 (d, 1H), 8.27 (s, 2H), 8.48 (d, 1H), 8.55 (s, 1H), 8.72 (s, 1H), 9.89 (s, 1H).

Example 111

Synthesis of 2-((2-oxa-6-azaspiro[3.4]octan-6-yl)methyl)-3-methyl-5-(2-methyl-4-(6-(trifluoromethyl)quinazolin-2-yl)phenyl)-6,7-dihydropyrazolo[1,5-a]pyrazin-4 (5H)-one

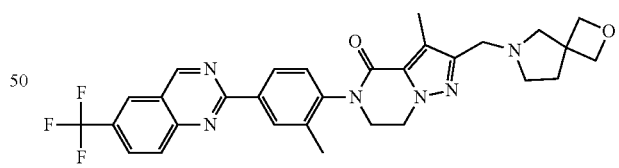

Proceeding analogously as described in Example 61, but substituting morpholine with 2-oxa-6-azaspiro[3.4]octane gave crude product. Purification by Prep-TLC (CH$_2$Cl$_2$/MeOH 40:1) gave the title compound as a white solid. LC-MS: (ES, m/z): [M+H]$^+$ 563.4; 1H-NMR: (300 MHz, DMSO-d$_6$, ppm): δ 9.91 (s, 1H), 8.73 (s, 1H), 8.56 (s, 1H), 8.50 (d, 1H), 8.28 (t, 2H), 7.57 (d, 1H), 4.47-4.65 (m, 6H), 4.29-4.36 (m, 1H), 4.05 (s, 1H), 3.92-3.97 (m, 2H), 3.44-3.47 (s, 2H), 3.16-3.18 (s, 1H), 2.35-2.51 (m, 8H), 1.55 (s, 1H).

Example 112

Synthesis of 3-methyl-5-(2-methyl-4-(6-(trifluoromethyl)quinazolin-2-yl)phenyl)-2-(1-morpholinoethyl)-6,7-dihydropyrazolo[1,5-a]pyrazin-4 (5H)-one

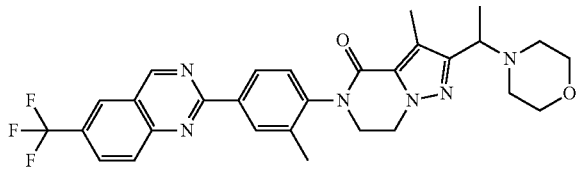 [SMILES: Cc1cc(-c2ncc3cc(C(F)(F)F)ccc3n2)ccc1N1CCn2nc(C(C)N3CCOCC3)c(C)c2C1=O]

Step 1: Synthesis of 2-(1-hydroxyethyl)-3-methyl-5-(2-methyl-4-(6-(trifluoromethyl)-quinazolin-2-yl)phenyl)-6,7-dihydropyrazolo[1,5-a]pyrazin-4 (5H)-one

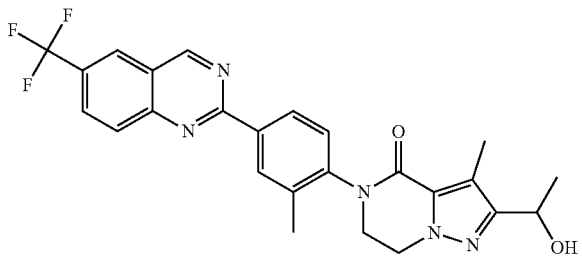 [SMILES: Cc1cc(-c2ncc3cc(C(F)(F)F)ccc3n2)ccc1N1CCn2nc(C(C)O)c(C)c2C1=O]

Into an 8-mL vial purged under N₂ atmosphere, were placed 3-methyl-5-(2-methyl-4-(6-(trifluoromethyl)quinazolin-2-yl)phenyl)-4-oxo-4,5,6,7-tetrahydropyrazolo[1,5-a]pyrazine-2-carbaldehyde (100.00 mg, 0.215 mmol, 1.00 equiv), and THF (1.00 mL, 12.343 mmol, 57.45 equiv). CH₃MgBr (128.10 mg, 1.074 mmol, equiv) was added at 0° C. and the resulting solution was stirred for 3 h at 0° C. After quenching the reaction mixture with water, the product was extracted with dichloromethane and the organic layer was concentrated. The residue was applied onto a Prep TLC and eluted with ethyl acetate/petroleum ether (1:1) to give in the title compound (60 mg, 58.00%) as a white solid.

Step 2: Synthesis of 2-(1-chloroethyl)-3-methyl-5-(2-methyl-4-(6-(trifluoromethyl)-quinazolin-2-yl)phenyl)-6,7-dihydropyrazolo[1,5-a]pyrazin-4 (5H)-one

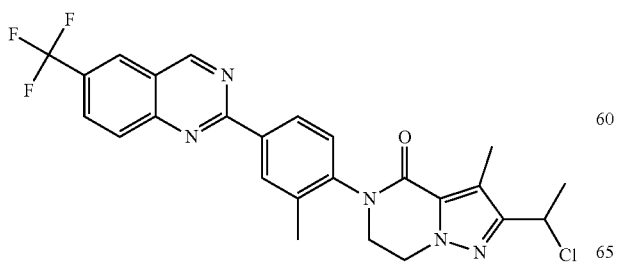

Into a 8-mL vial purged under N₂ atmosphere, were placed 2-(1-hydroxyethyl)-3-methyl-5-(2-methyl-4-(6-(trifluoromethyl)-quinazolin-2-yl)phenyl)-6,7-dihydropyrazolo[1,5-a]pyrazin-4 (5H)-one (60.00 mg, 0.125 mmol, 1.00 equiv), DCM (1.00 mL, 15.730 mmol, 126.23 equiv), and Et₃N (25.22 mg, 0.249 mmol, 2.00 equiv). MsCl (21.41 mg, 0.187 mmol, 1.50 equiv) was added at 0° C. and the resulting solution was stirred for 2 h at 0° C. The reaction was then quenched with water and extracted with dichloromethane. The organics were removed in vacuum and the residue was applied onto a Prep TLC and eluted with ethyl acetate/petroleum ether (1:2) to give the title compound (50 mg, 80.26%) as a white solid.

Step 3: Synthesis of 3-methyl-5-(2-methyl-4-(6-(trifluoromethyl)quinazolin-2-yl)phenyl)-2-(1-morpholinoethyl)-6,7-dihydropyrazolo[1,5-a]pyrazin-4 (5H)-one

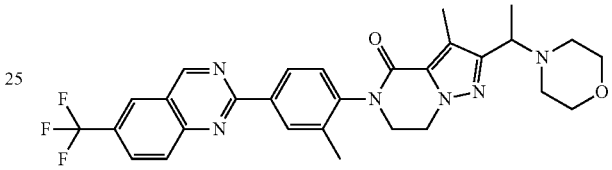

Into a 8-mL vial, were placed 2-(1-chloroethyl)-3-methyl-5-(2-methyl-4-(6-(trifluoromethyl)quinazolin-2-yl)phenyl)-6,7-dihydropyrazolo[1,5-a]pyrazin-4 (5H)-one (50.00 mg, 0.100 mmol, 1.00 equiv), morpholine (13.07 mg, 0.150 mmol, 1.50 equiv), acetone (1.00 mL, 13.602 mmol, 136.00 equiv), K₂CO₃ (41.47 mg, 0.300 mmol, 3.00 equiv), and KI (33.21 mg, 0.200 mmol, 2.00 equiv). The resulting solution was stirred at 25° C. The reaction mixture was quenched with water and extracted with dichloromethane. The residue was applied onto a Prep TLC and eluted with ethyl acetate/petroleum ether (1:1) to give the title compound (6.9 mg, 12.53%) as a white solid. LC-MS: (ES, m/z): [M+H]⁺ 551.4; ¹H-NMR: (400 MHz, CDCl₃, ppm): δ 1.25 (s, 3H), 1.41-1.52 (m, 2H), 2.45-2.80 (m, 8H), 3.67-3.98 (m, 6H), 4.23-4.31 (m, 1H), 4.51-4.54 (m, 2H), 7.39 (dd, 1H), 8.09 (d, 1H), 8.22 (d, 1H), 8.24 (s, 2H), 8.57 (d, 1H), 8.63 (s, 1H), 9.68 (s, 1H).

Example 113

Synthesis of 2-amino-3-methyl-5-(2-methyl-4-(6-(trifluoromethyl)quinazolin-2-yl)phenyl)-6,7-dihydropyrazolo[1,5-a]pyrazin-4 (5H)-one

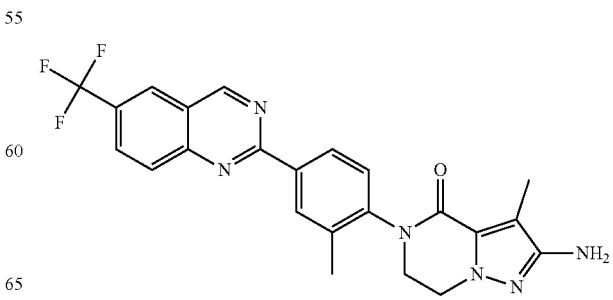

Into a 50-mL round-bottom flask under nitrogen atmosphere, were placed 2-bromo-3-methyl-5-(2-methyl-4-(6-(trifluoromethyl)quinazolin-2-yl)phenyl)-6,7-dihydropyrazolo[1,5-a]pyrazin-4 (5H)-one (200.00 mg, 0.387 mmol, 1.00 equiv), diphenylmethanimine (210.61 mg, 1.162 mmol, 3.00 equiv), toluene (5.00 mL, 46.995 mmol, 121.32 equiv), t-BuONa (74.45 mg, 0.775 mmol, 2.00 equiv), Xphos (73.86 mg, 0.155 mmol, 0.40 equiv), and Pd(dba)$_3$CHCl$_3$ (80.18 mg, 0.077 mmol, 0.20 equiv). The resulting solution was stirred overnight at 100° C. Then THF (2 mL) and HOAc (2 mL) were added and the resulting solution was stirred for overnight at 25° C. After quenching with water, the resulting solution was extracted with ethyl acetate and the organic layers combined and concentrated. The residue was applied onto a Prep TLC and eluted with dichloromethane/methanol (30:1) to give the title compound (90 mg, 51.35%) 0 as a white solid. LC-MS: (ES, m/z): [M+H]$^+$ 453.3; $^1$H-NMR: (400 MHz, DMSO-d$_6$, ppm): δ 2.08 (s, 3H), 2.33 (s, 3H), 3.82-3.88 (m, 1H), 4.25 (s, 3H), 4.82 (s, 2H), 7.53 (d, 1H), 8.29 (t, 2H), 8.48 (d, 1H), 8.55 (s, 1H), 8.73 (s, 1H), 9.91 (s, 1H).

Example 114

Synthesis of 7-(hydroxymethyl)-3-methyl-5-(2-methyl-4-(6-(trifluoromethyl)quinazolin-2-yl)phenyl)-6,7-dihydropyrazolo[1,5-a]pyrazin-4 (5H)-one

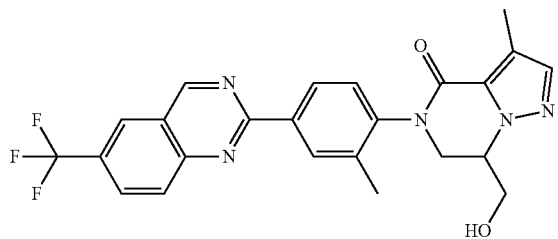

Proceeding analogously as described in Example 1, Step 9, but substituting 4-(2-(benzyloxy)ethoxy)-N-(4-bromo-2-methylphenyl)-1-methyl-1H-pyrazole-5-carboxamide with 7-((benzyloxy)methyl)-3-methyl-5-(2-methyl-4-(6-(trifluoromethyl)quinazolin-2-yl)phenyl)-6,7-dihydropyrazolo[1,5-a]pyrazin-4 (5H)-one gave crude product. Purification by Prep TLC with dichloromethane/methanol (50:1) gave the title compound as a white solid.

LCMS: (ES, m/z): [M+H]$^+$ 468.3; $^1$H-NMR: (300 MHz, DMSO-d$_6$, ppm): δ 2.26 (s, 3H), 2.35 (s, 3H), 3.77-3.79 (m, 1H), 3.89-3.93 (m, 1H), 4.15 (s, 1H), 4.37-4.62 (m, 2H), 5.19-5.31 (m, 1H), 7.51-7.59 (m, 2H), 8.27 (t, 2H), 8.49 (d, 1H), 8.55 (s, 1H), 8.73 (s, 1H), 9.87-9.91 (s, 1H).

Example 115

Synthesis of 5-(4-(4-hydroxy-6-(trifluoromethyl) quinazolin-2-yl)-2-methylphenyl)-3-methyl-6,7-dihydropyrazolo[1,5-a]pyrazin-4 (5H)-one

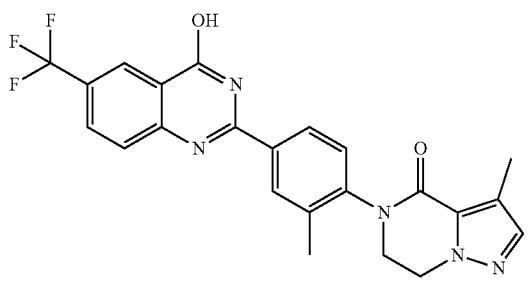 [SMILES: Cc1cc(-c2nc(O)c3cc(C(F)(F)F)ccc3n2)ccc1N1CCn2ncc(C)c2C1=O]

To a stirred mixture of 3-methyl-5-(2-methyl-4-(6-(trifluoromethyl)quinazolin-2-yl)phenyl)-6,7-dihydropyrazolo[1,5-a]pyrazin-4 (5H)-one (100.00 mg, 0.230 mmol, 1.00 equiv) in HCl (1M) (5.00 mL) was added KMnO$_4$ (90.00 mg, 0.570 mmol, 2.50 equiv) in portions under nitrogen atmosphere. The resulting mixture was stirred for overnight at 100° C. under nitrogen atmosphere. The mixture was allowed to cool to room temperature and then neutralized to pH 7 with saturated NaHCO$_3$ (aq.). The resulting mixture was extracted with EtOAc and concentrated under reduced pressure. The residue was purified by Prep-TLC (PE/EtOAc 5:1) to afford the title compound (10 mg) as a white solid. LC-MS: ES, m/z): [M+H]$^+$ 454.3; $^1$H-NMR: (300 MHz, DMSO-d$_6$, ppm): δ 2.26 (s, 3H), 2.31 (s, 3H), 3.87-3.92 (m, 1H), 4.28-4.30 (m, 1H), 4.50-4.54 (m, 2H), 7.49 (s, 1H), 7.55 (d, 1H), 7.96-7.98 (m, 2H), 8.08-8.20 (m, 3H), 8.41 (s, 1H).

Biological Example

HEPG2 and HEPA1C1C7 cells were maintained in MEM and αMEM without nucleosides supplemented with 10% heat inactivated FBS respectively. Stably integrated DRE-luciferase cell lines were generated by transducing the both cell lines with Cignal XRE luciferase reporter (Qiagen) lentiviral particles according to the manufacturer protocol. For both cell lines stably integrated reporter cell lines were selected for the presence of 2 μg/mL puromycin. Following selection of stably integrated cell line pools, clonal cell lines were isolated by limiting dilution in 96-well plates. Transcriptional assays were performed by seeding 100 μL of cells at a density of 250,000 or 100,000 cells/mL, for HEPG2 and HEPA1C1C7 DRE-Luc cells respectively, into 96-well cell culture plates in OptiMEM supplemented with 0.5% heat inactivated FBS and allowed to attach overnight. For modulator assays, the compounds were added in a semi-log dose response using a D300e Digital Dispenser (Tecan) followed normalization with vehicle (DMSO). Immediately following compound addition 10 μL of 2,3,7,8-Tetrachlorodibenzo-p-dioxin (TCDD) was added to the cells to a final concentration of 3 nM or 0.3 nM for the HEPG2 and HEPA1C1C7 DRE-Luc cells respectively. Following 24-hour incubation, the medium was removed and the cells were lysed in 25 μL of Reporter Lysis Buffer (Promega). Firefly luciferase activity was measured immediately following the addition of 50 μL Luciferase Assay Reagent (Promega). The percent maximal activity for each point was determined using the following equation: (RLU$_{sample}$−RLU$_{vehicle-TCDD}$)/(RLU$_{vehicle+TCDD}$ RLU$_{vehicle-TCDD}$)*100. The relative IC$_{50}$, defined as the compound concentration required to reduce the TCDD induced response between the top and bottom plateau of each individual dose response curve by half, for each compound was determined using Prism 7 (GraphPad Software).

TABLE 1

| Example No. | IC$_{50}$ hAhR (antagonist mode) |
|---|---|
| 001 | ++++ |
| 002 | ++++ |
| 003 | +++ |
| 004 | ++++ |
| 005 | ++++ |
| 006 | ++++ |
| 007 | ++++ |
| 008 | ++++ |

TABLE 1-continued

| Example No. | IC$_{50}$ hAhR (antagonist mode) |
|---|---|
| 009 | ++++ |
| 010 | + |
| 011 | ++++ |
| 012 | ++ |
| 013 | ++++ |
| 014 | ++++ |
| 015 | ++++ |
| 016 | ++++ |
| 017 | ++++ |
| 018 | +++ |
| 019 | ++++ |
| 020 | ++++ |
| 021 | ++++ |
| 022 | ++++ |
| 023 | + |
| 024 | ++++ |
| 025 | ++++ |
| 026 | ++++ |
| 027 | ++++ |
| 028 | ++++ |
| 029 | ++++ |
| 030 | ++++ |
| 031 | ++++ |
| 032 | + |
| 033 | ++++ |
| 034 | +++ |
| 035 | ++++ |
| 036 | ++++ |
| 037 | ++++ |
| 038 | ++++ |
| 039 | |
| 040 | + |
| 041 | |
| 042 | +++ |
| 043 | + |
| 044 | ++++ |
| 045 | ++++ |
| 046 | ++++ |
| 047 | ++++ |
| 048 | ++++ |
| 049 | ++++ |
| 050 | ++++ |
| 051 | +++ |
| 052 | ++ |
| 053 | +++ |
| 054 | +++ |
| 055 | +++ |
| 056 | ++++ |
| 057 | ++++ |
| 058 | ++++ |
| 059 | ++++ |
| 060 | +++ |
| 061 | ++++ |
| 062 | ++++ |
| 063 | ++++ |
| 064 | ++++ |
| 065 | ++ |
| 066 | ++++ |
| 067 | ++++ |
| 068 | ++++ |
| 069 | |
| 070 | ++++ |
| 071 | ++ |
| 072 | + |
| 073 | + |
| 074 | + |
| 075 | + |
| 076 | + |
| 077 | + |
| 078 | + |
| 079 | ++++ |
| 080 | ++++ |
| 081 | ++++ |
| 082 | ++++ |
| 083 | ++++ |
| 084 | ++++ |
| 085 | ++++ |
| 086 | ++++ |
| 087 | ++++ |
| 088 | ++++ |
| 089 | ++++ |
| 090 | ++++ |
| 091 | ++++ |
| 092 | ++++ |
| 093 | ++++ |
| 094 | ++++ |
| 095 | ++++ |
| 096 | ++++ |
| 097 | ++++ |
| 098 | ++++ |
| 099 | ++++ |
| 100 | ++++ |
| 101 | ++++ |
| 102 | ++++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | ++++ |
| 113 | ++++ |
| 114$_i$ | ++++ |

(+) IC$_{50}$ = 10 μM-1 μM;
(++) IC$_{50}$ = 1 μM-500 nM;
(+++) IC$_{50}$ = 500 nM-200 nM;
(++++) IC$_{50}$ < 200 nM

What is claimed is:

1. A compound of formula (I'):

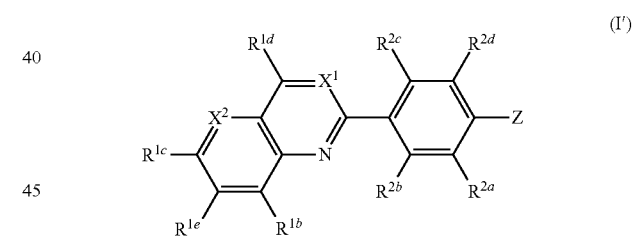

or a pharmaceutically acceptable salt, solvate or hydrate thereof, wherein:

$X^1$ is $C(R^{1a})$ and $X^2$ is N;

Z is selected from the group consisting of:

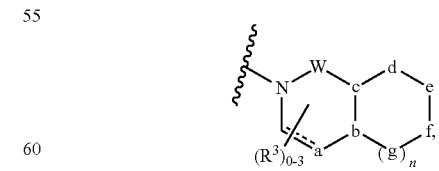

A'

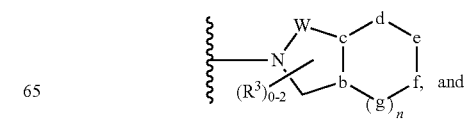

B' and

-continued

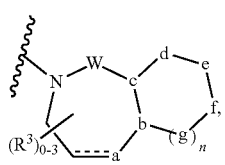

C' wherein:
the dashed bonds are single or double bonds,
n is 0 or 1, and
W is —C(O)— or —SO$_2$—;
each of ring vertices a, b, c, d, e, f, and g are independently selected from the group consisting of O, S, N, C(R$^4$), and N(R$^4$), and the bonds joining the ring vertices are independently single or double bonds;
each R$^{1a}$, R$^{1b}$, R$^{1c}$, R$^{1d}$ and R$^{1e}$ is independently selected from the group consisting of hydrogen, deuterium, halogen, —CN, —NO$_2$, —R$^c$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^a$, and —S(O)$_2$NR$^a$R$^b$, wherein each R$^a$ and R$^b$ is independently selected from hydrogen, C$_{1-8}$ alkyl, C$_{3-6}$ cycloalkyl, and C$_{1-8}$ haloalkyl, or R$^a$ and R$^b$, when attached to the same nitrogen atom, can be combined with the nitrogen atom to form a four-, five-, or six-membered ring having from 0 to 2 additional heteroatoms as ring members selected from N, O, S, SO, and SO$_2$; each R$^c$ is independently selected from the group consisting of C$_{1-8}$ alkyl, C$_{1-8}$ haloalkyl, C$_{1-8}$ deuteroalkyl, C$_{2-6}$ alkenyl, C$_{2-6}$ alkynyl, and C$_{3-6}$ cycloalkyl, and wherein the aliphatic and cyclic portions of R$^a$, R$^b$ and R$^c$ can be further substituted with from one to three halogen, hydroxy, C$_{1-4}$ alkyl, C$_{1-4}$ alkoxy, amino, C$_{1-4}$ alkylamino, di C$_{1-4}$ alkylamino, or carboxylic acid groups;
each R$^{2a}$, R$^{2b}$, R$^{2c}$ and R$^{2d}$ is independently selected from the group consisting of hydrogen, halogen, C$_{1-3}$ alkyl, C$_{1-3}$ deuteroalkyl, C$_{1-3}$ haloalkyl, C$_{1-3}$ alkoxy, C$_{1-3}$ deuteroalkoxy, and C$_{1-3}$ haloalkoxy;
R$^3$ is selected from the group consisting of hydrogen, deuterium, C$_{1-3}$ alkyl, C$_{1-3}$ deuteroalkyl, C$_{1-3}$ alkylene-OR$^d$, C$_{1-3}$ alkylene-CO$_2$R$^d$, C$_{1-3}$ alkylene-NR$^d$R$^e$, C$_{1-3}$ alkylene-CONR$^d$R$^e$, C$_{1-3}$ alkylene-OC(O)NR$^d$R$^e$, and C$_{1-3}$ alkylene-NR$^e$C(O)$_2$R$^f$;
each R$^4$ is independently selected from the group consisting of hydrogen, halogen, —CN, —R$^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^e$C(O)NR$^d$R$^e$, —NR$^d$R$^e$, —OR$^d$, —S(O)$_2$NR$^d$R$^e$, —X$^a$—CN, —X$^a$—CO$_2$R$^d$, —X$^a$—CONR$^d$R$^e$, —X$^a$—C(O) R$^d$, —X$^a$—OC(O)NR$^d$R$^e$, —X$^a$—NR$^e$C(O)R$^d$, —X$^a$—NR$^e$C(O)$_2$R$^f$, —X$^a$—NR$^e$C(O)NR$^d$R$^e$, —X$^a$—NR$^d$R$^e$, —X$^a$—OR$^d$, —X$^a$—S(O)$_2$NR$^d$R$^e$, and —X$^a$—OP(O)(OH)$_2$, wherein each X$^a$ is independently C$_{1-6}$ alkylene;
each R$^d$ and R$^e$ is independently selected from hydrogen, C$_{1-8}$ alkyl, and C$_{1-8}$ haloalkyl, or R$^d$ and R$^e$, when attached to the same nitrogen atom, can be combined with the nitrogen atom to form either (i) a four-, five-, or six-membered ring having from 0 to 3 additional heteroatoms as ring members selected from N, O, C(O), S, SO, and SO$_2$, or (ii) a spiroheterocycloalkyl ring;
each R$^f$ is independently selected from the group consisting of C$_{1-8}$ alkyl, C$_{1-8}$ haloalkyl, C$_{1-8}$ deuteroalkyl, C$_{3-6}$ cycloalkyl, C$_{3-6}$ heterocycloalkyl, phenyl, and 5- or 6-membered heteroaryl; and
the aliphatic and cyclic portions of R$^d$, R$^e$ and R$^f$ can be further substituted with from one to three halogen, hydroxy, benzyloxy, C$_{1-4}$ alkyl, C$_{1-4}$ alkoxy, amino, C$_{1-4}$ alkylamino, di C$_{1-4}$ alkylamino, tetrazolyl, or carboxylic acid groups.

2. The compound of claim 1, wherein:
the dashed bonds are single bonds;
vertex a is selected from the group consisting of O, S, N, CH(R$^4$), and N(R$^4$); each of ring vertices b, c, d, e, f, and g are independently selected from the group consisting of O, S, N, C(R$^4$), and N(R$^4$); and
the bonds joining the ring vertices are independently single or double bonds.

3. The compound of claim 2, wherein Z has subformula A'.

4. The compound of claim 2, wherein Z has subformula C'.

5. The compound of claim 3, wherein Z is selected from the group consisting of:

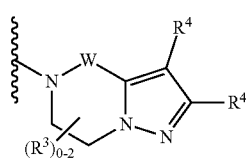

A'1

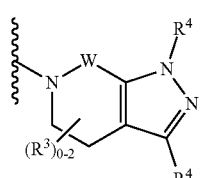

A'2

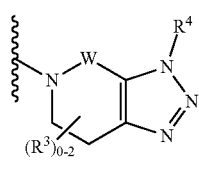

A'3

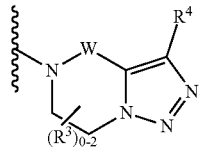

A'4

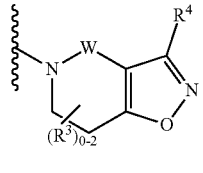

A'5

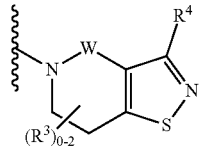

A'6

-continued

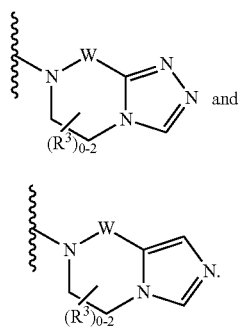

A'7

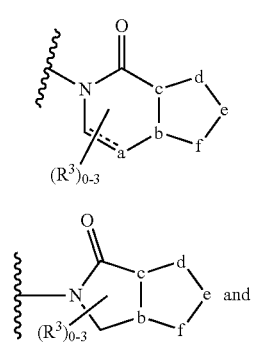

A'8

6. The compound of claim 5, wherein W is —C(O)—.

7. The compound of claim 5, wherein $R^{1b}$ is selected from the group consisting of H, deuterium, halogen, $C_{1-4}$ alkyl, —$OC_{1-4}$ alkyl, $C_{1-4}$ haloalkyl, and —$OC_{1-4}$ haloalkyl.

8. The compound of claim 7, wherein $R^{1c}$, $R^{1d}$ and $R^{1e}$ are each independently selected from the group consisting of H, deuterium, halogen, $C_{1-4}$ alkyl, $C_{1-4}$ haloalkyl, and $OC_{1-4}$ haloalkyl.

9. The compound of claim 8, wherein $R^{2a}$, $R^{2b}$, $R^{2c}$, $R^{2d}$ are independently selected from the group consisting of H, deuterium, halogen, $C_{1-4}$ alkyl, and $C_{1-4}$ haloalkyl.

10. The compound of claim 9, wherein each $R^4$ is independently selected from the group consisting of H, halogen, CN, —$R^f$, —$CO_2R^d$, —$CONR^dR^e$, —$C(O)R^d$, —$NR^eC(O)R^d$, —$NR^eC(O)_2R^f$, —$NR^dC(O)NR^dR^e$, —$NR^dR^e$, —$OR^d$, —$X^a$—CN, —$X^a$—$CO_2R^d$, —$X^a$—$CONR^dR^e$, —$X^a$—C(O)$R^d$, —$X^a$—OC(O)$NR^dR^e$, —$X^a$—$NR^eC(O)R^d$, —$X^a$—$NR^eC(O)_2R^f$, —$X^a$—$NR^dC(O)NR^dR^e$, —$X^a$—$NR^dR^e$, and —$X^a$—$OR^d$; wherein each $X^a$ is independently $C_{1-4}$alkylene.

11. The compound of claim 1, having a structure of formula (I):

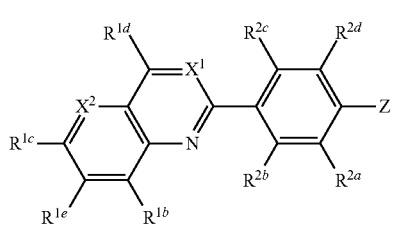

(I)

wherein:
Z is selected from the group consisting of:

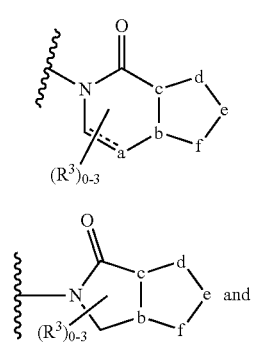

A

B

-continued

C each $R^4$ is independently selected from the group consisting of hydrogen, halogen, —CN, —$R^f$, —$CO_2R^d$, —$CONR^dR^e$, —C(O) $R^d$, —$OC(O)NR^dR^e$, —$NR^eC(O)R^d$, —$NR^eC(O)_2R^f$, —$NR^dC(O)NR^dR^e$, —$NR^dR^e$, —$OR^d$, —$S(O)_2NR^dR^e$, —$X^a$—CN, —$X^a$—$CO_2R^d$, —$X^a$—$CONR^dR^e$, —$X^a$—C(O) $R^d$, —$X^a$—OC(O)$NR^dR^e$, —$X^a$—$NR^eC(O)$ $R^d$, —$X^a$—$NR^eC(O)_2R^f$, —$X^a$—$NR^eC(O)NR^dR^e$, —$X^a$—$NR^dR^e$, —$X^a$—$OR^d$, and —$X^a$—$S(O)_2NR^dR^e$; wherein each $X^a$ is independently $C_{1-6}$alkylene; and each $R^d$ and $R^e$ is independently selected from hydrogen, $C_{1-8}$ alkyl, and $C_{1-8}$ haloalkyl, or $R^d$ and $R^e$, when attached to the same nitrogen atom, can be combined with the nitrogen atom to form a four-, five-, or six-membered ring having from 0 to 2 additional heteroatoms as ring members selected from N, O, S, SO, and $SO_2$; and the aliphatic and cyclic portions of $R^d$, $R^e$ and $R^f$ can be further substituted with from one to three halogen, hydroxy, $C_{1-4}$ alkyl, $C_{1-4}$ alkoxy, amino, $C_{1-4}$ alkylamino, di $C_{1-4}$ alkylamino, or carboxylic acid groups.

12. The compound of claim 11, having formula (IIc), (IId), (IIIb), (IIId), (IVc), or (IVd):

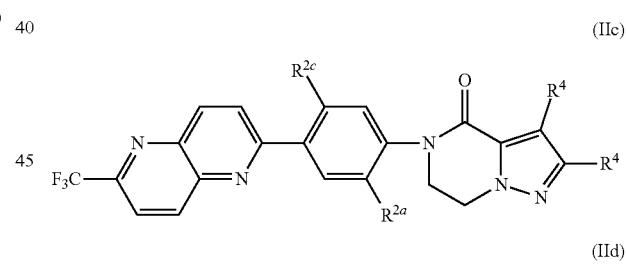

(IIc)

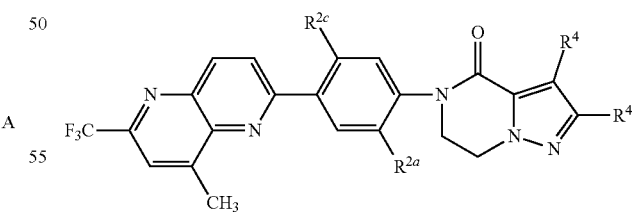

(IId)

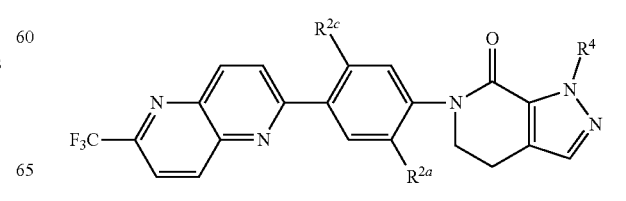

(IIIb)

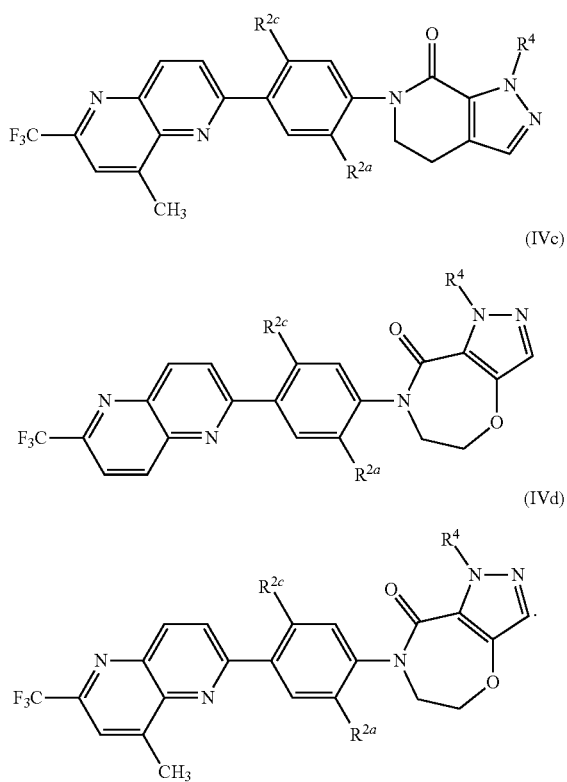

13. The compound of claim 1, selected from:
- 7-(2,5-dimethyl-4-(8-methyl-6-(trifluoromethyl)-1,5-naphthyridin-2-yl)phenyl)-1-methyl-6,7-dihydro-1H-pyrazolo[3,4-f][1,4]oxazepin-8 (5H)-one;
- 3-methyl-5-(2-methyl-4-(6-(trifluoromethyl)-1,5-naphthyridin-2-yl)phenyl)-6,7-dihydropyrazolo[1,5-a]pyrazin-4 (5H)-one;
- 5-(2-fluoro-5-methyl-4-(6-(trifluoromethyl)-1,5-naphthyridin-2-yl)phenyl)-3-methyl-6,7-dihydropyrazolo[1,5-a]pyrazin-4 (5H)-one;
- 6-(2,5-dimethyl-4-(6-(trifluoromethyl)-1,5-naphthyridin-2-yl)phenyl)-1-methyl-1,4,5,6-tetrahydro-7H-pyrazolo[3,4-c]pyridin-7-one;
- 6-(2-fluoro-5-methyl-4-(6-(trifluoromethyl)-1,5-naphthyridin-2-yl)phenyl)-1-methyl-1,4,5,6-tetrahydro-7H-pyrazolo[3,4-c]pyridin-7-one;
- 7-(2-fluoro-5-methyl-4-(6-(trifluoromethyl)-1,5-naphthyridin-2-yl)phenyl)-1-methyl-6,7-dihydro-1H-pyrazolo[3,4-f][1,4]oxazepin-8 (5H)-one;
- 3-methyl-5-(2-methyl-4-(8-methyl-6-(trifluoromethyl)-1,5-naphthyridin-2-yl)phenyl)-6,7-dihydropyrazolo[1,5-a]pyrazin-4 (5H)-one;
- 5-(2,5-dimethyl-4-(6-(trifluoromethyl)-1,5-naphthyridin-2-yl)phenyl)-3-methyl-6,7-dihydropyrazolo[1,5-a]pyrazin-4 (5H)-one;
- 5-(2,5-dimethyl-4-(8-methyl-6-(trifluoromethyl)-1,5-naphthyridin-2-yl)phenyl)-3-methyl-6,7-dihydropyrazolo[1,5-a]pyrazin-4 (5H)-one;
- 5-(2-fluoro-5-methyl-4-(8-methyl-6-(trifluoromethyl)-1,5-naphthyridin-2-yl)phenyl)-3-methyl-6,7-dihydropyrazolo[1,5-a]pyrazin-4 (5H)-one;
- 1-methyl-6-(2-methyl-4-(6-(trifluoromethyl)-1,5-naphthyridin-2-yl)phenyl)-1,4,5,6-tetrahydro-7H-pyrazolo[3,4-c]pyridin-7-one; 1-methyl-6-(2-methyl-4-(8-methyl-6-(trifluoromethyl)-1,5-naphthyridin-2-yl)phenyl)-1,4,5,6-tetrahydro-7H-pyrazolo[3,4-c]pyridin-7-one;
- 1-methyl-7-(2-methyl-4-(6-(trifluoromethyl)-1,5-naphthyridin-2-yl)phenyl)-6,7-dihydro-1H-pyrazolo[3,4-f][1,4]oxazepin-8 (5H)-one;
- 1-methyl-7-(2-methyl-4-(8-methyl-6-(trifluoromethyl)-1,5-naphthyridin-2-yl)phenyl)-6,7-dihydro-1H-pyrazolo[3,4-f][1,4]oxazepin-8 (5H)-one;
- 7-(2,5-dimethyl-4-(6-(trifluoromethyl)-1,5-naphthyridin-2-yl)phenyl)-1-methyl-6,7-dihydro-1H-pyrazolo[3,4-f][1,4]oxazepin-8 (5H)-one;
- 7-(2-methyl-4-(6-(trifluoromethyl)-1,5-naphthyridin-2-yl)phenyl)-6,7-dihydro-3H-[1,2,3]triazolo [4,5-f][1,4]oxazepin-8 (5H)-one;
- 2-methyl-7-(2-methyl-4-(6-(trifluoromethyl)-1,5-naphthyridin-2-yl)-phenyl)-6,7-dihydro-2H-[1,2,3]triazolo [4,5-f][1,4]oxazepin-8 (5H)-one;
- 6-methyl-7-(2-methyl-4-(6-(trifluoromethyl)-1,5-naphthyridin-2-yl)phenyl)-6,7-dihydro-1H-pyrazolo[3,4-f][1,4]oxazepin-8 (5H)-one;
- 2-methyl-7-(2-methyl-4-(6-(trifluoromethyl)-1,5-naphthyridin-2-yl)phenyl)-6,7-dihydro-2H-pyrazolo[3,4-f][1,4]oxazepin-8 (5H)-one;
- 7-(4-(6-fluoro-1,5-naphthyridin-2-yl)-2-methylphenyl)-1-methyl-6,7-dihydro-1H-pyrazolo[3,4-f][1,4]oxazepin-8 (5H)-one; and
- 3-methyl-5-(2-methyl-4-(6-(trifluoromethyl)-1,5-naphthyridin-2-yl)phenyl)-2-(morpholinomethyl)-6,7-dihydropyrazolo[1,5-a]pyrazin-4 (5H)-one, or a pharmaceutically acceptable salt thereof.

14. A pharmaceutical composition comprising a compound of claim 1 and a pharmaceutically acceptable excipient.

* * * * *